US011376272B2

(12) United States Patent
Barsotti et al.

(10) Patent No.: US 11,376,272 B2
(45) Date of Patent: Jul. 5, 2022

(54) METHODS OF MODULATING IMMUNE ACTIVITY

(71) Applicant: Flagship Pioneering Innovations V, Inc., Cambridge, MA (US)

(72) Inventors: Anthony Michael Barsotti, New York, NY (US); Alexandra Masu Cantley, New York, NY (US); Jason Park, West Newton, MA (US); Douglas Gowers Cole, Wayland, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 0 days.

(21) Appl. No.: 17/313,296

(22) Filed: May 6, 2021

(65) Prior Publication Data

US 2021/0299155 A1 Sep. 30, 2021

Related U.S. Application Data

(63) Continuation of application No. PCT/US2020/031190, filed on May 1, 2020.

(60) Provisional application No. 62/857,797, filed on Jun. 5, 2019, provisional application No. 62/857,809, filed on Jun. 5, 2019, provisional application No. 62/857,812, filed on Jun. 5, 2019, provisional application No. 62/843,266, filed on May 3, 2019.

(51) Int. Cl.
*A61K 31/7084* (2006.01)
*A61P 35/00* (2006.01)
*A61K 45/06* (2006.01)

(52) U.S. Cl.
CPC .......... *A61K 31/7084* (2013.01); *A61K 45/06* (2013.01); *A61P 35/00* (2018.01)

(58) Field of Classification Search
CPC ...... A61K 31/7084; A61K 45/05; A61P 35/00
See application file for complete search history.

(56) References Cited

U.S. PATENT DOCUMENTS

| 2014/0205653 | A1 | 7/2014 | Dubensky, Jr. et al. | |
|---|---|---|---|---|
| 2015/0297623 | A1* | 10/2015 | Jiang | A61K 31/522 514/47 |
| 2018/0125876 | A1* | 5/2018 | Perfettini | A61K 48/00 |

FOREIGN PATENT DOCUMENTS

| WO | 2003/028712 | A2 | 4/2003 |
|---|---|---|---|
| WO | 2005/112947 | A2 | 12/2005 |
| WO | 2009/001673 | A1 | 12/2008 |
| WO | 2010/139352 | A1 | 12/2010 |
| WO | 2014/099824 | A1 | 6/2014 |
| WO | 2015/061294 | A2 | 4/2015 |
| WO | WO2018/200812 | | * 11/2018 |
| WO | 2019/033710 | A1 | 2/2019 |

OTHER PUBLICATIONS

Nylund et al. (Autonomic Neuroscience: Basic and Clinical, 2004, 112, 69-79). (Year: 2004).*
Kermanian et al., Effects of adenosine A2a receptor agonist and antagonist on hippocampal nuclear factor-kB expression preceded by MDMA toxicity. Metab Brain Dis. Mar. 2013;28(1):45-52.
Khalafalla et al., P2X7 receptor antagonism prevents IL-1 beta release from salivary epithelial cells and reduces inflammation in a mouse model of autoimmune exocrinopathy. J Biol Chem. Oct. 6, 2017;292(40):16626-16637.
Mosser et al., Exploring the full spectrum of macrophage activation. Nat Rev Immunol. Dec. 2008;8(12):958-69.
Paredes-Juarez et al., DAMP production by human islets under low oxygen and nutrients in the presence or absence of an immunoisolating-capsule and necrostatin-1. Scientific Reports. Sep. 30, 2015;5:14623, 12 pages.
Savio et al., Immunomodulatory effects of P2X7 receptor in intracellular parasite infections. Curr Opin Pharmacol. Aug. 2019;47:53-58.
Theatre et al., A P2X ion channel-triggered NF-kappaB pathway enhances TNF-alpha-induced IL-8 expression in airway epithelial cells. Am J Respir Cell Mol Biol Dec. 2009;41(6):705-13.
Van Langevelde et al.. Antibiotic-induced lipopolysaccharide (LPS) release from *Salmonella typhi*: delay between killing by ceftazidime and imipenem and release of LPS. Antimicrob Agents Chemother. Apr. 1998;42(4):739-43.
Zhang et al., Virus-Triggered ATP Release Limits Viral Replication through Facilitating IFN-beta Production in a P2X7-Dependent Manner. J Immunol. Aug. 15, 2017;199(4):1372-1381.
Zhou et al.. Blockade of the Phagocytic Receptor MerTK on Tumor-Associated Macrophages Enhances P2X7R-Dependent STING Activation by Tumor-Derived cGAMP. Immunity Feb. 18, 2020;52(2):357-373.
International Search Resport and Written Opinion for Application No. PCT/US2020/031190, dated Nov. 18, 2020, 37 pages.
Invitation to Pay Additional Fees for Application No. PCT/US2020/031190, dated Aug. 7, 2020,26 pages.
International Preliminary Report on Patentability for Application No. PCT/US2020/031190, dated Nov. 18, 2021, 29 pages.

* cited by examiner

*Primary Examiner* — Genevieve S Alley
(74) *Attorney, Agent, or Firm* — McCarter & English, LLP; Jill Mello

(57) ABSTRACT

In one aspect, the invention provides methods of increasing immune response by administering postcellular signaling factors produced by cells exposed to a stress condition. In one aspect, the invention provides methods of increasing immune response by administering in combination (a) a Stimulator of Interferon Genes (STING) agonist and (b) a purinergic receptor agonist. The increase in immune response may be used, for example, for treatment of infection or cancer. The invention also provides screening assays for identification of compounds that induce production of postcellular signaling factors which are also immunostimulatory agents. The invention further provides methods for identifying postcellular signaling factors with immunostimulatory activity. In another aspect, the invention provides methods of decreasing immune response by administering to a cell, tissue or subject a purinergic receptor antagonist alone or in combination with a Stimulator of Interferon Genes (STING) antagonist.

30 Claims, 16 Drawing Sheets

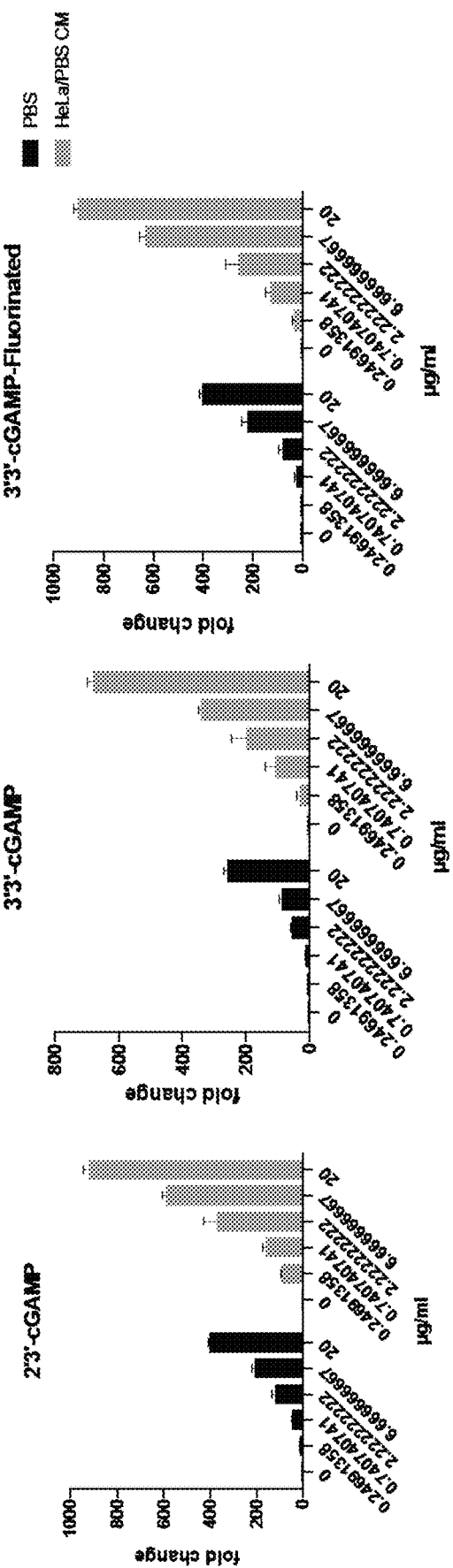

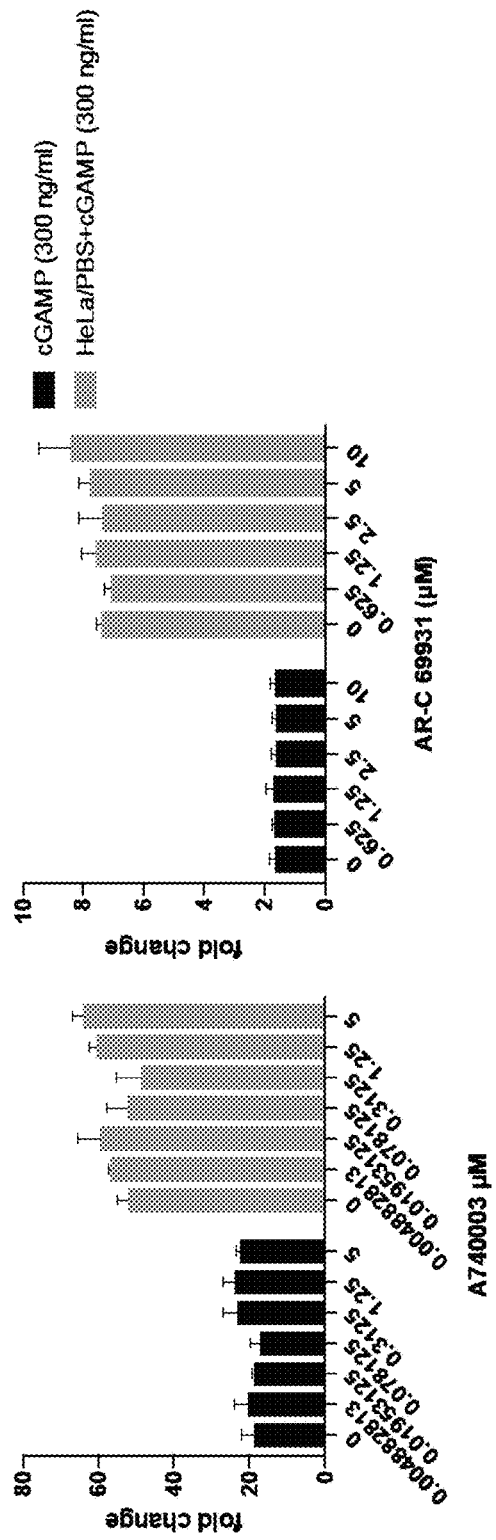
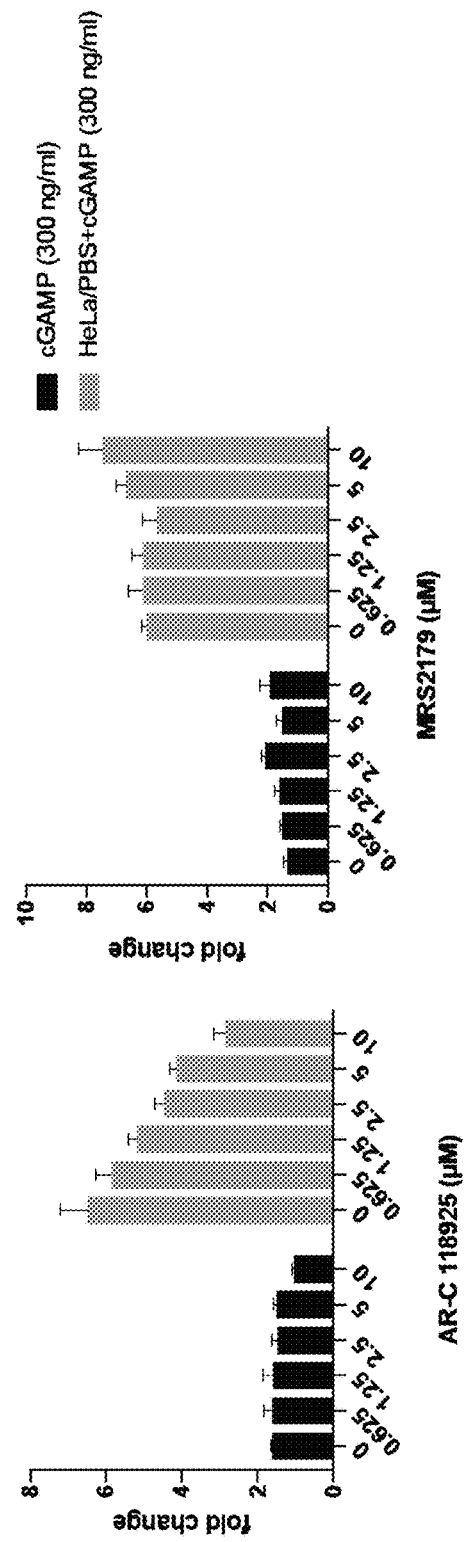
FIG. 6A
FIG. 6B
FIG. 6C
FIG. 6D

METHODS OF MODULATING IMMUNE ACTIVITY

RELATED APPLICATIONS

This application is a continuation under 35 U.S.C. § 111(a) of International Application No. PCT/US2020/031190, filed May 1, 2020 which, in turn, claims priority to U.S. Provisional Application No. 62/843,266, filed on May 3, 2019, U.S. Provisional Application No. 62/857,812, filed on Jun. 5, 2019, U.S. Provisional Application No. 62/857,797, filed on Jun. 5, 2019, and U.S. Provisional Application No. 62/857,809, filed on Jun. 5, 2019, the entire contents of each of which are expressly incorporated herein by reference.

BACKGROUND

In multicellular organisms, cell death is a critical and active process that is believed to maintain tissue homeostasis and eliminate potentially harmful cells.

SUMMARY OF THE INVENTION

In certain aspects, the disclosure relates to a method of increasing immune activity in a target cell, tissue or subject, the method comprising administering to the target cell, tissue or subject, in combination (a) a Stimulator of Interferon Genes (STING) agonist and (b) a purinergic receptor agonist, wherein the STING agonist and the purinergic receptor agonist are administered in an amount sufficient to increase the immune activity relative to a cell, tissue or subject that is not treated with the STING agonist and/or the purinergic receptor agonist. In one embodiment, the STING agonist and the purinergic receptor agonist act synergistically.

In certain aspects, the disclosure relates to a method of increasing the level or activity of IRF or STING in a target cell, tissue or subject, comprising administering to the target cell, tissue or subject, in combination (a) a Stimulator of Interferon Genes (STING) agonist and (b) a purinergic receptor agonist, wherein the STING agonist and the purinergic receptor agonist are administered in an amount sufficient to increase the level or activity of IRF or STING relative to a cell, tissue or subject that is not treated with the STING agonist and/or the purinergic receptor agonist. In one embodiment, the STING agonist and the purinergic receptor agonist act synergistically. In one embodiment, the subject is in need of an increased level or activity of RF or STING. In one embodiment, the level or activity of RF or STING is increased by at least 10%, 20%, 30%, 40%, 50%, 60%, 70%, 80%, 90% or 100%, or by at least 2-fold, 4-fold, 6-fold, 8-fold, or 10-fold relative to a cell, tissue or subject that is not treated with the the STING agonist and/or the purinergic receptor agonist.

In certain aspects, the disclosure relates to a method of treating a subject in need of increased immune activity, the method comprising administering to the subject, in combination (a) a Stimulator of Interferon Genes (STING) agonist and (b) a purinergic receptor agonist, wherein the STING agonist and the purinergic receptor agonist are administered in an amount sufficient to increase the immune activity in the subject relative to a subject that is not treated with the STING agonist and/or the purinergic receptor agonist. In one embodiment, the STING agonist and the purinergic receptor agonist act synergistically.

In one embodiment, the subject has cancer. In one embodiment, the subject has a chronic infection. In embodiments, the chronic infection is selected from HIV infection, HCV infection, HBV infection, HPV infection, Hepatitis B infection, Hepatitis C infection, EBV infection, CMV infection, TB infection, and infection with a parasite.

In certain aspects, the disclosure relates to a method of treating a subject diagnosed with cancer, comprising administering to the subject, in combination (a) a Stimulator of Interferon Genes (STING) agonist and (b) a purinergic receptor agonist, thereby treating the cancer in the subject. In one embodiment, the STING agonist and the purinergic receptor agonist act synergistically. In one embodiment, a response of the cancer to treatment is improved relative to a treatment with the STING agonist alone or the purinergic receptor agonist alone. In one embodiment, the response is improved, e.g., in a population of subjects, by at least 5%, at least 10%, at least 15%, at least 20%, at least 30%, at least 40%, at least 50%, at least 60%, at least 70%, or at least 80% relative to treatment with the STING agonist alone or the purinergic receptor agonist alone. In one embodiment, the response comprises any one or more of reduction in tumor burden, reduction in tumor size, inhibition of tumor growth, achievement of stable cancer in a subject with a progressive cancer prior to treatment, increased time to progression of the cancer, and increased time of survival. In one embodiment, the cancer is a cancer responsive to an immune checkpoint therapy. In one embodiment, the cancer is selected from a carcinoma, sarcoma, lymphoma, melanoma, and leukemia.

In one embodiment, the STING agonist is a cyclic dinucleotide. In one embodiment, the cyclic dinucleotide is selected from the group consisting of cGAMP, 2'3'-cGAMP, 3'3'-cGAMP, 3'3'-cGAMP-F, c-di-GMP, c-di-GMP-F, Rp/Sp, MK-1454, ADU-S100 (also known as ML RR-S2 CDA or MIW815), and Disodium dithio-(RP, RP)-[cyclic [A(2',5')pA(3',5')p]] [Rp,Rp]-Cyclic(adenosine-(2',5') monophosphorothioateadenosine-(3',5')-monophosphorothioate) (also known as disodium ADU-S100). In one embodiment, the STING agonist is a flavonoid. In one embodiment, the flavonoid is selected from the group consisting of 10-(carboxymethyl)-9(10H)acridone (CMA), 5,6-Dimethylxanthenone-4-acetic acid (DMXAA) or vadimezan, methoxyvone, 6, 4'-dimethoxyflavone, 4'-methoxyflavone, 3', 6'-dihydroxyflavone, 7, 2'-dihydroxyflavone, daidzein, formononetin, retusin 7-methyl ether, xanthone, or any combination thereof. In one embodiment, the STING agonist is an amidobenzimidazole compound or a dimeric amidobenzimidizole compound. In one embodiment, the STING agonist is DNA. In one embodiment, the STING agonist is a type I interferon (IFN). In one embodiment, the type I IFN is interferon-0 or interferon-α.

In one embodiment, the purinergic receptor agonist is a small molecule. In one embodiment, the purinergic receptor agonist is a cyclic dinucleotide. In one embodiment, the purinergic receptor agonist is a P2 receptor agonist. In one embodiment, the purinergic receptor agonist is a P2Y2, P2Y4 or P2Y6 receptor agonist. In one embodiment, the purinergic receptor agonist is a nucleotide-based compound represented by one of the following structural formulas:

In one embodiment, the purinergic receptor agonist is a nucleotide-based compound represented by one of the following structural formulas:

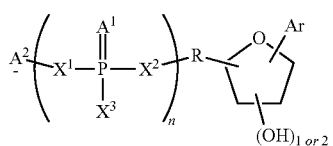

or a pharmaceutically acceptable salt, free acid, an analogue, a regioisomer, a stereoisomer or a tautomer thereof wherein $X^1$, $X^2$ and $X^3$, for each instance is independently selected from O, S, halogen, imido, methyl or methylene (as valency permits), ethyl or ethylene (as valency permits), halomethyl or halomethylene (as valency permits), haloethyl or haloethylene (as valency permits), wherein at least one instance of $X^1$, $X^2$ and $X^3$ is O or S; $A^1$ and $A^2$ are each independently O or S; R is selected from O, S, methoxy, thiomethoxy, ethoxy, and thioethoxy; and Ar is an optionally substituted monocyclic or bicyclic heteroaryl having at least one nitrogen atom (e.g., 1, 2, 3 or 4) and optionally one or more heteroatoms selected from O and S; and wherein n is 1, 2 or 3, preferably 2 or 3, preferably 3.

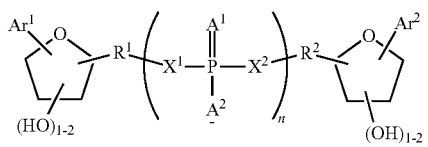

or a pharmaceutically acceptable salt, free acid, an analogue, a regioisomer, a stereoisomer or a tautomer thereof wherein $X^1$ and $X^2$, for each instance is independently selected from O, S, halogen, imido, methyl or methylene (as valency permits), ethyl or ethylene (as valency permits), halomethyl or halomethylene (as valency permits), haloethyl or haloethylene (as valency permits), wherein at least one instance of $X^1$ and $X^2$ is O or S; $A^1$ and $A^2$ are each independently O or S; R is selected from O, S, methoxy, thiomethoxy, ethoxy, and thioethoxy; and $Ar^1$ and $Ar^2$ are each and independently an optionally substituted monocyclic or bicyclic heteroaryl having at least one nitrogen atom (e.g., 1, 2, 3 or 4) and optionally one or more heteroatoms selected from O and S; n is an integer from 1 to 20.

In one embodiment, Ar, $Ar^1$ and $Ar^2$ in the two structural formulas described above for nucleotide-based purinergic receptor are each independently selected from the group consisting of:

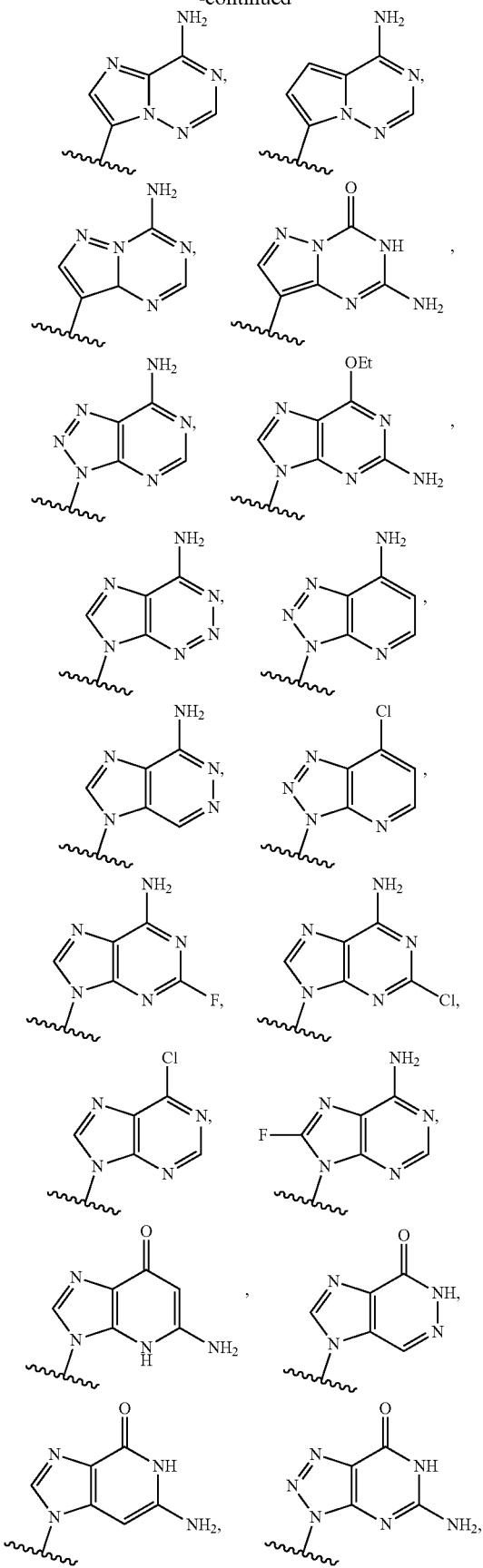

-continued
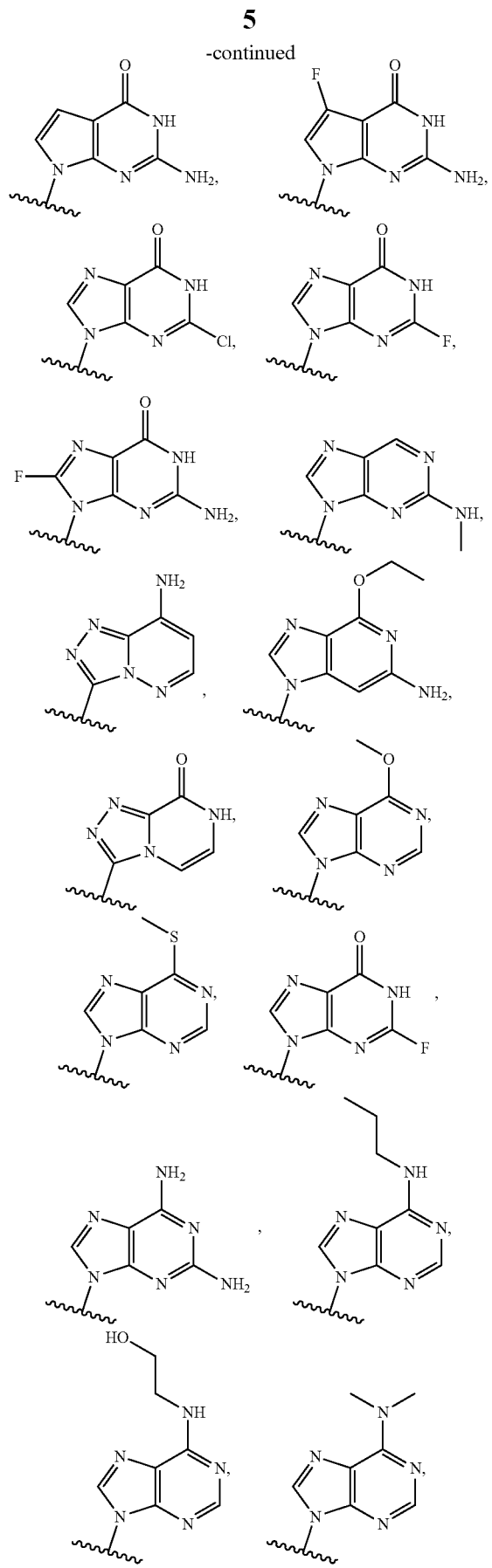
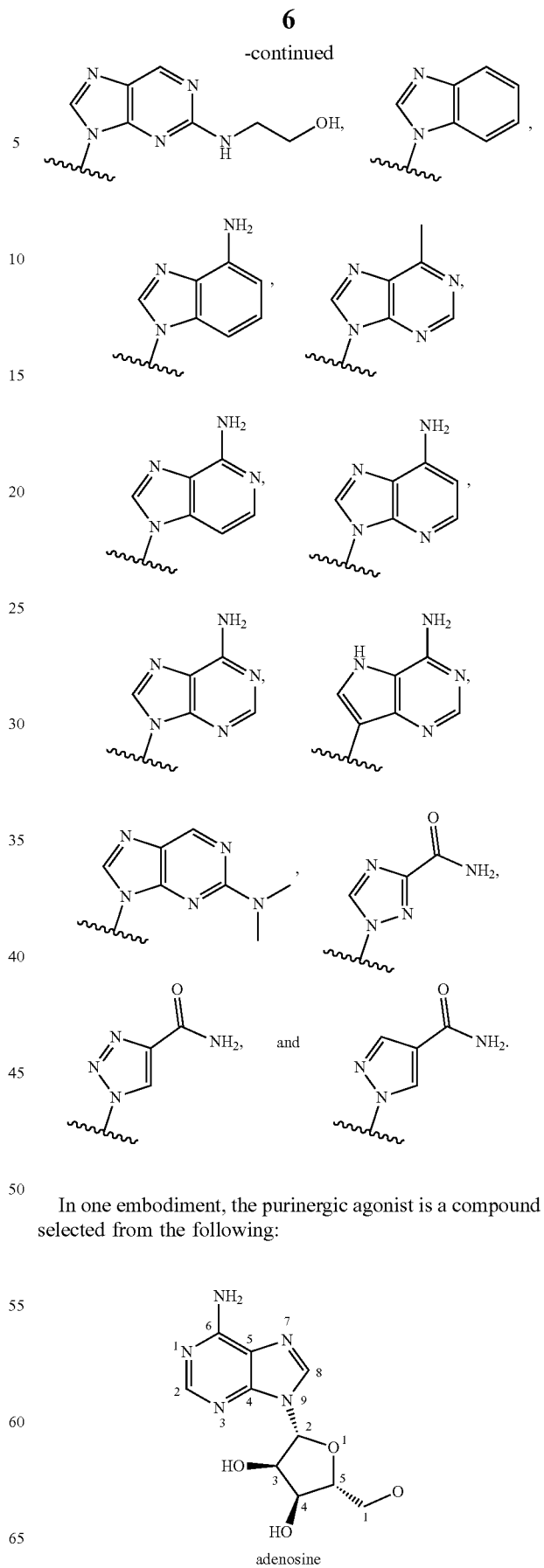
In one embodiment, the purinergic agonist is a compound selected from the following:
adenosine

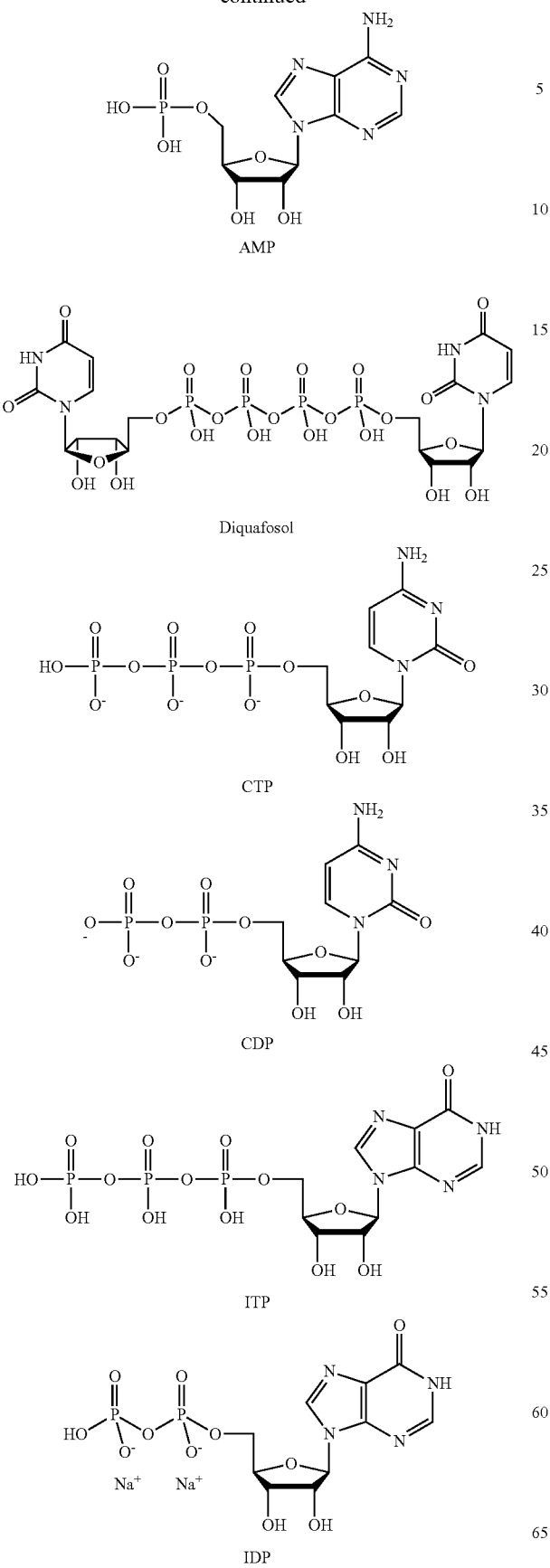
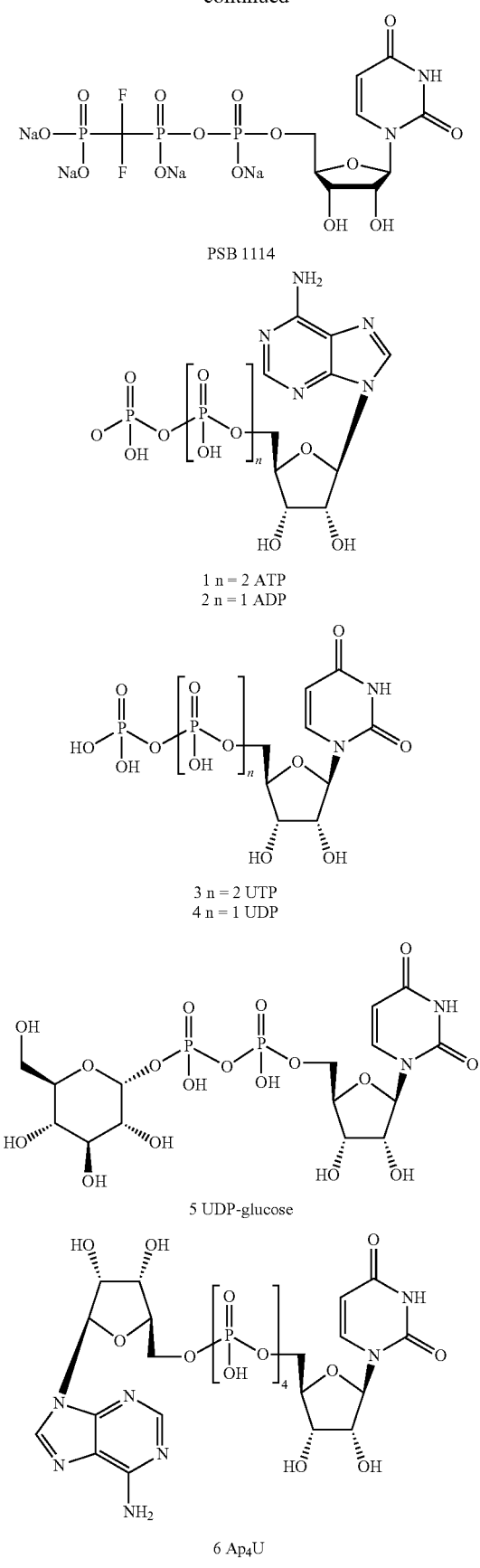

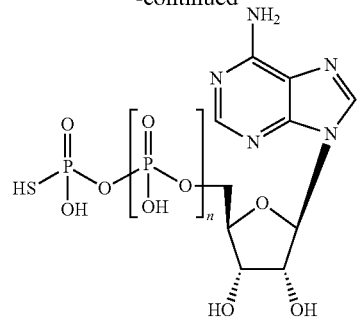
7 n = 2 ATP S
8 n = 1 ADP S
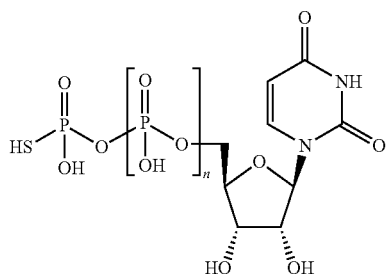
9 n = 2 UTP S
10 n = 1 UDP S
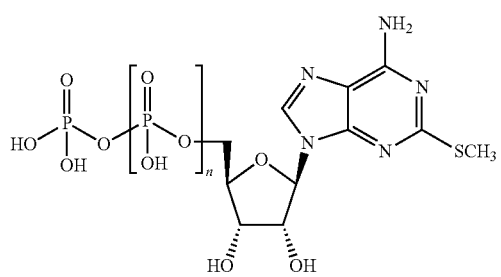
11 n = 2
12 n = 1
13 n = 0
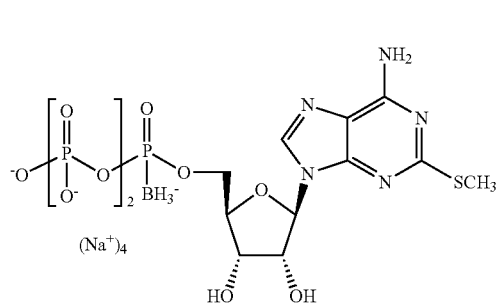
14
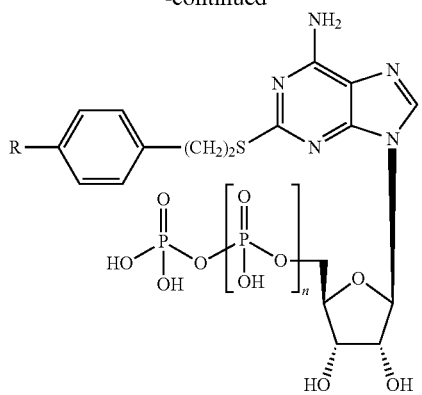
15 n = 2 R = NH$_2$
16 n = 1 R = N$_3$
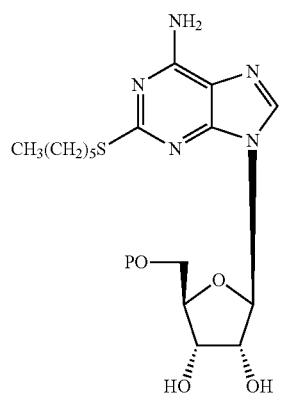
17 HT-AMP
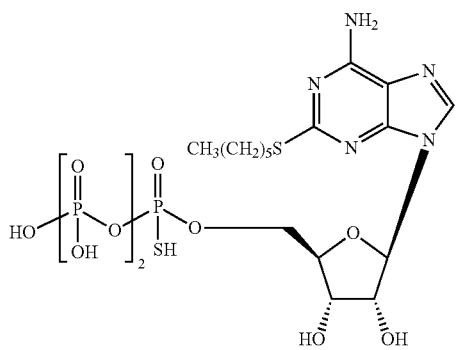
18

-continued
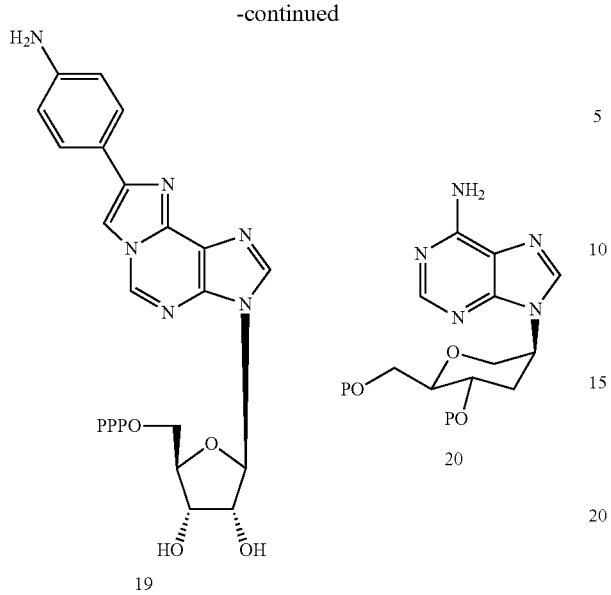
19
21 (N)-mcATP
22 (S)-mcATP
23
-continued
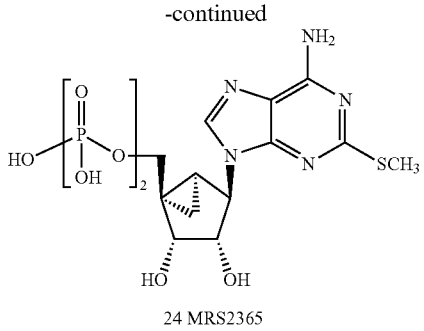
24 MRS2365
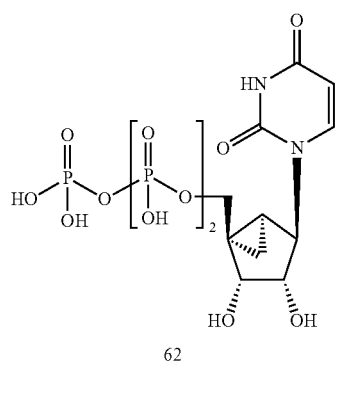
62
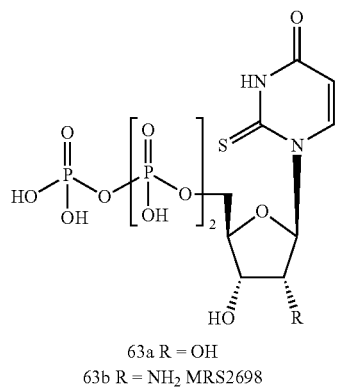
63a R = OH
63b R = NH₂ MRS2698
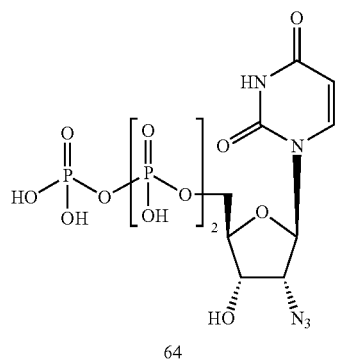
64

-continued
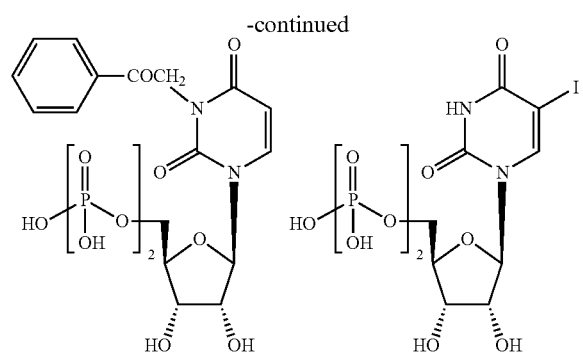
65
66 MRS2693
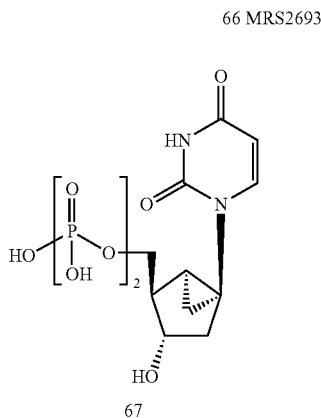
67
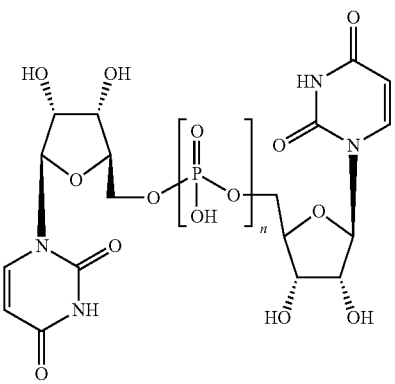
68a n = 2 Up$_2$U
68b n = 3 Up$_3$U
68c n = 4 Up$_4$U, Diquafosol
68d n = 6 Up$_6$U
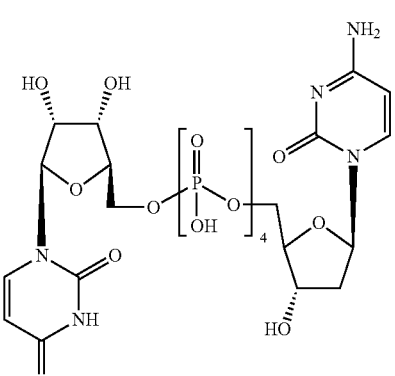
69 Up$_4$dC, INS37217, Denufosol
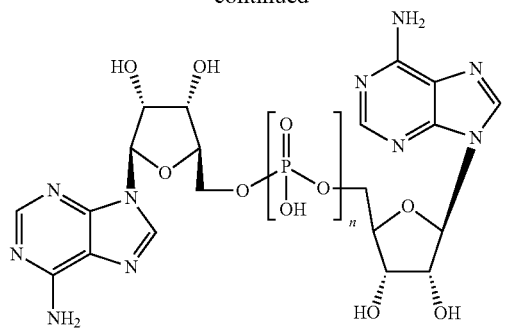
70a n = 3 Ap$_3$A
70b n = 4 Ap$_4$A
70c n = 5 Ap$_5$A
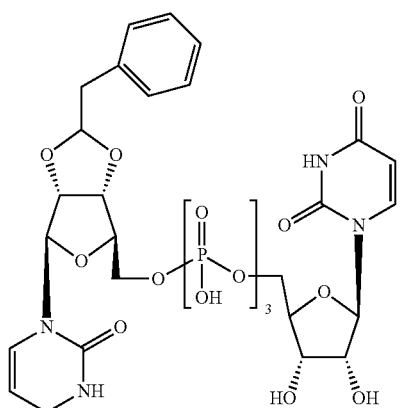
71 INS48823
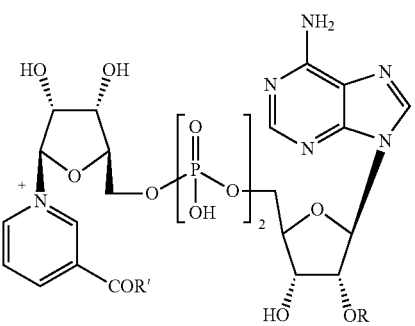
72 R = H, R' = NH$_2$ -NAD$^+$
73 R = PO$_3$H$_2$, R' = OH NAADP$^+$
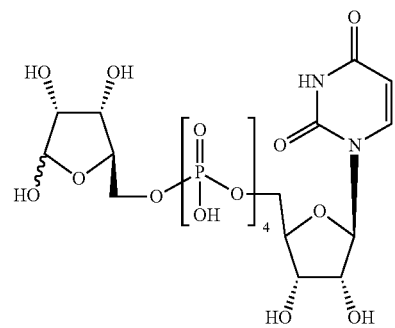
74

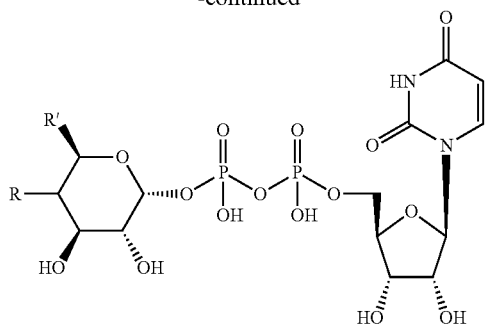
R =
75 R = HO⋯ R' = COOH
76 R = HO— R' = CH₂OH
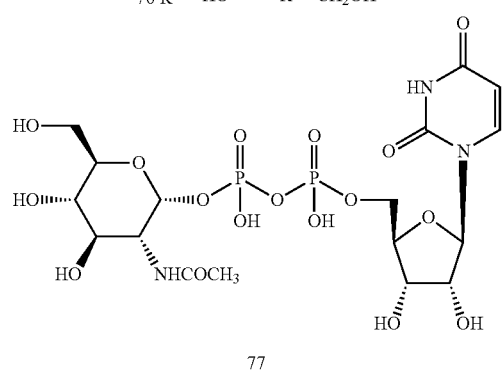
77
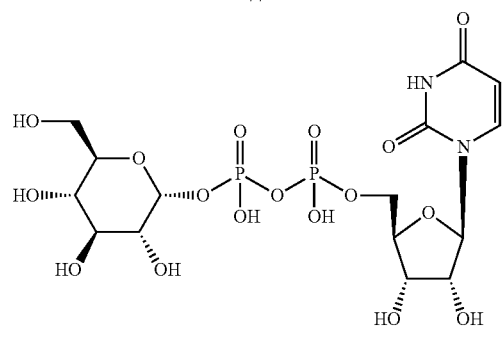
78 MRS2690
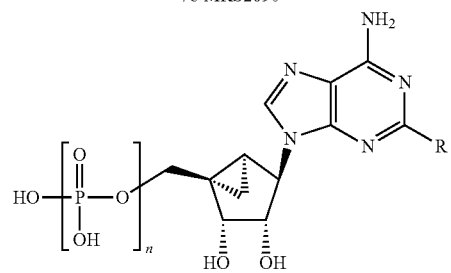
R = H, n = 3 MRS2340
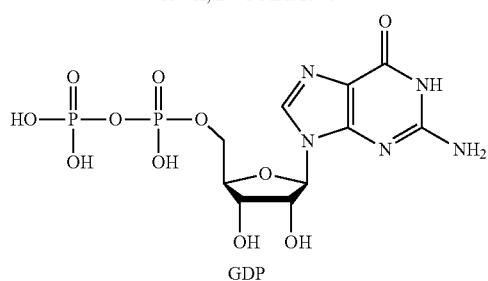
GDP
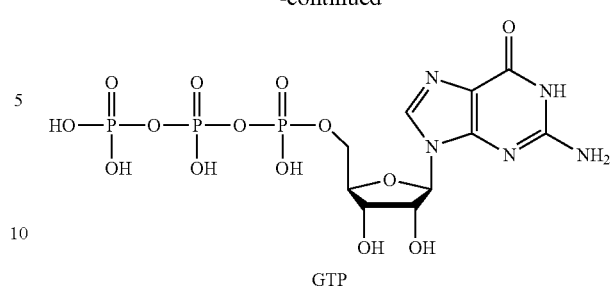
GTP
or a pharmaceutically acceptable salt, free acid, an analogue, a regioisomer, a stereoisomer or a tautomer thereof.
In one particular embodiment, the purinergic receptor agonist is a P2Y2, P2Y4 or P2Y6 receptor agonist and is a compound selected from the following:
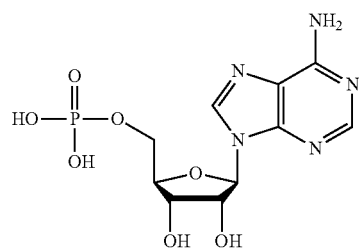
abenosine
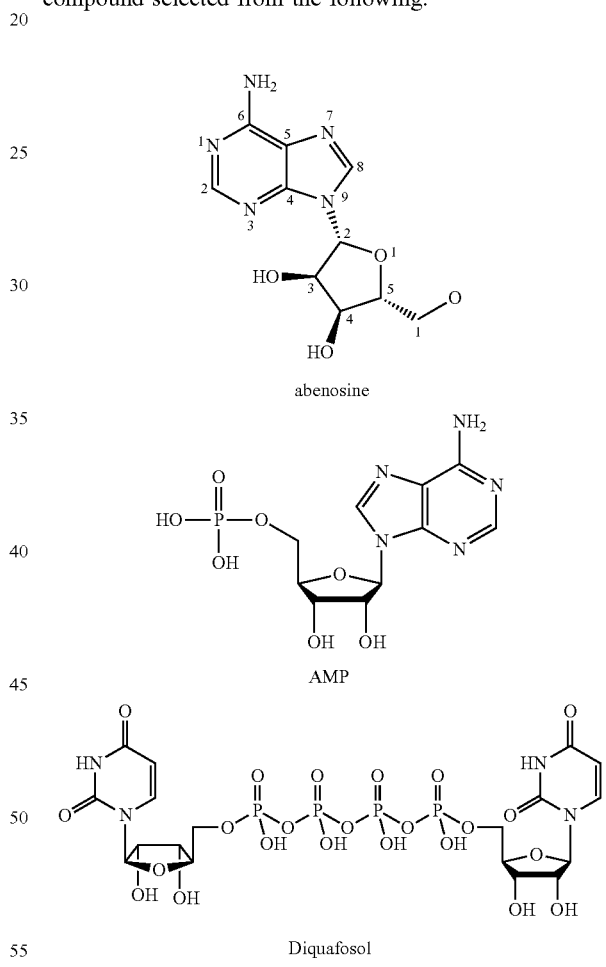
AMP
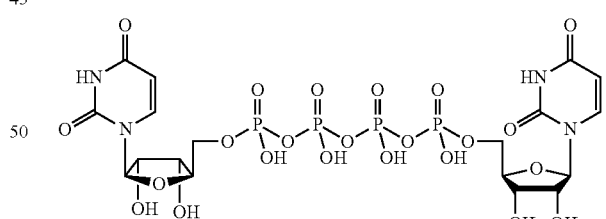
Diquafosol
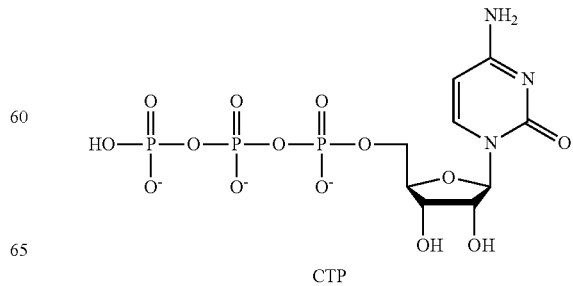
CTP

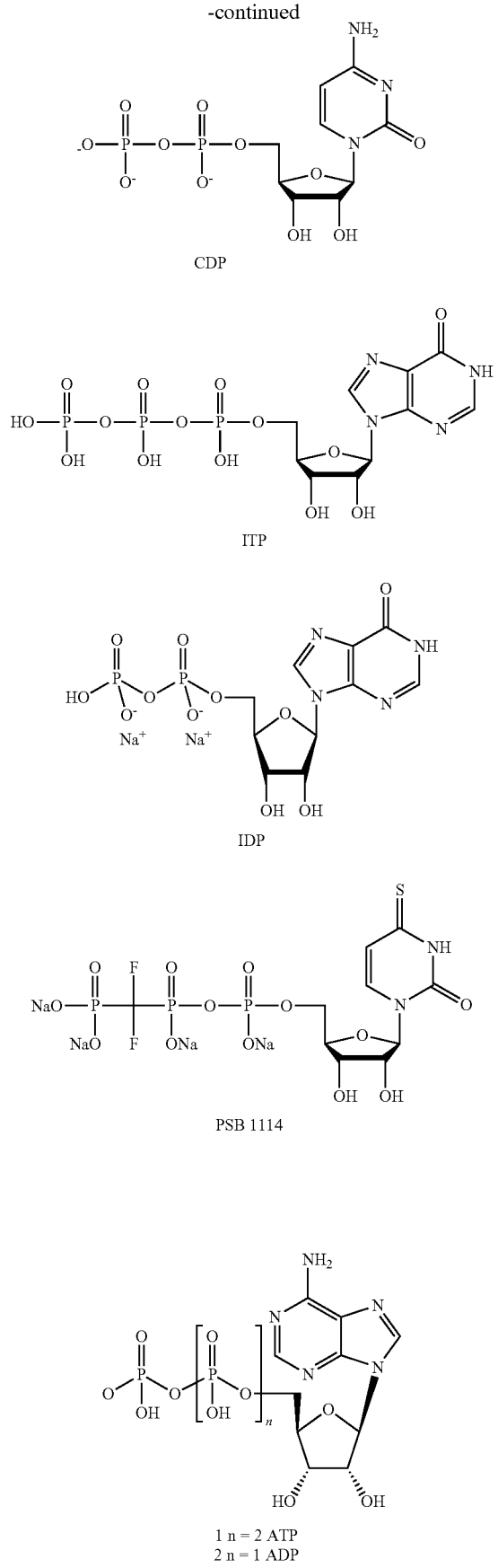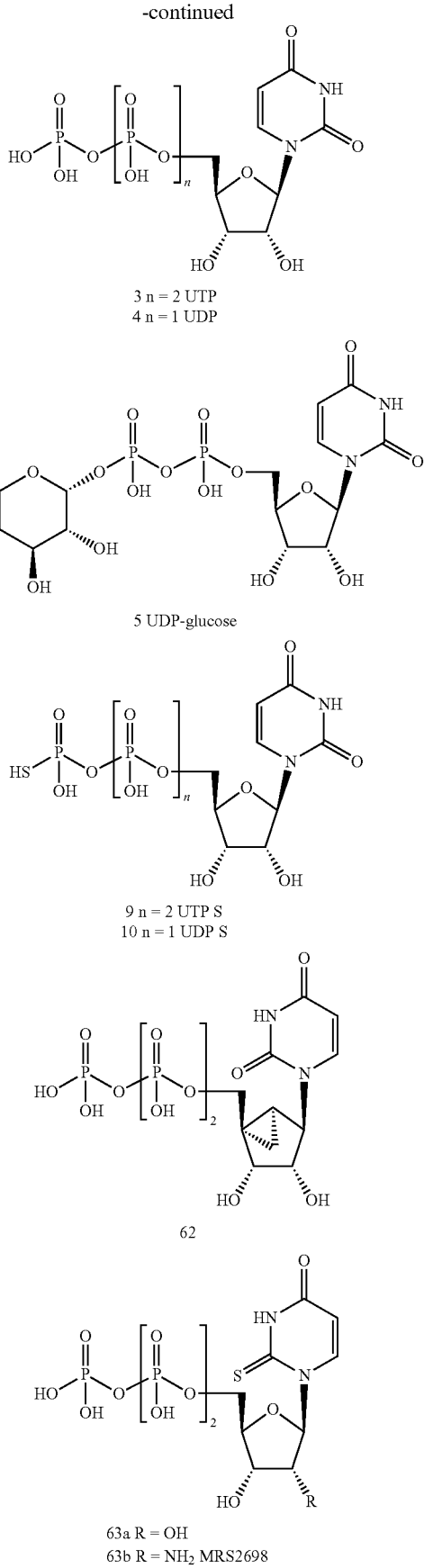

-continued
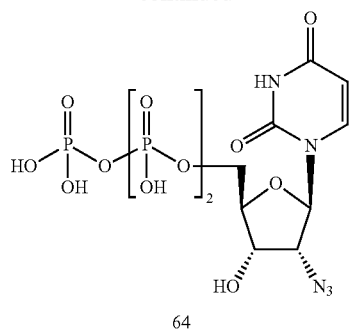
64
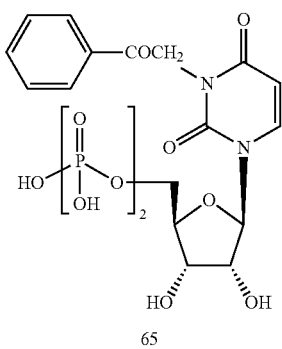
65
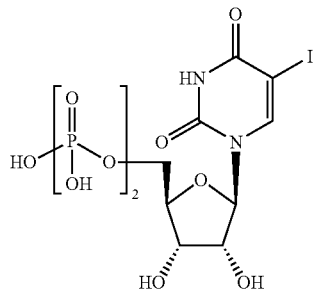
66 MRS2693
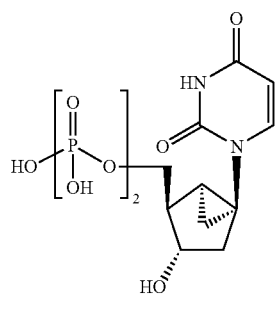
67
-continued
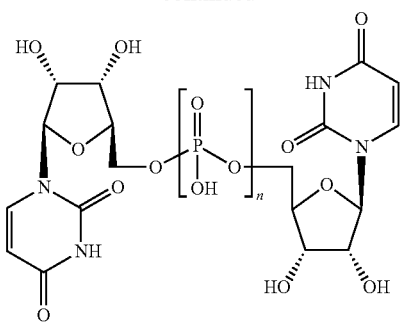
68a n = 2 Up$_2$U
68b n = 3 Up$_3$U
68c n = 4 Up$_4$U, Diquafosol
68d n = 6 Up$_6$U
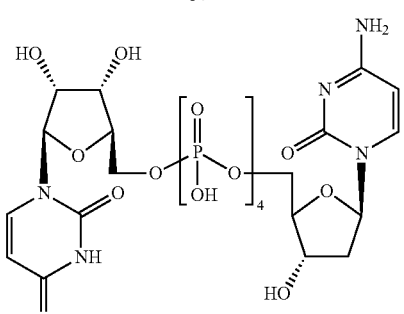
69 Up$_4$dC, INS37217, Denufosol
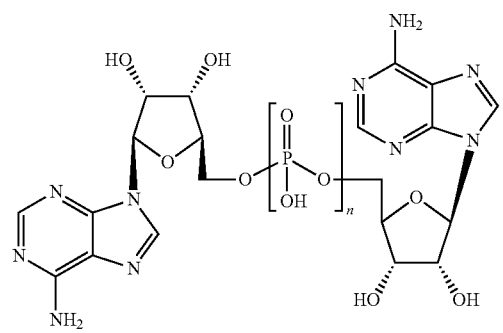
70a n = n = 3 Ap$_3$A
70b n = n = 4 Ap$_4$A
70c n = n = 5 Ap$_5$A
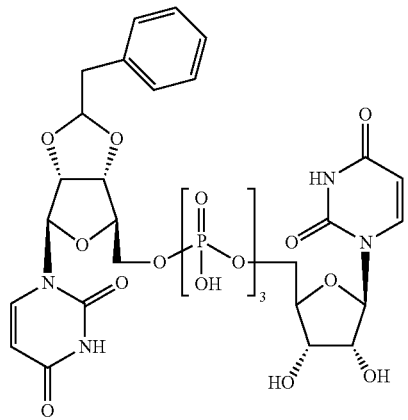
71 INS48823

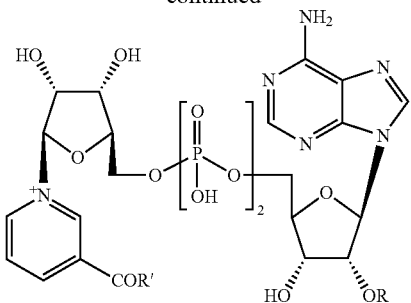

72 R = H, R' = NH₂ -NAD⁺
73 R = PO₃H₂, R' = OH NAADP⁺

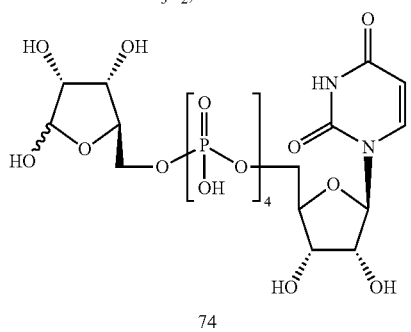

74

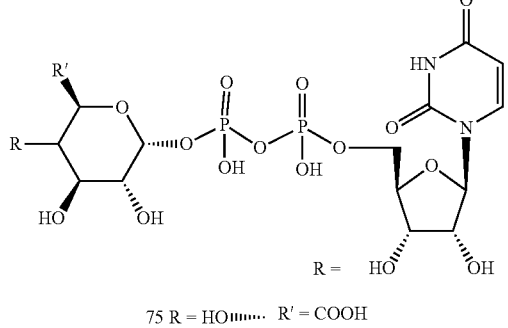

75 R = HO⸺, R' = COOH

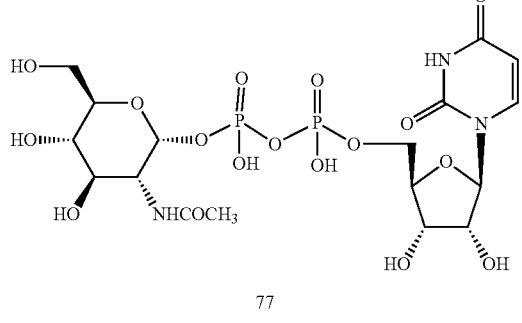

77

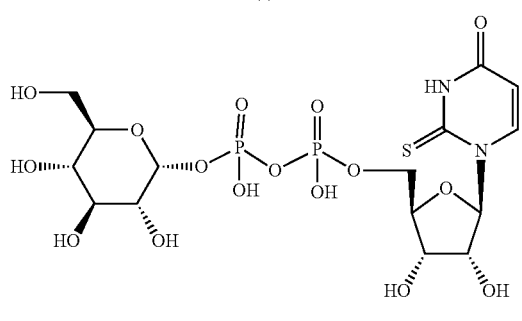

78 MRS2690 or a pharmaceutically acceptable salt, free acid, an analogue, a regioisomer, a stereoisomer or a tautomer thereof.

In one embodiment, the purinergic receptor agonist is a compound represented by the following structural formula, or a pharmaceutically acceptable salt, free acid, an analogue, a regioisomer, a stereoisomer or a tautomer thereof.

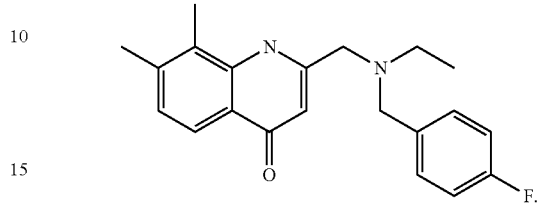

In one embodiment, the purinergic receptor agonist is selected from ATP disodium salt ATPγS tetralithium salt, BzATP triethylammonium salt, α,β-Methyleneadenosine 5'-triphosphate trisodium salt, 2-Methylthioadenosine diphosphate trisodium salt, 2-Methylthioadenosine triphosphate tetrasodium salt, MRS 2693 trisodium salt, MRS 2768 tetrasodium salt, MRS 2905, MRS 2957 triethylammonium salt, MRS 4062 triethylammonium salt, NF 546, 5-OMe-UDP trisodium salt, PSB 0474, 2-ThioUTP tetrasodium salt, and UTPγS trisodium salt.

In some embodiments, the purinergic receptor agonist is selected from the group consisting of ATP, adenosine, cytidine, inosine, uridine, guanosine, AMP, CMP, IMP, GMP, cAMP, UMP, ADP, GDP, CDP, IDP, UDP, CTP, GTP, ITP, UTP and cGMP.

In one embodiment of the methods described herein, the subject is in need of an increased immune activity. In one embodiment, the subject is human. In one embodiment, the STING agonist and the purinergic receptor agonist are administered in an amount sufficient to increase in the cell, tissue or subject one or more of the level or activity of type I interferon, the level or activity of TBK1, the level or activity of IRF, the level or activity of NFkB, the level or activity of macrophages, the level or activity of monocytes, the level or activity of dendritic cells, the level or activity of T cells, the level or activity of CD4+, CD8+ or CD3+ cells, and the level or activity of a pro-immune cytokine.

In one embodiment, the method further comprises administering an immunotherapeutic to the subject. In one embodiment, the immunotherapeutic is selected from the group consisting of a Toll-like receptor (TLR) agonist, a cell-based therapy, a cytokine, a cancer vaccine, and an immune checkpoint modulator of an immune checkpoint molecule. In one embodiment, the TLR agonist is selected from Coley's toxin and Bacille Calmette-Guerin (BCG). In one embodiment, the immune checkpoint molecule is selected from CD27, CD28, CD40, CD122, OX40, GITR, ICOS, 4-1BB, ADORA2A, B7-H3, B7-H4, BTLA, CTLA-4, IDO, KIR, LAG-3, PD-1, PD-L1, PD-L2, TIM-3, and VISTA.

In one embodiment, the immune checkpoint molecule is a stimulatory immune checkpoint molecule and the immune checkpoint modulator is an agonist of the stimulatory immune checkpoint molecule. In one embodiment, the immune checkpoint molecule is an inhibitory immune checkpoint molecule and the immune checkpoint modulator is an antagonist of the inhibitory immune checkpoint molecule. In one embodiment, the immune checkpoint modulator is selected from a small molecule, an inhibitory RNA, an antisense molecule, and an immune checkpoint molecule binding protein. In one embodiment, the immune checkpoint molecule is PD-1 and the immune checkpoint modulator is a PD-1 inhibitor. In one embodiment, the PD-1 inhibitor is selected from pembrolizumab, nivolumab, pidilizumab, SHR-1210, MEDI0680R01, BBg-A317, TSR-042, REGN2810 and PF-06801591. In one embodiment, the immune checkpoint molecule is PD-L1 and the immune checkpoint modulator is a PD-L1 inhibitor. In one embodiment, the PD-L1 inhibitor is selected from durvalumab, atezolizumab, avelumab, MDX-1105, AMP-224 and LY3300054. In one embodiment, the immune checkpoint molecule is CTLA-4 and the immune checkpoint modulator is a CTLA-4 inhibitor. In one embodiment, the CTLA-4 inhibitor is selected from ipilimumab, tremelimumab, JMW-3B3 and AGEN1884.

In certain aspects, the disclosure relates to a method of increasing immune activity in a target cell, tissue or subject, the method comprising administering to the target cell, tissue or subject a composition comprising one or more postcellular signaling factors produced by cells exposed to a stress condition, wherein the composition is administered in an amount sufficient to increase the immune activity relative to a cell, tissue or subject that is not treated with the composition.

In certain aspects, the disclosure relates to a method of increasing the level or activity of IRF or STING in a cell, tissue or subject, comprising administering to the cell, tissue or subject a composition comprising one or more postcellular signaling factors produced by cells exposed to a stress condition, wherein the composition is administered in an amount sufficient to increase the level or activity of IRF or STING relative to a cell, tissue or subject that is not treated with the composition. In one embodiment, the subject is in need of an increased level or activity of IRF or STING. In one embodiment, the level or activity of IRF or STING is increased by at least 10%, 20%, 30%, 40%, 50%, 60%, 70%, 80%, 90% or 100%, or by at least 2-fold, 4-fold, 6-fold, 8-fold, or 10-fold relative to a cell, tissue or subject that is not treated with the composition.

In certain aspects, the disclosure relates to a method of treating a subject in need of increased immune activity, the method comprising administering to the subject a composition comprising one or more postcellular signaling factors produced by cells exposed to a stress condition, wherein the composition is administered in an amount sufficient to increase the immune activity in the subject relative to a subject that is not treated with the composition. In one embodiment, the subject has cancer. In one embodiment, the subject has a chronic infection. In embodiments, the chronic infection is selected from HIV infection, HCV infection, HBV infection, HPV infection, Hepatitis B infection, Hepatitis C infection, EBV infection, CMV infection, TB infection, and infection with a parasite.

In certain aspects, the disclosure relates to a method of treating a subject diagnosed with cancer, comprising administering to the subject a composition comprising one or more postcellular signaling factors produced by cells exposed to a stress condition, thereby treating the cancer in the subject.

In certain aspects, the disclosure relates to a method of increasing immune activity in a target cell, tissue or subject, the method comprising administering to the target cell, tissue or subject, in combination (a) a composition comprising one or more postcellular signaling factors produced by cells exposed to a stress condition, and (b) a Stimulator of Interferon Genes (STING) agonist, wherein the composition and the STING agonist are administered in an amount sufficient to increase the immune activity relative to a cell, tissue or subject that is not treated with the composition and/or the STING agonist. In one embodiment, the STING agonist is a cyclic dinucleotide. In one embodiment, the cyclic dinucleotide is selected from the group consisting of cGAMP, 2'3'-cGAMP, 3'3'-cGAMP, 3'3'-cGAMP-F, c-di-GMP, c-di-GMP-F, Rp/Sp, MK-1454, ADU-S100 (also known as ML-RR-S2 CDA or MIW815), and Disodium dithio-(RP, RP)-[cyclic [A(2',5')pA(3',5')p]] [Rp,Rp]-Cyclic (adenosine-(2',5') monophosphorothioateadenosine-(3',5')-monophosphorothioate) (also known as disodium ADU-S100).

In one embodiment, the STING agonist is a flavonoid. In one embodiment, the flavonoid is selected from the group consisting of 10-(carboxymethyl)-9(10H)acridone (CMA), 5,6-Dimethylxanthenone-4-acetic acid (DMXAA) or vadimezan, methoxyvone, 6, 4'-dimethoxyflavone, 4'-methoxyflavone, 3', 6'-dihydroxyflavone, 7, 2'-dihydroxyflavone, daidzein, formononetin, retusin 7-methyl ether, xanthone, or any combination thereof. In one embodiment, the STING agonist is an amidobenzimidazole compound or a dimeric amidobenzimidizole compound. In one embodiment, the STING agonist is DNA. In one embodiment, the STING agonist is a type I interferon (IFN). In one embodiment, the type I IFN is interferon-0 or interferon-α.

In certain aspects, the disclosure relates to a method of treating a subject diagnosed with cancer, comprising administering to the subject in combination (a) composition comprising one or more postcellular signaling factors produced by cells exposed to a stress condition, and (b) a Stimulator of Interferon Genes (STING) agonist, thereby treating the cancer in the subject. In one embodiment, a response of the cancer to treatment is improved relative to a treatment with the STING agonist alone or the composition alone. In one embodiment, the response is improved, e.g., in a population of subjects, by at least 5%, at least 10%, at least 15%, at least 20%, at least 30%, at least 40%, at least 50%, at least 60%, at least 70%, or at least 80% relative to treatment with the STING agonist alone or the composition alone. In one embodiment, the response comprises any one or more of reduction in tumor burden, reduction in tumor size, inhibition of tumor growth, achievement of stable cancer in a subject with a progressive cancer prior to treatment, increased time to progression of the cancer, and increased time of survival. In one embodiment, the STING agonist and the composition act synergistically. In one embodiment, the cancer is a cancer responsive to an immune checkpoint therapy. In one embodiment, the cancer is selected from a carcinoma, sarcoma, lymphoma, melanoma, and leukemia. In one embodiment, the cancer is selected from the group consisting of cervical cancer, breast cancer, pancreatic cancer and reticulosarcoma.

In one embodiment of the methods disclosed herein, the composition comprises a cell-free extract prepared from cells exposed to a stress condition. In one embodiment, the composition does not comprise intact cells. In one embodiment, the composition comprises conditioned media from cells exposed to a stress condition. In one embodiment, the composition comprises a functional fraction of the conditioned media. In one embodiment, the functional fraction is prepared by isolating molecules with a molecular weight of 3 kDa or less from the conditioned media. In one embodiment, the functional fraction is inhibited by a P2Y2 inhibitor. In one embodiment, the one or more postcellular signaling factors are isolated from the cells.

In one embodiment, the one or more postcellular signaling factors comprise an agonist of a purinergic receptor. In one embodiment, the purinergic receptor is P2Y2, P2Y4 or P2Y6. In one embodiment, the one or more postcellular signaling factors comprise a cyclic dinucleotide. In one embodiment, the stress condition comprises nutrient deprivation. In one embodiment, nutrient deprivation comprises culturing the cells in a culture medium selected from the group consisting of HBSS and PBS. In one embodiment, the stress condition comprise exposure to an agent that induces regulatory cell death. In one embodiment, the agent that induces regulatory cell death comprises a chemotherapeutic agent. In one embodiment, the stress condition does not comprise radiation. In one embodiment, the stress condition does not comprise UV radiation. In one embodiment, the stress condition does not comprise exposure to an agent that induces iron-dependent cellular disassembly. In one embodiment, the cells exposed to a stress condition are allogeneic to the target cell, tissue or subject. In one embodiment, the cells exposed to a stress condition are autologous to the target cell, tissue or subject. In one embodiment, the cells exposed to a stress condition are cancer cells.

In one embodiment, the cancer cells are immortalized. In one embodiment, the cancer cells are primary cells isolated from a subject. In one embodiment, the cells exposed to a stress condition do not comprise leukocytes. In one embodiment, the cells exposed to a stress condition do not comprise peripheral blood mononuclear cells (PBMCs). In one embodiment, the cells exposed to a stress condition do not comprise T-cells. In one embodiment, the cells exposed to a stress condition do not comprise malignant T-cells.

In one embodiment, the subject is in need of an increased immune activity. In one embodiment, the subject is human. In one embodiment, the composition is administered in an amount sufficient to increase in the cell, tissue or subject one or more of the level or activity of type I interferon, the level or activity of TBK1, the level or activity of IRF, the level or activity of NFκB, the level or activity of macrophages, the level or activity of monocytes, the level or activity of dendritic cells, the level or activity of T cells, the level or activity of CD4+, CD8+ or CD3+ cells, and the level or activity of a pro-immune cytokine.

In one embodiment, the method further comprises administering an immunotherapeutic to the subject. In one embodiment, the immunotherapeutic is selected from the group consisting of a Toll-like receptor (TLR) agonist, a cell-based therapy, a cytokine, a cancer vaccine, and an immune checkpoint modulator of an immune checkpoint molecule. In one embodiment, the TLR agonist is selected from Coley's toxin and Bacille Calmette-Guerin (BCG). In one embodiment, the immune checkpoint molecule is selected from CD27, CD28, CD40, CD122, OX40, GITR, ICOS, 4-1BB, ADORA2A, B7-H3, B7-H4, BTLA, CTLA-4, IDO, KIR, LAG-3, PD-1, PD-L1, PD-L2, TIM-3, and VISTA. In one embodiment, the immune checkpoint molecule is a stimulatory immune checkpoint molecule and the immune checkpoint modulator is an agonist of the stimulatory immune checkpoint molecule. In one embodiment, the immune checkpoint molecule is an inhibitory immune checkpoint molecule and the immune checkpoint modulator is an antagonist of the inhibitory immune checkpoint molecule. In one embodiment, the immune checkpoint modulator is selected from a small molecule, an inhibitory RNA, an antisense molecule, and an immune checkpoint molecule binding protein. In one embodiment, the immune checkpoint molecule is PD-1 and the immune checkpoint modulator is a PD-1 inhibitor. In one embodiment, the PD-1 inhibitor is selected from pembrolizumab, nivolumab, pidilizumab, SHR-1210, MEDI0680R01, BBg-A317, TSR-042, REGN2810 and PF-06801591. In one embodiment, the immune checkpoint molecule is PD-L1 and the immune checkpoint modulator is a PD-L1 inhibitor. In one embodiment, the PD-L1 inhibitor is selected from durvalumab, atezolizumab, avelumab, MDX-1105, AMP-224 and LY3300054. In one embodiment, the immune checkpoint molecule is CTLA-4 and the immune checkpoint modulator is a CTLA-4 inhibitor. In one embodiment, the CTLA-4 inhibitor is selected from ipilimumab, tremelimumab, JMW-3B3 and AGEN1884.

In certain aspects, the disclosure relates to a method of screening for an agent that induces production of immunostimulatory postcellular signaling factors in a cell, the method comprising: (a) providing a plurality of test agents (e.g., a library of test agents); (b) evaluating each of the plurality of test agents for the ability to induce production of immunostimulatory postcellular signaling factors in a cell. In one embodiment, the evaluating step (b) comprises contacting cells or tissue with each of the plurality of test agents. In one embodiment, evaluating each of the plurality of test agents for the ability to induce production of immunostimulatory postcellular signaling factors comprises culturing an immune cell together with cells contacted with the test agent or exposing an immune cell to postcellular signaling factors produced by cells contacted with the test agent and measuring the level or activity of NFκB, IRF or STING in the immune cell. In one embodiment, the immune cell is a THP-1 cell.

In one embodiment, evaluating each of the plurality of test agents for the ability to induce production of immunostimulatory postcellular signaling factors comprises culturing T cells together with cells contacted with the test agent or exposing T cells to postcellular signaling factors produced by cells contacted with the test agent and measuring the activation and proliferation of the T cells.

In certain aspects, the disclosure relates to a method of identifying an immunostimulatory postcellular signaling factor, the method comprising:
(a) exposing a cell to a stress condition;
(b) isolating one or more posteellular signaling factors produced by the cell after exposure to the stress condition; and
(c) assaying the one or more postcellular signaling factors for the ability to stimulate immune response.

In one embodiment, the method further comprises:
i) measuring the level of the one or more postcellular signaling factors produced by the cell after exposure to the stress condition;
ii) comparing the level of the one or more postcellular signaling factors produced by the cell after exposure to the stress condition to the level of the one or more test agents in a control cell that is not exposed to the stress condition; and
iii) selecting postcellular signaling factors that exhibit increased levels in the cell exposed to the stress condition relative to the control cell to generate the one or more postcellular signaling factors for assaying in step (c).

In one embodiment, the assaying comprises administering the one or more postcellular signaling factors to an animal and measuring immune response in the animal. In one embodiment, the assaying comprises treating an immune cell with the one or more postcellular signaling factors and measuring the level or activity of NFκB activity in the immune cell. In one embodiment, the assaying comprises treating T cells with the one or more postcellular signaling factors and measuring the activation or proliferation of the T cells. In one embodiment, the assaying comprises contacting an immune cell with the one or more postcellular signaling factors and measuring the level or activity of NFκB, IRF or STING in the immune cell. In one embodiment, the immune cell is a THP-1 cell.

In certain aspects the disclosure relates to a method of decreasing immune activity in a target cell, tissue or subject, the method comprising administering to the target cell, tissue or subject a purinergic receptor antagonist, wherein the purinergic receptor antagonist is administered in an amount sufficient to decrease the immune activity relative to a cell, tissue or subject that is not treated with the purinergic receptor antagonist. In one embodiment, the subject is in need of decreased immune activity. In one embodiment, the purinergic receptor antagonist is administered in an amount sufficient to decrease in the cell, tissue or subject one or more of the level or activity of NFkB, the level or activity of IRF or STING, the level or activity of macrophages, the level or activity of monocytes, the level or activity of dendritic cells, the level or activity of T cells, the level or activity of CD4+, CD8+ or CD3+ cells, and the level or activity of a pro-immune cytokine.

In certain aspects the disclosure relates to a method of decreasing the level or activity of NFkB in a cell, tissue or subject, comprising administering to the cell, tissue or subject a purinergic receptor antagonist, wherein the purinergic receptor antagonist is administered in an amount sufficient to decrease the level or activity of NFkB relative to a cell, tissue or subject that is not treated with the purinergic receptor antagonist. In one embodiment, the subject is in need of a decreased level or activity of NFkB. In one embodiment, the level or activity of NFkB is decreased by at least 10%, 20%, 30%, 40%, 50%, 60%, 70%, 80%, 90% or 99%, or by at least 2-fold, 4-fold, 6-fold, 8-fold, or 10-fold relative to a cell, tissue or subject that is not treated with the the purinergic receptor antagonist.

In certain aspects the disclosure relates to a method of decreasing the level or activity of IRF or STING in a cell, tissue or subject, comprising administering to the cell, tissue or subject a purinergic receptor antagonist, wherein the purinergic receptor antagonist is administered in an amount sufficient to decrease the level or activity of IRF or STING relative to a cell, tissue or subject that is not treated with the purinergic receptor antagonist. In one embodiment, the subject is in need of a decreased level or activity of IRF or STING. In one embodiment, the level or activity of IRF or STING is increased by at least 10%, 20%, 30%, 40%, 50%, 60%, 70%, 80%, 90% or 99%, or by at least 2-fold, 4-fold, 6-fold, 8-fold, or 10-fold relative to a cell, tissue or subject that is not treated with the purinergic receptor antagonist.

In certain aspects the disclosure relates to a method of decreasing the level or activity of macrophages, monocytes, dendritic cells or T cells in a tissue or subject, comprising administering to the tissue or subject a purinergic receptor antagonist, wherein the purinergic receptor antagonist is administered in an amount sufficient to increase the level or activity of macrophages, monocytes, dendritic cells or T cells relative to a tissue or subject that is not treated with the purinergic receptor antagonist. In one embodiment, the subject is in need of a decreased level or activity of macrophages, monocytes, dendritic cells or T cells. In one embodiment, the level or activity of macrophages, monocytes, dendritic cells, or T cells is decreased by at least 10%, 20%, 30%, 40%, 50%, 60%, 70%, 80%, 90% or 99%, or by at least 2-fold, 4-fold, 6-fold, 8-fold, or 10-fold relative to a tissue or subject that is not treated with the purinergic receptor antagonist.

In certain aspects the disclosure relates to a method of decreasing the level or activity of CD4+, CD8+, or CD3+ cells in a tissue or subject, comprising administering to the subject a purinergic receptor antagonist, wherein the purinergic receptor antagonist is administered in an amount sufficient to decrease the level or activity of CD4+, CD8+, or CD3+ cells relative to a tissue or subject that is not treated with the purinergic receptor antagonist. In one embodiment, the subject is in need of a decreased level or activity of CD4+, CD8+, or CD3+ cells. In one embodiment, the level or activity of CD4+, CD8+, or CD3+ cells is decreased by at least 10%, 20%, 30%, 40%, 50%, 60%, 70%, 80%, 90% or 99%, or by at least 2-fold, 4-fold, 6-fold, 8-fold, or 10-fold relative to a tissue or subject that is not treated with the purinergic receptor antagonist.

In certain aspects the disclosure relates to a method of decreasing the level or activity of a pro-immune cytokine in a cell, tissue or subject, comprising administering to the cell, tissue or subject a purinergic receptor antagonist, wherein the purinergic receptor antagonist is administered in an amount sufficient to decrease the level or activity of the pro-immune cytokine relative to a cell, tissue or subject that is not treated with the purinergic receptor antagonist. In one embodiment, the subject is in need of a decreased level or activity of a pro-immune cytokine. In one embodiment, the level or activity of the pro-immune cytokine is decreased by at least 10%, 20%, 30%, 40%, 50%, 60%, 70%, 80%, 90% or 99%, or by at least 2-fold, 4-fold, 6-fold, 8-fold, or 10-fold relative to a cell, tissue or subject that is not treated with the purinergic receptor antagonist. In one embodiment, the pro-immune cytokine is selected from IFN-α, IL-1, IL-12, IL-18, IL-2, IL-15, IL-4, IL-6, TNF-α, IL-17 and GMCSF. In one embodiment of claims A-F, the method further includes, before the administration, evaluating the cell, tissue or subject for one or more of the level or activity of NFkB; the level or activity of macrophages; the level or activity of monocytes; the level or activity of dendritic cells; the level or activity of CD4+ cells, CD8+ cells, or CD3+ cells; the level or activity of T cells; and the level or activity of a pro-immune cytokine. In one embodiment of claims A-F, the method further includes, after the administration, evaluating the cell, tissue or subject for one or more of the level or activity of NFkB; the level or activity of macrophages; the level or activity of monocytes; the level or activity of dendritic cells; the level or activity of CD4+ cells, CD8+ cells or CD3+ cells; the level or activity of T cells; and the level or activity of a pro-immune cytokine. In embodiments, the pro-immune cytokine is selected from IFN-α, IL-1, IL-12, IL-18, IL-2, IL-15, IL-4, IL-6, TNF-α, IL-17 and GMCSF.

In certain aspects the disclosure relates to a method of treating a subject in need of decreased immune activity, the method comprising administering to the subject a purinergic receptor antagonist, wherein the purinergic receptor antagonist is administered in an amount sufficient to decrease the immune activity in the subject.

In certain aspects the disclosure relates to a method of decreasing immune activity in a target cell, tissue or subject, the method comprising administering to the target cell, tissue or subject, in combination (a) a Stimulator of Interferon Genes (STING) antagonist and (b) a purinergic receptor antagonist, wherein the STING antagonist and the purinergic receptor antagonist are administered in an amount sufficient to decrease the immune activity relative to a cell, tissue or subject that is not treated with the STING antagonist and/or the purinergic receptor antagonist. In one embodiment, the subject is in need of decreased immune activity. In one embodiment, the STING antagonist and purinergic receptor antagonist are administered in an amount sufficient to decrease in the cell, tissue or subject one or more of the level or activity of NFkB, the level or activity of IRF or STING, the level or activity of macrophages, the level or activity of monocytes, the level or activity of dendritic cells, the level or activity of T cells, the level or activity of CD4+, CD8+ or CD3+ cells, and the level or activity of a pro-immune cytokine.

In certain aspects the disclosure relates to a method of decreasing the level or activity of NFkB in a cell, tissue or subject, comprising administering to the cell, tissue or subject, in combination (a) a Stimulator of Interferon Genes (STING) antagonist and (b) a purinergic receptor antagonist, wherein the STING antagonist and the purinergic receptor antagonist are administered in an amount sufficient to decrease the level or activity of NFkB relative to a cell, tissue or subject that is not treated with the STING antagonist and/or the purinergic receptor antagonist. In one embodiment, the subject is in need of a decreased level or activity of NFkB.

In one embodiment, the level or activity of NFkB is decreased by at least 10%, 20%, 30%, 40%, 50%, 60%, 70%, 80%, 90% or 99%, or by at least 2-fold, 4-fold, 6-fold, 8-fold, or 10-fold relative to a cell, tissue or subject that is not treated with the STING antagonist and/or the purinergic receptor antagonist.

In certain aspects the disclosure relates to a method of decreasing the level or activity of IRF or STING in a cell, tissue or subject, comprising administering to the cell, tissue or subject, in combination (a) a Stimulator of Interferon Genes (STING) antagonist and (b) a purinergic receptor antagonist, wherein the STING antagonist and the purinergic receptor antagonist are administered in an amount sufficient to decrease the level or activity of IRF or STING relative to a cell, tissue or subject that is not treated with the STING antagonist and/or the purinergic receptor antagonist. In one embodiment, the subject is in need of a decreased level or activity of IRF or STING. In one embodiment, the level or activity of IRF or STING is increased by at least 10%, 20%, 30%, 40%, 50%, 60%, 70%, 80%, 90% or 99%, or by at least 2-fold, 4-fold, 6-fold, 8-fold, or 10-fold relative to a cell, tissue or subject that is not treated with the STING antagonist and/or the purinergic receptor antagonist.

In certain aspects the disclosure relates to a method of decreasing the level or activity of macrophages, monocytes, dendritic cells or T cells in a tissue or subject, comprising administering to the tissue or subject, in combination (a) a Stimulator of Interferon Genes (STING) antagonist and (b) a purinergic receptor antagonist, wherein the STING antagonist and the purinergic receptor antagonist are administered in an amount sufficient to increase the level or activity of macrophages, monocytes, dendritic cells or T cells relative to a tissue or subject that is not treated with the STING antagonist and/or the purinergic receptor antagonist. In one embodiment, the subject is in need of a decreased level or activity of macrophages, monocytes, dendritic cells or T cells. In one embodiment, the level or activity of macrophages, monocytes, dendritic cells, or T cells is decreased by at least 10%, 20%, 30%, 40%, 50%, 60%, 70%, 80%, 90% or 99%, or by at least 2-fold, 4-fold, 6-fold, 8-fold, or 10-fold relative to a tissue or subject that is not treated with the STING antagonist and/or the purinergic receptor antagonist.

In certain aspects the disclosure relates to a method of decreasing the level or activity of CD4+, CD8+, or CD3+ cells in a tissue or subject, comprising administering to the subject, in combination (a) a Stimulator of Interferon Genes (STING) antagonist and (b) a purinergic receptor antagonist, wherein the STING antagonist and the purinergic receptor antagonist are administered in an amount sufficient to decrease the level or activity of CD4+, CD8+, or CD3+ cells relative to a tissue or subject that is not treated with the STING antagonist and/or the purinergic receptor antagonist. In one embodiment, the subject is in need of a decreased level or activity of CD4+, CD8+, or CD3+ cells. In one embodiment, the level or activity of CD4+, CD8+, or CD3+ cells is decreased by at least 10%, 20%, 30%, 40%, 50%, 60%, 70%, 80%, 90% or 99%, or by at least 2-fold, 4-fold, 6-fold, 8-fold, or 10-fold relative to a tissue or subject that is not treated with the STING antagonist and/or the purinergic receptor antagonist.

In certain aspects the disclosure relates to a method of decreasing the level or activity of a pro-immune cytokine in a cell, tissue or subject, comprising administering to the cell, tissue or subject, in combination (a) a Stimulator of Interferon Genes (STING) antagonist and (b) a purinergic receptor antagonist, wherein the STING antagonist and the purinergic receptor antagonist are administered in an amount sufficient to decrease the level or activity of the pro-immune cytokine relative to a cell, tissue or subject that is not treated with the STING antagonist and/or the purinergic receptor antagonist. In one embodiment, the subject is in need of a decreased level or activity of a pro-immune cytokine. In one embodiment, the level or activity of the pro-immune cytokine is decreased by at least 10%, 20%, 30%, 40%, 50%, 60%, 70%, 80%, 90% or 99%, or by at least 2-fold, 4-fold, 6-fold, 8-fold, or 10-fold relative to a cell, tissue or subject that is not treated with the STING antagonist and/or the purinergic receptor antagonist. In one embodiment, the pro-immune cytokine is selected from IFN-α, IL-1, IL-12, IL-18, IL-2, IL-15, IL-4, IL-6, TNF-α, IL-17 and GMCSF. In one embodiment of the methods described herein, the method further includes, before the administration, evaluating the cell, tissue or subject for one or more of the level or activity of NFkB; the level or activity of macrophages; the level or activity of monocytes; the level or activity of dendritic cells; the level or activity of CD4+ cells, CD8+ cells, or CD3+ cells; the level or activity of T cells; and the level or activity of a pro-immune cytokine. In one embodiment of the methods described herein, the method further includes, after the administration, evaluating the cell, tissue or subject for one or more of the level or activity of NFkB; the level or activity of macrophages; the level or activity of monocytes; the level or activity of dendritic cells; the level or activity of CD4+ cells, CD8+ cells or CD3+ cells; the level or activity of T cells; and the level or activity of a pro-immune cytokine. In embodiments, the pro-immune cytokine is selected from IFN-α, IL-1, IL-12, IL-18, IL-2, IL-15, IL-4, IL-6, TNF-α, IL-17 and GMCSF.

In certain aspects the disclosure relates to a method of treating a subject in need of decreased immune activity, the method comprising administering to the subject, in combination (a) a Stimulator of Interferon Genes (STING) antagonist and (b) a purinergic receptor antagonist, wherein the STING antagonist and the purinergic receptor antagonist are administered in an amount sufficient to decrease the immune activity in the subject. In one embodiment of the methods described herein, the subject has an inflammatory disease or condition. In one embodiment, the inflammatory disease or condition is selected from the group consisting of inflammation, acute organ injury, tissue damage, sepsis, atherosclerosis, a neurodegenerative disorder, and an immune-related disease or condition. In one embodiment, the inflammation is selected from sterile inflammation, chronic inflammation, and acute inflammation in response to disease or injury. In one embodiment, the immune-related disease or condition is an autoimmune disease. In one embodiment, the autoimmune disease is selected from systemic lupus erythematosus (SLE), rheumatoid arthritis, Type I diabetes, Type II diabetes, multiple sclerosis (MS), amyotrophic lateral sclerosis (ALS), graft-vs-host disease (GVHD), psoriasis, and ulcerative colitis. In one embodiment, the immune-related disease or condition is an allergy or asthma. In one embodiment, the immune-related disease or condition is an autoinflammatory condition. In one embodiment of claims A-N, the purinergic receptor antagonist is a P2Y receptor antagonist. In one embodiment, the P2Y receptor antagonist is a P2Y2 receptor antagonist, a P2Y4 receptor antagonist, or a P2Y6 receptor antagonist. In one embodiment, the purinergic receptor antagonist is a compound selected from the group consisting of:

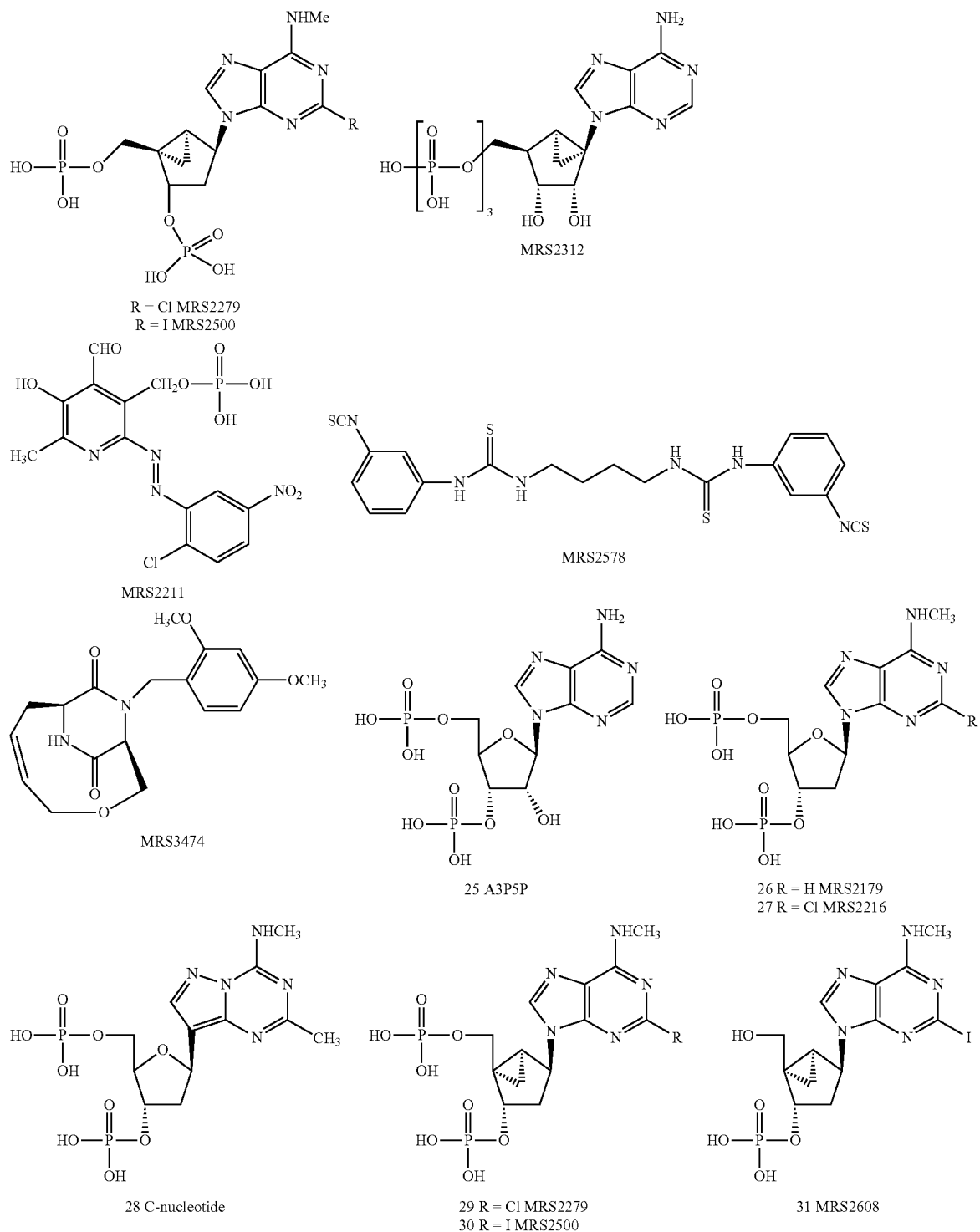

33    -continued    34
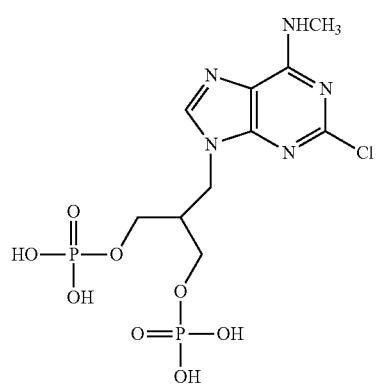
32 MRS2298
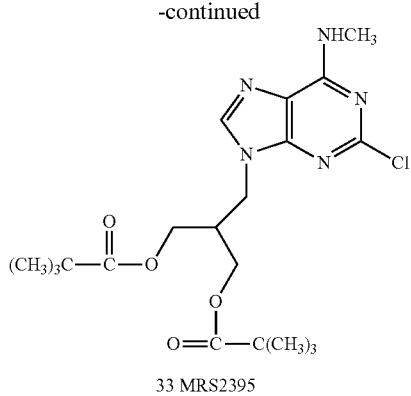
33 MRS2395
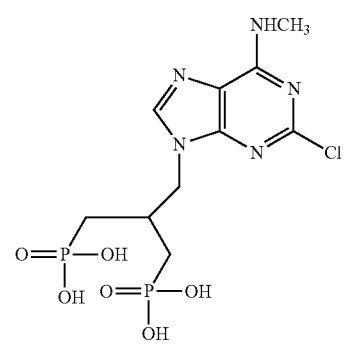
34 MRS2496
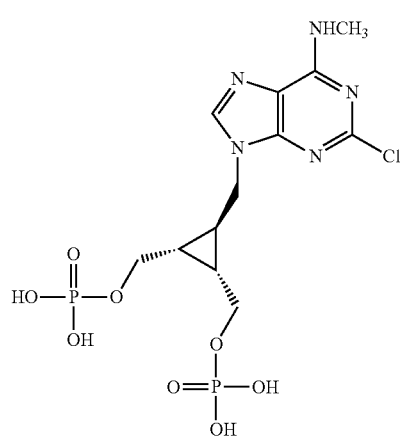
35 MRS2290
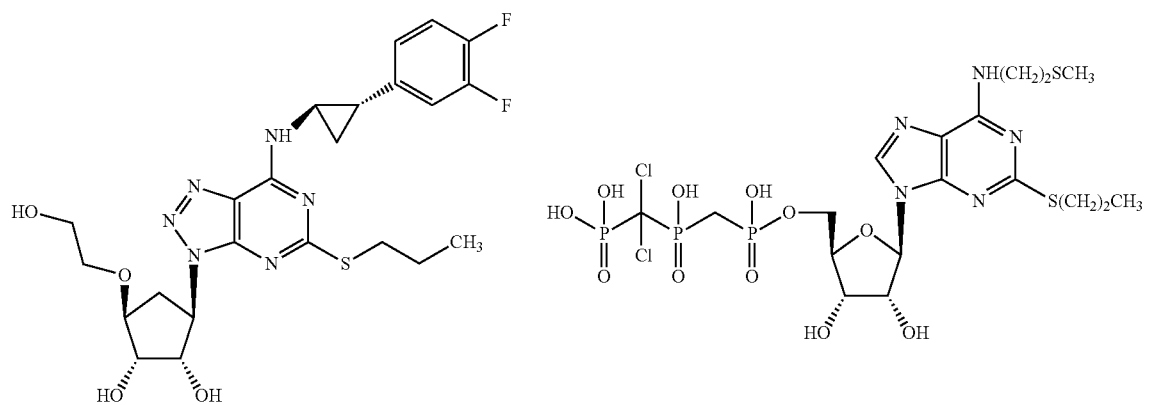

35
36
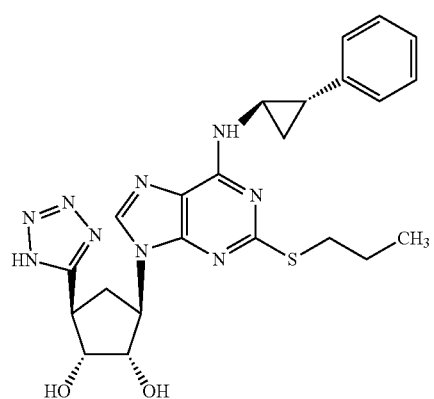
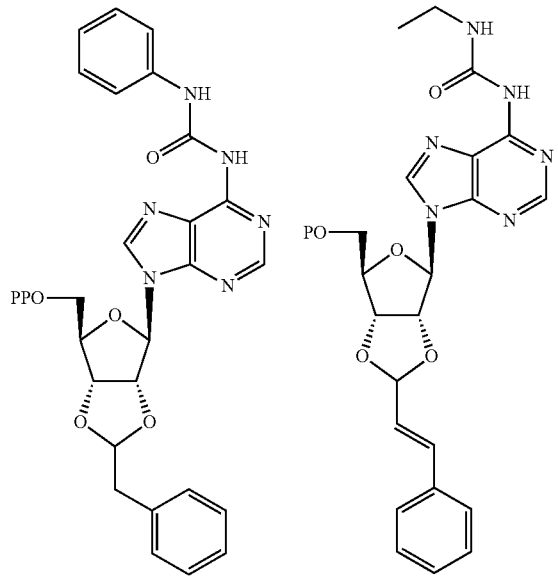
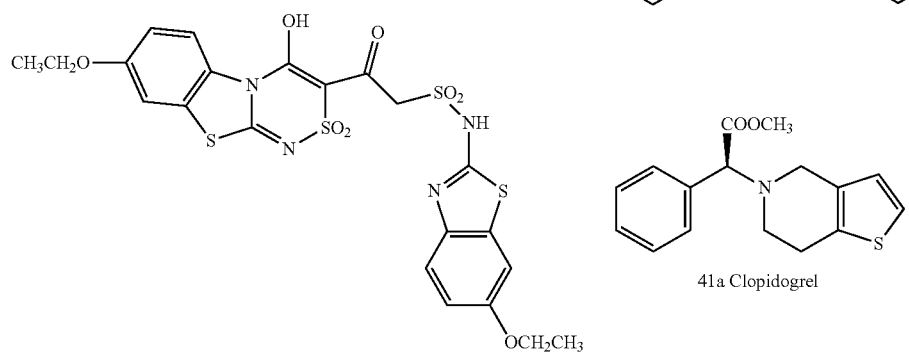
43
41a Clopidogrel
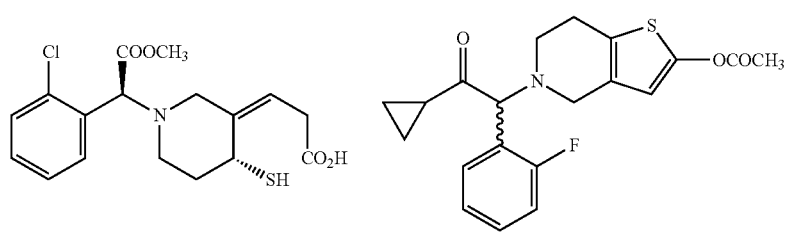
42 Prasugrel
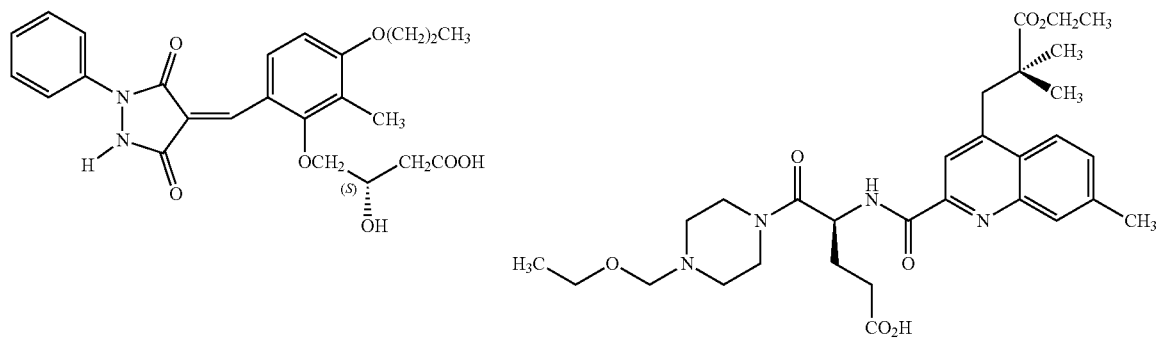
45 BX677

-continued
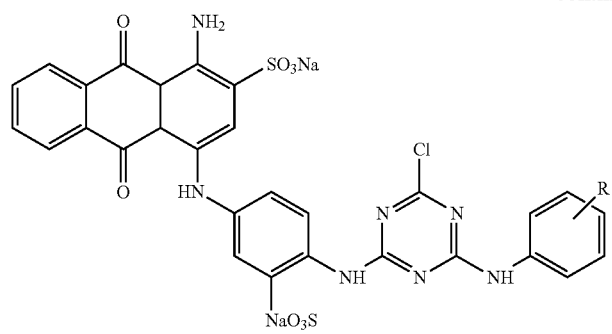
46a R = SO₃Na m- and p-
mixture
Reactive Blue 2
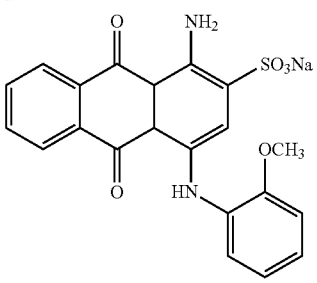
46B PSB-716
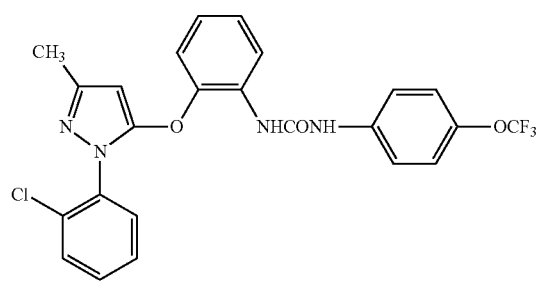
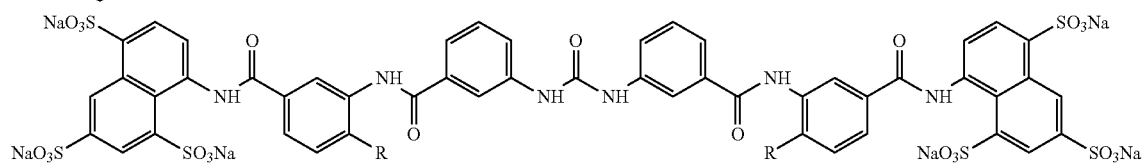
48a R = CH₃ Suramin
48b R = F NF157
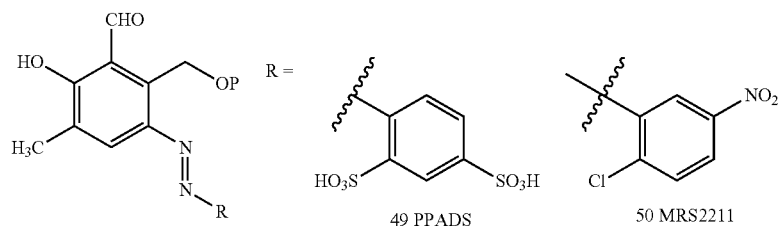
49 PPADS    50 MRS2211
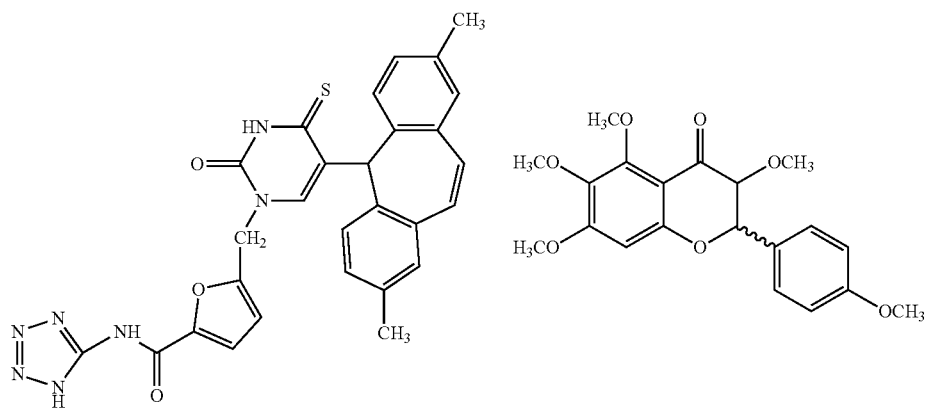
53 AR-C118925

-continued
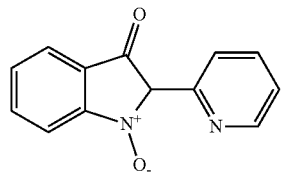
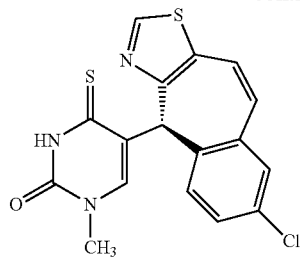
52-AR-C-126313
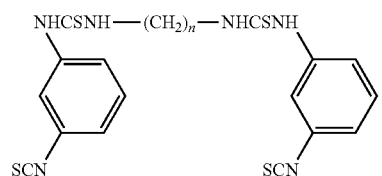
55 n = 4 MRS2578
56 n = 3 MRS2577
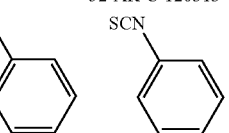
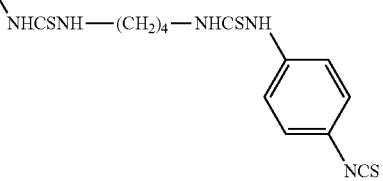
57 MRS2576
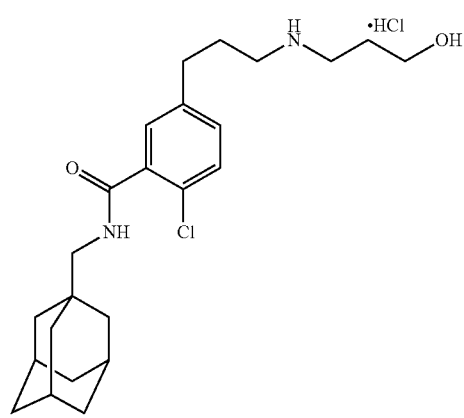
(AZD9056)
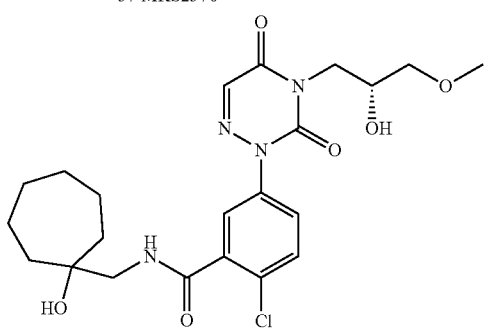
(CE-224,535)
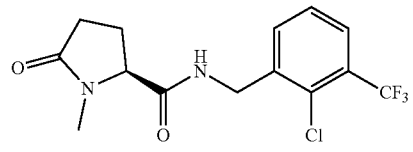
(GSK1482160)
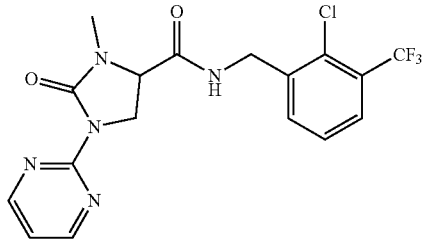
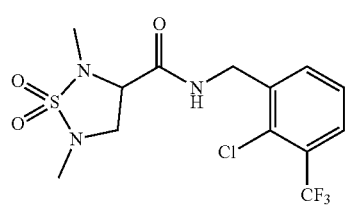
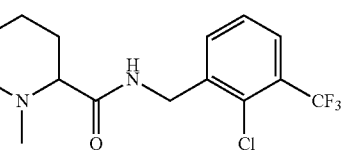

-continued
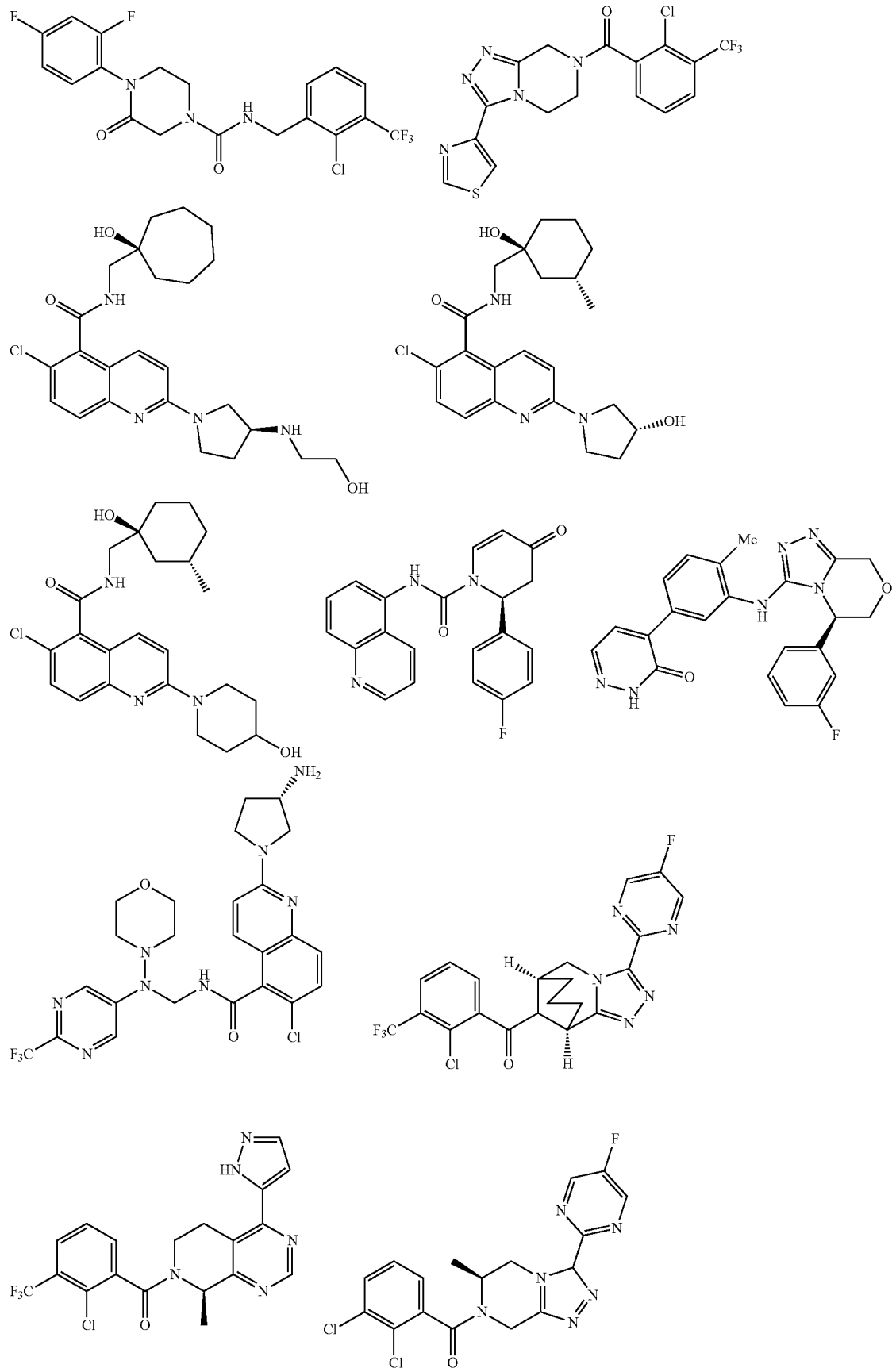

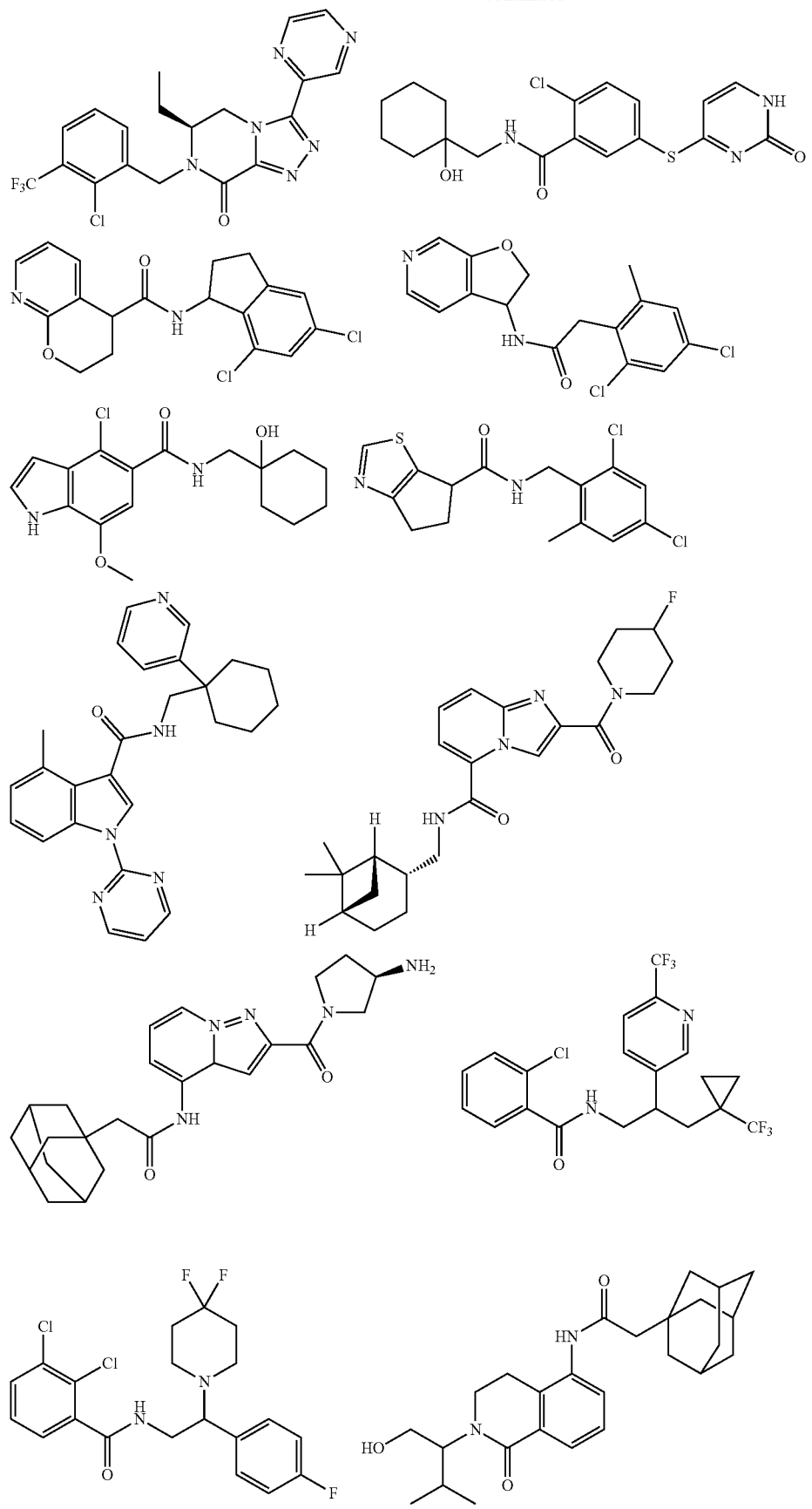

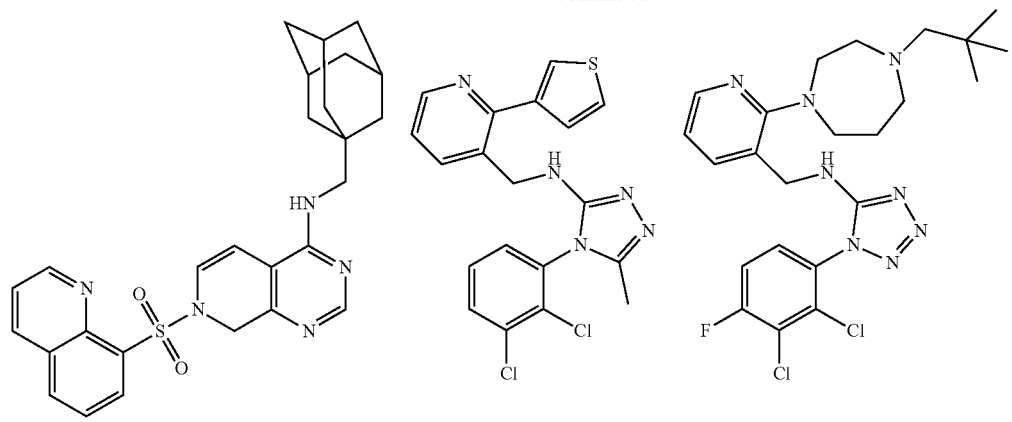
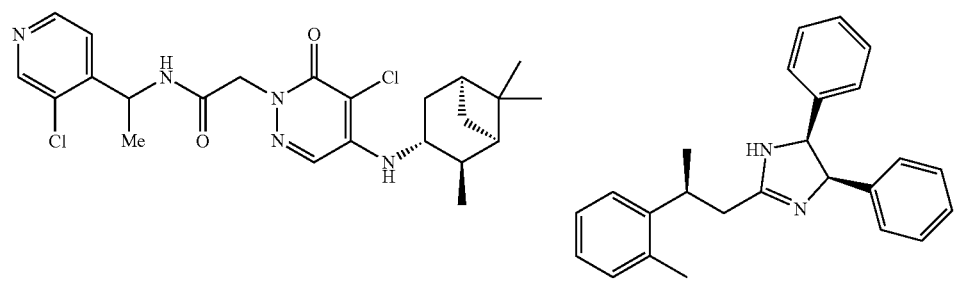
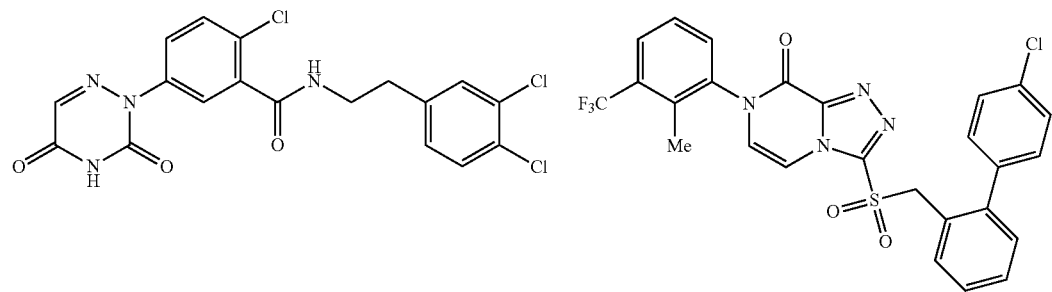
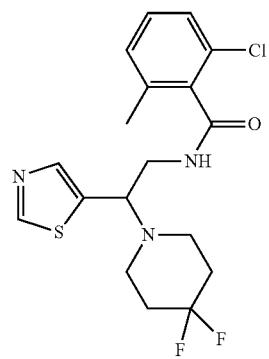

EVT 401, and AFC-5128, and a pharmaceutically acceptable salt, free acid, an analogue, a regioisomer, a stereoisomer or a tautomer thereof.

In one embodiment, the purinergic receptor antagonist is a P2Y2, P2Y4 or P2Y6 antagonist, and is a compound selected from the group consisting of:

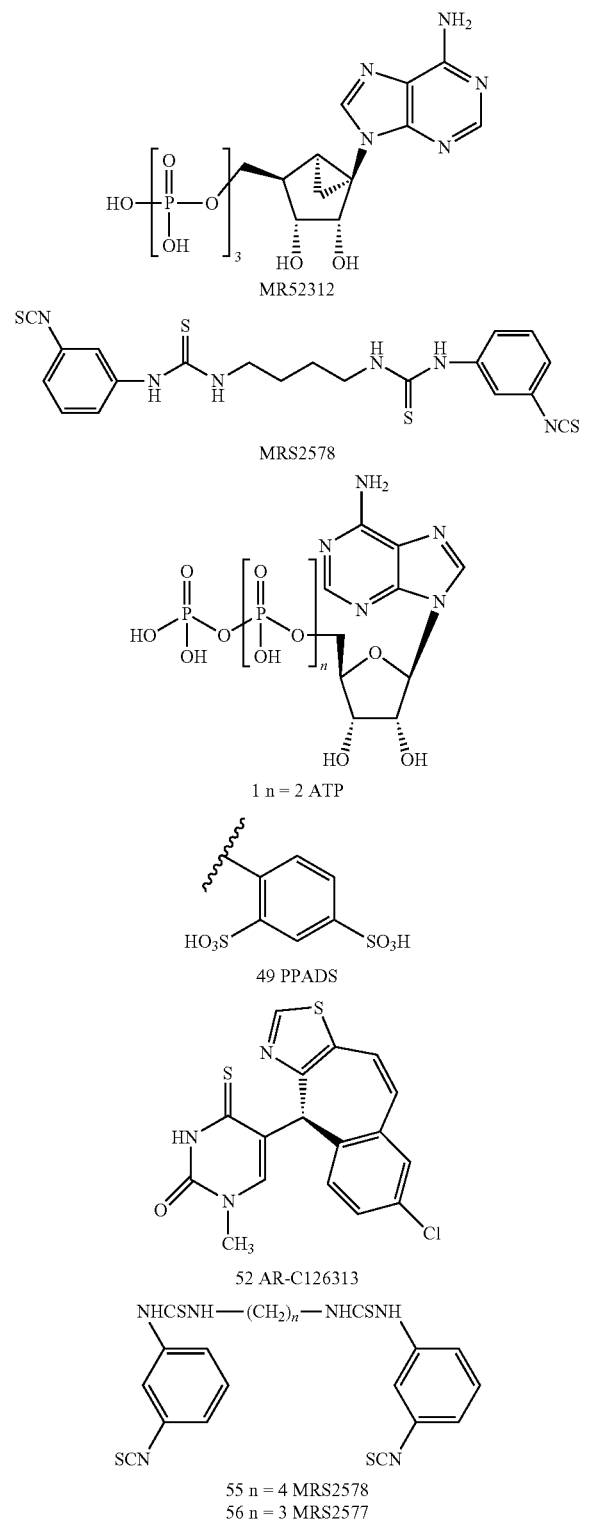

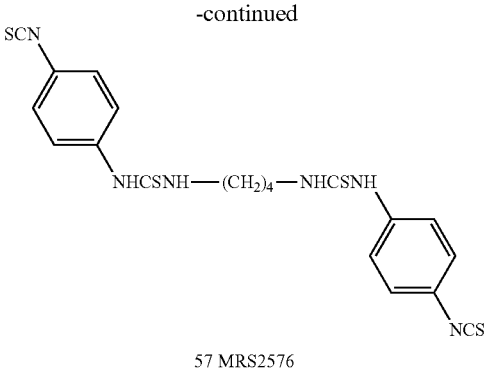

57 MRS2576 and a pharmaceutically acceptable salt, free acid, an analogue, a regioisomer, a stereoisomer or a tautomer thereof.

In one embodiment of the methods described herein, the STING antagonist is a protein, a nucleic acid or a small molecule. In one embodiment, the protein is an oncoprotein selected from the group consisting of E6, E7, E1A and SV40 Large T antigen. In one embodiment, the nucleic acid is an oncogene encoding an oncoprotein selected from the group consisting of E6, E7, E1A and SV40 Large T antigen. In one embodiment, the STING antagonist is a kinase inhibitor. In one embodiment, the kinase inhibitor is a TBK1 kinase inhibitor. In one embodiment, the TBK1 kinase inhibitor is selected from the group consisting of staurosporine, BX765 and MRT67307. In one embodiment, the STING antagonist is a cyclic dinucleotide (CDN) compound. In one embodiment, the CDN compound is represented by the following structural formula:

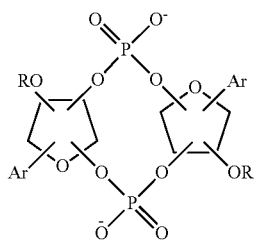

or a pharmaceutically acceptable salt, a free acid, a regioisomer, a stereoisomer or a tautomer thereof wherein Ar, for each instance, is independently optionally substituted monocyclic or bicyclic heteroaryl having at least one nitrogen atom (e.g., 1, 2, 3 or 4) and optionally one or more heteroatoms selected from O and S; wherein R, for each instance, is independently hydrogen or an optionally substituted $C_1$-$C_4$ alkyl; wherein each oxygen atom in the two phosphate groups and the OR groups is optionally and independently substituted with S; wherein each OR group and each O⁻ is optionally substituted with a halogen (e.g., F, Cl). In one embodiment, each Ar is independently selected from the group consisting of:

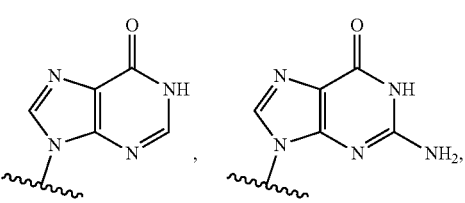

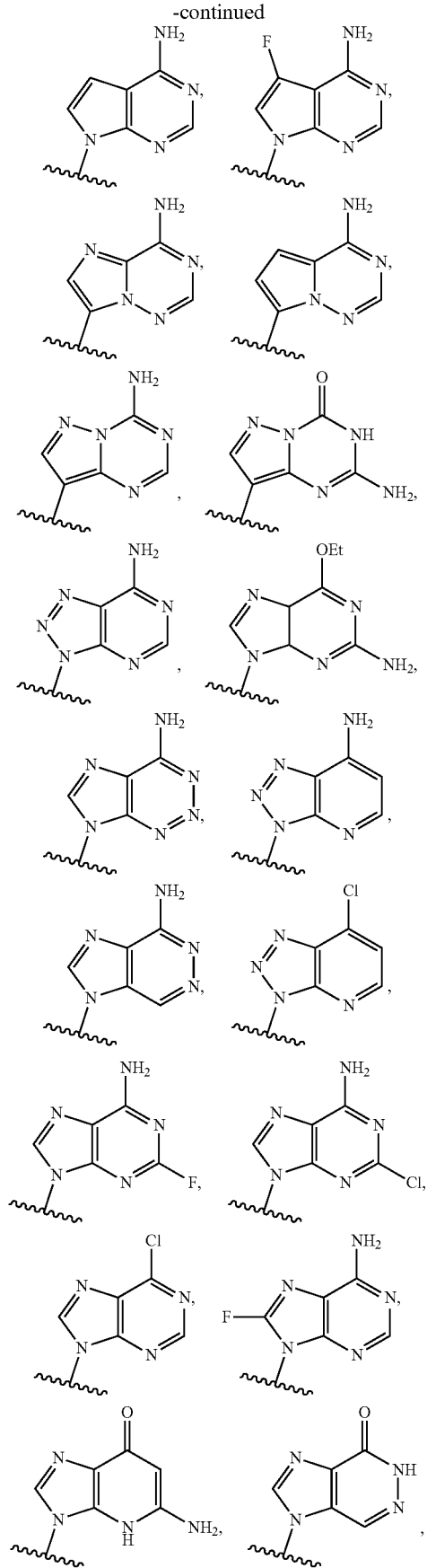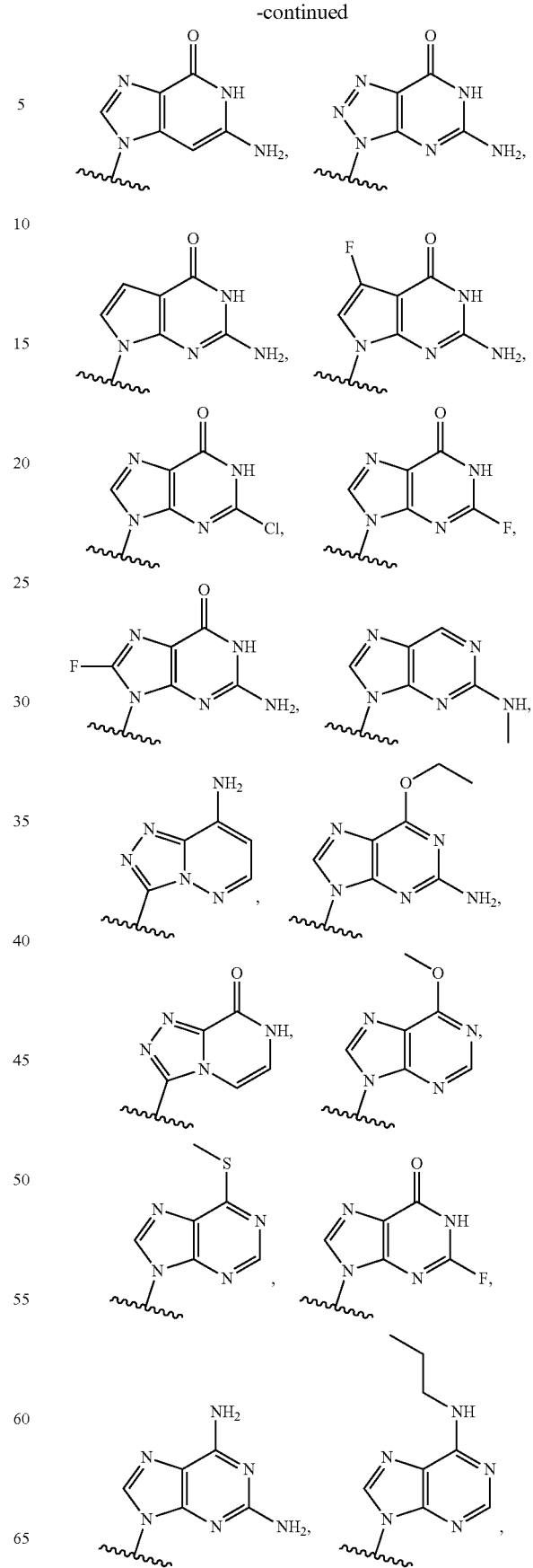

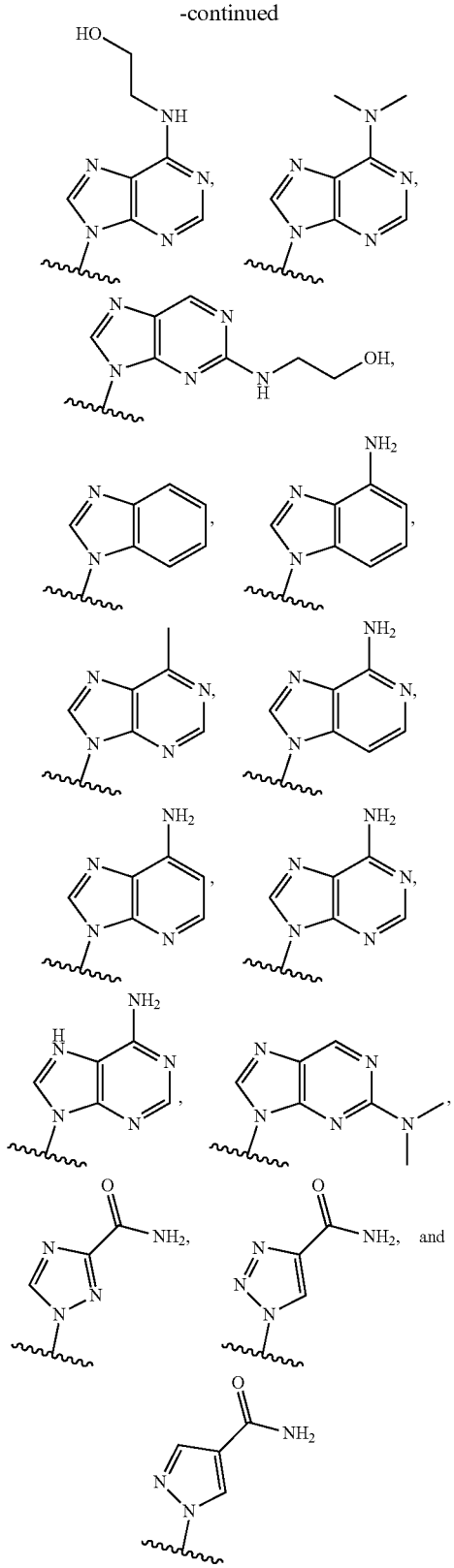

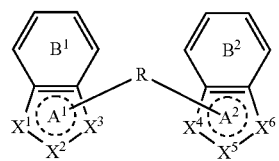

or a pharmaceutically acceptable salt, a free acid, a regioisomer, a stereoisomer or a tautomer thereof wherein one or two of $X^1$, $X^2$ and $X^3$ is/are nitrogen while the other(s) is/are carbon; wherein one or two of $X^4$, $X^5$ and $X^6$ is/are nitrogen while the other(s) is/are carbon; wherein R is an optionally substituted $C_1$-$C_6$ alkyl, $C_2$-$C_6$ alkenyl or $C_2$-$C_6$ alkynyl covalently linked to ring $A^1$ and ring $A^2$; each of rings $A^1$, $A^2$, $B^1$ and $B^2$ is optionally substituted.

In one embodiment, the STING antagonist is an amido-substituted bi-heterocyclic compound represented by the following formula:

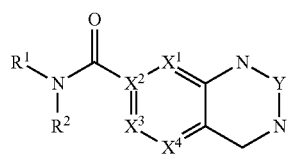

or a pharmaceutically acceptable salt, a free acid, a regioisomer, a stereoisomer or a tautomer thereof the bi-heterocyclic ring is optionally further substituted; wherein Y is C, O, or S; $X^1$, $X^2$, $X^3$ and $X^4$ are each independent C or N; and R1 and R2 are each independently an optionally substituted alkyl, an optionally substituted alkenyl, an optionally substituted alkynyl, an optionally substituted cycloalkyl, an optionally substituted aryl, an optionally substituted heteroaryl, or an optionally substituted heterocyclyl.

In one embodiment, the STING antagonist is a compound selected from the following:

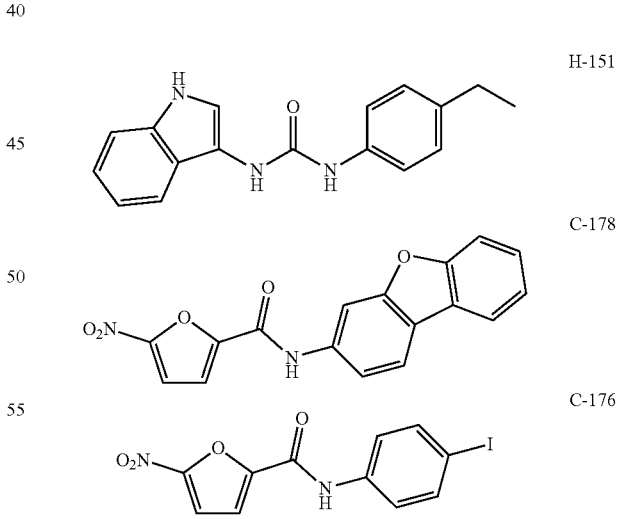

or a pharmaceutically acceptable salt, a free acid, a regioisomer, a stereoisomer or a tautomer thereof.

Figure 1A:
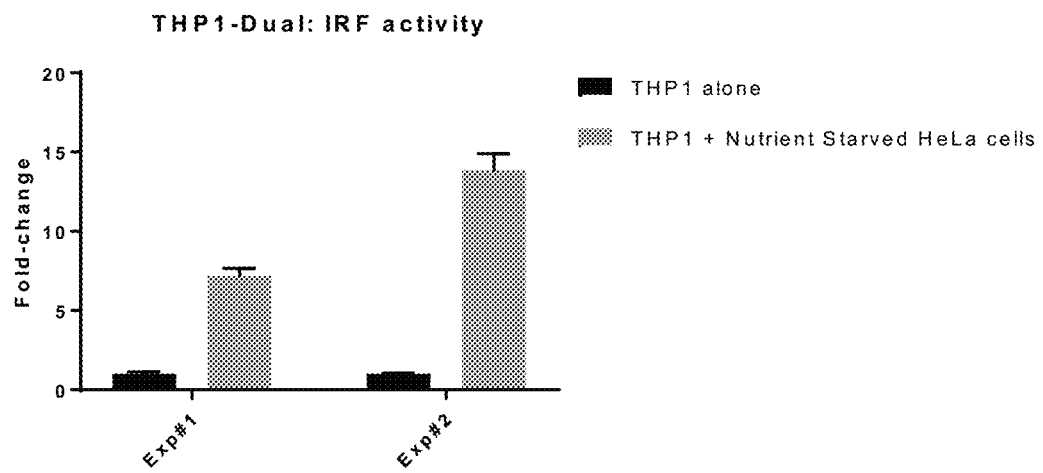
FIG. 1A shows IRF transcriptional activity in THP1 monocytes co-cultured with nutrient-starved HeLa cells.
Figure 1B:
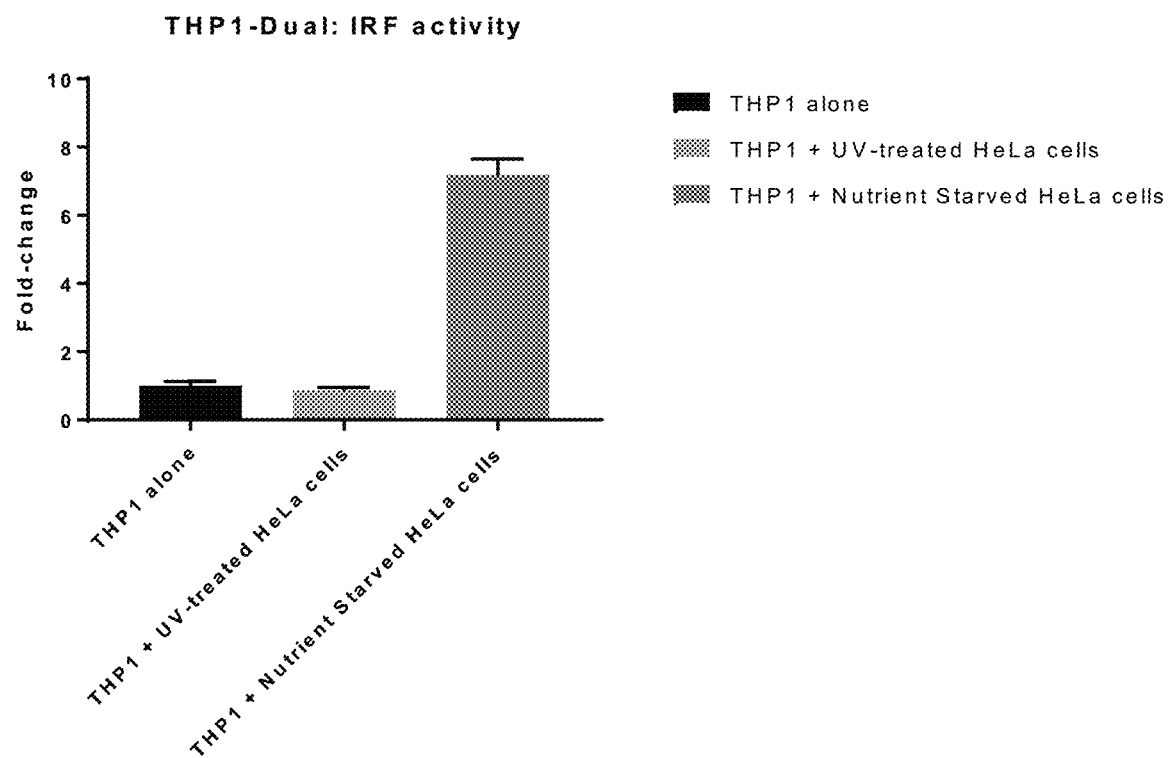

In one embodiment, the STING antagonist is an imidazole derivative. In one embodiment, the imidazole derivative is a dimeric compound. In one embodiment, the dimeric compound is represented by the following structural formula:

FIG. 1B shows IRF transcriptional activity in THP1 monocytes co-cultured with nutrient-starved HeLa cells or UV-treated HeLa cells.

Figure 2A:
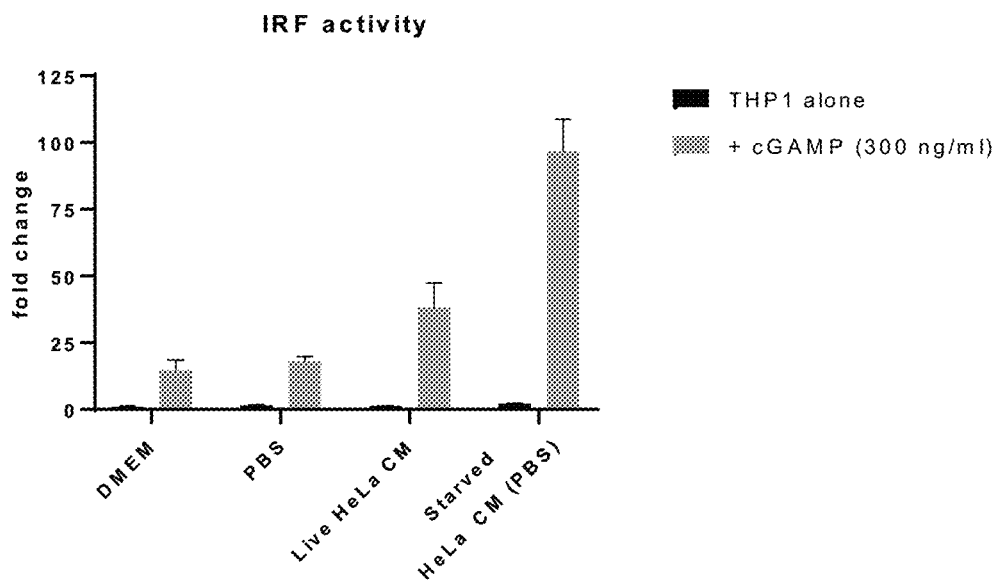
Figure 2B:
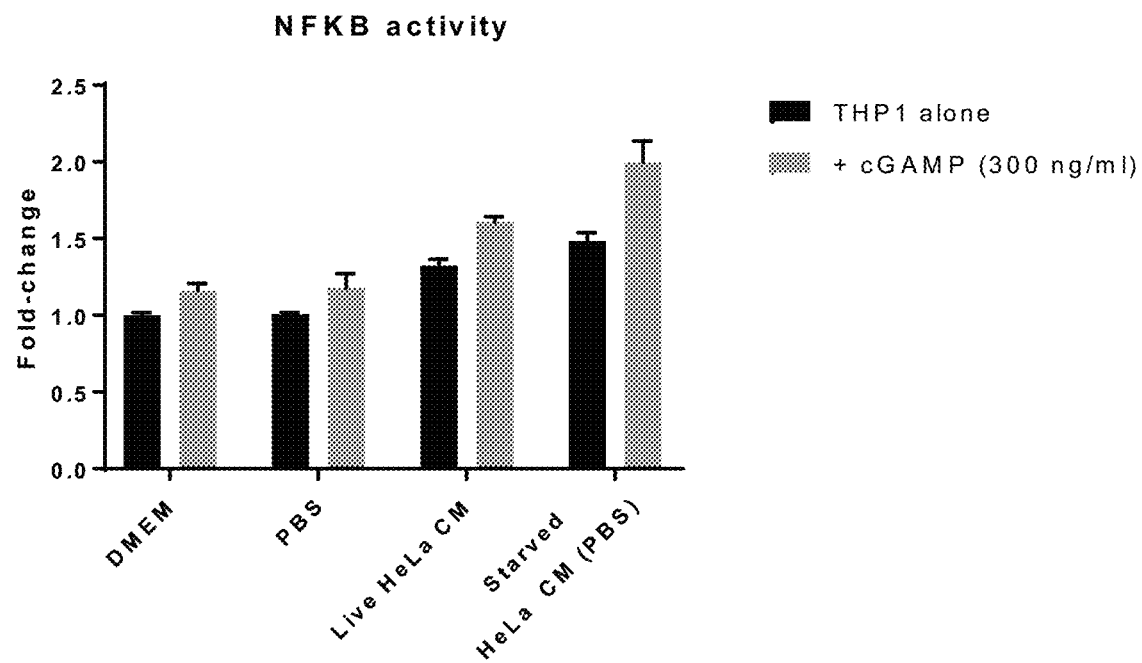

FIG. 2A shows IRF transcriptional activity in THP1 monocytes treated with conditioned medium from nutrient-starved HeLa cells. FIG. 2B shows NFKB activity in THP1 monocytes treated with conditioned medium from nutrient-starved HeLa cells.

Figure 3A:
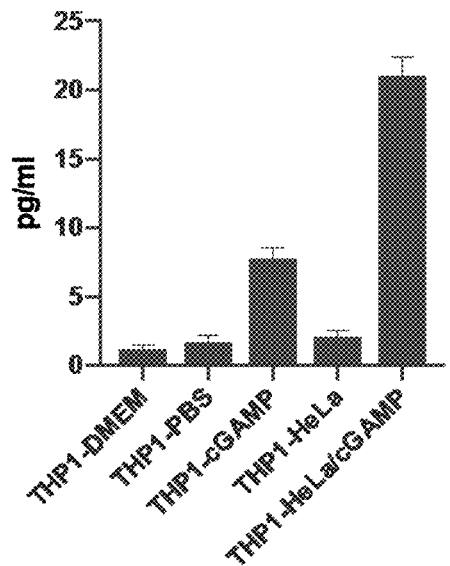
Figure 3B:
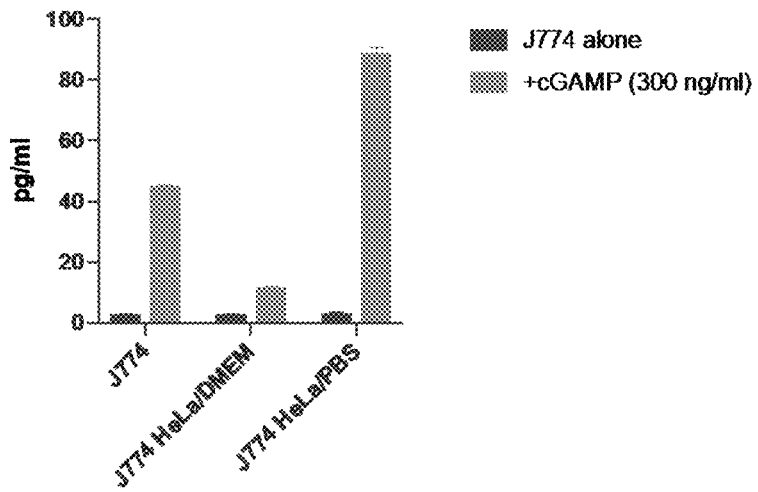
Figure 5A:
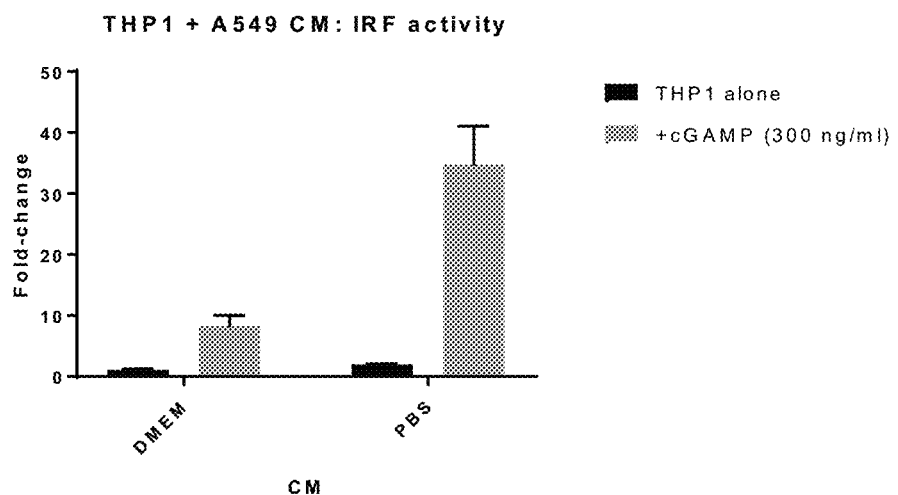
Figure 5B:
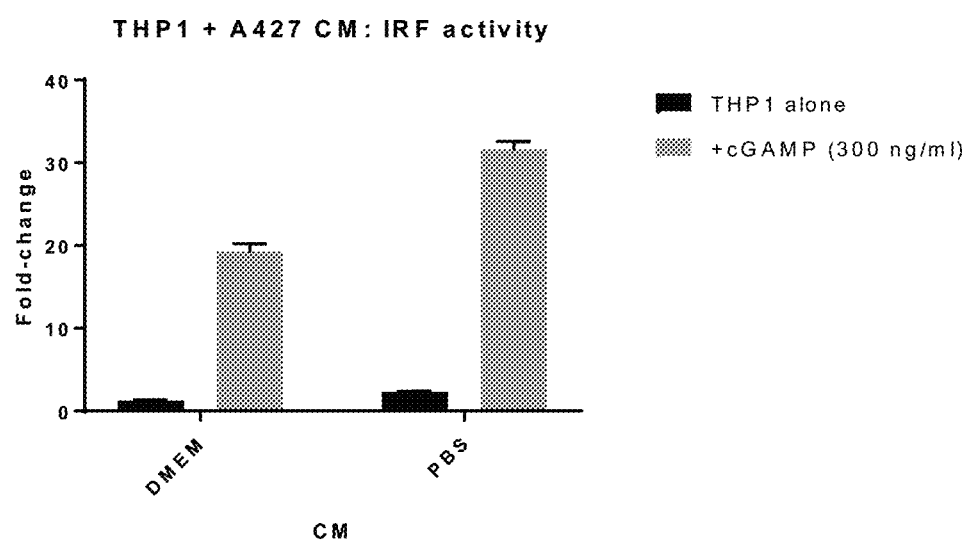
Figure 5C:
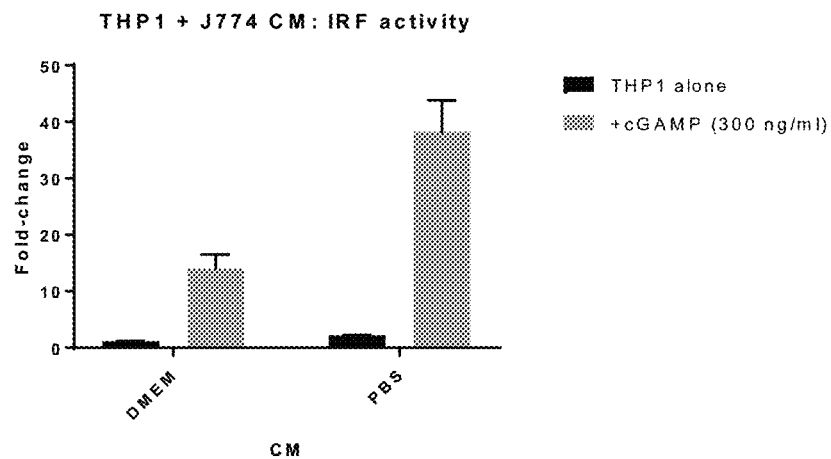
Figure 5D:
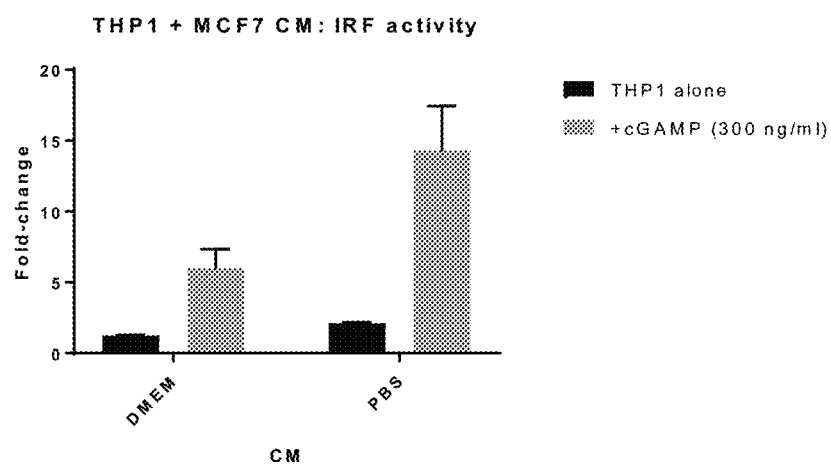
Figure 5E:
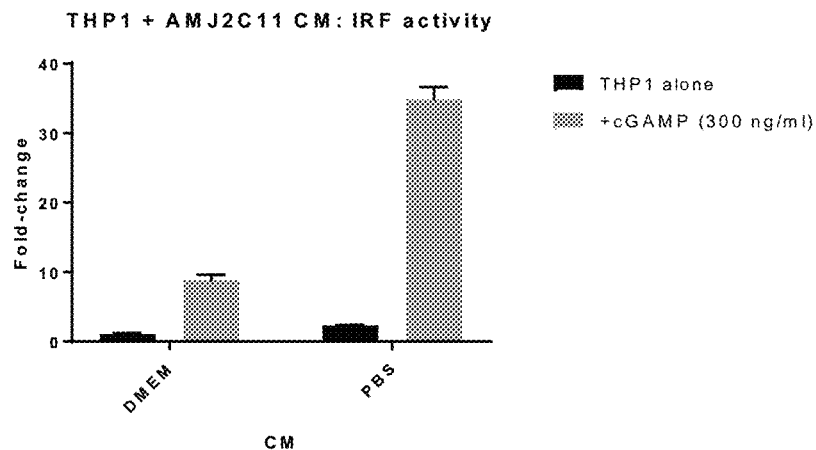
Figure 5F:
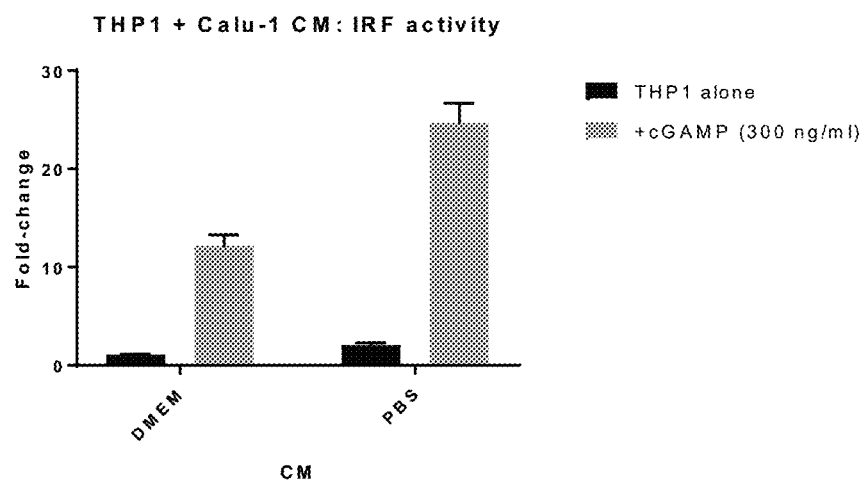
Figure 5G:
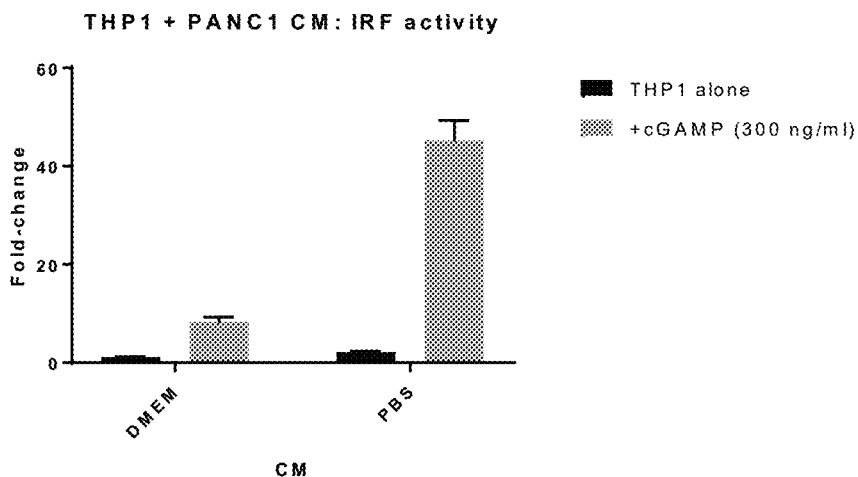
Figure 5H:
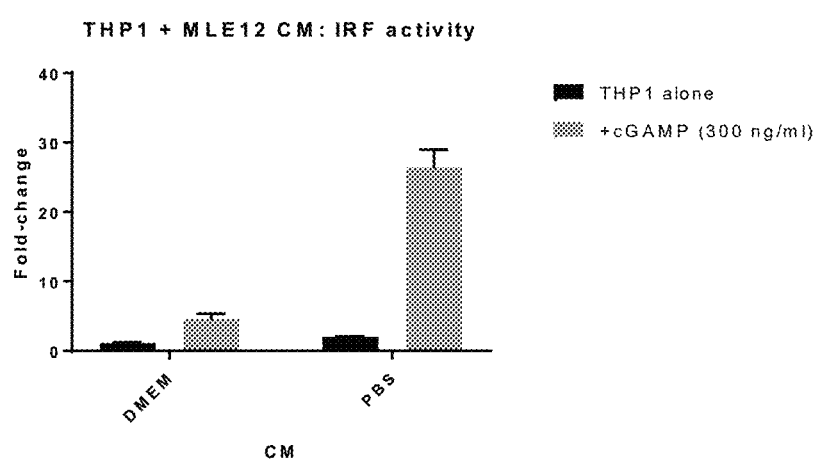
Figure 5I:
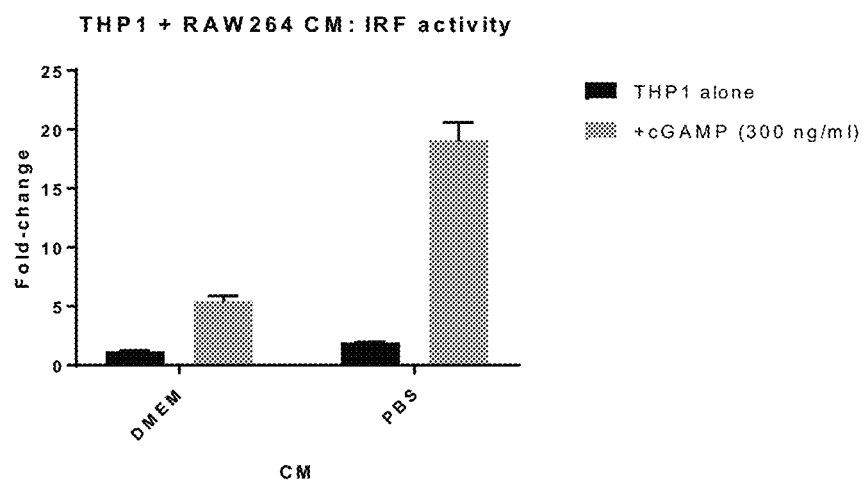

FIG. 3A shows IFN-beta secretion in THP1 monocytes exposed to HeLa/PBS conditioned media in combination with 2'3'-cGAMP. FIG. 3B shows IFN-beta secretion in J774 macrophages exposed to HeLa/PBS conditioned media in combination with 2'3'-cGAMP.

FIG. 4A-4F shows that each cyclic dinucleotide (CDN) displayed IRF inducing activity on its own in THP1-Dual cells, and each of these CDNs also displayed synergistic activation of IRF when combined with HeLa-PBS conditioned media.

FIG. 5A-5I show conditioned media from several different nutrient-deprived cells in combination with 2'3'-cGAMP induced IRF activation in human THP1 monocytes.

FIGS. 6A-6D show induction of IRF activity by cGAMP in combination with HeLa-PBS conditioned media was inhibited by AR-C 118925, which is a P2Y2 specific purinergic receptor antagonist.

Figure 7A:
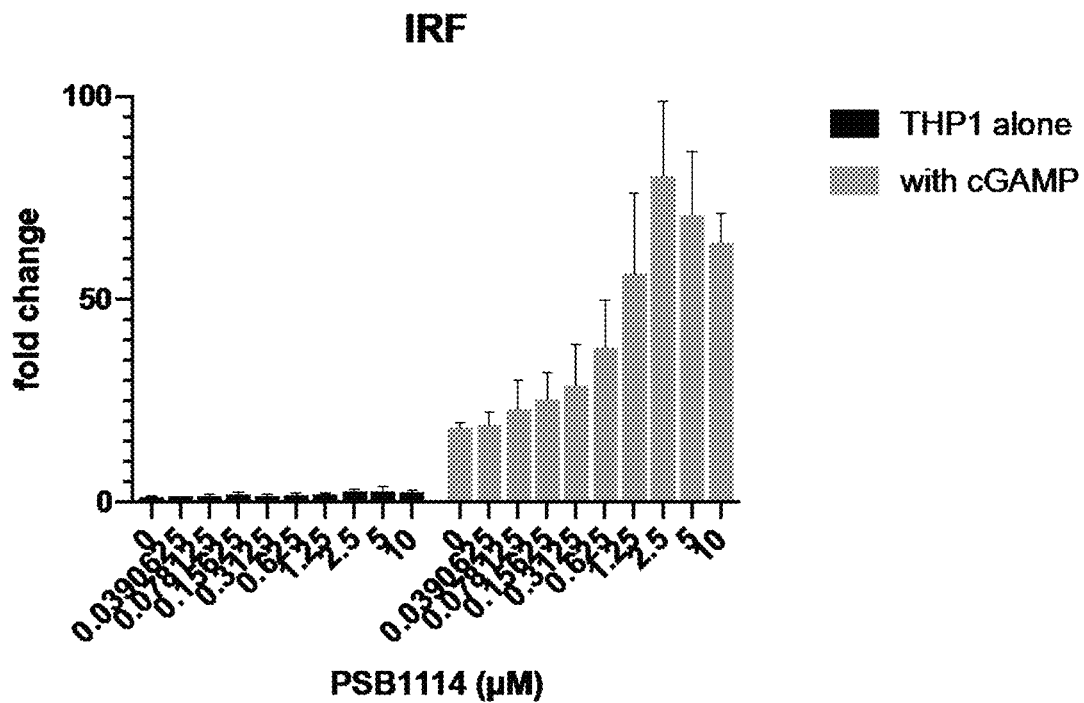
Figure 7B:
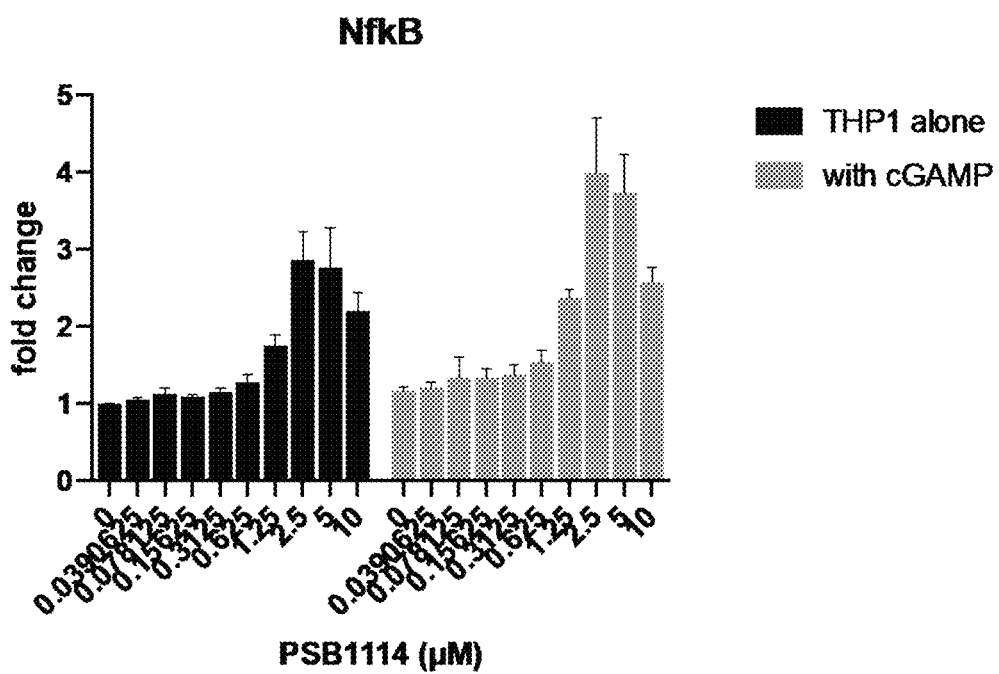

FIGS. 7A and 7B show the combination of PSB 1114 (a P2Y2 agonist) and 2'3'-cGAMP (a STING agonist) induced IRF signaling in human THP1 monocytes.

Figure 8A:
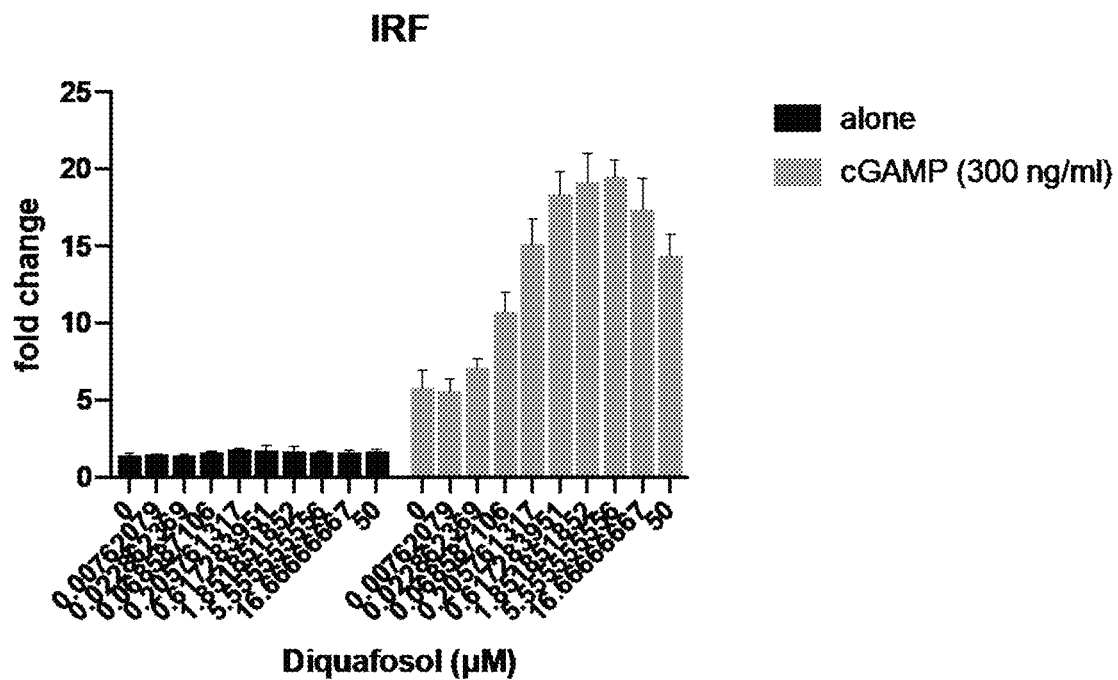
Figure 8B:
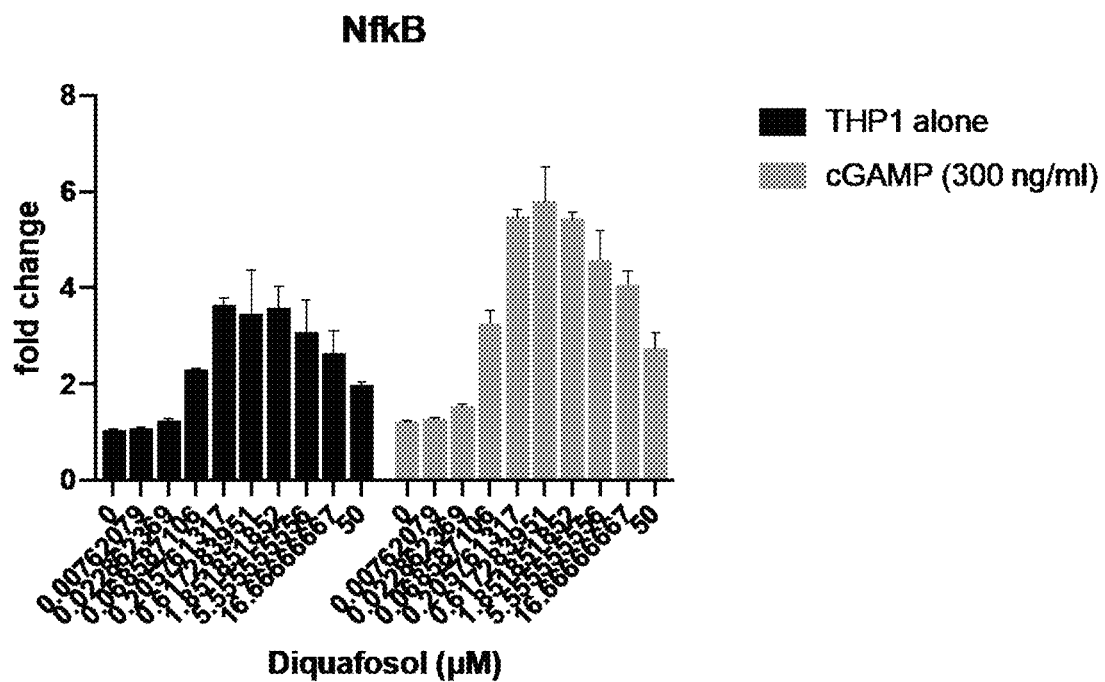

FIGS. 8A and 8B show a combination of the P2Y2 agonist Diquafosol and the STING agonist cGAMP induced IRF signaling in human THP1 monocytes.

Figure 9:
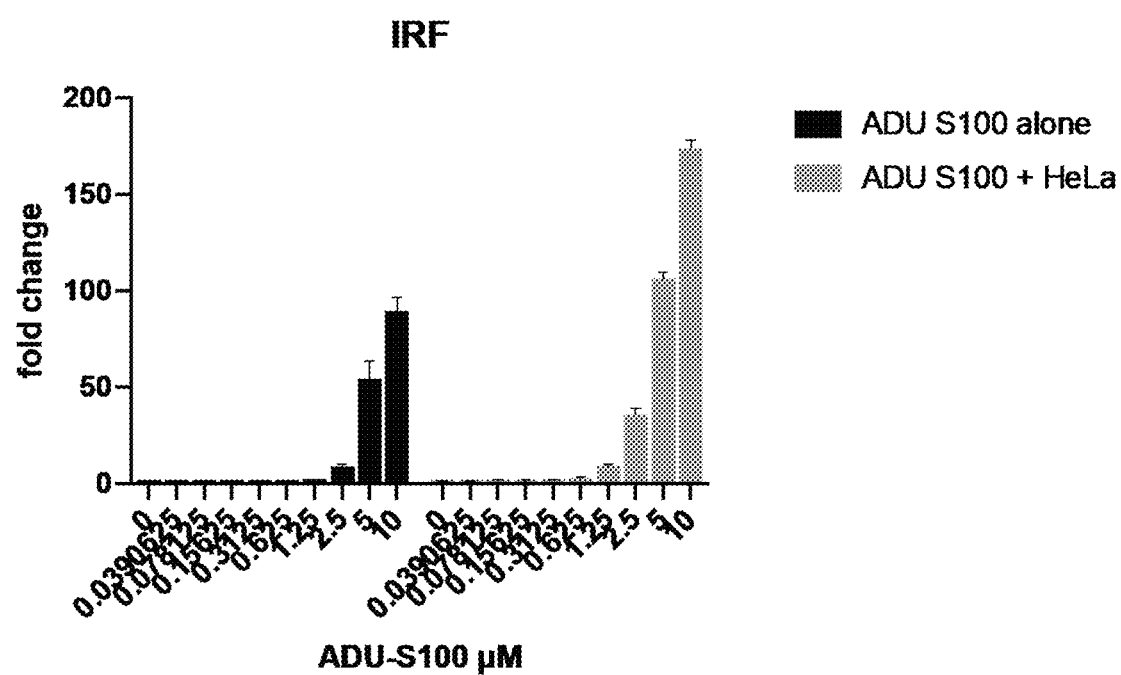

FIG. 9 shows treatment of THP1 monocytes with nutrient starved (PBS) HeLa conditioned media in combination with the STING agonist ADU-S100 strongly increased IRF signaling.

Figure 10A:
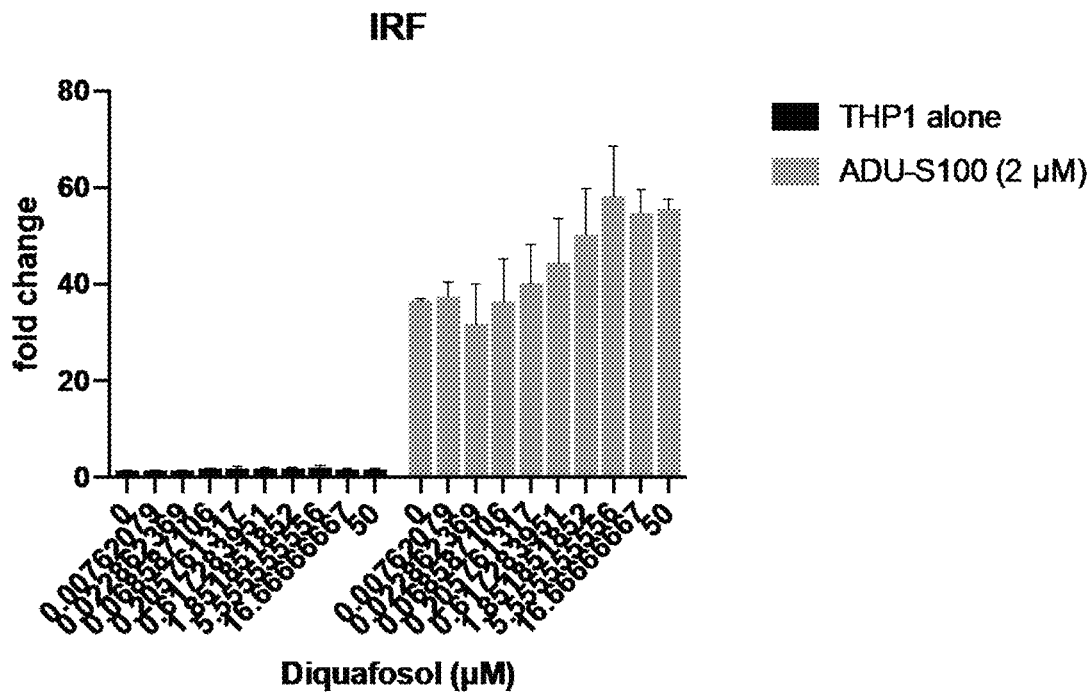
Figure 10B:
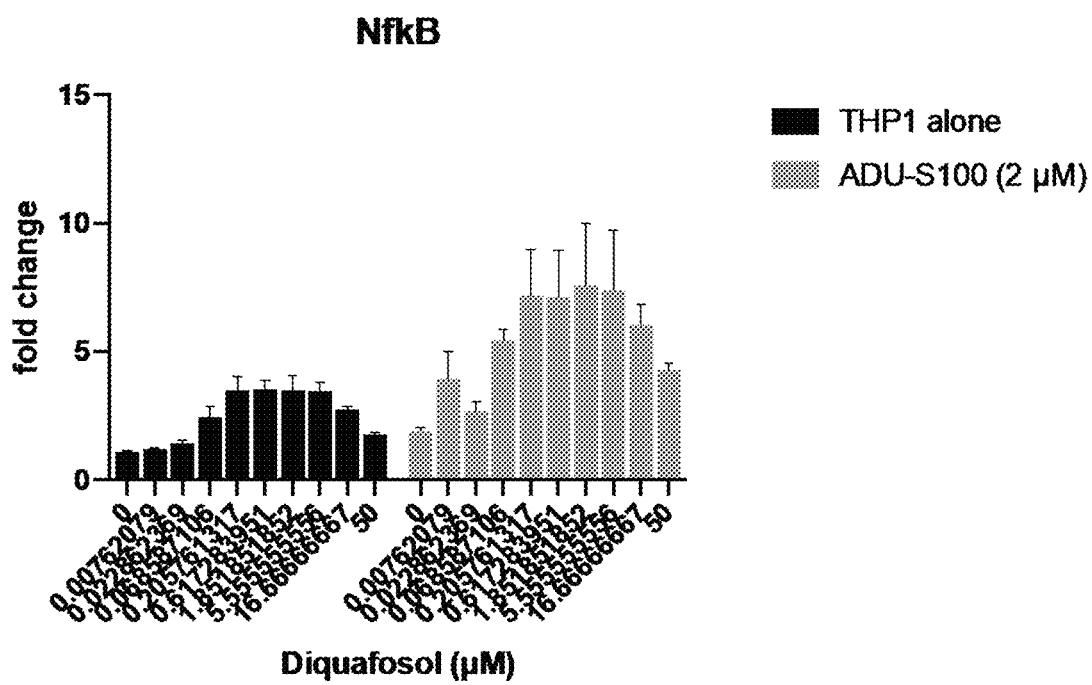

FIGS. 10A and 10B show the STING agonist ADU-S100 synergizes with the P2Y2 agonist Diquafosol to induce IRF signaling in human monocytes.

Figure 11:
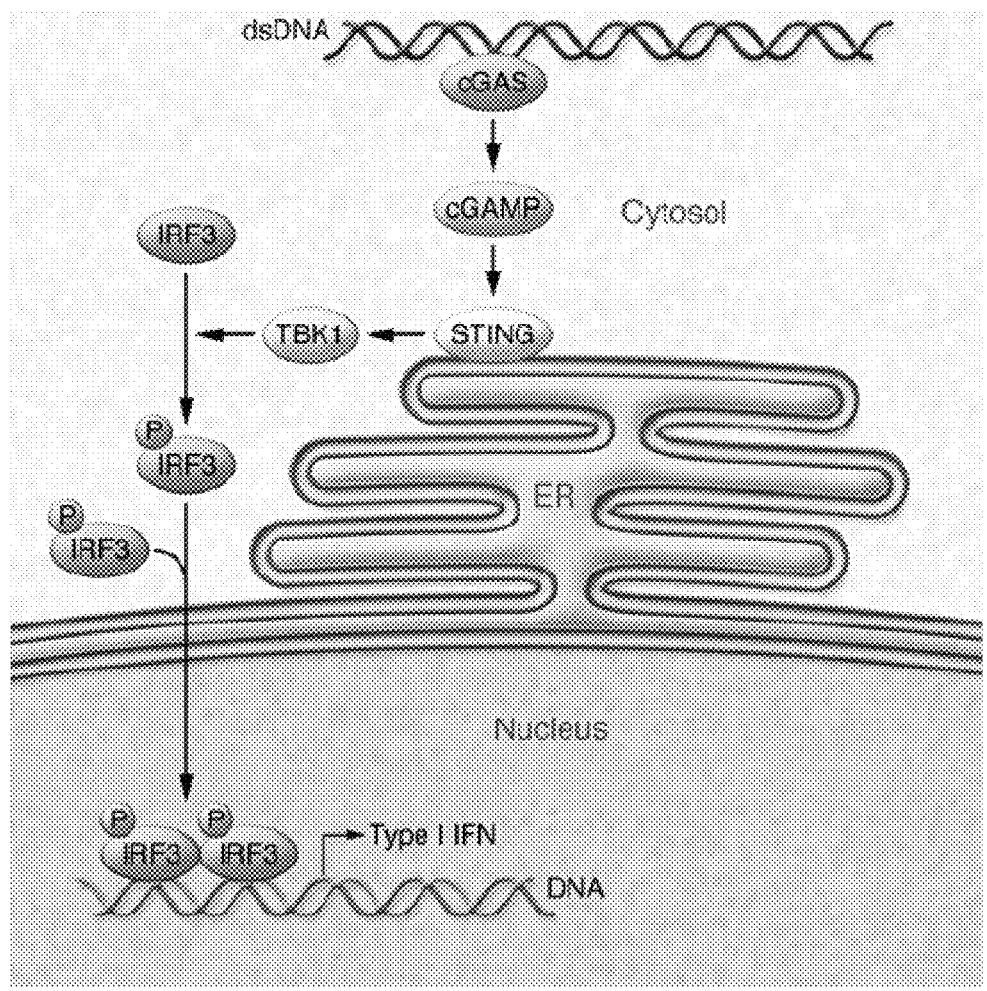

FIG. 11 shows a diagram of the STING pathway. Cytosolic DNA is recognized by cGAS, which catalyzes the generation of cGAMP. cGAMP binds to STING and leads to its activation, which involves translocation from the ER to perinuclear sites. This translocation results in the recruitment and activation of TBK1 by autophosphorylation. Active TBK1, in turn, phosphorylates the transcription factor IRF3, which translocates to the nucleus to induce transcription of type I IFN genes. See Corrales et al., 2016, J Clin. Invest. 126(7): 2404-2411, the entire content of which is incorporated herein by reference.

Figure 12:
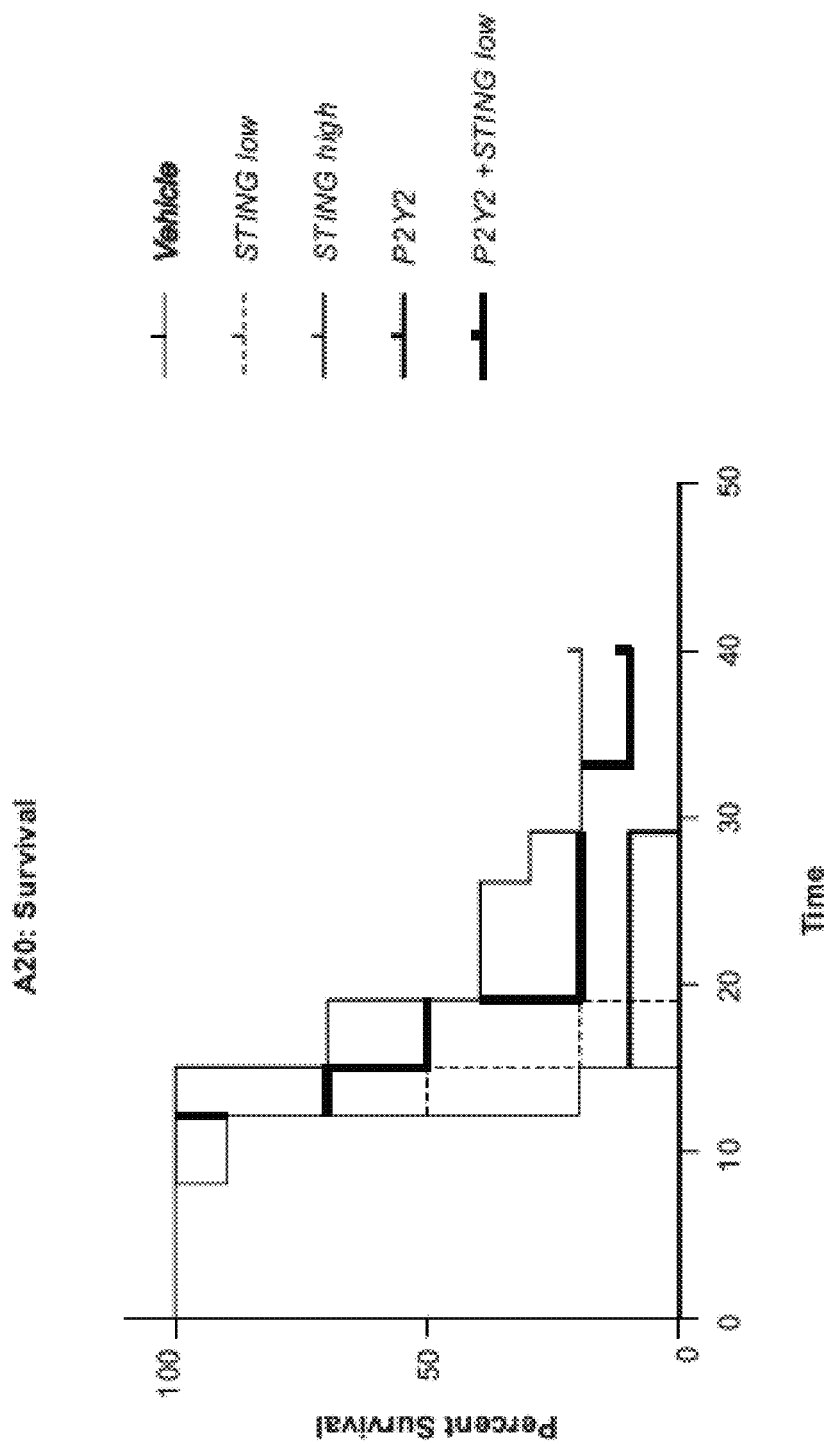

FIG. 12 shows percent survival in a mouse model of B-cell lymphoma treated with a STING agonist (ADU-S100) and a purinergic receptor agonist (diquafasol tetrasodium), either alone or in combination. Vehicle is PBS administered intratumorally once per day. STING low is 1 µg/kg of STING agonist (ADU-S100) administered intratumorally once per day. STING high is 50 µg/kg of STING agonist (ADU-S100) administered intratumorally once per day. P2Y2 is 10 mg/animal of P2Y2 purinergic receptor agonist (diquafosol testrasodium) administered intratumorally once per day. Time is shown in days.

DETAILED DESCRIPTION

In certain aspects, the present disclosure relates to methods of increasing immune activity in a target cell, tissue or subject, the methods comprising administering to the target cell, tissue or subject a composition comprising one or more postcellular signaling factors produced by cells exposed to a stress condition. Applicants have surprisingly shown that postcellular signaling factors produced by cells exposed to a stress condition increase immune response as evidenced by increases in NFKB and IRF activity in immune cells. Accordingly, administration of postcellular signaling factors produced by cells exposed to a stress condition may be used to treat disorders that would benefit from increased immune activity, such as cancer or an infection.

In certain aspects, the present disclosure relates to methods of increasing immune activity in a target cell, tissue or subject, the methods comprising administering to the target cell, tissue or subject, in combination (a) a Stimulator of Interferon Genes (STING) agonist and (b) a purinergic receptor agonist. Applicants have surprisingly found that combinations of a STING agonist and a purinergic receptor agonist (e.g., a P2Y receptor agonist, such as a P2Y2, P2Y4 or P2Y6 agonist) unexpectedly and synergistically increase immune response as evidenced by increases in IRF activity in immune cells. Accordingly, administration of combinations of a STING agonist and a purinergic receptor agonist (e.g., a P2Y receptor agonist, such as a P2Y2, P2Y4 or P2Y6 agonist) may be used to treat disorders that would benefit from increased immune activity, such as cancer or an infection.

In certain aspects, the present disclosure relates to methods of decreasing immune activity in a cell, tissue or subject comprising administering to the cell, tissue or subject, a purinergic receptor antagonist. As discussed above, Applicants have surprisingly found that combinations of a STING agonist and a purinergic receptor agonist (e.g., a P2Y receptor agonist, such as a P2Y2, P2Y4 or P2Y6 agonist) unexpectedly and synergistically increase immune response as evidenced by increases in IRF activity in immune cells. Based on these results, a purinergic receptor antagonist (e.g., a P2Y receptor antagonist, such as a P2Y2, P2Y4 or P2Y6 antagonist), optionally in combination with a STING antagonist, is expected to decrease immune response by preventing the induction of immunostimulatory activity.

Accordingly, administration of a purinergic receptor antagonist (e.g., a P2Y receptor antagonist, such as a P2Y2, P2Y4 or P2Y6 antagonist), optionally in combination with a STING antagonist, may be used to treat disorders that would benefit from decreased immune activity, such as inflammatory diseases.

I. Definitions

The terms "administer", "administering" or "administration" include any method of delivery of a pharmaceutical composition or agent into a subject's system or to a particular region in or on a subject.

As used herein, "administering in combination", "co-administration" or "combination therapy" is understood as administration of two or more active agents using separate formulations or a single pharmaceutical formulation, or consecutive administration in any order such that, there is a time period while both (or all) active agents overlap in exerting their biological activities. It is contemplated herein that one active agent (e.g., a postcellular signaling factor) can improve the activity of a second therapeutic agent, for example, can sensitize target cells, e.g., cancer cells, to the activities of the second therapeutic agent or can have a syngergistic effect with the second therapeutic agent. "Administering in combination" does not require that the agents are administered at the same time, at the same frequency, or by the same route of administration. As used herein, "administering in combination", "co-administration" or "combination therapy" includes administration of a composition comprising one or more postcellular signaling factors produced by cells exposed to a stress condition with one or more additional therapeutic agents, e.g., a STING agonist or an immunotherapeutic (e.g. an immune checkpoint modulator). Examples of STING agonists and immunotherapeutics are provided herein.

"Cellular disassembly" refers to a dynamic process that reorders and disseminates the material within a cell and results in the production and release from the cell of postcellular signaling factors.

As used herein, the terms "increasing" (or "activating") and "decreasing" refer to modulating resulting in, respectively, greater or lesser amounts, function or activity of a parameter relative to a reference. For example, subsequent to administration of a preparation described herein, a parameter (e.g., activation of NFkB, activation of macrophages, size or growth of a tumor) may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the parameter prior to administration. Generally, the metric is measured subsequent to administration at a time that the administration has had the recited effect, e.g., at least one day, one week, one month, 3 months, 6 months, after a treatment regimen has begun. Similarly, pre-clinical parameters (such as activation of NFkB of cells in vitro, and/or reduction in tumor burden of a test mammal, by a preparation described herein) may be increased or decreased by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the parameter prior to administration.

As used herein, "an anti-neoplastic agent" refers to a drug used for the treatment of cancer. Anti-neoplastic agents include chemotherapeutic agents (e.g., alkylating agents, antimetabolites, anti-tumor antibiotics, topoisomerase inhibitors, mitotic inhibitors corticosteroids, and enzymes), biologic anti-cancer agents, and immune checkpoint modulators.

A "cancer treatment regimen" or "anti-neoplastic regimen" is a clinically accepted dosing protocol for the treatment of cancer that includes administration of one or more anti-neoplastic agents to a subject in specific amounts on a specific schedule.

As used herein, an "immune checkpoint" or "immune checkpoint molecule" is a molecule in the immune system that modulates a signal. An immune checkpoint molecule can be a stimulatory checkpoint molecule, i.e., increase a signal, or inhibitory checkpoint molecule, i.e., decrease a signal. A "stimulatory checkpoint molecule" as used herein is a molecule in the immune system that increases a signal or is co-stimulatory. An "inhibitory checkpoint molecule", as used herein is a molecule in the immune system that decreases a signal or is co-inhibitory.

As used herein, an "immune checkpoint modulator" is an agent capable of altering the activity of an immune checkpoint in a subject. In certain embodiments, an immune checkpoint modulator alters the function of one or more immune checkpoint molecules including, but not limited to, CD27, CD28, CD40, CD122, OX40, GITR, ICOS, 4-1BB, ADORA2A, B7-H3, B7-H4, BTLA, CTLA-4, IDO, KIR, LAG-3, PD-1, PD-L1, PD-L2, TIM-3, and VISTA. The immune checkpoint modulator may be an agonist or an antagonist of the immune checkpoint. In some embodiments, the immune checkpoint modulator is an immune checkpoint binding protein (e.g., an antibody, antibody Fab fragment, divalent antibody, antibody drug conjugate, scFv, fusion protein, bivalent antibody, or tetravalent antibody). In other embodiments, the immune checkpoint modulator is a small molecule. In a particular embodiment, the immune checkpoint modulator is an anti-PD1, anti-PD-L1, or anti-CTLA-4 binding protein, e.g., antibody or antibody fragment.

An "immunotherapeutic" as used herein refers to a pharmaceutically acceptable compound, composition or therapy that induces or enhances an immune response. Immunotherapeutics include, but are not limited to, immune checkpoint modulators, Toll-like receptor (TLR) agonists, cell-based therapies, cytokines and cancer vaccines.

As used herein, "oncological disorder" or "cancer" or "neoplasm" refer to all types of cancer or neoplasm found in humans, including, but not limited to: leukemias, lymphomas, melanomas, carcinomas and sarcomas. As used herein, the terms "oncological disorder", "cancer," and "neoplasm," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells.

Specific criteria for the staging of cancer are dependent on the specific cancer type based on tumor size, histological characteristics, tumor markers, and other criteria known by those of skill in the art. Generally, cancer stages can be described as follows: (i) Stage 0, Carcinoma in situ; (ii) Stage I, Stage II, and Stage III, wherein higher numbers indicate more extensive disease, including larger tumor size and/or spread of the cancer beyond the organ in which it first developed to nearby lymph nodes and/or tissues or organs adjacent to the location of the primary tumor; and (iii) Stage IV, wherein the cancer has spread to distant tissues or organs.

"Posteellular signaling factors" are molecules and cell fragments produced by a cell undergoing cellular disassembly that are ultimately released from the cell and influence the biological activity of other cells. Postcellular signaling factors can include proteins, peptides, carbohydrates, lipids, nucleic acids, small molecules, and cell fragments (e.g. vesicles and cell membrane fragments).

A "solid tumor" is a tumor that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. The tumor does not need to have measurable dimensions.

A "subject" to be treated by the methods of the invention can mean either a human or non-human animal, preferably a mammal, more preferably a human. In certain embodiments, a subject has a detectable or diagnosed cancer prior to initiation of treatments using the methods of the invention. In certain embodiments, a subject has a detectable or diagnosed infection, e.g., chronic infection, prior to initiation of treatments using the methods of the invention.

"Therapeutically effective amount" means the amount of a compound that, when administered to a patient for treating a disease, is sufficient to effect such treatment for the disease. When administered for preventing a disease, the amount is sufficient to avoid or delay onset of the disease. The "therapeutically effective amount" will vary depending on the compound, the disease and its severity and the age, weight, etc., of the patient to be treated. A therapeutically effective amount need not be curative. A therapeutically effective amount need not prevent a disease or condition from ever occurring. Instead a therapeutically effective amount is an amount that will at least delay or reduce the onset, severity, or progression of a disease or condition.

As used herein, "treatment", "treating" and cognates thereof refer to the medical management of a subject with the intent to improve, ameliorate, stabilize, prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy).

II. Cellular Disassembly and Production of Postcellular Signaling Factors

Cellular disassembly is a dynamic process that re-orders and disseminates the material within a cell, and which results in the production and release of postcellular signaling factors that can have a profound effect on the biological activity of other cells. Cellular disassembly may occur during the process of regulated cell death and is controlled by multiple molecular mechanisms. Different types of cellular disassembly result in the production of different postcellular signaling factors and thereby mediate different biological effects. For example, Applicants have surprisingly shown that exposure of a cell to stress (e.g. nutrient deprivation) can result in the production of postcellular signaling factors that increase immune response as evidenced by increases in NFKB and IRF activity in immune cells.

Induction of Cellular Disassembly and Production of Postcellular Signaling Factors by Stress Conditions The methods provided herein involve stress conditions that induce cellular disassembly and production of postcellular signaling factors. Stress conditions suitable for carrying out the methods of the invention include, but are not limited to, nutrient deprivation, heat, cold, radiation, hypoxia, osmotic pressure, pH, and exposure to an agent that induces cellular disassembly.

Nutrient deprivation suitable for inducing cellular disassembly and producing postcellular signaling factors may comprise culturing cells in a medium lacking sufficient nutrients for sustained cell growth, such as Hank's Balanced Salt Solution (HBSS) or phosphate buffered saline (PBS).

Heat stress conditions suitable for inducing cellular disassembly and producing postcellular signaling factors may comprise exposing a cell to a temperature that is at least 1, 2, 3, 4, 5, 6, 7, 8, 9, 10, 11, 12, 13, 14, 15, 16, 17, 18, 10, 20, 30, 40 or 50° C. higher than the optimal cultivation temperature for the cell, e.g. 37° C. Cold stress conditions suitable for inducing cellular disassembly and producing postcellular signaling factors may comprise exposing a cell to a temperature that is at least 1, 2, 3, 4, 5, 6, 7, 8, 9, 10, 11, 12, 13, 14, 15, 16, 17, 18, 10, 20, 30, 40 or 50° C. lower than the optimal cultivation temperature for the cell, e.g. 37° C.

Radiation stress conditions suitable for inducing cellular disassembly and producing postcellular signaling factors may comprise, for example, UV radiation, gamma radiation, X-rays, infrared radiation or microwaves. Methods of treating cells with radiation are known in the art and are described, for example, in US 2012/0045418, which is incorporated by reference herein in its entirety. Cells may be irradiated with, for example, at least 10, 20, 30, 40 or 50 Gy to induce cellular disassembly. In some embodiments, the stress condition does not comprise radiation. In some embodiments, the stress condition does not comprise one or more of UV radiation, gamma radiation, X-rays, infrared radiation or microwaves.

Hypoxia is a condition in which a cell is deprived of adequate oxygen supply. Hypoxia stress conditions suitable for inducing cellular disassembly and producing postcellular signaling factors may comprise exposing a cell to oxygen concentrations that are at least 5%, 10%, 15%, 20%, 25%, 30%, 40%, 50%, 60%, 70%, 80% or 90% lower than the optimal oxygen concentration for the cell.

Osmotic pressure may be increased by the addition of salt (e.g. NaCl) to the culture medium of a cell. Osmotic pressure stress conditions suitable for inducing cellular disassembly and producing postcellular signaling factors may comprise exposing a cell to osmotic pressure that is at least 5%, 10%, 15%, 20%, 25%, 30%, 40%, 50%, 60%, 70%, 80%, 90%, 100%, 200%, 300%, 400%, or 500% higher than the optimal osmotic pressure for a cell.

Cellular disassembly and production of postcellular signaling factors may also be induced in a cell by exposing the cell to a pH that is higher or lower than the optimal pH for the cell. The pH of the culture medium for the cell may be adjusted by adding acids or bases to the culture medium. In some embodiments, the pH of the culture medium for the cell is at least 5.0, 5.5, 6.0, 6.5, 7.0, 7.2, 7.5 or 8.0. In some embodiments, the pH of the culture medium for the cell is less than 8.0, 7.5, 7.2, 7.0, 6.5, 6.0, 5.5 or 6.0. Any of these values may be used to define a range for the pH of the culture medium. For example, in some embodiments, the pH of the culture medium is 6.5 to 7.2, 7.5 to 8.0, or 6.0 to 6.5.

Agents that induce cellular disassembly and produce postcellular signaling factors may include small molecules, nucleic acids or proteins. As used herein, a "small molecule" is a molecule that has a molecular weight of less than 1000 Da. In some embodiments, the small molecule has a molecular weight of less than 900, 800, 700, 600 or 500 Da. In certain embodiments, a small molecule does not include a nucleic acid molecule. In certain embodiments, a small molecule does not include a peptide more than three amino acids in length. Nucleic acids that induce cellular disassembly may include, but are not limited to, antisense DNA molecules, antisense RNA molecules, double stranded RNA, siRNA, cDNA, or a Clustered Regularly Interspaced Short Palindromic Repeats (CRISPR)—CRISPR associated (Cas) (CRISPR-Cas) system guide RNA. In some embodiments, the nucleic acid encodes a protein that induces cellular disassembly and release of posteellular signaling factors when expressed in a cell. In some embodiments, the nucleic acid induces cellular disassembly and release of postcellular signaling factors by inhibiting expression of one or more genes in the cell. Proteins that induce cellular disassembly may include proteins (e.g. monoclonal or polyclonal antibodies) that inhibit activity of one or more proteins in the cell.

In some embodiments, the agent that induces cellular disassembly is a chemotherapeutic agent or antineoplastic agent, for example, any of the chemotherapeutic agents or antineoplastic agents described herein. In some embodiments, the agent that induces cellular disassembly is not an agent that induces iron-dependent cellular disassembly, e.g. ferroptosis.

Such stress conditions are capable of inducing the process of cellular disassembly when present in sufficient amount or intensity and for a sufficient period of time. In certain embodiments, the stress condition that induces cellular disassembly induces the production of postcellular signaling factors (e.g. immunostimulatory postcellular signaling factors) but does not result in cell death. In some embodiments, the stress condition induces cellular disassembly in a portion of a cell population, e.g., 10%, 20%, 30%, 40%, 50%, 60%, 70%, 80%, 90%, 95% or more cells of the population, such that postcellular signaling factors (e.g., immunostimulatory postcellular signaling factors), are produced by the portion of cells in the cell population. Cell death may occur in all or only a fraction of the portion of cells in the cell population.

According to the methods of the invention, the cells are exposed to the stress condition for a sufficient time to induce production of postcellular signaling factors. In some embodiments, the cell is exposed to the stress condition for at least 1, 2, 3, 4, 5, 6, 7, 8, 9, 10, 20, 30, 40, 50 or 60 minutes. In some embodiments, the cell is exposed to the stress condition for at least 1, 2, 3, 4, 5, 6, 7, 8, 9, 10, 11, 12, 24, 36, 48, 60 or 72 hours.

Any type of cell may be exposed to the stress conditions described herein for the production of postcellular signaling factors. In one embodiment, the cells exposed to a stress condition are cancer cells, for example, cells of any of the cancers described herein. In one embodiment, the cancer cells are immortalized. In one embodiment, the cancer cells are primary cells isolated from a subject. In some embodiments, the cells exposed to a stress condition do not comprise a cancer cell.

In some embodiments, the cells exposed to a stress condition are immune cells, including but not limited to any of the immune cells described herein. In other embodiments, the cells exposed to a stress condition do not comprise immune cells.

In some embodiments, the cells exposed to a stress condition are blood cells, e.g. erythrocytes, leukocytes (e.g. peripheral blood mononuclear cells (PBMCs)), or thrombocytes. In other embodiments, the cells exposed to a stress condition do not comprise blood cells. In some embodiments, the cells exposed to a stress condition do not comprise leukocytes. In some embodiments, the cells exposed to a stress condition do not comprise peripheral blood mononuclear cells (PBMCs). In some embodiments, the cells exposed to a stress condition do not comprise T-cells. In some embodiments, the cells exposed to a stress condition do not comprise malignant T-cells.

The source of the cells exposed to a stress condition is not limited, and may include cells isolated from the target tissue or subject to which the composition comprising one or more postcellular signaling factors is administered. For example, in some embodiments, the cells exposed to a stress condition are autologous to the target cell, tissue or subject. In some embodiments, the cells exposed to a stress condition are allogeneic to the target cell, tissue or subject.

Compositions Comprising Postcellular Signaling Factors

According to the methods provided herein, the composition comprising one or more postcellular signaling factors produced by cells exposed to a stress condition may contain various components in addition to the one or more postcellular signaling factors, depending, for example, on the method of preparing the composition. For example, in some embodiments, the composition comprises the cells exposed to a stress condition in addition to the one or more postcelluar signaling factors produced by these cells, e.g., the cells comprise the one or more postcellular signaling factors. In other embodiments, the cells exposed to a stress condition may be separated from the one or more postcellular cellular signaling fators to prepare the composition. For example, in some embodiments, the composition comprises a cell-free extract prepared from cells exposed to a stress condition, e.g., the cell-free extract comprises the one or more postcellular signaling factors. Cell-free extracts may be prepared, for example, by centrifuging cells suspended in a culture medium and collecting the supernatant. In one embodiment, the composition comprising one or more postcellular signaling factors does not comprise the cells that were exposed to the stress condition. In one embodiment, the composition comprising one or more postcellular signaling factors does not comprise intact cells.

The composition comprising the one or more postcellular signaling factors may be prepared by culturing cells in a culture medium and exposing the cells to a stress condition as described herein. In one embodiment, conditioned medium containing the one or more postcellular signaling factors is collected from the cell culture after exposure to the stress condition. The cells may be further cultured after exposure to the stress condition to allow for release of additional postcellular signaling factors. In some embodiments, the cells are cultured for at least 5, 10, 15, 20, 30, 45 or 60 minutes, or at least 2, 3, 4, 5, 6, 7, 8, 9, 10, 11, 12, 24, 36, 48 or 72 hours after exposure to the stress condition. In one embodiment, the composition comprises conditioned medium from cells exposed to a stress condition. In one embodiment, the one or more postcellular signaling factors are isolated from the cells exposed to the stress condition, such that the composition comprising one or more postcellular signaling factors does not contain intact cells.

The composition comprising the one or more postcellular signaling factors may be fractionated to isolate or concentrate one or more postcellular signaling factors with immunostimulatory activity. For example, in one embodiment, the composition comprises a functional fraction of the conditioned medium from the cells exposed to the stress condition. In some embodiments, the functional fraction is prepared by treating the conditioned medium with an enzyme (e.g. a protease) to degrade a particular class of compounds in the conditioned medium (e.g. proteins) and increase the relative abundance of other molecules (e.g. small molecules and nucleic acids). Suitable enzymes include, but are not limited to, proteases and nucleases (e.g. RNases or DNases). In some embodiments, the functional fraction comprising the one or more postcellular signaling factors is resistant to protease digestion or nuclease digestion (e.g. RNAse digestion or DNAse digestion). In some embodiments, the one or more postcellular signaling factors are resistant to protease digestion or nuclease digestion (e.g. RNAse digestion or DNAse digestion).

Functional fractions of the conditioned medium may also be prepared by isolating molecules based on their molecular weight. For example, in some embodiments, postcellular signaling factors with a molecular weight of less than 50, 40, 30, 20, 10, 9, 8, 7, 6, 5, 4, 3, 2, 1 or 0.5 are isolated from the conditioned medium. In some embodiments, postcellular signaling factors with a molecular weight of less than 50, 40, 30, 20, 10, 9, 8, 7, 6, 5, 4, 3, 2, 1 or 0.5 kDa are isolated from the conditioned medium. Any of these values may be used to define a range for the size of the one or more postcellular signaling factors in the composition. For example, in some embodiments, the one or more postcellular signaling factors in the composition have a molecular weight of less than 50, 40, 30, 20, 10, 9, 8, 7, 6, 5, 4, 3, 2, 1 or 0.5 kDa. In some embodiments, the one or more postcellular signaling factors in the composition have a molecular weight of greater than 50, 40, 30, 20, 10, 9, 8, 7, 6, 5, 4, 3, 2, 1 or 0.5 kDa. In some embodiments, the one or more postcellular signaling factors in the composition have a molecular weight of between 0.5 and 50 kDa, between 0.5 and 25 kDa, between 25 and 50 kDa, between 10 and 20 kDa, between 20 and 30 kDa, between 30 and 40 kDa or between 40 and 50 kDa. Methods for isolating compounds of a particular molecular weight are known in the art. For example, in some embodiments, the conditioned medium is extracted with organic solvent followed by HPLC fractionation. In other embodiments, the conditioned medium is subjected to size exclusion chromatography and different fractions are collected. For example, conditioned medium may be applied to a size exclusion column and fractionated on FPLC.

The functional fractions of the conditioned medium may be evaluated to identify fractions with a particular activity, e.g. immunostimulatory activity. Any of the methods described herein for measuring immune response may be used to identify functional fractions of the conditioned medium with immunostimulatory activity. For example, fractions with immunostimulatory activity may be identified by exposing an immune cell (e.g. a THP-1 human monocyte) to fractions of the conditioned medium and measuring the level or activity of NFκB, IRF or STING in, or produced by, the immune cell.

The fractions may also be evaluated to identify particular functions associated with immunostimulatory activity, e.g. activation of a purinergic receptor. For example, in some embodiments, the fractions may be administered to the immune cell in combination with an inhibitor (e.g. a purinergic receptor inhibitor) to identify fractions whose immunostimulatory activity is attenuated by the inhibitor. Suitable purinergic receptors include, but are not limited to, P2Y2, P2Y4 and P2Y6. In this way, it is possible to identify functional fractions with a particular activity, e.g. purinergic receptor activation. In one embodiment, the functional fraction is inhibited by a purinergic receptor inhibitor, e.g. a P2Y2 inhibitor. In one embodiment, the one or more postcellular signaling factors comprises an agonist of a purinergic receptor.

The skilled artisan will recognize that, in addition to the utility of a functional fraction of the conditioned medium, the functional fraction may be further analyzed to identify, for example, a single postcellular signaling factor having immunostimulatory activity, and/or having a particular activity, such as purinergic receptor activation. In some embodiments, the composition comprises only one postcellular signaling factor isolated from a cell exposed to a stress condition, and which has immunostimulatory activity, and/or has a particular activity, such as purinergic receptor activation. In some embodiments, the composition comprises 2, 3, 4, 5, 6, 7, 8, 9, or 10 postcellular signaling factors isolated from a cell exposed to a stress condition, and which have immunostimulatory activity, and/or have a particular activity, such as purinergic receptor activation.

III. Purinergic Receptor Agonists

Purinergic receptors, also known as purinoceptors, are a family of plasma membrane molecules that are found in almost all mammalian tissues. Within the field of purinergic signalling, these receptors have been implicated in learning and memory, locomotor and feeding behavior, and sleep. More specifically, they are involved in several cellular functions, including proliferation and migration of neural stem cells, vascular reactivity, apoptosis and cytokine secretion. These functions have not been well characterized and the effect of the extracellular microenvironment on their function is also poorly understood.

There are five known distinct classes of purinergic receptors, known as P1, P2X, P2Y, P2Z, P2U and P2T receptors, and they are so classified based on their respective activation molecules. For instance, P1 receptors such as $A_1$, $A_{2A}$, $A_{2B}$ and $A_3$ receptors, are G protein-coupled receptors activated by adenosine. P2Y receptors, such as P2Y2, P2Y4, P2Y6, P2Y11, P2Y12, P2Y13 and P2Y14, are also G protein-coupled receptors but are activated by nucleotides such as ATP, ADP, UTP, UDP and UDP-glucose. P2X receptors are ligand-gated ion channels activated by ATP.

The term "purinergic receptor agonist" as used herein refers to any chemical entity, including but not limited to a small molecule, a nucleoside, a nucleotide, a nucleobase, a sugar, a nucleotide-sugar, an N-acetylated nucleotide-sugar, a nucleic acid, an amino acid, a polysaccharide, a peptide, a polypeptide, a protein, an antibody, an aptamer (e.g., DNA/RNA/XNA/peptide aptamers) or a complex comprising any combination of the aforementioned chemical entities, that activates a purinergic receptor.

A "P2Y receptor agonist" as used herein refers to any chemical entity, including but not limited to a small molecule, a nucleoside, a nucleotide, a nucleobase, a sugar, a nucleotide-sugar, an N-acetylated nucleotide-sugar, a nucleic acid, an amino acid, a polysaccharide, a peptide, a polypeptide, a protein, an antibody, an aptamer (e.g., DNA/RNA/XNA/peptide aptamers) or a complex comprising any combination of the aforementioned chemical entities, that activates a P2Y receptor (e.g., P2Y1, P2Y2, P2Y4, P2Y6, P2Y11 or P2Y12 receptor agonist).

P2Y receptors initiate an intracellular cascade of events that lead to an increase in the cytosolic concentration of calcium ions. Accordingly, in some embodiments, a P2Y receptor agonist may be identified by treating a cell with a chemical entity and measuring intracellular calcium ion concentrations. For example, commercially available fluorescent dyes such as fluo-4 and fura-2 (Thermo Fisher Scientific, Waltham, Mass.) that fluoresce at greater intensity when bound to $Ca^{2+}$ may be used to measure intracellular $Ca^{2+}$ concentrations. Cells such as 1321N1 astrocytoma cells may be stably transfected with a P2Y receptor for use in the assay. Fluorescence may be measured, for example, by using a TriStar LB 942 plate reader (Berthold Technologies GmbH & Co. KG, Bad Wildbad, Germany). An increase in intracellular $Ca^{2+}$ concentrations in response to treatment with the chemical entity would indicate that the chemical entity is a P2Y receptor agonist.

In some embodiments, the P2Y receptor agonist activates Phospholipase-C(PLC) and/or Protein Kinase-C(PKC). Accordingly, in some embodiments, a P2Y receptor agonist may be identified by assaying for activation of PLC and/or PKC using assays commonly known in the art, for example as described in Durban et al., 2007, European Journal of Lipid Science and Technology 109(5): 469-473; and Glickman et al., 2004, Assay Guidance Manual, Editors Sittampalam et al., Eli Lilly & Company and the National Center for Advancing Translational Sciences, Bethesda (Md.); the entire content of which is incorporated by reference herein in their entirety. An increase in PLC and/or PKC activation in response to treatment with the chemical entity would indicate that the chemical entity is a P2Y receptor agonist.

In some embodiments, the P2Y2 receptor agonist regulates chemotaxis of macrophages and immune cells. In some embodiments, the P2Y2 receptor agonist regulates neutrophil degranulation. In some embodiments, the P2Y2 receptor agonist regulates proliferation and migration of smooth muscle cells. In some embodiments, the P2Y2 receptor agonist regulates secretion of chloridion in epithelial cells. In some embodiments, the P2Y2 receptor agonist regulates secretion of water and mucin from epithelial cells. Accordingly, in some embodiments, a P2Y2 receptor agonist may be identified by assaying for any one or more of chemotaxis of macrophages and immune cells, neutrophil degranulation, proliferation and migration of smooth muscle cells, secretion of chloridion in epithelial cells, and/or secretion of water and mucin from epithelial cells using utilizing assays commonly known in the art, for example as described in Xu et al., 2018, Bioorganic and Medicinal Chemistry 26: 366-374; and Linden et al., 2019, Annual Review of Immunology 37:325-47, Liu et al., 2012, Med Chem 20: 1155; Muller et al., 2017, Oncotarget 8: 35962-72; the contents of each of which are incorporated by reference herein in its entirety. A modulation of chemotaxis of macrophages and immune cells, neutrophil degranulation, proliferation and migration of smooth muscle cells, secretion of chloridion in epithelial cells, and/or secretion of water and mucin from epithelial cells in response to treatment with the chemical entity would indicate that the chemical entity is a P2Y (e.g., P2Y2) receptor agonist.

In one embodiment, the purinergic receptor agonist (e.g., P2Y receptor agonist, such as P2Y2, P2Y4 or P2Y6 agonist) administered in combination with a STING agonist is a small molecule compound or a nucleotide as defined herein. Non-limiting examples of small molecule and nucleotide-based purinergic receptor agonists are described in International Patent Application Nos. WO 2004/047749, WO 1998/034593, WO 1991/016056, WO 2001/1045691, Jacobson et al. (*Novartis Found. Symp.,* 2006, 276:58-281), and Sakuma et al. (*Nature Scientific Reports,* 2017, 7:6050), each of which is incorporated herein by reference in its entirety.

In one embodiment, the purinergic receptor agonist used in a method of the invention is a P2 receptor agonist. In one embodiment, the purinergic receptor agonist is a P2Y receptor agonist (e.g., P2Y1, P2Y2, P2Y4, P2Y6, P2Y11 or P2Y12 receptor agonist). In one embodiment, the purinergic receptor agonist is a P2Y2, P2Y4 or P2Y6 receptor agonist. In one embodiment, the purinergic receptor agonist is a P2Y2 receptor agonist. In one embodiment, the purinergic receptor agonist is a P2Y4 receptor agonist. In another embodiment, the purinergic receptor agonist is a P2Y6 receptor agonist. In one embodiment, the purinergic receptor agonist is a P2Y1 receptor agonist. In one embodiment, the purinergic receptor agonist is a P2Y11 receptor agonist. In one embodiment, the purinergic receptor agonist is a P2Y12 receptor agonist.

In one embodiment, the purinergic receptor agonist (e.g., P2Y receptor agonist, such as P2Y2, P2Y4 or P2Y6 agonist) is a nucleotide-based compound represented by the following structural formula:

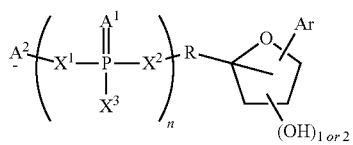

or a pharmaceutically acceptable salt, free acid, an analogue, a regioisomer, a stereoisomer or a tautomer thereof wherein $X^1$, $X^2$ and $X^3$, for each instance is independently selected from O, S, halogen, imido, methyl or methylene (as valency permits), ethyl or ethylene (as valency permits), halomethyl or halomethylene (as valency permits), haloethyl or haloethylene (as valency permits), wherein at least one instance of $X^1$, $X^2$ and $X^3$ is O or S; $A^1$ and A2 are each independently O or S; R is selected from O, S, methoxy, thiomethoxy, ethoxy, and thioethoxy; and Ar is an optionally substituted monocyclic or bicyclic heteroaryl having at least one nitrogen atom (e.g., 1, 2, 3 or 4) and optionally one or more heteroatoms selected from O and S; and wherein n is 1, 2 or 3, preferably 2 or 3, preferably 3.

In one embodiment, the purinergic receptor agonist (e.g., P2Y receptor agonist, such as P2Y2, P2Y4 or P2Y6 agonist) is a nucleotide-based compound represented by the following structural formula:

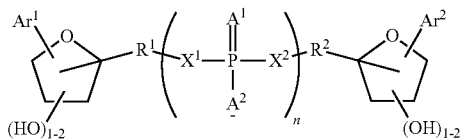

or a pharmaceutically acceptable salt, free acid, an analogue, a regioisomer, a stereoisomer or a tautomer thereof wherein $X^1$ and $X^2$, for each instance is independently selected from O, S, halogen, imido, methyl or methylene (as valency permits), ethyl or ethylene (as valency permits), halomethyl or halomethylene (as valency permits), haloethyl or haloethylene (as valency permits), wherein at least one instance of $X^1$ and $X^2$ is O or S; $A^1$ and $A^2$ are each independently O or S; R is selected from O, S, methoxy, thiomethoxy, ethoxy, and thioethoxy; and $Ar^1$ and $Ar^2$ are each and independently an optionally substituted monocyclic or bicyclic heteroaryl having at least one nitrogen atom (e.g., 1, 2, 3 or 4) and optionally one or more heteroatoms selected from O and S; n is an integer from 1 to 20.

In one embodiment, Ar, $Ar^1$ and $Ar^2$ in the two structural formulas described above for nucleotide-based purinergic receptor are each independently selected from the group consisting of:

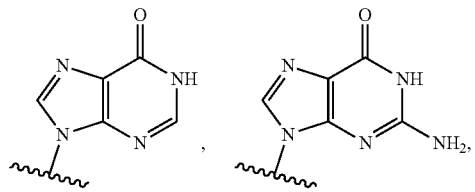

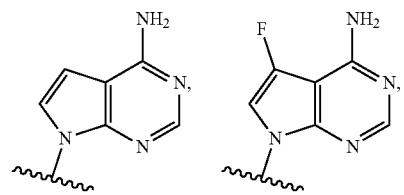

65
-continued
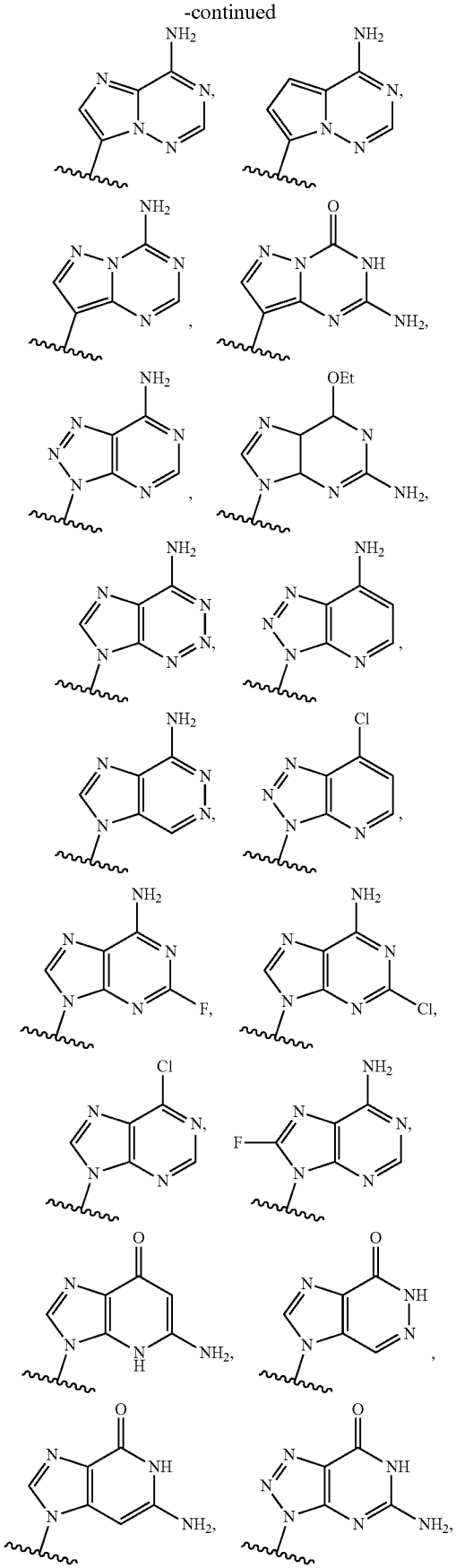
66
-continued
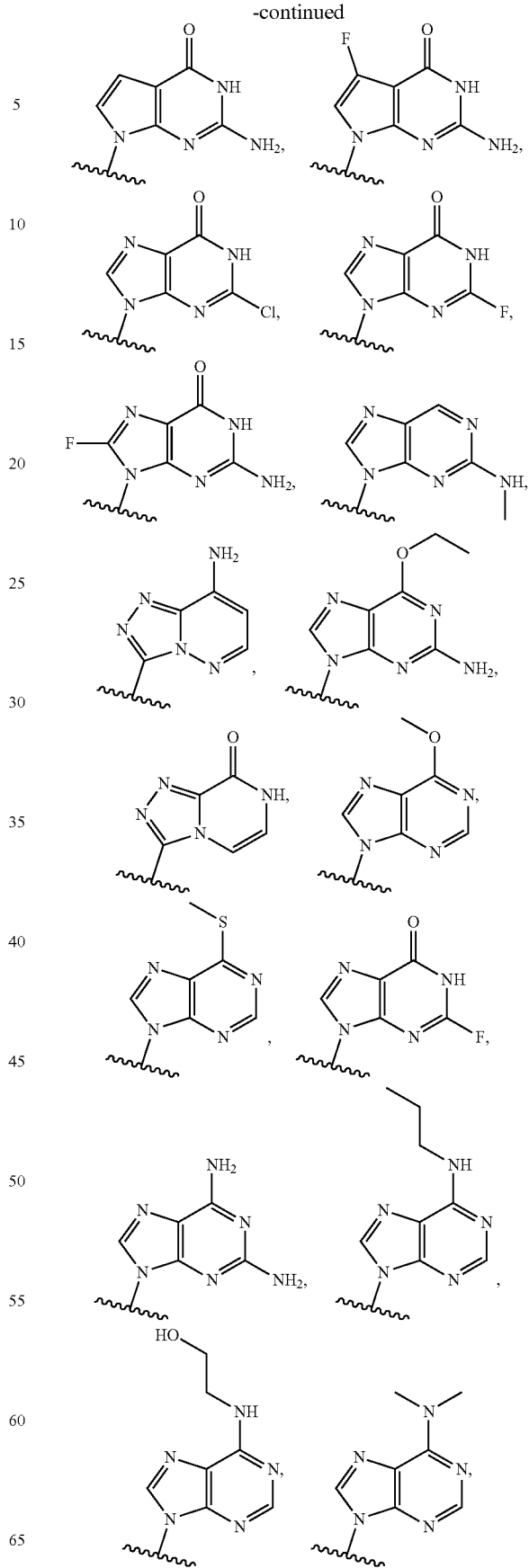

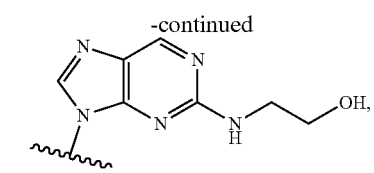
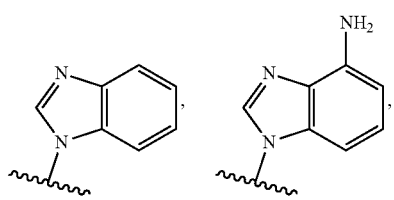
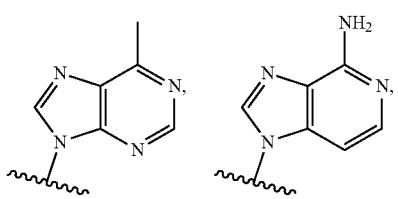
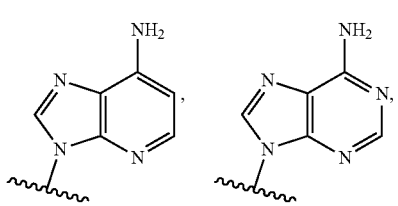
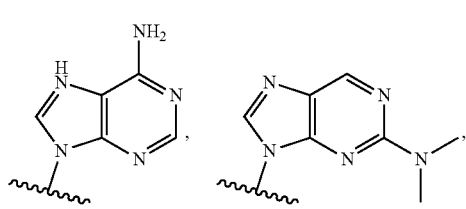
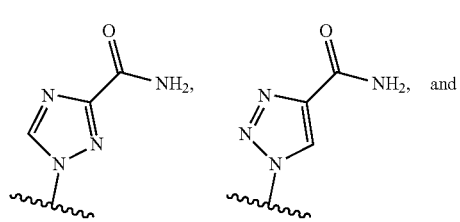
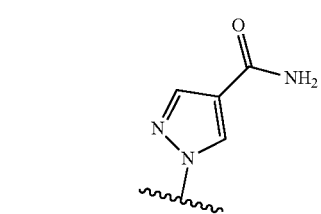
In one embodiment, the purinergic receptor agonist (e.g., P2Y receptor agonist, such as P2Y2, P2Y4 or P2Y6 agonist) is a compound selected from the following:
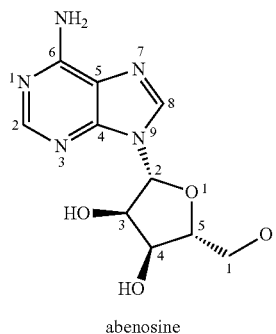
abenosine
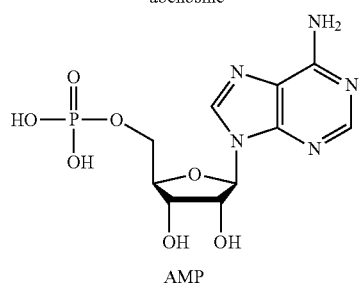
AMP
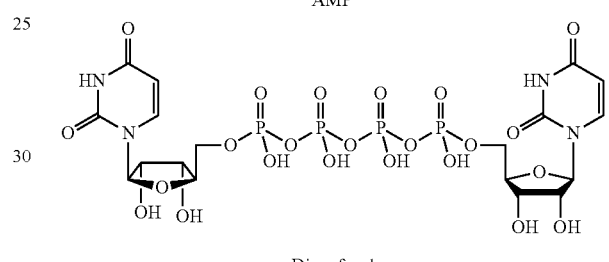
Diquafosol
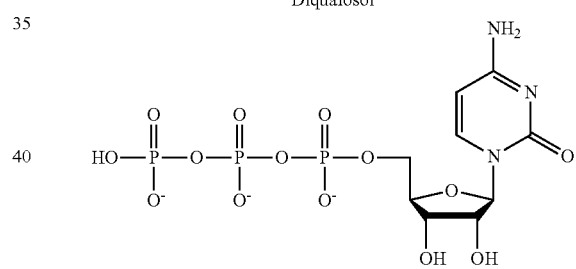
CTP
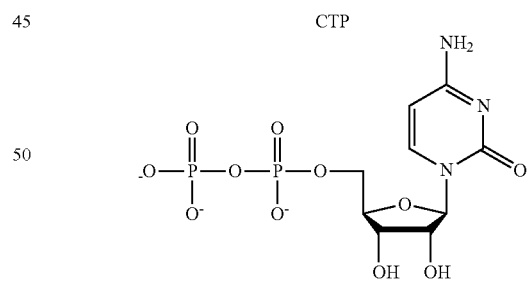
CDP
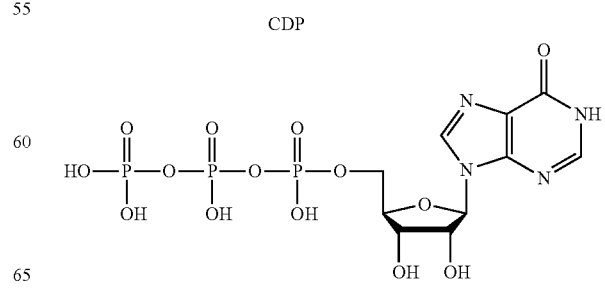
ITP

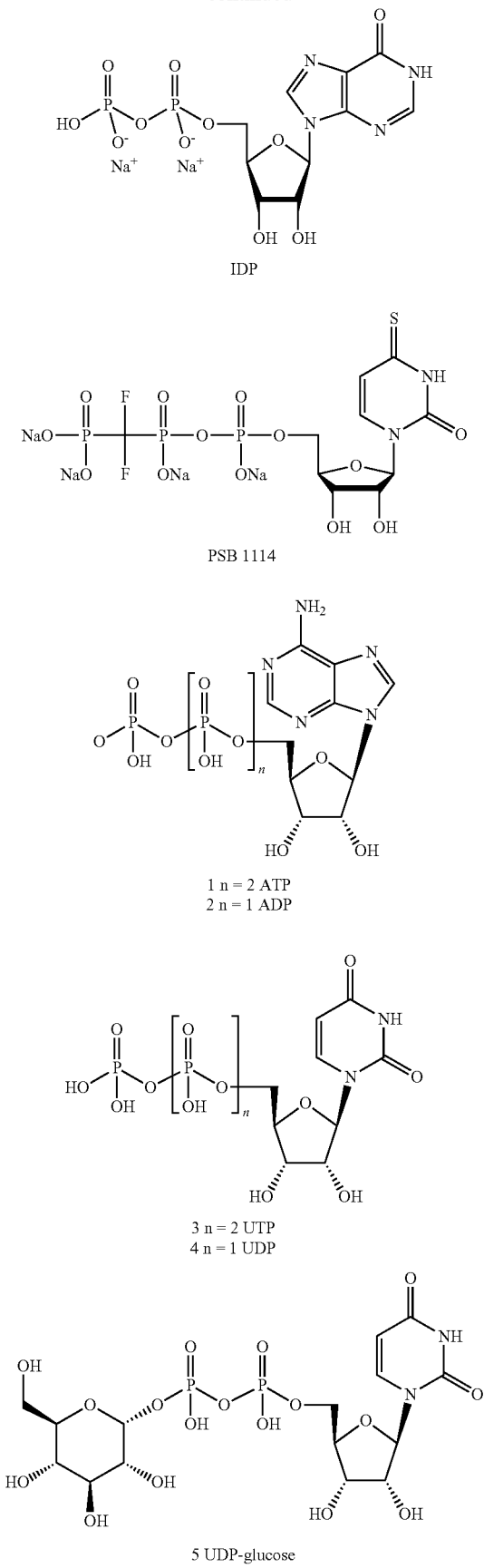

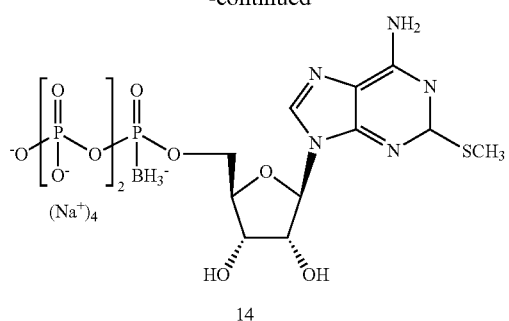
14
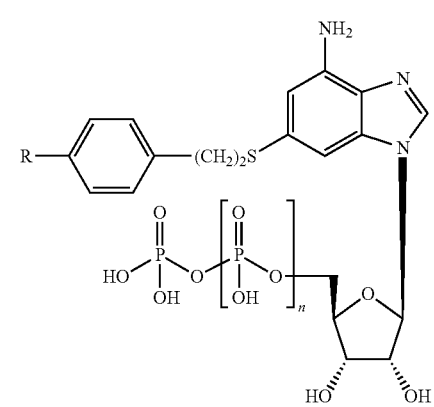
15 n = 2 R = NH₂
16 n = 1 R = N₃
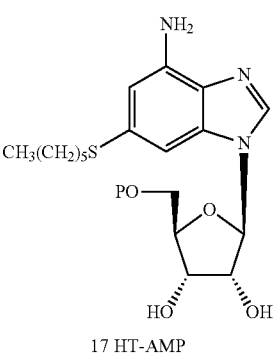
17 HT-AMP
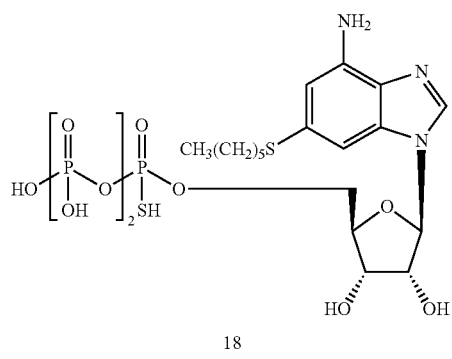
18
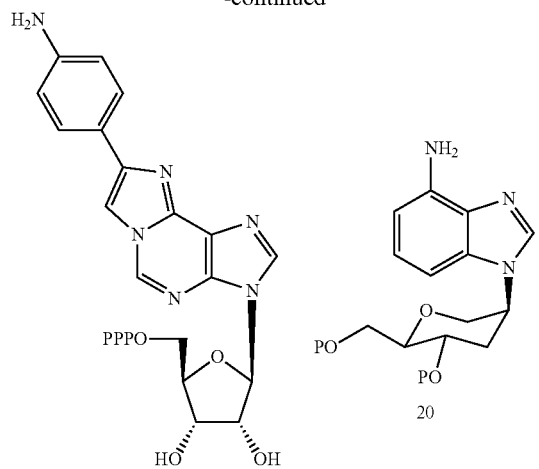
19
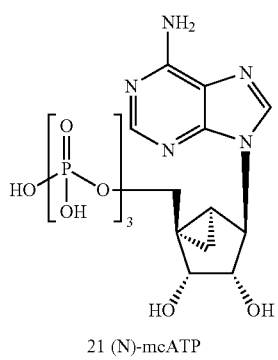
21 (N)-mcATP
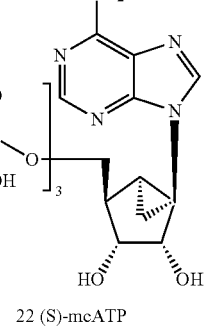
22 (S)-mcATP
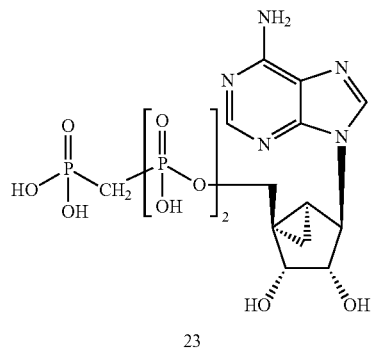
23

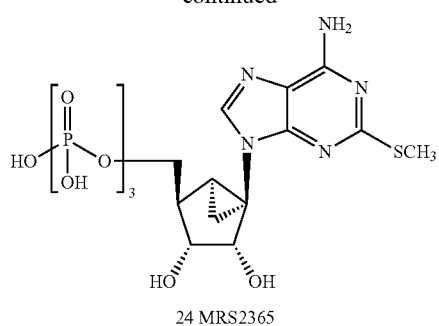
24 MRS2365
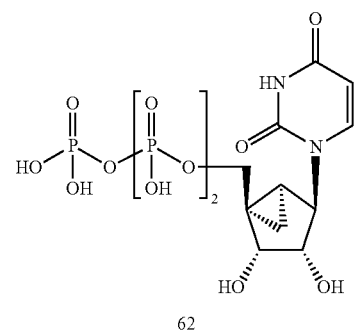
62
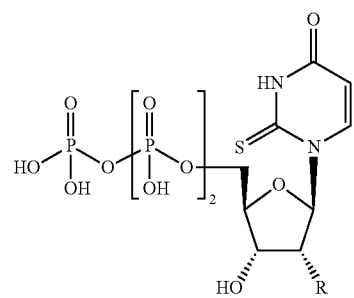
63a R = OH
63b R = NH₂ MRS2698
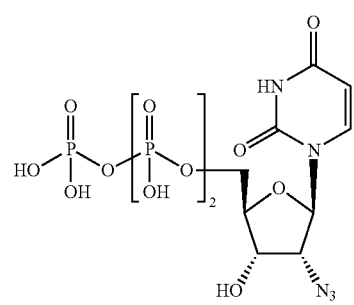
64
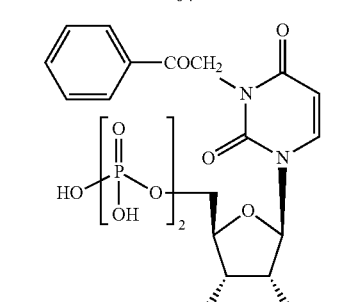
65
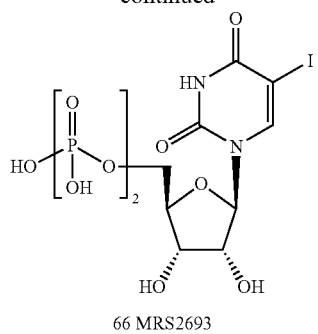
66 MRS2693
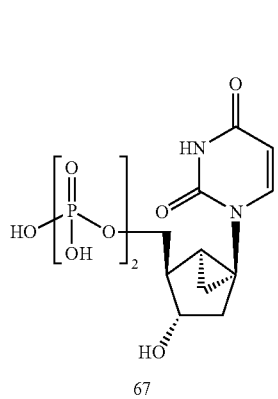
67
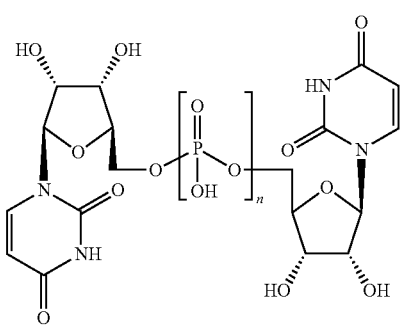
68a n = 2 Up$_2$U
68b n = 3 Up$_3$U
68c n = 4 Up$_4$U, Diquafosol
68d n = 6 Up$_6$U
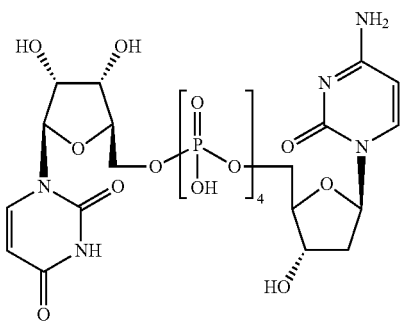
69 Up$_4$dC, INS37217, Denufosol 75
-continued
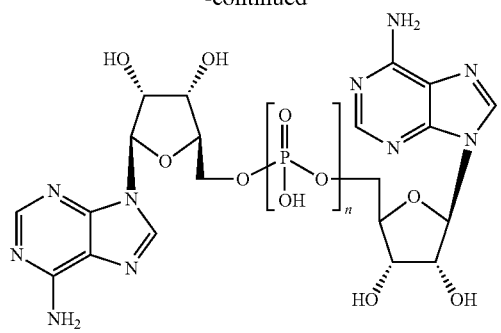
70a n = n = 3 Ap₃A
70b n = n = 4 Ap₄A
70c n = n = 5 Ap₅A
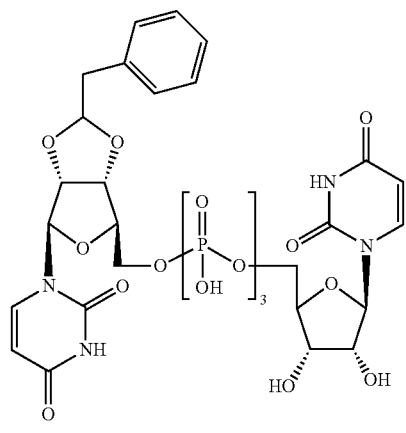
71 INS48823
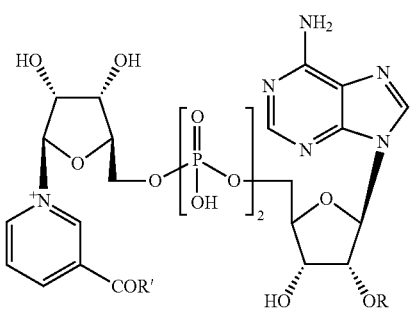
72 R = H, R' = NH$_2$ -NAD$^+$
73 R = PO$_3$H$_2$, R' = OH NAADP$^+$
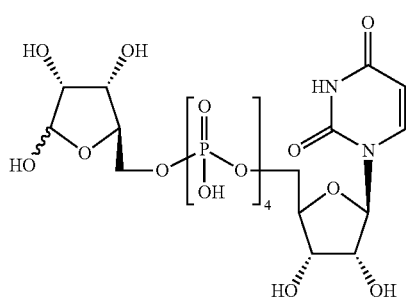
74
76
-continued
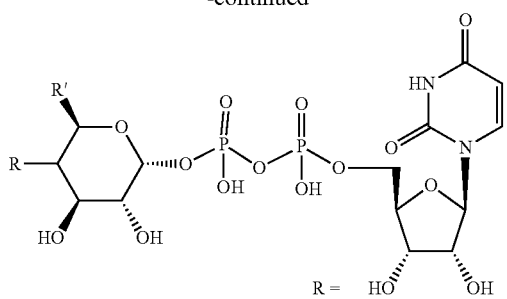
75 R = HO····  R' = COOH
76 R = HO—  R' = CH$_2$OH
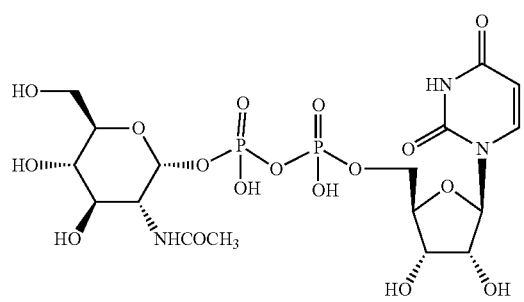
77
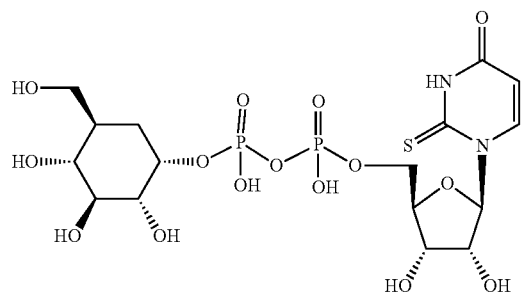
78 MRS2690
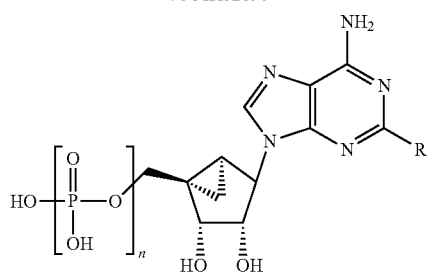
R = H, n = 3 MRS2340
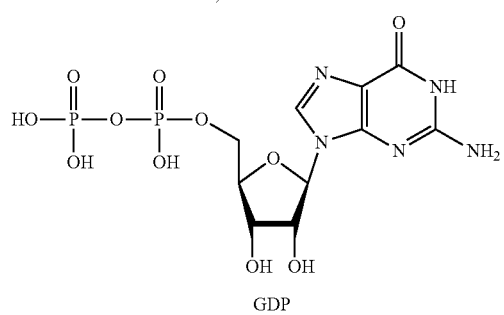
GDP

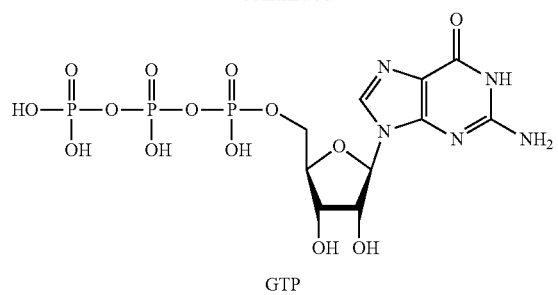
GTP
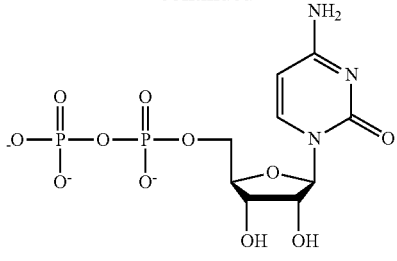
CDP
or a pharmaceutically acceptable salt, free acid, an analogue, a regioisomer, a stereoisomer or a tautomer thereof.
In one particular embodiment, the purinergic receptor agonist is a P2Y2, P2Y4 or P2Y6 receptor agonist and is a compound selected from the following:
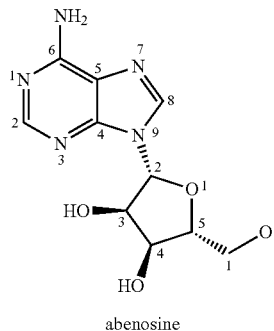
abenosine
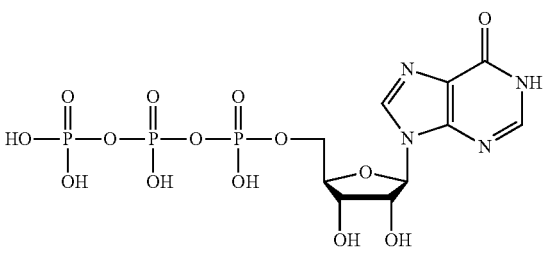
ITP
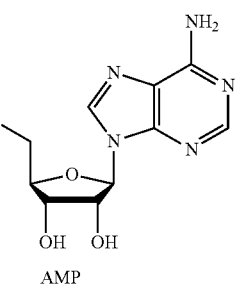
AMP
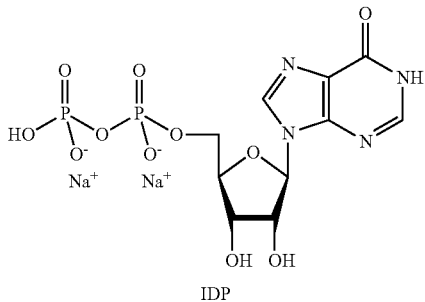
IDP
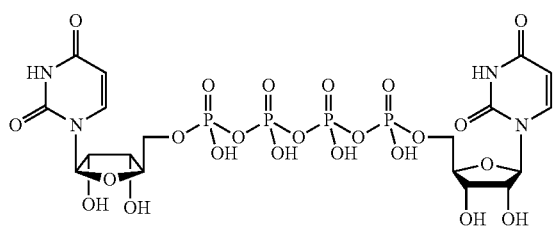
Diquafosol
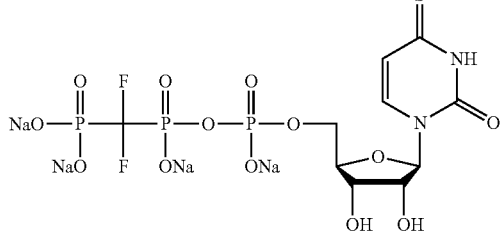
PSB 1114
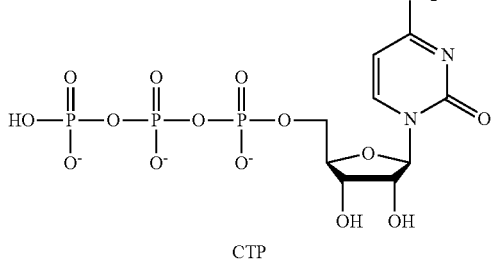
CTP
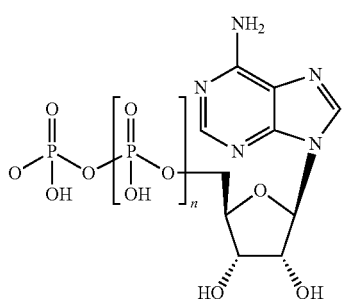
1 n = 2 ATP
2 n = 1 ADP

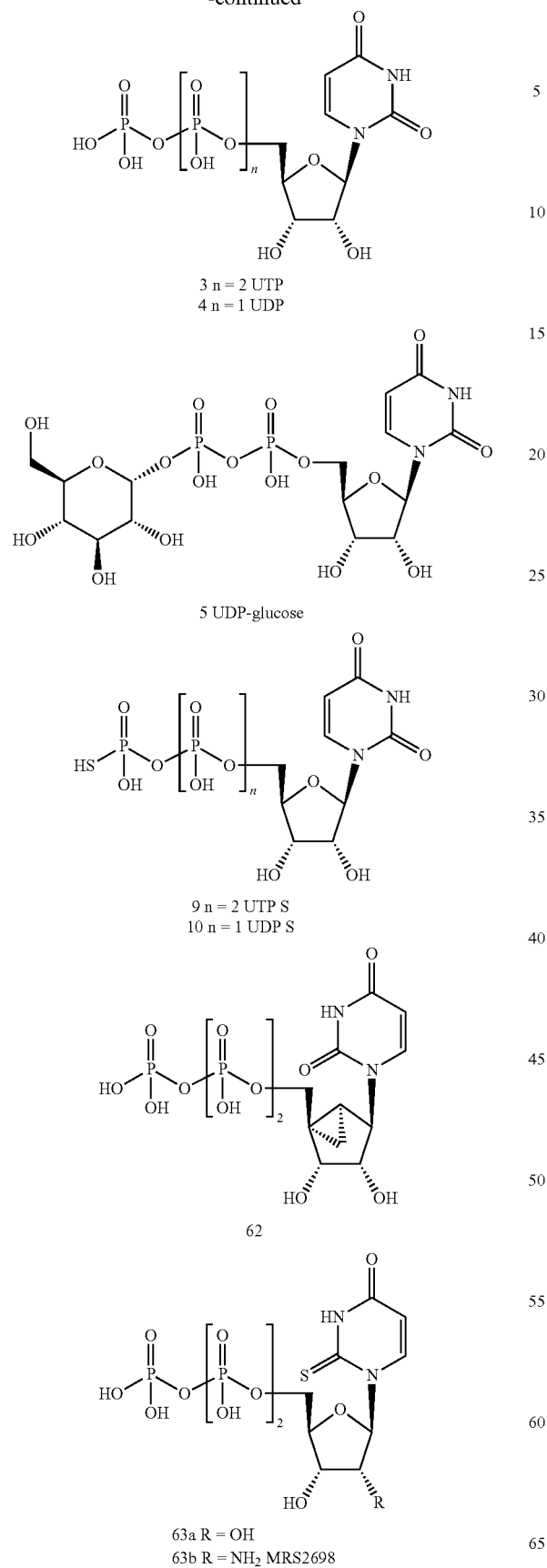

-continued
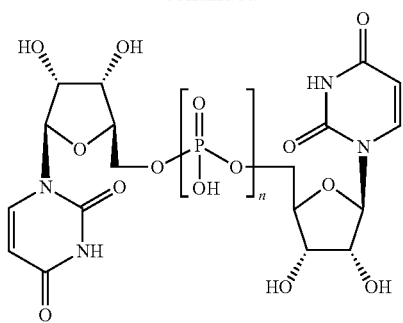
68a n = 2 Up₂U
68b n = 3 Up₃U
68c n = 4 Up₄U, Diquafosol
68d n = 6 Up₆U
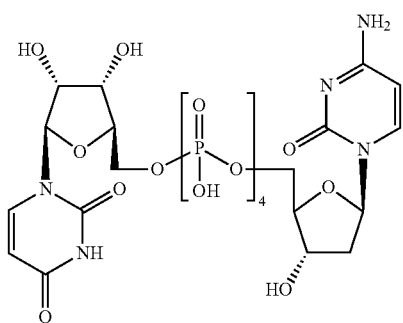
69 Up₄dC, INS37217,
Denufosol
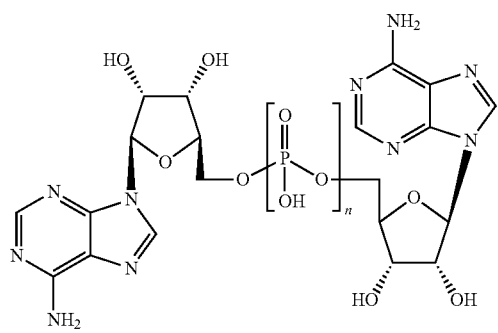
70a n = n = 3 Ap₃A
70b n = n = 4 Ap₄A
70c n = n = 5 Ap₅A
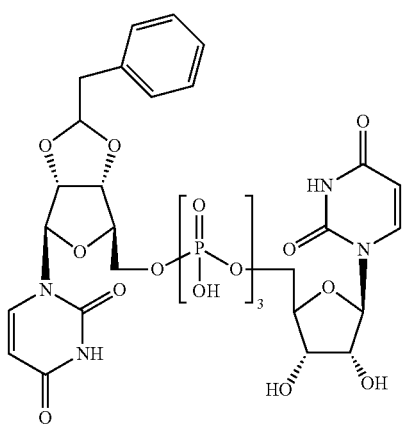
71 INS48823
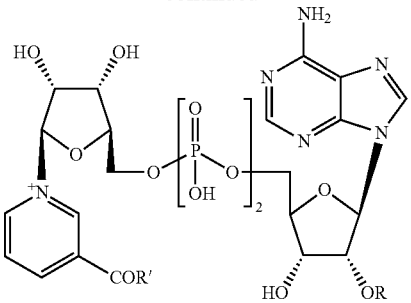
72 R = H, R' = NH₂ -NAD⁺
73 R = PO₃H₂, R' = OH NAADP⁺
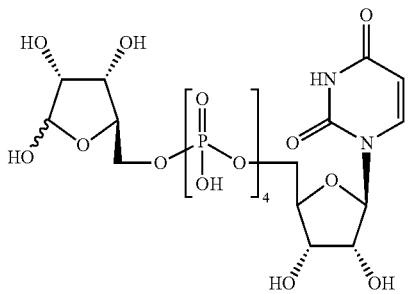
74
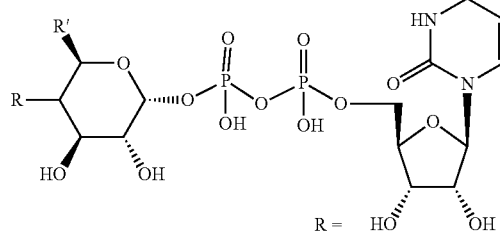
75 R = HO⋯ R' = COOH
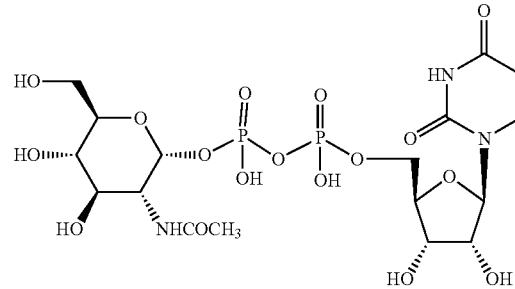
77
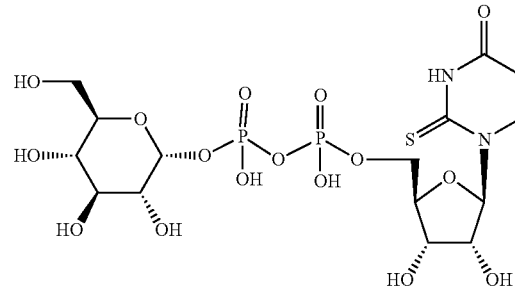
78 MRS2690 or a pharmaceutically acceptable salt, free acid, an analogue, a regioisomer, a stereoisomer or a tautomer thereof.

In one embodiment, the purinergic receptor agonist (e.g., P2Y receptor agonist, such as P2Y2, P2Y4 or P2Y6 agonist) is a compound represented by the following structural formula, or a pharmaceutically acceptable salt, free acid, an analogue, a regioisomer, a stereoisomer or a tautomer thereof:

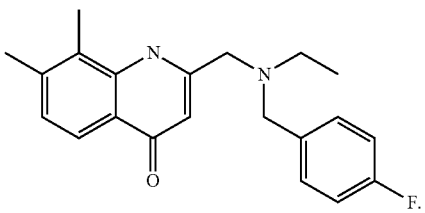 [SMILES: CCN(Cc1ccc(F)cc1)Cc1cc(=O)c2ccc(C)c(C)c2[nH]1]

In one embodiment, the purinergic receptor agonist (e.g., P2Y receptor agonist, such as P2Y2, P2Y4 or P2Y6 agonist) is selected from ATP disodium salt ATPγS tetralithium salt, BzATP triethylammonium salt, α,β-Methyleneadenosine 5'-triphosphate trisodium salt, 2-Methylthioadenosine diphosphate trisodium salt, 2-Methylthioadenosine triphosphate tetrasodium salt, MRS 2693 trisodium salt, MRS 2768 tetrasodium salt, MRS 2905,
MRS 2957 triethylammonium salt, MRS 4062 triethylammonium salt, NF 546, 5-OMe-UDP trisodium salt, PSB 0474, 2-ThioUTP tetrasodium salt, and UTPγS trisodium salt.

In some embodiments, the purinergic receptor agonist (e.g., P2Y receptor agonist, such as P2Y2, P2Y4 or P2Y6 agonist) is selected from the group consisting of ATP, adenosine, cytidine, inosine, uridine, guanosine, AMP, CMP, IMP, GMP, cAMP, UMP, ADP, GDP, CDP, IDP, UDP, CTP, GTP, ITP, UTP and cGMP. In some embodiments, the purinergic receptor agonist (e.g., P2Y receptor agonist, such as P2Y2, P2Y4 or P2Y6 agonist) is selected from the group consisting of ATP, adenosine, AMP, UMP, ADP, GDP, IDP, UDP, CTP, GTP, ITP and UTP.

IV. STING Agonists

STING is an adaptor protein anchored in the ER. In its basal state, STING exists as a dimer, with its C-terminal domain residing in the cytosol; however, in the presence of cytosolic DNA (typically due to viral, bacterial, or parasitic infections) STING undergoes conformational changes and transits from the ER through the Golgi to perinuclear endosomes. Consequently, STING recruits TANK-binding kinase 1 (TBK1), which phosphorylates STING, rendering it more accessible for the binding of the transcription factor IFN-regulatory factor 3 (IRF3). TBK1 then phosphorylates IRF3, which translocates to the nucleus to drive transcription of interferon-0 (IFN-0) and other innate immune genes. Bacterial cyclic-dinucleotides (CDNs) are natural ligands of STING and link the presence of cytosolic DNA to the activation of STING. For example, bacteria and mammalian cells generate CDNs via the DNA sensor cyclic GMP-AMP synthase (cGAS/MB21D1), which catalyzes the synthesis of cyclic GMP-AMP (cGAMP) from GTP and ATP upon DNA binding. Cells from cGAS-deficient mice were unable to produce type I IFNs in response to cytosolic DNA. Upon DNA exposure within the cytosol, cGAS is the major receptor that directly binds DNA, leading to cGAMP pro-duction, which in turn engages STING to trigger the remaining signaling events that drive IFN-β expression. STING pathway activation within antigen presenting cells (APCs) in the tumor microenvironment leads to production of IFN-β and the spontaneous generation of antitumor CD8+ T cell responses, allowing for control of the growth of several transplantable tumor cell models. See Corrales et al., 2016, J Clin. Invest. 126(7): 2404-2411.

The term "STING agonist" as used herein refers to any chemical entity, including but not limited to a small molecule, a nucleoside, a nucleotide, a nucleobase, a sugar, a nucleic acid, an amino acid, a polysaccharide, a peptide, a polypeptide, a protein, an antibody, an aptamer (e.g., DNA/RNA/XNA/peptide aptamers) or a complex comprising any combination of the aforementioned chemical entities, that activates the STING pathway. In some embodiments, the STING agonist interacts directly with the STING protein. In some embodiments, the STING agonist interacts with a component of the STING pathway, for example, GMP-AMP synthase, TBK1, IRF3 or IFN-β. In some embodiments, the STING agonist increases the level or activity of one or more components of the STING pathway, for example, STING, GMP-AMP synthase, TBK1, IRF3 and/or IFN-β. In a particular embodiment, the STING agonist increases the level or activity of IRF3.

A chemical entity may be identified as a STING agonist, for example, by treating a cell with the chemical entity and measuring IRF3 activity. For example, an IRF reporter cell such as THP1-Dual™ cells (InvivoGen) may used to identify STING agonists. THP1-Dual™ ells are human THP1 monocytes that have been engineered to contain an inducible IRF reporter construct. IRF activity is measured in these cells by assessing the activity of a secreted luciferase. An increase in IRF activity in cells treated with the chemical entity would indicate that the compound is a STING agonist.

A chemical entity may also be identified as a STING agonist by treating a cell with the chemical entity and measuring IFN-β expression and/or activity. For example, antigen presenting cells (APCs), PBMCs, dendritic cells or the THP1-Dual™ cells described above may be treated with the chemical entity and IFN-β expression measured by methods known in the art, such as ELISA. An IFN-β reporter cell line such as B16-Blue IFN reporter cells (InvivoGen) may also be used to measure IFN-β expression in response to treatment with the chemical entity. For the reporter cell line, IFN-β expression may be measured by adding the substrate QUANTI-Blue (InvivoGen) and measuring color intensity using a spectrophotometer at 620-655 nm. See Woo et al., 2014, Immunity 41(5): 830-842, which is incorporated by reference herein in its entirety. An increase in IFN-β expression and/or activity in the cells treated with the chemical entity would indicate that the compound is a STING agonist.

Another method for identifying a chemical entity as a STING agonist is through a HepAD38-derived reporter cell line that expresses firefly luciferase in response to the activation of the cyclic GMP-AMP synthase (cGAS)-STING pathway. The reporter cells are treated with the chemical entity and the luciferase signal produced by the cells is measured several hours after treatment. See Liu et al., 2017, Antiviral Research 147: 37-46, which is incorporated by reference herein in its entirety. An increase in luciferase activity in the reporter cells treated with the chemical entity would indicate that the compound is a STING agonist.

In one embodiment, the STING agonist is a small molecule compound as defined herein. Examples of small molecule STING agonists are described in U.S. Pat. Nos. 9,724,408; 10,011,630; 10,045,961; and 10,106,574; International Patent Application Publication Nos. WO2014/189805, WO 2013/185052, WO 2017/075477, WO 2018/198076, WO 2014/093936, WO 2018/009466, WO 2016/145102, WO 2016/096577, WO2017/027645, WO 2017/027646, WO 2018/100558, WO 2018/098203, WO 2018/067423, WO 2018/118665, WO2018/118664, WO 2018/234808, WO 2018/234807, WO 2018/234805, WO2019/069275, WO2019/051489, WO2019/046511, WO2019/027858, WO 2019/027857, WO 2018/208667, WO 2017/100305 and WO 2018/200812 (STING agonists can be conjugated to antibodies), WO 2018/172206, WO 2018/138685, WO 2018/138684, WO 2018/045204, WO 2017/180769, Ramanjulu et al., 2018, Nature 564(7736):439-443, and Corrales et al., 2016, J Clin. Invest. 126(7): 2404-2411, each of which is incorporated by reference herein in its entirety.

In some embodiments, the STING agonist is a cyclic dinucleotide (CDN). Suitable cyclic dinucleotides include, but are not limited to, cGAMP, 2'3'-cGAMP, 3'3'-cGAMP, 3'3'-cGAMP-F, c-di-GMP, c-di-GMP-F, Rp/Sp, MK-1454, ADU-S100 (also known as ML-RR-S2 CDA or MIW815), and Disodium dithio-(RP, RP)-[cyclic [A(2',5')pA(3',5')p]] [Rp,Rp]-Cyclic(adenosine-(2',5') monophosphorothioateadenosine-(3',5')-monophosphorothioate) (also known as disodium ADU-S100) the structures of some of which are shown below:

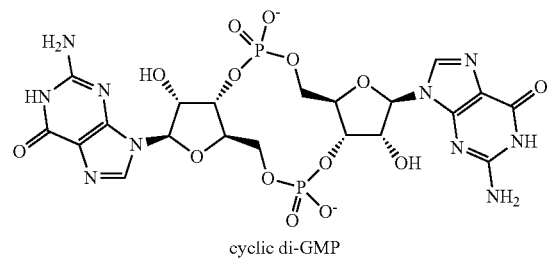
cyclic di-GMP

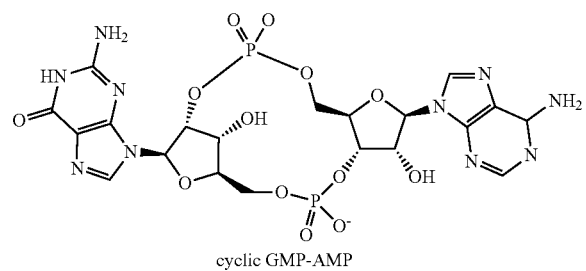
cyclic GMP-AMP

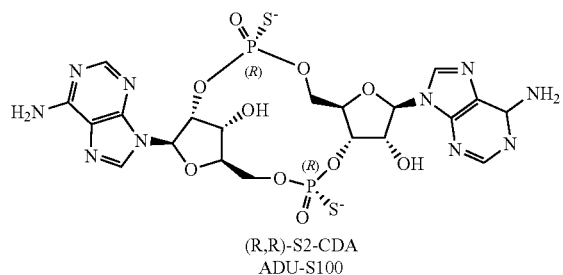
(R,R)-S2-CDA
ADU-S100

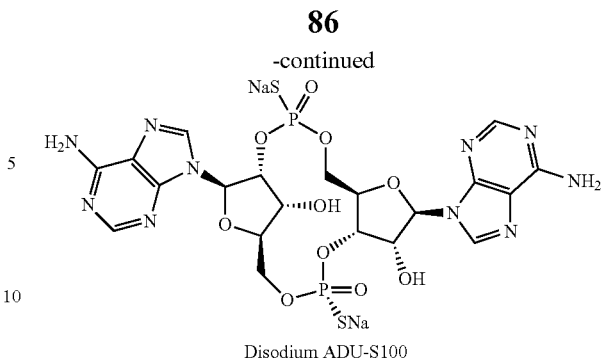
Disodium ADU-S100

In one embodiment, the STING agonist is a CDN compound represented by the following structural formula:

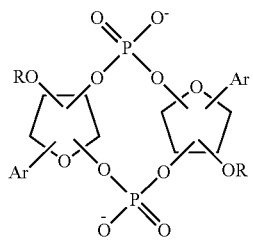

or a pharmaceutically acceptable salt, a free acid, a regioisomer, a stereoisomer or a tautomer thereof wherein Ar, for each instance, is independently optionally substituted monocyclic or bicyclic heteroaryl having at least one nitrogen atom (e.g., 1, 2, 3 or 4) and optionally one or more heteroatoms selected from O and S; wherein R, for each instance, is independently hydrogen or an optionally substituted $C_1$-$C_4$ alkyl; wherein each oxygen atom in the two phosphate groups and the OR groups is optionally and independently substituted with S; wherein each OR group and each O⁻ is optionally substituted with a halogen (e.g., F, Cl). In one embodiment, each Ar is independently selected from the group consisting of

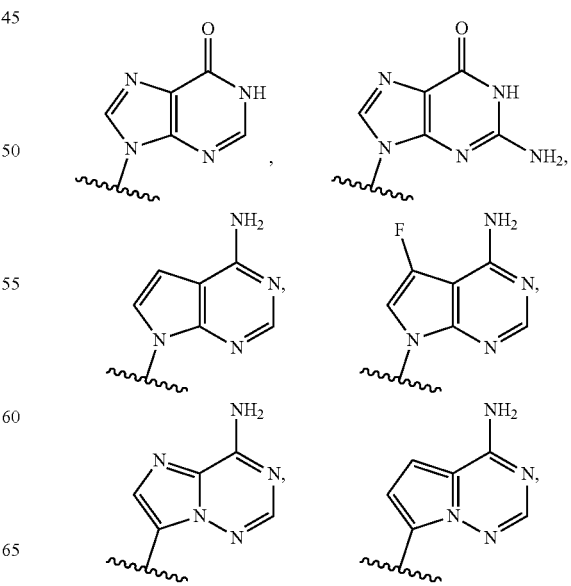

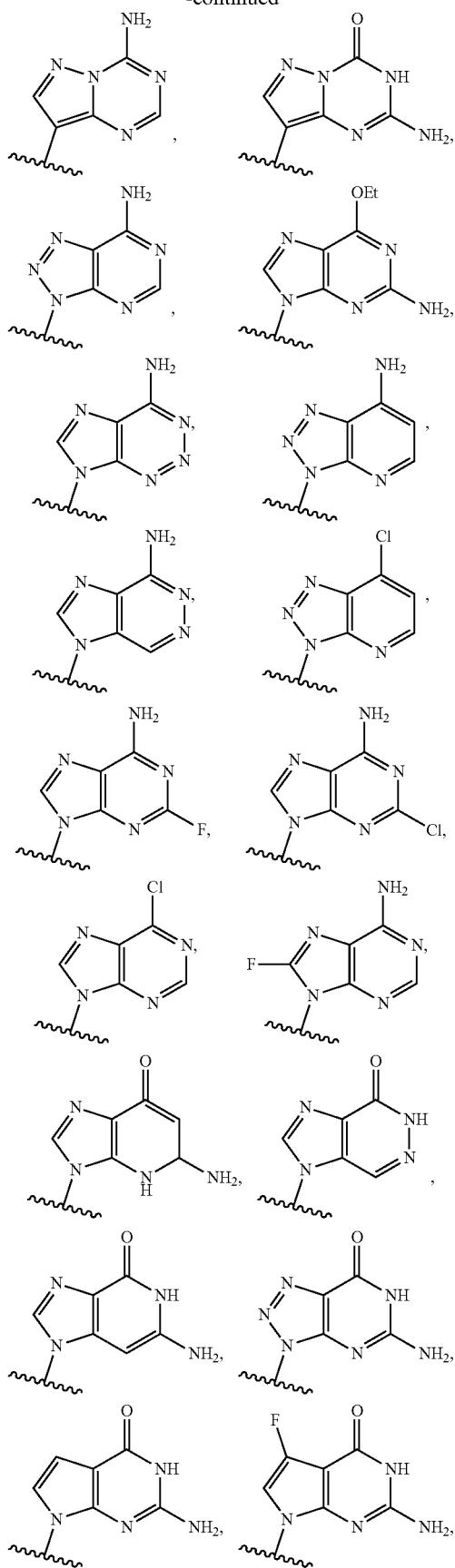
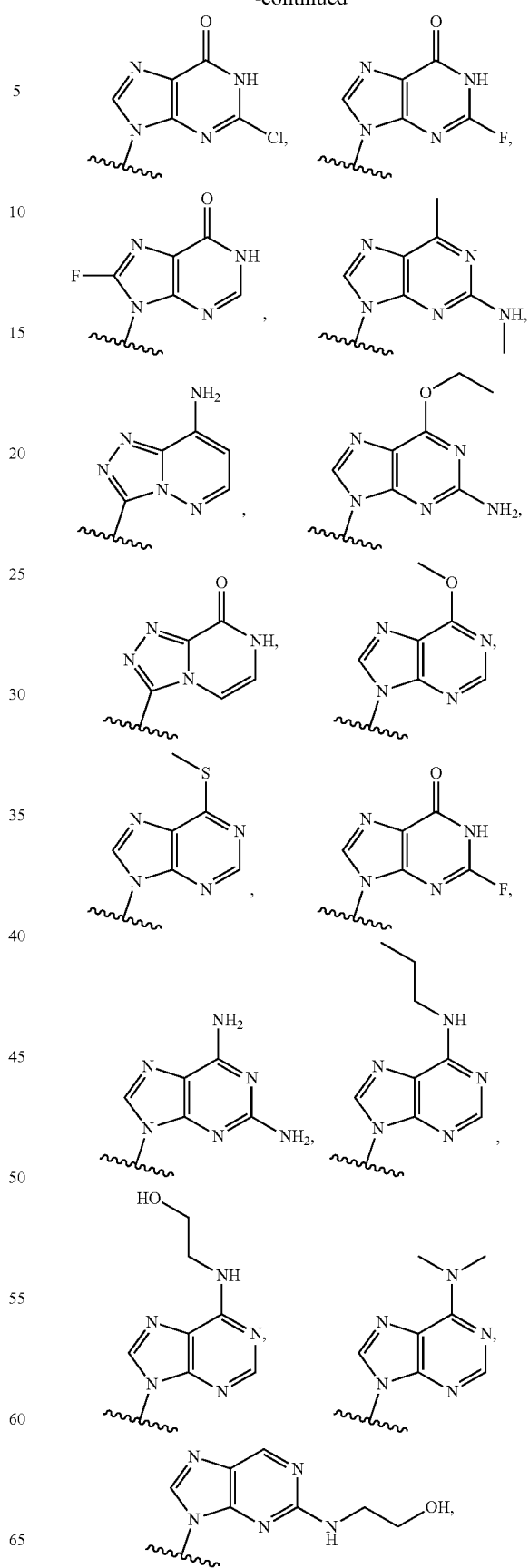

-continued

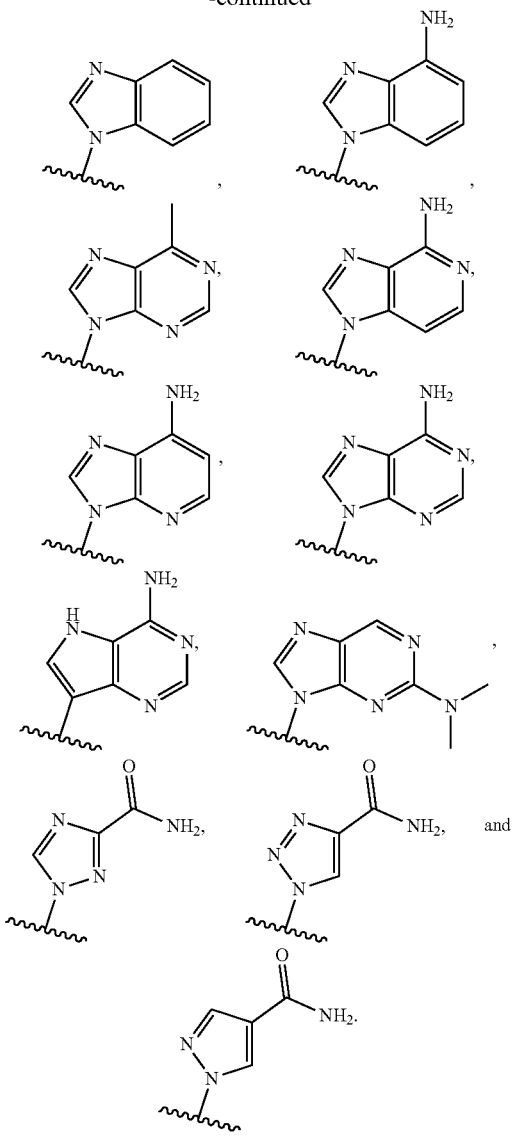

ADU-S100 (ML RR-S2 CDA) is a rationally designed synthetic CDN STING agonist and exhibits enhanced stability, human STING activation, cellular uptake, and antitumor efficacy, as well as low reactogenicity compared with the natural STING ligands produced by bacteria or host cell cGAS. See Corrales et al., 2015, Cell Reports 11(7): 1018-1030. To increase affinity for human STING, ADU-S100 (ML RR-S2 CDA) contains a noncanonical structure defined by a phosphate bridge with one 2'-5' and one 3'-5' mixed phosphodiester linkages (2',3' CDNs). The 2',3' mixed linkage structure confers increased STING binding affinity and is also found in endogenous cGAMP produced by eukaryotic cGAS. ADU-S100 (ML RR-S2 CDA) was shown to broadly activate all known human STING alleles in a HEK293T cellular STING signaling assay and induced dose-dependent expression of IFN-β in human peripheral blood monocytes (PBMCs) isolated from multiple donors with different STING genotypes. ADU-S100 (ML RR-S2 CDA) was evaluated in multiple syngeneic mouse tumor models, including B16.F10 melanoma, 4T1 mammary carcinoma, and CT26 colon carcinoma, and demonstrated a potent antitumor immune response and significant tumor regression in each model. ADU-S100 activates all known human and mouse STINGs, and effectively induces the expression of cytokines and chemokines, leading to a robust and durable antigen-specific T-cell mediated immune response against cancer cells. See Corrales et al., 2015, Cell Reports 11(7): 1018-1030.

In some embodiments, the STING agonist is a flavonoid. Suitable flavonoids include, but are not limited to, 10-(carboxymethyl)-9(10H)acridone (CMA), 5,6-Dimethylxanthenone-4-acetic acid (DMXAA) or vadimezan, methoxyvone, 6, 4'-dimethoxyflavone, 4'-methoxyflavone, 3', 6'-dihydroxyflavone, 7, 2'-dihydroxyflavone, daidzein, formononetin, retusin 7-methyl ether, xanthone, or any combination thereof. In certain embodiments, the STING agonist is not DMXAA.

In some embodiments, the STING agonist is a flavonoid and comprises one of the following basic ring structures, where further substitutions on any position of any ring, further ring fusions, and alternative stereochemistry are permissible:

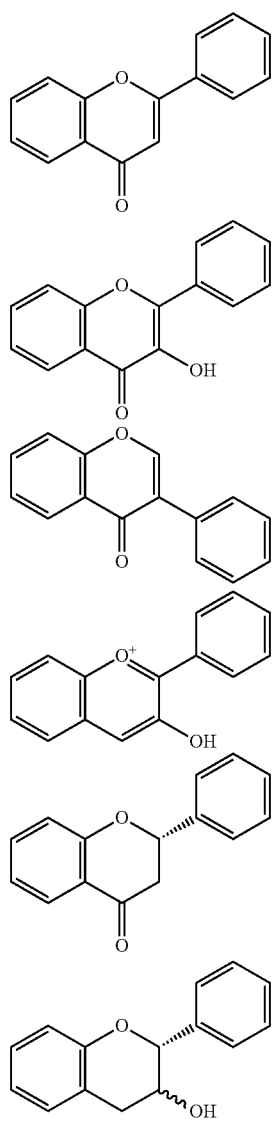

In some embodiments, the STING agonist is an amidobenzimidazole compound or a dimeric amidobenzimidazole compound. Amidobenzimidazole-based compounds exhibit enhanced binding to STING and strong anti-tumour activity. See Ramanjulu et al., 2018, Nature 564(7736):439-443, which is incorporated by reference herein in its entirety.

In one embodiment, the STING agonist is a dimeric compound represented by the following structural formula:

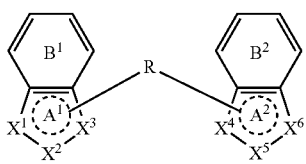

or a pharmaceutically acceptable salt, a free acid, a regioisomer, a stereoisomer or a tautomer thereof wherein one or two of $X^1$, $X^2$ and $X^3$ is/are nitrogen while the other(s) is/are carbon; wherein one or two of $X^4$, $X^5$ and $X^6$ is/are nitrogen while the other(s) is/are carbon; wherein R is an optionally substituted $C_1$-$C_6$ alkyl, $C_2$-$C_6$ alkenyl or $C_2$-$C_6$ alkynyl covalently linked to ring $A^1$ and ring $A^2$; each of rings $A^1$, $A^2$, $B^1$ and $B^2$ is optionally substituted. In one embodiment, each of rings $B^1$ and $B^2$ is substituted with an amido group or an alkyl substituted with an amido group. In one embodiment, the STING agonist is a dimeric amidobenzimidazole compound represented by one of the following formulas:

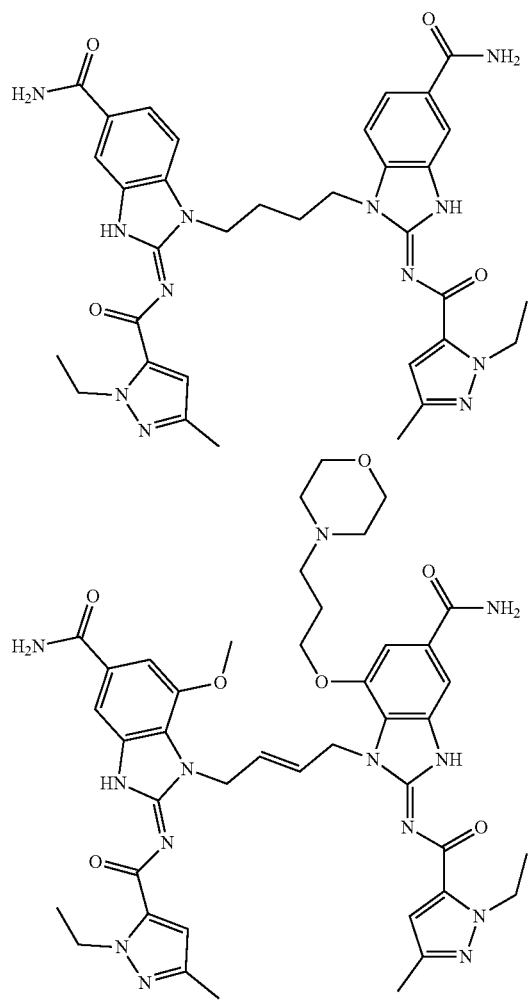

or a pharmaceutically acceptable salt, a free acid, a regioisomer, a stereoisomer or a tautomer thereof.

In some embodiments, the STING agonist is DNA. Suitable types of DNA include, but are not limited to, viral DNA, bacterial DNA, and double-stranded DNA. Because DNA binding to GMIP-AMP synthase catalyzes the synthesis of cGAMP, which in turn engages STING to trigger the remaining signaling events that drive IFN-β expression, DNA may be used as a STING agonist to induce production of cGAMP and activation of the STING pathway.

In some embodiments, the STING agonist increases the level or activity of a type I interferon (IFN), e.g. IFN-β or interferon-α (IFN-α). Activation of the transcription factor IRF3 in the STING pathway leads to increased expression of type I IFNs. Type I IFNs can act at several levels within the generation of an adaptive T cell response, promoting cross-priming of antigens by APCs and their migration to lymph nodes, thereby enhancing the effector functions of cytotoxic T-lymphocytes (CTLs) and supporting the survival of memory CTLs. See Zitvogel et al., 2015, Nat. Rev. Immunol. 15(7): 405-414.

V. Methods of Increasing Immune Activity

In certain aspects, the postcellular signaling factors described herein may be used to increase immune activity in a cell, tissue or in a subject, for example, a subject who would benefit from increased immune activity. In some aspects, the disclosure relates to a method of increasing immune activity in a target cell, the method comprising contacting the target cell with a composition comprising one or more postcellular signaling factors produced by cells exposed to a stress condition, wherein the composition is administered in an amount sufficient to increase the immune activity relative to a cell that is not treated with the composition.

In some aspects, the disclosure relates to a method of increasing immune activity in a target tissue, the method comprising administering to the target tissue a composition comprising one or more postcellular signaling factors produced by cells exposed to a stress condition, wherein the composition is administered in an amount sufficient to increase the immune activity relative to a tissue that is not treated with the composition.

In some aspects, the disclosure relates to a method of increasing immune activity in a subject, the method comprising administering to the subject a composition comprising one or more postcellular signaling factors produced by cells exposed to a stress condition, wherein the composition is administered in an amount sufficient to increase the immune activity relative to a subject that is not treated with the composition. In one embodiment, the subject is in need of an increased immune activity.

The combinations of a STING agonist and a purinergic receptor agonist described herein may be used to increase immune activity in a cell, tissue or in a subject, for example, a subject who would benefit from increased immune activity. In some aspects, the disclosure relates to a method of increasing immune activity in a target cell, the method comprising contacting the target cell with a combination of a STING agonist and a purinergic receptor agonist, wherein the STING agonist and the purinergic receptor agonist are administered in an amount sufficient to increase the immune activity relative to a cell that is not treated with the STING agonist and/or the purinergic receptor agonist.

In some aspects, the disclosure relates to a method of increasing immune activity in a cell, the method comprising administering to the cell, in combination, a STING agonist and a purinergic receptor agonist (e.g., P2Y receptor agonist, such as P2Y2, P2Y4 or P2Y6 agonist), wherein the STING agonist and purinergic receptor agonist are administered in an amount sufficient to increase the immune activity relative to a cell that is not treated with the STING agonist and/or the purinergic receptor agonist.

In some aspects, the disclosure relates to a method of increasing immune activity in a target tissue, the method comprising administering to the target tissue, in combination, a STING agonist and a purinergic receptor agonist (e.g., P2Y receptor agonist, such as P2Y2, P2Y4 or P2Y6 agonist), wherein the STING agonist and purinergic receptor agonist are administered in an amount sufficient to increase the immune activity relative to a tissue that is not treated with the STING agonist and/or the purinergic receptor agonist.

In some aspects, the disclosure relates to a method of increasing immune activity in a subject, the method comprising administering to the subject, in combination, a STING agonist and a purinergic receptor agonist (e.g., P2Y receptor agonist, such as P2Y2, P2Y4 or P2Y6 agonist), wherein the STING agonist and the purinergic receptor agonist are administered in an amount sufficient to increase the immune activity relative to a subject that is not treated with the STING agonist and/or the purinergic receptor agonist. In one embodiment, the subject is in need of an increased immune activity.

According to some methods of the disclosure, immune activity may be regulated by interaction of the postcellular signaling factors with a broad range of immune cells, including, for example, any one or more of mast cells, Natural Killer (NK) cells, basophils, neutrophils, monocytes, macrophages, dendritic cells, eosinophils, lymphocytes (e.g. B-lymphocytes (B-cells)), and T-lymphocytes (T-cells)).

According to some methods of the disclosure, immune activity may be regulated by interaction of the STING agonist and the purinergic receptor agonist with a broad range of immune cells, including, for example, any one or more of mast cells, Natural Killer (NK) cells, basophils, neutrophils, monocytes, macrophages, dendritic cells, eosinophils, lymphocytes (e.g. B-lymphocytes (B-cells)), and T-lymphocytes (T-cells)).

Types of Immune Cells

Mast cells are a type of granulocyte containing granules rich in histamine and heparin, an anti-coagulant. When activated, a mast cell releases inflammatory compounds from the granules into the local microenvironment. Mast cells play a role in allergy, anaphylaxis, wound healing, angiogenesis, immune tolerance, defense against pathogens, and blood-brain barrier function.

Natural Killer (NK) cells are cytotoxic lymphocytes that lyse certain tumor and virus infected cells without any prior stimulation or immunization. NK cells are also potent producers of various cytokines, e.g. IFN-gamma (IFNγ), TNF-alpha (TNFα), GM-CSF and IL-3. Therefore, NK cells are also believed to function as regulatory cells in the immune system, influencing other cells and responses. In humans, NK cells are broadly defined as CD56+CD3− lymphocytes. The cytotoxic activity of NK cells is tightly controlled by a balance between the activating and inhibitory signals from receptors on the cell surface. A main group of receptors that inhibits NK cell activation are the inhibitory killer immunoglobulin-like receptors (KIRs). Upon recognition of self MHIC class I molecules on the target cells, these receptors deliver an inhibitory signal that stops the activating signaling cascade, keeping cells with normal MHC class I expression from NK cell lysis. Activating receptors include the natural cytotoxicity receptors (NCR) and NKG2D that push the balance towards cytolytic action through engagement with different ligands on the target cell surface. Thus, NK cell recognition of target cells is tightly regulated by processes involving the integration of signals delivered from multiple activating and inhibitory receptors.

Monocytes are bone marrow-derived mononuclear phagocyte cells that circulate in the blood for few hours/days before being recruited into tissues. See Wacleche et al., 2018, Viruses (10)2: 65. The expression of various chemokine receptors and cell adhesion molecules at their surface allows them to exit the bone marrow into the blood and to be subsequently recruited from the blood into tissues. Monocytes belong to the innate arm of the immune system providing responses against viral, bacterial, fungal or parasitic infections. Their functions include the killing of pathogens via phagocytosis, the production of reactive oxygen species (ROS), nitric oxide (NO), myeloperoxidase and inflammatory cytokines. Under specific conditions, monocytes can stimulate or inhibit T-cell responses during cancer as well as infectious and autoimmune diseases. They are also involved in tissue repair and neovascularization.

Macrophages engulf and digest substances such as cellular debris, foreign substances, microbes and cancer cells in a process called phagocytosis. Besides phagocytosis, macrophages play a critical role in nonspecific defense (innate immunity) and also help initiate specific defense mechanisms (adaptive immunity) by recruiting other immune cells such as lymphocytes. For example, macrophages are important as antigen presenters to T cells. Beyond increasing inflammation and stimulating the immune system, macrophages also play an important anti-inflammatory role and can decrease immune reactions through the release of cytokines. Macrophages that encourage inflammation are called M1 macrophages, whereas those that decrease inflammation and encourage tissue repair are called M2 macrophages.

Dendritic cells (DCs) play a critical role in stimulating immune responses against pathogens and maintaining immune homeostasis to harmless antigens. DCs represent a heterogeneous group of specialized antigen-sensing and antigen-presenting cells (APCs) that are essential for the induction and regulation of immune responses. In the peripheral blood, human DCs are characterized as cells lacking the T-cell (CD3, CD4, CD8), the B-cell (CD19, CD20) and the monocyte markers (CD14, CD16) but highly expressing HLA-DR and other DC lineage markers (e.g., CD1a, CD1c). See Murphy et al., Janeway's Immunobiology. 8th ed. Garland Science; New York, N.Y., USA: 2012. 868p.

The term "lymphocyte" refers to a small white blood cell formed in lymphatic tissue throughout the body and in normal adults making up about 22-28% of the total number of leukocytes in the circulating blood that plays a large role in defending the body against disease. Individual lymphocytes are specialized in that they are committed to respond to a limited set of structurally related antigens through recombination of their genetic material (e.g. to create a T cell receptor and a B cell receptor). This commitment, which exists before the first contact of the immune system with a given antigen, is expressed by the presence of receptors specific for determinants (epitopes) on the antigen on the lymphocyte's surface membrane. Each lymphocyte possesses a unique population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions. (Paul, W. E., "Chapter 1: The immune system: an introduction," Fundamental Immunology, 4th Edition, Ed. Paul, W. E., Lippicott-Raven Publishers, Philadelphia, (1999), at p. 102).

Lymphocytes include B-lymphocytes (B-cells), which are precursors of antibody-secreting cells, and T-lymphocytes (T-cells).

B-Lymphocytes (B-cells)

B-lymphocytes are derived from hematopoietic cells of the bone marrow. A mature B-cell can be activated with an antigen that expresses epitopes that are recognized by its cell surface. The activation process may be direct, dependent on cross-linkage of membrane Ig molecules by the antigen (cross-linkage-dependent B-cell activation), or indirect, via interaction with a helper T-cell, in a process referred to as cognate help. In many physiological situations, receptor cross-linkage stimuli and cognate help synergize to yield more vigorous B-cell responses (Paul, W. E., "Chapter 1: The immune system: an introduction," Fundamental Immunology, 4th Edition, Ed. Paul, W. E., Lippicott-Raven Publishers, Philadelphia, (1999)).

Cross-linkage dependent B-cell activation requires that the antigen express multiple copies of the epitope complementary to the binding site of the cell surface receptors, because each B-cell expresses Ig molecules with identical variable regions. Such a requirement is fulfilled by other antigens with repetitive epitopes, such as capsular polysaccharides of microorganisms or viral envelope proteins. Cross-linkage-dependent B-cell activation is a major protective immune response mounted against these microbes (Paul, W. E., "Chapter 1: The immune system: an introduction", Fundamental Immunology, 4th Edition, Ed. Paul, W. E., Lippicott-Raven Publishers, Philadelphia, (1999)).

Cognate help allows B-cells to mount responses against antigens that cannot cross-link receptors and, at the same time, provides costimulatory signals that rescue B cells from inactivation when they are stimulated by weak cross-linkage events. Cognate help is dependent on the binding of antigen by the B-cell's membrane immunoglobulin (Ig), the endocytosis of the antigen, and its fragmentation into peptides within the endosomal/lysosomal compartment of the cell. Some of the resultant peptides are loaded into a groove in a specialized set of cell surface proteins known as class II major histocompatibility complex (MHC) molecules. The resultant class II/peptide complexes are expressed on the cell surface and act as ligands for the antigen-specific receptors of a set of T-cells designated as $CD4^+$ T-cells. The $CD4^+$ T-cells bear receptors on their surface specific for the B-cell's class II/peptide complex. B-cell activation depends not only on the binding of the T cell through its T cell receptor (TCR), but this interaction also allows an activation ligand on the T-cell (CD40 ligand) to bind to its receptor on the B-cell (CD40) signaling B-cell activation. In addition, T helper cells secrete several cytokines that regulate the growth and differentiation of the stimulated B-cell by binding to cytokine receptors on the B cell (Paul, W. E., "Chapter 1: The immune system: an introduction, "Fundamental Immunology, 4th Edition, Ed. Paul, W. E., Lippicott-Raven Publishers, Philadelphia, (1999)).

During cognate help for antibody production, the CD40 ligand is transiently expressed on activated $CD4^+$ T helper cells, and it binds to CD40 on the antigen-specific B cells, thereby transducing a second costimulatory signal. The latter signal is essential for B cell growth and differentiation and for the generation of memory B cells by preventing apoptosis of germinal center B cells that have encountered antigen. Hyperexpression of the CD40 ligand in both B and T cells is implicated in pathogenic autoantibody production in human SLE patients (Desai-Mehta, A. et al., "Hyperexpression of CD40 ligand by B and T cells in human lupus and its role in pathogenic autoantibody production," J. Clin. Invest. Vol. 97(9), 2063-2073, (1996)).

T-Lymphocytes (T-cells)

T-lymphocytes derived from precursors in hematopoietic tissue, undergo differentiation in the thymus, and are then seeded to peripheral lymphoid tissue and to the recirculating pool of lymphocytes. T-lymphocytes or T cells mediate a wide range of immunologic functions. These include the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on T cell expression of specific cell surface molecules and the secretion of cytokines (Paul, W. E., "Chapter 1: The immune system: an introduction", Fundamental Immunology, 4th Edition, Ed. Paul, W. E., Lippicott-Raven Publishers, Philadelphia, (1999)).

T cells differ from B cells in their mechanism of antigen recognition. Immunoglobulin, the B cell's receptor, binds to individual epitopes on soluble molecules or on particulate surfaces. B-cell receptors see epitopes expressed on the surface of native molecules. While antibody and B-cell receptors evolved to bind to and to protect against microorganisms in extracellular fluids, T cells recognize antigens on the surface of other cells and mediate their functions by interacting with, and altering the behavior of these antigen-presenting cells (APCs). There are three main types of APCs in peripheral lymphoid organs that can activate T cells: dendritic cells, macrophages and B cells. The most potent of these are the dendritic cells, whose only function is to present foreign antigens to T cells. Immature dendritic cells are located in tissues throughout the body, including the skin, gut, and respiratory tract. When they encounter invading microbes at these sites, they endocytose the pathogens and their products, and carry them via the lymph to local lymph nodes or gut associated lymphoid organs. The encounter with a pathogen induces the dendritic cell to mature from an antigen-capturing cell to an APC that can activate T cells. APCs display three types of protein molecules on their surface that have a role in activating a T cell to become an effector cell: (1) MHC proteins, which present foreign antigen to the T cell receptor; (2) costimulatory proteins which bind to complementary receptors on the T cell surface; and (3) cell-cell adhesion molecules, which enable a T cell to bind to the APC for long enough to become activated ("Chapter 24: The adaptive immune system," Molecular Biology of the Cell, Alberts, B. et al., Garland Science, NY, (2002)).

T-cells are subdivided into two distinct classes based on the cell surface receptors they express. The majority of T cells express T cell receptors (TCR) consisting of α and β-chains. A small group of T cells express receptors made of γ and δ chains. Among the α/β T cells are two sub-lineages: those that express the coreceptor molecule CD4 ($CD4^+$ T cells); and those that express CD8 ($CD8^+$ T cells). These cells differ in how they recognize antigen and in their effector and regulatory functions.

$CD4^+$ T cells are the major regulatory cells of the immune system. Their regulatory function depends both on the expression of their cell-surface molecules, such as CD40 ligand whose expression is induced when the T cells are activated, and the wide array of cytokines they secrete when activated.

T cells also mediate important effector functions, some of which are determined by the patterns of cytokines they secrete. The cytokines can be directly toxic to target cells and can mobilize potent inflammatory mechanisms.

In addition, T cells, particularly CD8$^+$ T cells, can develop into cytotoxic T-lymphocytes (CTLs) capable of efficiently lysing target cells that express antigens recognized by the CTLs (Paul, W. E., "Chapter 1: The immune system: an introduction," Fundamental Immunology, 4th Edition, Ed. Paul, W. E., Lippicott-Raven Publishers, Philadelphia, (1999)).

T cell receptors (TCRs) recognize a complex consisting of a peptide derived by proteolysis of the antigen bound to a specialized groove of a class II or class I MHC protein. CD4$^+$ T cells recognize only peptide/class II complexes while CD8$^+$ T cells recognize peptide/class I complexes (Paul, W. E., "Chapter 1: The immune system: an introduction," Fundamental Immunology, 4th Edition, Ed. Paul, W. E., Lippicott-Raven Publishers, Philadelphia, (1999)).

The TCR's ligand (i.e., the peptide/MHC protein complex) is created within APCs. In general, class II MIC molecules bind peptides derived from proteins that have been taken up by the APC through an endocytic process. These peptide-loaded class II molecules are then expressed on the surface of the cell, where they are available to be bound by CD4$^+$ T cells with TCRs capable of recognizing the expressed cell surface complex. Thus, CD4$^+$ T cells are specialized to react with antigens derived from extracellular sources (Paul, W. E., "Chapter 1: The immune system: an introduction," Fundamental Immunology, 4th Edition, Ed. Paul, W. E., Lippicott-Raven Publishers, Philadelphia, (1999)).

In contrast, class I MHC molecules are mainly loaded with peptides derived from internally synthesized proteins, such as viral proteins. These peptides are produced from cytosolic proteins by proteolysis by the proteosome and are translocated into the rough endoplasmic reticulum. Such peptides, generally composed of nine amino acids in length, are bound into the class I MHC molecules and are brought to the cell surface, where they can be recognized by CD8$^+$ T cells expressing appropriate receptors. This gives the T cell system, particularly CD8$^+$ T cells, the ability to detect cells expressing proteins that are different from, or produced in much larger amounts than, those of cells of the remainder of the organism (e.g., viral antigens) or mutant antigens (such as active oncogene products), even if these proteins in their intact form are neither expressed on the cell surface nor secreted (Paul, W. E., "Chapter 1: The immune system: an introduction," Fundamental Immunology, 4th Edition, Ed. Paul, W. E., Lippicott-Raven Publishers, Philadelphia, (1999)).

T cells can also be classified based on their function as helper T cells; T cells involved in inducing cellular immunity; suppressor T cells; and cytotoxic T cells.

Helper T Cells

Helper T cells are T cells that stimulate B cells to make antibody responses to proteins and other T cell-dependent antigens. T cell-dependent antigens are immunogens in which individual epitopes appear only once or a limited number of times such that they are unable to cross-link the membrane immunoglobulin (Ig) of B cells or do so inefficiently. B cells bind the antigen through their membrane Ig, and the complex undergoes endocytosis. Within the endosomal and lysosomal compartments, the antigen is fragmented into peptides by proteolytic enzymes, and one or more of the generated peptides are loaded into class II MHC molecules, which traffic through this vesicular compartment. The resulting peptide/class II MHC complex is then exported to the B-cell surface membrane. T cells with receptors specific for the peptide/class II molecular complex recognize this complex on the B-cell surface. (Paul, W. E., "Chapter 1: The immune system: an introduction," Fundamental Immunology, 4th Edition, Ed. Paul, W. E., Lippicott-Raven Publishers, Philadelphia (1999)).

B-cell activation depends both on the binding of the T cell through its TCR and on the interaction of the T-cell CD40 ligand (CD40L) with CD40 on the B cell. T cells do not constitutively express CD40L. Rather, CD40L expression is induced as a result of an interaction with an APC that expresses both a cognate antigen recognized by the TCR of the T cell and CD80 or CD86. CD80/CD86 is generally expressed by activated, but not resting, B cells so that the helper interaction involving an activated B cell and a T cell can lead to efficient antibody production. In many cases, however, the initial induction of CD40L on T cells is dependent on their recognition of antigen on the surface of APCs that constitutively express CD80/86, such as dendritic cells. Such activated helper T cells can then efficiently interact with and help B cells. Cross-linkage of membrane Ig on the B cell, even if inefficient, may synergize with the CD40L/CD40 interaction to yield vigorous B-cell activation. The subsequent events in the B-cell response, including proliferation, Ig secretion, and class switching of the Ig class being expressed, either depend or are enhanced by the actions of T cell-derived cytokines (Paul, W. E., "Chapter 1: The immune system: an introduction," Fundamental Immunology, 4th Edition, Ed. Paul, W. E., Lippicott-Raven Publishers, Philadelphia, (1999)).

CD4$^+$ T cells tend to differentiate into cells that principally secrete the cytokines IL-4, IL-5, IL-6, and IL-10 ($T_H2$ cells) or into cells that mainly produce IL-2, IFN-γ, and lymphotoxin ($T_H1$ cells). The $T_H2$ cells are very effective in helping B-cells develop into antibody-producing cells, whereas the $T_H1$ cells are effective inducers of cellular immune responses, involving enhancement of microbicidal activity of monocytes and macrophages, and consequent increased efficiency in lysing microorganisms in intracellular vesicular compartments. Although CD4+ T cells with the phenotype of $T_H2$ cells (i.e., IL-4, IL-5, IL-6 and TL-10) are efficient helper cells, $T_H1$ cells also have the capacity to be helpers (Paul, W. E., "Chapter 1: The immune system: an introduction, "Fundamental Immunology, 4th Edition, Ed. Paul, W. E., Lippicott-Raven Publishers, Philadelphia, (1999)).

T Cell Involvement in Cellular Immunity Induction

T cells also may act to enhance the capacity of monocytes and macrophages to destroy intracellular microorganisms. In particular, interferon-gamma (IFN-γ) produced by helper T cells enhances several mechanisms through which mononuclear phagocytes destroy intracellular bacteria and parasitism including the generation of nitric oxide and induction of tumor necrosis factor (TNF) production. $T_H1$ cells are effective in enhancing the microbicidal action, because they produce IFN-γ. In contrast, two of the major cytokines produced by $T_H2$ cells, IL-4 and IL-10, block these activities (Paul, W. E., "Chapter 1: The immune system: an introduction," Fundamental Immunology, 4th Edition, Ed. Paul, W. E., Lippicott-Raven Publishers, Philadelphia, (1999)).

Regulatory T (Treg) Cells

Immune homeostasis is maintained by a controlled balance between initiation and downregulation of the immune response. The mechanisms of both apoptosis and T cell anergy (a tolerance mechanism in which the T cells are intrinsically functionally inactivated following an antigen encounter (Schwartz, R. H., "T cell anergy", Annu. Rev. Immunol., Vol. 21: 305-334 (2003)) contribute to the down-regulation of the immune response. A third mechanism is provided by active suppression of activated T cells by suppressor or regulatory CD4$^+$ T (Treg) cells (Reviewed in Kronenberg, M. et al., "Regulation of immunity by self-reactive T cells", Nature, Vol. 435: 598-604 (2005)). CD4$^+$ Tregs that constitutively express the IL-2 receptor alpha (IL-2R$\alpha$) chain (CD4$^+$ CD25$^+$) are a naturally occurring T cell subset that are anergic and suppressive (Taams, L. S. et al., "Human anergic/suppressive CD4$^+$CD25$^+$ T cells: a highly differentiated and apoptosis-prone population", Eur. J. Immunol. Vol. 31: 1122-1131 (2001)). Human CD4$^+$ CD25$^+$ Tregs, similar to their murine counterpart, are generated in the thymus and are characterized by the ability to suppress proliferation of responder T cells through a cell-cell contact-dependent mechanism, the inability to produce IL-2, and the anergic phenotype in vitro. Human CD4$^+$CD25$^+$ T cells can be split into suppressive (CD25$^{high}$) and nonsuppressive (CD25$^{low}$) cells, according to the level of CD25 expression. A member of the forkhead family of transcription factors, FOXP3, has been shown to be expressed in murine and human CD4$^+$CD25$^+$ Tregs and appears to be a master gene controlling CD4$^+$CD25$^+$ Treg development (Battaglia, M. et al., "Rapamycin promotes expansion of functional CD4$^+$CD25$^+$Foxp3$^+$ regulator T cells of both healthy subjects and type 1 diabetic patients", J. Immunol., Vol. 177: 8338-8347, (2006)). Accordingly, in some embodiments, an increase in immune response may be associated with a lack of activation or proliferation of regulatory T cells.

Cytotoxic T Lymphocytes

CD8$^+$ T cells that recognize peptides from proteins produced within the target cell have cytotoxic properties in that they lead to lysis of the target cells. The mechanism of CTL-induced lysis involves the production by the CTL of perforin, a molecule that can insert into the membrane of target cells and promote the lysis of that cell. Perforin-mediated lysis is enhanced by granzymes, a series of enzymes produced by activated CTLs. Many active CTLs also express large amounts of fas ligand on their surface. The interaction of fas ligand on the surface of CTL with fas on the surface of the target cell initiates apoptosis in the target cell, leading to the death of these cells. CTL-mediated lysis appears to be a major mechanism for the destruction of virally infected cells.

Lymphocyte Activation

The term "activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase C$\gamma$1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the APC.

T-Memory Cells

Following the recognition and eradication of pathogens through adaptive immune responses, the vast majority (90-95%) of T cells undergo apoptosis with the remaining cells forming a pool of memory T cells, designated central memory T cells (TCM), effector memory T cells (TEM), and resident memory T cells (TRM) (Clark, R. A., "Resident memory T cells in human health and disease", Sci. Transl. Med., 7, 269rv1, (2015)).

Compared to standard T cells, these memory T cells are long-lived with distinct phenotypes such as expression of specific surface markers, rapid production of different cytokine profiles, capability of direct effector cell function, and unique homing distribution patterns. Memory T cells exhibit quick reactions upon re-exposure to their respective antigens in order to eliminate the reinfection of the offender and thereby restore balance of the immune system rapidly. Increasing evidence substantiates that autoimmune memory T cells hinder most attempts to treat or cure autoimmune diseases (Clark, R. A., "Resident memory T cells in human health and disease", Sci. Transl. Med., Vol. 7, 269rv1, (2015)).

Increasing Immune Activity

In some embodiments, the postcellular signaling factors described herein may increase immune activity in a tissue or subject by increasing the level or activity of any one or more of the immune cells described herein, for example, macrophages, monocytes, dendritic cells, and CD4+, CD8+ or CD3+ cells (e.g. CD4+, CD8+ or CD3+ T cells) in the tissue or subject. For example, in one embodiment, the composition comprising postcellular signaling factors is administered in an amount sufficient to increase in the tissue or subject one or more of the level or activity of macrophages, the level or activity of monocytes, the level or activity of dendritic cells, the level or activity of T cells, and the level or activity of CD4+, CD8+ or CD3+ cells (e.g. CD4+, CD8+ or CD3+ T cells).

The postcellular signaling factors may also increase immune activity in a cell, tissue or subject by increasing the level or activity of a pro-immune cytokine. For example, in some embodiments, the composition comprising postcellular signaling factors is administered in an amount sufficient to increase in a cell, tissue or subject the level or activity of a pro-immune cytokine. In one embodiment, the pro-immune cytokine is selected from IFN-$\alpha$, IL-1, IL-12, IL-18, IL-2, IL-15, IL-4, IL-6, TNF-$\alpha$, IL-17 and GMCSF.

The postcellular signaling factors may also increase immune activity in a cell, tissue or subject by increasing the level or activity of positive regulators of the immune response such as nuclear factor kappa-light-chain-enhancer of activated B cells (NFkB), interferon regulatory factor (IRF), and stimulator of interferon genes (STING). For example, in some embodiments, the composition comprising postcellular signaling factors is administered in an amount sufficient to increase in a cell, tissue or subject the level or activity of NFkB, IRF and/or STING.

In some aspects, the disclosure relates to a method of increasing the level or activity of NFkB in a cell, tissue or subject, comprising administering to the cell, tissue or subject a composition comprising one or more postcellular signaling factors produced by cells exposed to a stress condition in an amount sufficient to increase the level or activity of NFkB relative to a cell, tissue or subject that is not treated with the composition.

In one embodiment, the subject is in need of an increased level or activity of NFkB.

In one embodiment, the level or activity of NFkB is increased by at least 10%, 20%, 30%, 40%, 50%, 60%, 70%, 80%, 90% or 100%, or by at least 2-fold, 4-fold, 6-fold, 8-fold, or 10-fold relative to a cell, tissue or subject that is not treated with the composition comprising one or more postcellular signaling factors produced by cells exposed to a stress condition.

In some aspects, the disclosure relates to a method of increasing the level or activity of IRF or STING in a cell, tissue or subject, comprising administering to the cell, tissue or subject a composition comprising one or more postcellular signaling factors produced by cells exposed to a stress condition in an amount sufficient to increase the level or activity of IRF or STING relative to a cell, tissue or subject that is not treated with the composition.

In one embodiment, the subject is in need of an increased level or activity of IRF or STING.

In one embodiment, the level or activity of IRF or STING is increased by at least 10%, 20%, 30%, 40%, 50%, 60%, 70%, 80%, 90% or 100%, or by at least 2-fold, 4-fold, 6-fold, 8-fold, or 10-fold relative to a cell, tissue or subject that is not treated with the composition comprising one or more posteellular signaling factors.

In some aspects, the disclosure relates to a method of increasing the level or activity of macrophages, monocytes, T cells and/or dendritic cells in a tissue or subject, comprising administering to the tissue or subject a composition comprising one or more postcellular signaling factors produced by cells exposed to a stress condition in an amount sufficient to increase the level or activity of macrophages, monocytes, T cells and/or dendritic cells relative to a tissue or subject that is not treated with the composition.

In one embodiment, the subject is in need of an increased level or activity of macrophages, monocytes or dendritic cells.

In one embodiment, the level or activity of macrophages, monocytes, T cells or dendritic cells is increased by at least 10%, 20%, 30%, 40%, 50%, 60%, 70%, 80%, 90% or 100%, or by at least 2-fold, 4-fold, 6-fold, 8-fold, or 10-fold relative to a tissue or subject that is not treated with the composition comprising one or more postcellular signaling factors.

In some aspects, the disclosure relates to a method of increasing the level or activity of CD4+, CD8+, or CD3+ cells in a tissue or subject, comprising administering to the subject a composition comprising one or more postcellular signaling factors produced by cells exposed to a stress condition in an amount sufficient to increase the level or activity of CD4+, CD8+, or CD3+ cells relative to a tissue or subject that is not treated with the composition.

In one embodiment, the subject is in need of an increased level or activity of CD4+, CD8+, or CD3+ cells.

In one embodiment, the level or activity of CD4+, CD8+, or CD3+ cells is increased by at least 10%, 20%, 30%, 40%, 50%, 60%, 70%, 80%, 90% or 100%, or by at least 2-fold, 4-fold, 6-fold, 8-fold, or 10-fold relative to a tissue or subject that is not treated with the composition comprising one or more postcellular signaling factors.

In some aspects, the disclosure relates to a method of increasing the level or activity of a pro-immune cytokine in a cell, tissue or subject, comprising administering to the cell, tissue or subject a composition comprising one or more postcellular signaling factors produced by cells exposed to a stress condition in an amount sufficient to increase the level or activity of the pro-immune cytokine relative to a cell, tissue or subject that is not treated with the composition.

In one embodiment, the subject is in need of an increased level or activity of a pro-immune cytokine.

In one embodiment, the level or activity of the pro-immune cytokine is increased by at least 10%, 20%, 30%, 40%, 50%, 60%, 70%, 80%, 90% or 100%, or by at least 2-fold, 4-fold, 6-fold, 8-fold, or 10-fold relative to a cell, tissue or subject that is not treated with the composition comprising one or more postcellular signaling factors.

In one embodiment, the pro-immune cytokine is selected from IFN-α, IL-1, IL-12, IL-18, IL-2, IL-15, IL-4, IL-6, TNF-α, IL-17 and GMCSF.

In some embodiments, the methods of the invention further include, before administration of the composition comprising one or more postcellular signaling factors produced by cells exposed to a stress condition, evaluating the cell, tissue or subject for one or more of the level or activity of NFkB; the level or activity of macrophages; the level or activity of monocytes; the level or activity of dendritic cells; the level or activity of CD4+ cells, CD8+ cells, or CD3+ cells; the level or activity of T cells; and the level or activity of a pro-immune cytokine.

In one embodiment, the methods of the invention further include, after administration of the composition comprising one or more postcellular signaling factors produced by cells exposed to a stress condition, evaluating the cell, tissue or subject for one or more of the level or activity of NFkB, IRF or STING; the level or activity of macrophages; the level or activity of monocytes; the level or activity of dendritic cells; the level or activity of CD4+ cells, CD8+ cells or CD3+ cells; the level or activity of T cells; and the level or activity of a pro-immune cytokine.

Methods of measuring the level or activity of NFkB, IRF or STING; the level or activity of macrophages; the level or activity of monocytes; the level or activity of dendritic cells; the level or activity of CD4+ cells, CD8+ cells or CD3+ cells; the level or activity of T cells; and the level or activity of a pro-immune cytokine are known in the art.

For example, the protein level or activity of NFkB, IRF or STING may be measured by suitable techniques known in the art including ELISA, Western blot or in situ hybridization. The level of a nucleic acid (e.g. an mRNA) encoding NFkB, IRF or STING may be measured using suitable techniques known in the art including polymerase chain reaction (PCR) amplification reaction, reverse-transcriptase PCR analysis, quantitative real-time PCR, single-strand conformation polymorphism analysis (SSCP), mismatch cleavage detection, heteroduplex analysis, Northern blot analysis, in situ hybridization, array analysis, deoxyribonucleic acid sequencing, restriction fragment length polymorphism analysis, and combinations or sub-combinations thereof.

Methods for measuring the level and activity of macrophages are described, for example, in Chitu et al., 2011, Curr Protoc Immunol 14: 1-33. The level and activity of monocytes may be measured by flow cytometry, as described, for example, in Henning et al., 2015, Journal of Immunological Methods 423: 78-84. The level and activity of dendritic cells may be measured by flow cytometry, as described, for example in Dixon et al., 2001, Infect Immun. 69(7): 4351-4357. Each of these references is incorporated by reference herein in its entirety.

The level or activity of T cells may be assessed using a human CD4+ T-cell-based proliferative assay. For example, cells are labeled with the fluorescent dye 5,6-carboxyfluorescein diacetate succinimidyl ester (CFSE). Those cells that proliferate show a reduction in CFSE fluorescence intensity, which is measured directly by flow cytometry. Alternatively, radioactive thymidine incorporation can be used to assess the rate of growth of the T cells.

In some embodiments, an increase in immune response may be associated with reduced activation of regulatory T cells (Tregs). Functional activity T regs may be assessed using an in vitro Treg suppression assay. Such an assay is described in Collinson and Vignali (Methods Mol Biol. 2011; 707: 21-37, incorporated by reference in its entirety herein).

The level or activity of a pro-immune cytokine may be quantified, for example, in CD8+ T cells. In embodiments, the pro-immune cytokine is selected from interferon alpha (IFN-α), interleukin-1 (IL-1), IL-12, IL-18, IL-2, IL-15, IL-4, IL-6, tumor necrosis factor alpha (TNF-α), IL-17, and granulocyte-macrophage colony-stimulating factor (GMCSF). Quantitation can be carried out using the ELISPOT (enzyme-linked immunospot) technique, that detects T cells that secrete a given cytokine (e.g. IFN-α) in response to an antigenic stimulation. T cells are cultured with antigen-presenting cells in wells which have been coated with, e.g., anti-IFN-α antibodies. The secreted IFN-α is captured by the coated antibody and then revealed with a second antibody coupled to a chromogenic substrate. Thus, locally secreted cytokine molecules form spots, with each spot corresponding to one IFN-α-secreting cell. The number of spots allows one to determine the frequency of IFN-α-secreting cells specific for a given antigen in the analyzed sample. The ELISPOT assay has also been described for the detection of TNF-α, interleukin-4 (IL-4), IL-6, IL-12, and GMCSF. In some embodiments, the combinations of a STING agonist and a purinergic receptor agonist described herein may increase immune activity in a tissue or subject by increasing the level or activity of any one or more of the immune cells described herein, for example, macrophages, monocytes, dendritic cells, and CD4+, CD8+ or CD3+ cells (e.g. CD4+, CD8+ or CD3+ T cells) in the tissue or subject. For example, in one embodiment, the STING agonist and the purinergic receptor agonist are administered in an amount sufficient to increase in the tissue or subject one or more of the level or activity of macrophages, the level or activity of monocytes, the level or activity of dendritic cells, the level or activity of T cells, and the level or activity of CD4+, CD8+ or CD3+ cells (e.g. CD4+, CD8+ or CD3+ T cells).

The combination of the STING agonist and the purinergic receptor agonist may also increase immune activity in a cell, tissue or subject by increasing the level or activity of a pro-immune cytokine. For example, in some embodiments, the STING agonist and the purinergic receptor agonist are administered in an amount sufficient to increase in a cell, tissue or subject the level or activity of a pro-immune cytokine. In one embodiment, the pro-immune cytokine is selected from IFN-α, IL-1, IL-12, IL-18, IL-2, IL-15, IL-4, IL-6, TNF-α, IL-17 and GMCSF.

The combination of the STING agonist and the purinergic receptor agonist may also increase immune activity in a cell, tissue or subject by increasing the level or activity of positive regulators of the immune response such as nuclear factor kappa-light-chain-enhancer of activated B cells (NFkB), interferon regulatory factor (IRF), and stimulator of interferon genes (STING). For example, in some embodiments, the STING agonist and the purinergic receptor agonist are administered in an amount sufficient to increase in a cell, tissue or subject the level or activity of NFkB, IRF and/or STING.

In some aspects, the disclosure relates to a method of increasing the level or activity of NFkB in a cell, tissue or subject, comprising administering to the cell, tissue or subject, in combination, a STING agonist and a purinergic receptor agonist (e.g., P2Y receptor agonist, such as P2Y2, P2Y4 or P2Y6 agonist) in an amount sufficient to increase the level or activity of NFkB relative to a cell, tissue or subject that is not treated with the STING agonist and/or the purinergic receptor agonist.

In one embodiment, the subject is in need of an increased level or activity of NFkB.

In one embodiment, the level or activity of NFkB is increased by at least 10%, 20%, 30%, 40%, 50%, 60%, 70%, 80%, 90% or 100%, or by at least 2-fold, 4-fold, 6-fold, 8-fold, or 10-fold relative to a cell, tissue or subject that is not treated with the STING agonist and/or the purinergic receptor agonist.

In some aspects, the disclosure relates to a method of increasing the level or activity of IRF or STING in a cell, tissue or subject, comprising administering to the cell, tissue or subject, in combination, a STING agonist and a purinergic receptor agonist (e.g., P2Y receptor agonist, such as P2Y2, P2Y4 or P2Y6 agonist) in an amount sufficient to increase the level or activity of IRF or STING relative to a cell, tissue or subject that is not treated with the STING agonist and/or the purinergic receptor agonist.

In one embodiment, the subject is in need of an increased level or activity of IRF or STING.

In one embodiment, the level or activity of IRF or STING is increased by at least 10%, 20%, 30%, 40%, 50%, 60%, 70%, 80%, 90% or 100%, or by at least 2-fold, 4-fold, 6-fold, 8-fold, or 10-fold relative to a cell, tissue or subject that is not treated with the STING agonist and/or the purinergic receptor agonist.

In some aspects, the disclosure relates to a method of increasing the level or activity of macrophages, monocytes, T cells and/or dendritic cells in a tissue or subject, comprising administering to the tissue or subject, in combination, STING agonist and a purinergic receptor agonist (e.g., P2Y receptor agonist, such as P2Y2, P2Y4 or P2Y6 agonist) in an amount sufficient to increase the level or activity of macrophages, monocytes, T cells and/or dendritic cells relative to a tissue or subject that is not treated with the STING agonist and/or the purinergic receptor agonist.

In one embodiment, the subject is in need of an increased level or activity of macrophages, monocytes or dendritic cells.

In one embodiment, the level or activity of macrophages, monocytes, T cells or dendritic cells is increased by at least 10%, 20%, 30%, 40%, 50%, 60%, 70%, 80%, 90% or 100%, or by at least 2-fold, 4-fold, 6-fold, 8-fold, or 10-fold relative to a tissue or subject that is not treated with the STING agonist and/or the purinergic receptor agonist.

In some aspects, the disclosure relates to a method of increasing the level or activity of CD4+, CD8+, or CD3+ cells in a tissue or subject, comprising administering to the subject, in combination, a STING agonist and apurinergic receptor agonist (e.g., P2Y receptor agonist, such as P2Y2, P2Y4 or P2Y6 agonist) in an amount sufficient to increase the level or activity of CD4+, CD8+, or CD3+ cells relative to a tissue or subject that is not treated with the STING agonist and/or the purinergic receptor agonist.

In one embodiment, the subject is in need of an increased level or activity of CD4+, CD8+, or CD3+ cells.

In one embodiment, the level or activity of CD4+, CD8+, or CD3+ cells is increased by at least 10%, 20%, 30%, 40%, 50%, 60%, 70%, 80%, 90% or 100%, or by at least 2-fold, 4-fold, 6-fold, 8-fold, or 10-fold relative to a tissue or subject that is not treated with the STING agonist and/or the purinergic receptor agonist.

In some aspects, the disclosure relates to a method of increasing the level or activity of a pro-immune cytokine in a cell, tissue or subject, comprising administering to the cell, tissue or subject, in combination, a STING agonist and a purinergic receptor agonist (e.g., P2Y receptor agonist, such as P2Y2, P2Y4 or P2Y6 agonist) in an amount sufficient to increase the level or activity of the pro-immune cytokine relative to a cell, tissue or subject that is not treated with the STING agonist and/or the purinergic receptor agonist.

In one embodiment, the subject is in need of an increased level or activity of a pro-immune cytokine.

In one embodiment, the level or activity of the pro-immune cytokine is increased by at least 10%, 20%, 30%, 40%, 50%, 60%, 70%, 80%, 90% or 100%, or by at least 2-fold, 4-fold, 6-fold, 8-fold, or 10-fold relative to a cell, tissue or subject that is not treated with the STING agonist and/or the purinergic receptor agonist.

In one embodiment, the pro-immune cytokine is selected from IFN-α, IL-1, IL-12, IL-18, IL-2, IL-15, IL-4, IL-6, TNF-α, IL-17 and GMCSF.

In some embodiments, the methods of the invention further include, before administration of the combination of the STING agonist and the purinergic receptor agonist, evaluating the cell, tissue or subject for one or more of the level or activity of NFkB; the level or activity of macrophages; the level or activity of monocytes; the level or activity of dendritic cells; the level or activity of CD4+ cells, CD8+ cells, or CD3+ cells; the level or activity of T cells; and the level or activity of a pro-immune cytokine.

In one embodiment, the methods of the invention further include, after administration of the combination of the STING agonist and the purinergic receptor agonist, evaluating the cell, tissue or subject for one or more of the level or activity of NFkB, IRF or STING; the level or activity of macrophages; the level or activity of monocytes; the level or activity of dendritic cells; the level or activity of CD4+ cells, CD8+ cells or CD3+ cells; the level or activity of T cells; and the level or activity of a pro-immune cytokine.

VI. Methods of Treating Disorders That Would Benefit from Increased Immune Activity Applicants have shown that treatment of target cells (e.g. immune cells) with postcellular signaling factors produced by cells exposed to a stress condition (e.g. nutrient deprivation) results in an increase in immune activity, as evidenced by increases in NFKB and IRF activity in immune cells. Accordingly, postcellular signaling factors that increase immune activity may be used in the treatment of disorders that may benefit from increased immune activity, such as cancer and infections.

Applicants have also shown that treatment of target cells (e.g. immune cells) with a combination of a STING agonist and a purinergic receptor agonist results in an increase in immune activity, as evidenced by increases in IRF activity in immune cells. Accordingly, combinations of a STING agonist and a purinergic receptor agonist (e.g., P2Y receptor agonist, such as P2Y2, P2Y4 or P2Y6 agonist) that increase immune activity may be used in the treatment of disorders that may benefit from increased immune activity, such as cancer and infections.

Infectious Diseases

As provided herein, postcellular signaling factors produced by cells exposed to a stress condition can activate immune cells (e.g., T cells, B cells, NK cells, etc.) and, therefore, can enhance immune cell functions such as inhibiting bacterial and/or viral infection, and/or restoring immune surveillance and immune memory function to treat infection. Accordingly, in some embodiments, the compositions of the invention, e.g., comprising postcellular signaling factors produced by cells exposed to a stress condition, are used to treat an infection or infectious disease in a subject, for example, a chronic infection.

As also provided herein, combinations of a STING agonist and a purinergic receptor agonist can activate immune cells (e.g., T cells, B cells, NK cells, etc.) and, therefore, can enhance immune cell functions such as inhibiting bacterial and/or viral infection, and/or restoring immune surveillance and immune memory function to treat infection. Accordingly, in some embodiments, the combinations of the STING agonist and the purinergic receptor agonist (e.g., P2Y receptor agonist, such as P2Y2, P2Y4 or P2Y6 agonist) are used to treat an infection or infectious disease in a subject, for example, a chronic infection.

As used herein, the term "infection" refers to any state in which cells or a tissue of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections including, but not limited to, viral infections, e.g., retrovirus, lentivirus, hepadna virus, herpes viruses, pox viruses, or human papilloma viruses; intracellular bacterial infections, e.g., *Mycobacterium, Chlamydophila, Ehrlichia, Rickettsia, Brucella, Legionella, Francisella, Listeria, Coxiella, Neisseria, Salmonella, Yersinia* sp, or *Helicobacter pylori*; and intracellular protozoan pathogens, e.g., *Plasmodium* sp, *Trypanosoma* sp., Giardia sp., *Toxoplasma* sp., or *Leishmania* sp.

Infectious diseases that can be treated using the compositions described herein include but are not limited to: HIV, Influenza, Herpes, Giardia, Malaria, *Leishmania*, pathogenic infection by the virus Hepatitis (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumonococci, meningococci and conococci, *klebsiella, proteus, serratia, pseudomonas, E. coli, legionella*, diphtheria, *salmonella*, bacilli, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus Mucorales (*mucor, absidia*, rhizophus), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleria fowleri*,

*Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and/or *Nippostrongylus brasiliensis*.

The term "chronic infection" refers to an infection lasting about one month or more, for example, for at least one month, two months, three months, four months, five months, or six months. In some embodiments, a chronic infection is associated with the increased production of anti-inflammatory chemokines in and/or around the infected area(s). Chronic infections include, but are not limited to, infections by HIV, HPV, Hepatitis B, Hepatitis C, EBV, CMV, *M. tuberculosis*, and intracellular bacteria and parasites. In some embodiments, the chronic infection is a bacterial infection. In some embodiments, the chronic infection is a viral infection.

Cancer

As provided herein, posteellular signaling factors produced by cells exposed to a stress condition can activate immune cells (e.g., T cells, B cells, NK cells, etc.) and, therefore, can enhance immune cell functions such as, for example, that involved in immunotherapies. Accordingly, in certain aspects, the disclosure relates to a method of treating a subject diagnosed with cancer, comprising administering to the subject, in combination (a) an immunotherapeutic anti-neoplastic agent and (b) a composition comprising one or more postcellular signaling factors produced by cells exposed to a stress condition, thereby treating the cancer in the subject.

As also provided herein, the combination of a STING agonist and a purinergic receptor agonist can activate immune cells (e.g., T cells, B cells, NK cells, etc.) and, therefore, can enhance immune cell functions such as, for example, that involved in immunotherapies. Accordingly, in certain aspects, the disclosure relates to a method of treating a subject diagnosed with cancer, comprising administering to the subject, in combination, a STING agonist and a purinergic receptor agonist, thereby treating the cancer in the subject.

The ability of cancer cells to harness a range of complex, overlapping mechanisms to prevent the immune system from distinguishing self from non-self represents the fundamental mechanism of cancers to evade immunesurveillance. Mechanism(s) include disruption of antigen presentation, disruption of regulatory pathways controlling T cell activation or inhibition (immune checkpoint regulation), recruitment of cells that contribute to immune suppression (Tregs, MDSC) or release of factors that influence immune activity (IDO, PGE2). (See Harris et al., 2013, J Immunotherapy Cancer 1:12; Chen et al., 2013, Immunity 39:1; Pardoll, et al., 2012, Nature Reviews: Cancer 12:252; and Sharma et al., 2015, Cell 161:205, each of which is incorporated by reference herein in its entirety.) Cancers for treatment using the methods described herein include, for example, all types of cancer or neoplasm or malignant tumors found in mammals, including, but not limited to: sarcomas, melanomas, carcinomas, leukemias, and lymphomas.

The term "sarcoma" generally refers to a tumor which is made up of a substance like the embryonic connective tissue and is generally composed of closely packed cells embedded in a fibrillar or homogeneous substance. Examples of sarcomas which can be treated with the methods of the invention include, for example, a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, uterine sarcoma, myxoid liposarcoma, leiomyosarcoma, spindle cell sarcoma, desmoplastic sarcoma, and telangiectaltic sarcoma.

The term "melanoma" is taken to mean a tumor arising from the melanocytic system of the skin and other organs. Melanomas which can be treated with the methods of the invention include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the methods of the invention, as described herein, include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, colon adenocarcinoma of colon, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, merkel cell carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, cervical squamous cell carcinoma, tonsil squamous cell carcinoma, and carcinoma *villosum*. In a particular embodiment, the cancer is renal cell carcinoma.

The term "leukemia" refers to a type of cancer of the blood or bone marrow characterized by an abnormal increase of immature white blood cells called "blasts". Leukemia is a broad term covering a spectrum of diseases. In turn, it is part of the even broader group of diseases affecting the blood, bone marrow, and lymphoid system, which are all known as hematological neoplasms. Leukemias can be divided into four major classifications, acute lymphocytic (or lymphoblastic) leukemia (ALL), acute myelogenous (or myeloid or non-lymphatic) leukemia (AML), chronic lymphocytic leukemia (CLL), and chronic myelogenous leukemia (CML). Further types of leukemia include Hairy cell leukemia (HCL), T-cell prolymphocytic leukemia (T-PLL), large granular lymphocytic leukemia, and adult T-cell leukemia. In certain embodiments, leukemias include acute leukemias. In certain embodiments, leukemias include chronic leukemias.

The term "lymphoma" refers to a group of blood cell tumors that develop from lymphatic cells. The two main categories of lymphomas are Hodgkin lymphomas (HL) and non-Hodgkin lymphomas (NHL) Lymphomas include any neoplasms of the lymphatic tissues. The main classes are cancers of the lymphocytes, a type of white blood cell that belongs to both the lymph and the blood and pervades both.

In some embodiments, the compositions are used for treatment of various types of solid tumors, for example breast cancer (e.g. triple negative breast cancer), bladder cancer, genitourinary tract cancer, colon cancer, rectal cancer, endometrial cancer, kidney (renal cell) cancer, pancreatic cancer, prostate cancer, thyroid cancer (e.g. papillary thyroid cancer), skin cancer, bone cancer, brain cancer, cervical cancer, liver cancer, stomach cancer, mouth and oral cancers, esophageal cancer, adenoid cystic cancer, neuroblastoma, testicular cancer, uterine cancer, thyroid cancer, head and neck cancer, kidney cancer, lung cancer (e.g. small cell lung cancer, non-small cell lung cancer), mesothelioma, ovarian cancer, sarcoma, stomach cancer, uterine cancer, cervical cancer, medulloblastoma, and vulvar cancer. In certain embodiments, skin cancer includes melanoma, squamous cell carcinoma, and cutaneous T-cell lymphoma (CTCL).

Additional cancers which can be treated with the compositions of the invention include, for example, multiple myeloma, primary thrombocytosis, primary macroglobulinemia, malignant pancreatic insulanoma, malignant carcinoid, malignant hypercalcemia, endometrial cancer, adrenal cortical cancer, and malignant fibrous histiocytoma.

In some embodiments, the compositions and combination therapies described herein may be administered to a subject that has previously failed treatment for a cancer with another anti-neoplastic (e.g. chemotherapeutic) regimen. For example, in some embodiments, the compositions and combination therapies described herein may be administered to a subject that has failed treatment for a cancer with an anti-neoplastic regimen comprising administration of one or more STING agonists. A "subject who has failed an anti-neoplastic regimen" is a subject with cancer that does not respond, or ceases to respond to treatment with a anti-neoplastic regimen per RECIST 1.1 criteria, i.e., does not achieve a complete response, partial response, or stable disease in the target lesion; or does not achieve complete response or non-CR/non-PD of non-target lesions, either during or after completion of the anti-neoplastic regimen, either alone or in conjunction with surgery and/or radiation therapy which, when possible, are often clinically indicated in conjunction with anti-neoplastic therapy. The RECIST 1.1 criteria are described, for example, in Eisenhauer et al., 2009, Eur. J. Cancer 45:228-24 (which is incorporated herein by reference in its entirety), and discussed in greater detail below. A failed anti-neoplastic regimen results in, e.g., tumor growth, increased tumor burden, and/or tumor metastasis. A failed anti-neoplastic regimen as used herein includes a treatment regimen that was terminated due to a dose limiting toxicity, e.g., a grade III or a grade IV toxicity that cannot be resolved to allow continuation or resumption of treatment with the anti-neoplastic agent or regimen that caused the toxicity. In one embodiment, the subject has failed treatment with a anti-neoplastic regimen comprising administration of one or more anti-angiogenic agents.

A failed anti-neoplastic regimen includes a treatment regimen that does not result in at least stable disease for all target and non-target lesions for an extended period, e.g., at least 1 month, at least 2 months, at least 3 months, at least 4 months, at least 5 months, at least 6 months, at least 12 months, at least 18 months, or any time period less than a clinically defined cure. A failed anti-neoplastic regimen includes a treatment regimen that results in progressive disease of at least one target lesion during treatment with the anti-neoplastic agent, or results in progressive disease less than 2 weeks, less than 1 month, less than two months, less than 3 months, less than 4 months, less than 5 months, less than 6 months, less than 12 months, or less than 18 months after the conclusion of the treatment regimen, or less than any time period less than a clinically defined cure.

A failed anti-neoplastic regimen does not include a treatment regimen wherein the subject treated for a cancer achieves a clinically defined cure, e.g., 5 years of complete response after the end of the treatment regimen, and wherein the subject is subsequently diagnosed with a distinct cancer, e.g., more than 5 years, more than 6 years, more than 7 years, more than 8 years, more than 9 years, more than 10 years, more than 11 years, more than 12 years, more than 13 years, more than 14 years, or more than 15 years after the end of the treatment regimen.

RECIST criteria are clinically accepted assessment criteria used to provide a standard approach to solid tumor measurement and provide definitions for objective assessment of change in tumor size for use in clinical trials. Such criteria can also be used to monitor response of an individual undergoing treatment for a solid tumor. The RECIST 1.1 criteria are discussed in detail in Eisenhauer et al., 2009, Eur. J. Cancer 45:228-24, which is incorporated herein by reference. Response criteria for target lesions include:

Complete Response (CR): Disappearance of all target lesions. Any pathological lymph nodes (whether target or non-target) must have a reduction in short axis to <10 mm.

Partial Response (PR): At least a 30% decrease in the sum of diameters of target lesion, taking as a reference the baseline sum diameters.

Progressive Diseases (PD): At least a 20% increase in the sum of diameters of target lesions, taking as a reference the smallest sum on the study (this includes the baseline sum if that is the smallest on the study). In addition to the relative increase of 20%, the sum must also demonstrate an absolute increase of at least 5 mm. (Note: the appearance of one or more new lesions is also considered progression.)

Stable Disease (SD): Neither sufficient shrinkage to qualify for PR nor sufficient increase to qualify for PD, taking as a reference the smallest sum diameters while on study.

RECIST 1.1 criteria also consider non-target lesions which are defined as lesions that may be measureable, but need not be measured, and should only be assessed qualitatively at the desired time points. Response criteria for non-target lesions include: Complete Response (CR): Disappearance of all non-target lesions and normalization of tumor marker levels. All lymph nodes must be non-pathological in size (<10 mm short axis).

Non-CR/Non-PD: Persistence of one or more non-target lesion(s) and/or maintenance of tumor marker level above the normal limits.

Progressive Disease (PD): Unequivocal progression of existing non-target lesions. The appearance of one or more new lesions is also considered progression. To achieve "unequivocal progression" on the basis of non-target disease, there must be an overall level of substantial worsening of non-target disease such that, even in the presence of SD or PR in target disease, the overall tumor burden has increased sufficiently to merit discontinuation of therapy. A modest "increase" in the size of one or more non-target lesions is usually not sufficient to qualify for unequivocal progression status. The designation of overall progression solely on the basis of change in non-target disease in the face of SD or PR in target disease will therefore be extremely rare.

In some embodiments, the pharmaceutical compositions and combination therapies described herein may be administered to a subject having a refractory cancer. A "refractory cancer" is a malignancy for which surgery is ineffective, which is either initially unresponsive to chemo- or radiation therapy, or which becomes unresponsive to chemo- or radiation therapy over time.

The invention further provides methods of inhibiting tumor cell growth in a subject, comprising administering a composition comprising one or more postcellular signaling factors to the subject, such that tumor cell growth is inhibited. In certain embodiments, treating cancer comprises extending survival or extending time to tumor progression as compared to a control. In some embodiments, the control is a subject that is not treated with the composition comprising one or more postcellular signaling factors. In some embodiments, the control is not treated with the composition comprising one or more postcellular signaling factors, but is treated with another therapeutic agent, for example, one or more of the additional therapeutic agents described herein. In certain embodiments, the subject is a human subject. In some embodiments, the subject is identified as having a tumor prior to administration of the first dose of the composition comprising one or more posteellular signaling factors. In certain embodiments, the subject has a tumor at the time of the first administration of the composition comprising one or more postcellular signaling factors.

In one embodiment, administration of the composition comprising one or more postcellular signaling factors results in one or more of, reducing tumor size, weight or volume, increasing time to progression, inhibiting tumor growth and/or prolonging the survival time of a subject having an oncological disorder. In certain embodiments, administration of the composition comprising one or more postcellular signaling factors reduces tumor size, weight or volume, increases time to progression, inhibits tumor growth and/or prolongs the survival time of the subject by at least 1%, 2%, 3%, 4%, 5%, 10%, 20%, 30%, 40%, 50%, 60%, 70%, 80%, 90%, 100%, 200%, 300%, 400% or 500% relative to a corresponding control subject, e.g. a subject that is not administered the composition comprising one or more postcellular signaling factors. In certain embodiments, administration of the composition comprising one or more postcellular signaling factors reduces tumor size, weight or volume, increases time to progression, inhibits tumor growth and/or prolongs the survival time of a population of subjects afflicted with an oncological disorder by at least 1%, 2%, 3% 4%, 5%, 10%, 20%, 30%, 40%, 50%, 60%, 70%, 80%, 90%, 100%, 200%, 300%, 400% or 500% relative to a corresponding population of control subjects afflicted with the oncological disorder that is not administered the composition comprising one or more postcellular signaling factors. In other embodiments, administration of the composition comprising one or more postcellular signaling factors stabilizes the oncological disorder in a subject with a progressive oncological disorder prior to treatment.

The disclosure further provides methods of inhibiting tumor cell growth in a subject, comprising administering, in combination, a STING agonist and a purinergic receptor agonist, such that tumor cell growth is inhibited. In certain embodiments, treating cancer comprises extending survival or extending time to tumor progression as compared to a control. In some embodiments, the control is a subject that is not treated with STING agonist or the purinergic receptor agonist. In some embodiments, the control is a subject that is treated with the STING agonist, but is not treated with the purinergic receptor agonist. In some embodiments, the control is a subject that is not treated with the STING agonist but is treated with the purinergic receptor agonist. In certain embodiments, the subject is a human subject. In some embodiments, the subject is identified as having a tumor prior to administration of the first dose of the STING agonist and/or the purinergic receptor agonist. In certain embodiments, the subject has a tumor at the time of the first administration of the STING agonist and/or the purinergic receptor agonist.

In one embodiment, administration of the STING agonist and the purinergic receptor agonist results in one or more of reducing tumor size, weight or volume, increasing time to progression, inhibiting tumor growth and/or prolonging the survival time of a subject having an oncological disorder. In certain embodiments, administration of the STING agonist and the purinergic receptor agonist reduces tumor size, weight or volume, increases time to progression, inhibits tumor growth and/or prolongs the survival time of the subject by at least 1%, 2%, 3%, 4%, 5%, 10%, 20%, 30%, 40%, 50%, 60%, 70%, 80%, 90%, 100%, 200%, 300%, 400% or 500% relative to a corresponding control subject that is not administered the STING agonist and/or the purinergic receptor agonist. In certain embodiments, administration of the STING agonist and purinergic receptor agonist reduces tumor size, weight or volume, increases time to progression, inhibits tumor growth and/or prolongs the survival time of a population of subjects afflicted with an oncological disorder by at least 1%, 2%, 3%, 4%, 5%, 10%, 20%, 30%, 40%, 50%, 60%, 70%, 80%, 90%, 100%, 200%, 300%, 400% or 500% relative to a corresponding population of control subjects afflicted with the oncological disorder that is not administered the STING agonist and/or the purinergic receptor agonist. In other embodiments, administration of the STING agonist and purinergic receptor agonist stabilizes the oncological disorder in a subject with a progressive oncological disorder prior to treatment.

Combination Therapies

In some embodiments, the terms "administering in combination", "combination therapy", "co-administering" or "co-administration" refer to administration of a composition comprising one or more postcellular signaling factors (produced by cells exposed to a stress condition) prior to, concurrently or substantially concurrently with, subsequently to, or intermittently with administration of one or more additional therapeutic agents. In certain embodiments, the composition comprising one or more postcellular signaling factors is administered prior to administration of the one or more additional therapeutic agents. In certain embodiments, the composition comprising one or more postcellular signaling factors is administered concurrently with the immune checkpoint modulator. In certain embodiments, the composition comprising one or more postcellular signaling factors is administered after administration of the immune checkpoint modulator.

The posteellular signaling factors and the immune checkpoint modulator can act additively or synergistically. In one embodiment, the one or more postcellular signaling factors and the one or more additional therapeutic agents act synergistically. In some embodiments the synergistic effects are in the treatment of an oncological disorder or an infection. For example, in one embodiment, the combination of the one or more postcellular signaling factors and the one or more additional therapeutic agents improves the durability, i.e. extends the duration, of the immune response against a cancer. In some embodiments, the one or more postcellular signaling factors and the one or more additional therapeutic agents act additively.

In some embodiments, the additional therapeutic agent administered in combination with the composition comprising one or more postcellular signaling factors is a Stimulator of Interferon Genes (STING) agonist. Accordingly, in certain aspects, the disclosure relates to a method of increasing immune activity in a target cell, tissue or subject, the method comprising administering to the target cell, tissue or subject, in combination (a) a composition comprising one or more postcellular signaling factors produced by cells exposed to a stress condition, and (b) a Stimulator of Interferon Genes (STING) agonist, wherein the composition and the STING agonist are administered in an amount sufficient to increase the immune activity relative to a cell, tissue or subject that is not treated with the composition and/or the STING agonist.

In some embodiments, the terms "administering in combination", "combination therapy", "co-administering" or "co-administration" refer to administration of a STING agonist prior to, concurrently or substantially concurrently with, subsequently to, or intermittently with administration of a purinergic receptor agonist (e.g., P2Y receptor agonist, such as P2Y2, P2Y4 or P2Y6 agonist). In certain embodiments, the STING agonist is administered prior to administration of the purinergic receptor agonist. In certain embodiments, the STING agonist is administered concurrently with the purinergic receptor agonist. In certain embodiments, the STING agonist is administered after administration of the purinergic receptor agonist.

The STING agonist and the purinergic receptor agonist can act additively or synergistically. In one embodiment, the STING agonist and the purinergic receptor agonist act synergistically. In some embodiments the synergistic effects are in the treatment of an oncological disorder or an infection. For example, in one embodiment, the combination of the STING agonist and purinergic receptor agonist improves the durability, i.e. extends the duration, of the immune response against a cancer. In some embodiments, the STING agonist and the purinergic receptor agonist act additively.

The terms "administering in combination", "combination therapy", "co-administering" or "co-administration" may also refer to administration of the combination of the STING agonist and the purinergic receptor agonist in further combination with one or more additional therapeutic agents. The one or more additional therapeutic agents may be administered prior to, concurrently or substantially concurrently with, subsequently to, or intermittently with administration of the STING agonist and/or the purinergic receptor agonist. In certain embodiments, the one or more additional therapeutic agents is administered prior to administration of the STING agonist and/or the purinergic receptor agonist. In certain embodiments, the one or more additional therapeutic agents is administered concurrently with the STING agonist and/or the purinergic receptor agonist. In certain embodiments, the one or more additional therapeutic agents is administered after administration of the STING agonist and/or the purinergic receptor agonist.

The one or more additional therapeutic agents and the STING agonist and/or the purinergic receptor agonist can act additively or synergistically. In one embodiment, the one or more additional therapeutic agents and the STING agonist and/or the purinergic receptor agonist act synergistically. In some embodiments the synergistic effects are in the treatment of an oncological disorder or an infection. For example, in one embodiment, the combination of the one or more additional therapeutic agents and the STING agonist and/or the purinergic receptor agonist improves the durability, i.e. extends the duration, of the immune response against a cancer. In some embodiments, the one or more additional therapeutic agents and the STING agonist and/or the purinergic receptor agonist act additively.

1. Immune Checkpoint Modulators

In some embodiments, the additional therapeutic agent administered in combination with the composition comprising one or more postcellular signaling factors is an immune checkpoint modulator of an immune checkpoint molecule. In some embodiments, the additional therapeutic agent administered in combination with the STING agonist and the purinergic receptor agonist is an immune checkpoint modulator of an immune checkpoint molecule. Examples of immune checkpoint molecules include LAG-3 (Triebel et al., 1990, J. Exp. Med. 171: 1393-1405), TIM-3 (Sakuishi et al., 2010, J. Exp. Med. 207: 2187-2194), VISTA (Wang et al., 2011, J. Exp. Med. 208: 577-592), ICOS (Fan et al., 2014, J. Exp. Med. 211: 715-725), OX40 (Curti et al., 2013, Cancer Res. 73: 7189-7198) and 4-1BB (Melero et al., 1997, Nat. Med. 3: 682-685).

Immune checkpoints may be stimulatory immune checkpoints (i.e. molecules that stimulate the immune response) or inhibitory immune checkpoints (i.e. molecules that inhibit immune response). In some embodiments, the immune checkpoint modulator is an antagonist of an inhibitory immune checkpoint. In some embodiments, the immune checkpoint modulator is an agonist of a stimulatory immune checkpoint. In some embodiments, the immune checkpoint modulator is an immune checkpoint binding protein (e.g., an antibody, antibody Fab fragment, divalent antibody, antibody drug conjugate, scFv, fusion protein, bivalent antibody, or tetravalent antibody). In certain embodiments, the immune checkpoint modulator is capable of binding to, or modulating the activity of more than one immune checkpoint. Examples of stimulatory and inhibitory immune checkpoints, and molecules that modulate these immune checkpoints that may be used in the methods of the invention, are provided below.

i. Stimulatory Immune Checkpoint Molecules

CD27 supports antigen-specific expansion of naïve T cells and is vital for the generation of T cell memory (see, e.g., Hendriks et al. (2000) *Nat. Immunol.* 171 (5): 433-40). CD27 is also a memory marker of B cells (see, e.g., Agematsu et al. (2000) *Histol. Histopathol.* 15 (2): 573-6. CD27 activity is governed by the transient availability of its ligand, CD70, on lymphocytes and dendritic cells (see, e.g., Borst et al. (2005) Curr. Opin. Immunol. 17 (3): 275-81). Multiple immune checkpoint modulators specific for CD27 have been developed and may be used as disclosed herein. In some embodiments, the immune checkpoint modulator is an agent that modulates the activity and/or expression of CD27. In some embodiments, the immune checkpoint modulator is an agent that binds to CD27 (e.g., an anti-CD27 antibody). In some embodiments, the checkpoint modulator is a CD27 agonist. In some embodiments, the checkpoint modulator is a CD27 antagonist. In some embodiments, the immune checkpoint modulator is an CD27-binding protein (e.g., an antibody). In some embodiments, the immune checkpoint modulator is varlilumab (Celldex Therapeutics). Additional CD27-binding proteins (e.g., antibodies) are known in the art and are disclosed, e.g., in U.S. Pat. Nos. 9,248,183, 9,102,737, 9,169,325, 9,023,999, 8,481,029; U.S. Patent Application Publication Nos. 2016/0185870, 2015/0337047, 2015/0299330, 2014/0112942, 2013/0336976, 2013/0243795, 2013/0183316, 2012/0213771, 2012/0093805, 2011/0274685, 2010/0173324; and PCT Publication Nos. WO 2015/016718, WO 2014/140374, WO 2013/138586, WO 2012/004367, WO 2011/130434, WO 2010/001908, and WO 2008/051424, each of which is incorporated by reference herein.

CD28. Cluster of Differentiation 28 (CD28) is one of the proteins expressed on T cells that provide co-stimulatory signals required for T cell activation and survival. T cell stimulation through CD28 in addition to the T-cell receptor (TCR) can provide a potent signal for the production of various interleukins (IL-6 in particular). Binding with its two ligands, CD80 and CD86, expressed on dendritic cells, prompts T cell expansion (see, e.g., Prasad et al. (1994) Proc. Nat'l. Acad. Sci. USA 91(7): 2834-8). Multiple immune checkpoint modulators specific for CD28 have been developed and may be used as disclosed herein. In some embodiments, the immune checkpoint modulator is an agent that modulates the activity and/or expression of CD28. In some embodiments, the immune checkpoint modulator is an agent that binds to CD28 (e.g., an anti-CD28 antibody). In some embodiments, the checkpoint modulator is an CD28 agonist. In some embodiments, the checkpoint modulator is an CD28 antagonist. In some embodiments, the immune checkpoint modulator is an CD28-binding protein (e.g., an antibody). In some embodiments, the immune checkpoint modulator is selected from the group consisting of TAB08 (TheraMab LLC), lulizumab (also known as BMS-931699, Bristol-Myers Squibb), and FR104 (OSE Immunotherapeutics). Additional CD28-binding proteins (e.g., antibodies) are known in the art and are disclosed, e.g., in U.S. Pat. Nos. 9,119,840, 8,709,414, 9,085,629, 8,034,585, 7,939,638, 8,389,016, 7,585,960, 8,454,959, 8,168,759, 8,785,604, 7,723,482; U.S. Patent Application Publication Nos. 2016/0017039, 2015/0299321, 2015/0150968, 2015/0071916, 2015/0376278, 2013/0078257, 2013/0230540, 2013/0078236, 2013/0109846, 2013/0266577, 2012/0201814, 2012/0082683, 2012/0219553, 2011/0189735, 2011/0097339, 2010/0266605, 2010/0168400, 2009/0246204, 2008/0038273; and PCT Publication Nos. WO 2015198147, WO 2016/05421, WO 2014/1209168, WO 2011/101791, WO 2010/007376, WO 2010/009391, WO 2004/004768, WO 2002/030459, WO 2002/051871, and WO 2002/047721, each of which is incorporated by reference herein.

CD40. Cluster of Differentiation 40 (CD40, also known as TNFRSF5) is found on a variety of immune system cells including antigen presenting cells. CD40L, otherwise known as CD154, is the ligand of CD40 and is transiently expressed on the surface of activated CD4$^+$ T cells. CD40 signaling is known to 'license' dendritic cells to mature and thereby trigger T-cell activation and differentiation (see, e.g., O'Sullivan et al. (2003) *Crit. Rev. Immunol.* 23 (1): 83-107. Multiple immune checkpoint modulators specific for CD40 have been developed and may be used as disclosed herein. In some embodiments, the immune checkpoint modulator is an agent that modulates the activity and/or expression of CD40. In some embodiments, the immune checkpoint modulator is an agent that binds to CD40 (e.g., an anti-CD40 antibody). In some embodiments, the checkpoint modulator is a CD40 agonist. In some embodiments, the checkpoint modulator is an CD40 antagonist. In some embodiments, the immune checkpoint modulator is a CD40-binding protein selected from the group consisting of dacetuzumab (Genentech/Seattle Genetics), CP-870,893 (Pfizer), bleselumab (Astellas Pharma), lucatumumab (Novartis), CFZ533 (Novartis; see, e.g., Cordoba et al. (2015) *Am. J. Transplant.* 15(11): 2825-36), RG7876 (Genentech Inc.), FFP104 (PanGenetics, B. V.), APX005 (Apexigen), BI 655064 (Boehringer Ingelheim), Chi Lob 7/4 (Cancer Research UK; see, e.g., Johnson et al. (2015) *Clin. Cancer Res.* 21(6): 1321-8), ADC-1013 (BioInvent International), SEA-CD40 (Seattle Genetics), XmAb 5485 (Xencor), PG120 (PanGenetics B. V.), teneliximab (Bristol-Myers Squibb; see, e.g., Thompson et al. (2011) *Am. J. Transplant.* 11(5): 947-57), and AKH3 (Biogen; see, e.g., International Publication No. WO 2016/028810). Additional CD40-binding proteins (e.g., antibodies) are known in the art and are disclosed, e.g., in U.S. Pat. Nos. 9,234,044, 9,266,956, 9,109,011, 9,090,696, 9,023,360, 9,023,361, 9,221,913, 8,945,564, 8,926,979, 8,828,396, 8,637,032, 8,277,810, 8,088,383, 7,820,170, 7,790,166, 7,445,780, 7,361,345, 8,961,991, 8,669,352, 8,957,193, 8,778,345, 8,591,900, 8,551,485, 8,492,531, 8,362,210, 8,388,971; U.S. Patent Application Publication Nos. 2016/0045597, 2016/0152713, 2016/0075792, 2015/0299329, 2015/0057437, 2015/0315282, 2015/0307616, 2014/0099317, 2014/0179907, 2014/0349395, 2014/0234344, 2014/0348836, 2014/0193405, 2014/0120103, 2014/0105907, 2014/0248266, 2014/0093497, 2014/0010812, 2013/0024956, 2013/0023047, 2013/0315900, 2012/0087927, 2012/0263732, 2012/0301488, 2011/0027276, 2011/0104182, 2010/0234578, 2009/0304687, 2009/0181015, 2009/0130715, 2009/0311254, 2008/0199471, 2008/0085531, 2016/0152721, 2015/0110783, 2015/0086991, 2015/0086559, 2014/0341898, 2014/0205602, 2014/0004131, 2013/0011405, 2012/0121585, 2011/0033456, 2011/0002934, 2010/0172912, 2009/0081242, 2009/0130095, 2008/0254026, 2008/0075727, 2009/0304706, 2009/0202531, 2009/0117111, 2009/0041773, 2008/0274118, 2008/0057070, 2007/0098717, 2007/0218060, 2007/0098718, 2007/0110754; and PCT Publication Nos. WO 2016/069919, WO 2016/023960, WO 2016/023875, WO 2016/028810, WO 2015/134988, WO 2015/091853, WO 2015/091655, WO 2014/065403, WO 2014/070934, WO 2014/065402, WO 2014/207064, WO 2013/034904, WO 2012/125569, WO 2012/149356, WO 2012/

111762, WO 2012/145673, WO 2011/123489, WO 2010/ 123012, WO 2010/104761, WO 2009/094391, WO 2008/ 091954, WO 2007/129895, WO 2006/128103, WO 2005/ 063289, WO 2005/063981, WO 2003/040170, WO 2002/ 011763, WO 2000/075348, WO 2013/164789, WO 2012/ 075111, WO 2012/065950, WO 2009/062054, WO 2007/ 124299, WO 2007/053661, WO 2007/053767, WO 2005/ 044294, WO 2005/044304, WO 2005/044306, WO 2005/ 044855, WO 2005/044854, WO 2005/044305, WO 2003/ 045978, WO 2003/029296, WO 2002/028481, WO 2002/ 028480, WO 2002/028904, WO 2002/028905, WO 2002/ 088186, and WO 2001/024823, each of which is incorporated by reference herein.

CD122. CD122 is the Interleukin-2 receptor beta sub-unit and is known to increase proliferation of $CD8^+$ effector T cells. See, e.g., Boyman et al. (2012) *Nat. Rev. Immunol.* 12 (3): 180-190. Multiple immune checkpoint modulators specific for CD122 have been developed and may be used as disclosed herein. In some embodiments, the immune checkpoint modulator is an agent that modulates the activity and/or expression of CD122. In some embodiments, the immune checkpoint modulator is an agent that binds to CD122 (e.g., an anti-CD122 antibody). In some embodiments, the checkpoint modulator is an CD122 agonist. In some embodiments, the checkpoint modulator is an CD22 agonist. In some embodiments, the immune checkpoint modulator is humanized MiK-Beta-1 (Roche; see, e.g., Morris et al. (2006) Proc Nat'l. Acad. Sci. USA 103(2): 401-6, which is incorporated by reference). Additional CD122-binding proteins (e.g., antibodies) are known in the art and are disclosed, e.g., in U.S. Pat. No. 9,028,830, which is incorporated by reference herein.

OX40. The OX40 receptor (also known as CD134) promotes the expansion of effector and memory T cells. OX40 also suppresses the differentiation and activity of T-regulatory cells, and regulates cytokine production (see, e.g., Croft et al. (2009) Immunol. Rev. 229(1): 173-91). Multiple immune checkpoint modulators specific for OX40 have been developed and may be used as disclosed herein. In some embodiments, the immune checkpoint modulator is an agent that modulates the activity and/or expression of OX40. In some embodiments, the immune checkpoint modulator is an agent that binds to OX40 (e.g., an anti-OX40 antibody). In some embodiments, the checkpoint modulator is an OX40 agonist. In some embodiments, the checkpoint modulator is an OX40 antagonist. In some embodiments, the immune checkpoint modulator is a OX40-binding protein (e.g., an antibody) selected from the group consisting of MEDI6469 (AgonOx/Medimmune), pogalizumab (also known as MOXR0916 and RG7888; Genentech, Inc.), tavolixizumab (also known as MEDI0562; Medimmune), and GSK3174998 (GlaxoSmithKline). Additional OX-40-binding proteins (e.g., antibodies) are known in the art and are disclosed, e.g., in U.S. Pat. Nos. 9,163,085, 9,040,048, 9,006,396, 8,748,585, 8,614,295, 8,551,477, 8,283,450, 7,550,140; U.S. Patent Application Publication Nos. 2016/ 0068604, 2016/0031974, 2015/0315281, 2015/0132288, 2014/0308276, 2014/0377284, 2014/0044703, 2014/ 0294824, 2013/0330344, 2013/0280275, 2013/0243772, 2013/0183315, 2012/0269825, 2012/0244076, 2011/ 0008368, 2011/0123552, 2010/0254978, 2010/0196359, 2006/0281072; and PCT Publication Nos. WO 2014/ 148895, WO 2013/068563, WO 2013/038191, WO 2013/ 028231, WO 2010/096418, WO 2007/062245, and WO 2003/106498, each of which is incorporated by reference herein.

GITR. Glucocorticoid-induced TNFR family related gene (GITR) is a member of the tumor necrosis factor receptor (TNFR) superfamily that is constitutively or conditionally expressed on Treg, CD4, and CD8 T cells. GITR is rapidly upregulated on effector T cells following TCR ligation and activation. The human GITR ligand (GITRL) is constitutively expressed on APCs in secondary lymphoid organs and some nonlymphoid tissues. The downstream effect of GITR: GITRL interaction induces attenuation of Treg activity and enhances $CD4^+$ T cell activity, resulting in a reversal of Treg-mediated immunosuppression and increased immune stimulation. Multiple immune checkpoint modulators specific for GITR have been developed and may be used as disclosed herein. In some embodiments, the immune checkpoint modulator is an agent that modulates the activity and/or expression of GITR. In some embodiments, the immune checkpoint modulator is an agent that binds to GITR (e.g., an anti-GITR antibody). In some embodiments, the checkpoint modulator is an GITR agonist. In some embodiments, the checkpoint modulator is an GITR antagonist. In some embodiments, the immune checkpoint modulator is a GITR-binding protein (e.g., an antibody) selected from the group consisting of TRX518 (Leap Therapeutics), MK-4166 (Merck & Co.), MEDI-1873 (MedImmune), INCAGN1876 (Agenus/Incyte), and FPA154 (Five Prime Therapeutics). Additional GITR-binding proteins (e.g., antibodies) are known in the art and are disclosed, e.g., in U.S. Pat. Nos. 9,309,321, 9,255,152, 9,255,151, 9,228,016, 9,028,823, 8,709,424, 8,388,967; U.S. Patent Application Publication Nos. 2016/0145342, 2015/0353637, 2015/ 0064204, 2014/0348841, 2014/0065152, 2014/0072566, 2014/0072565, 2013/0183321, 2013/0108641, 2012/ 0189639; and PCT Publication Nos. WO 2016/054638, WO 2016/057841, WO 2016/057846, WO 2015/187835, WO 2015/184099, WO 2015/031667, WO 2011/028683, and WO 2004/107618, each of which is incorporated by reference herein.

ICOS. Inducible T-cell costimulator (ICOS, also known as CD278) is expressed on activated T cells. Its ligand is ICOSL, which is expressed mainly on B cells and dendritic cells. ICOS is important in T cell effector function. ICOS expression is up-regulated upon T cell activation (see, e.g., Fan et al. (2014) *J. Exp. Med.* 211(4): 715-25). Multiple immune checkpoint modulators specific for ICOS have been developed and may be used as disclosed herein. In some embodiments, the immune checkpoint modulator is an agent that modulates the activity and/or expression of ICOS. In some embodiments, the immune checkpoint modulator is an agent that binds to ICOS (e.g., an anti-ICOS antibody). In some embodiments, the checkpoint modulator is an ICOS agonist. In some embodiments, the checkpoint modulator is an ICOS antagonist. In some embodiments, the immune checkpoint modulator is a ICOS-binding protein (e.g., an antibody) selected from the group consisting of MEDI-570 (also known as JMab-136, Medimmune), GSK3359609 (GlaxoSmithKline/INSERM), and JTX-2011 (Jounce Therapeutics). Additional ICOS-binding proteins (e.g., antibodies) are known in the art and are disclosed, e.g., in U.S. Pat. Nos. 9,376,493, 7,998,478, 7,465,445, 7,465,444; U.S. Patent Application Publication Nos. 2015/0239978, 2012/ 0039874, 2008/0199466, 2008/0279851; and PCT Publication No. WO 2001/087981, each of which is incorporated by reference herein.

4-1BB. 4-1BB (also known as CD137) is a member of the tumor necrosis factor (TNF) receptor superfamily. 4-1BB (CD137) is a type II transmembrane glycoprotein that is inducibly expressed on primed $CD4^+$ and $CD8^+$ T cells, activated NK cells, DCs, and neutrophils, and acts as a T cell costimulatory molecule when bound to the 4-1BB ligand (4-1BBL) found on activated macrophages, B cells, and DCs. Ligation of the 4-1BB receptor leads to activation of the NF-κB, c-Jun and p38 signaling pathways and has been shown to promote survival of $CD8^+$ T cells, specifically, by upregulating expression of the antiapoptotic genes BcL-x(L) and Bfl-1. In this manner, 4-1BB serves to boost or even salvage a suboptimal immune response. Multiple immune checkpoint modulators specific for 4-1BB have been developed and may be used as disclosed herein. In some embodiments, the immune checkpoint modulator is an agent that modulates the activity and/or expression of 4-1BB. In some embodiments, the immune checkpoint modulator is an agent that binds to 4-1BB (e.g., an anti-4-1BB antibody). In some embodiments, the checkpoint modulator is an 4-1BB agonist. In some embodiments, the checkpoint modulator is an 4-1BB antagonist. In some embodiments, the immune checkpoint modulator is a 4-1BB-binding protein is urelumab (also known as BMS-663513; Bristol-Myers Squibb) or utomilumab (Pfizer). In some embodiments, the immune checkpoint modulator is a 4-1BB-binding protein (e.g., an antibody). 4-1BB-binding proteins (e.g., antibodies) are known in the art and are disclosed, e.g., in U.S. Pat. Nos. 9,382,328, 8,716,452, 8,475,790, 8,137,667, 7,829,088, 7,659,384; U.S. Patent Application Publication Nos. 2016/0083474, 2016/0152722, 2014/0193422, 2014/0178368, 2013/0149301, 2012/0237498, 2012/0141494, 2012/0076722, 2011/0177104, 2011/0189189, 2010/0183621, 2009/0068192, 2009/0041763, 2008/0305113, 2008/0008716; and PCT Publication Nos. WO 2016/029073, WO 2015/188047, WO 2015/179236, WO 2015/119923, WO 2012/032433, WO 2012/145183, WO 2011/031063, WO 2010/132389, WO 2010/042433, WO 2006/126835, WO 2005/035584, WO 2004/010947; and Martinez-Forero et al. (2013) *J. Immunol.* 190(12): 6694-706, and Dubrot et al. (2010) *Cancer Immunol. Immunother.* 59(8): 1223-33, each of which is incorporated by reference herein.

ii. Inhibitory Immune Checkpoint Molecules

ADORA2A. The adenosine A2A receptor (A2A4) is a member of the G protein-coupled receptor (GPCR) family which possess seven transmembrane alpha helices, and is regarded as an important checkpoint in cancer therapy. A2A receptor can negatively regulate overreactive immune cells (see, e.g., Ohta et al. (2001) Nature 414(6866): 916-20). Multiple immune checkpoint modulators specific for ADORA2A have been developed and may be used as disclosed herein. In some embodiments, the immune checkpoint modulator is an agent that modulates the activity and/or expression of ADORA2A. In some embodiments, the immune checkpoint modulator is an agent that binds to ADORA2A (e.g., an anti-ADORA2A antibody). In some embodiments, the immune checkpoint modulator is a ADORA2A-binding protein (e.g., an antibody). In some embodiments, the checkpoint modulator is an ADORA2A agonist. In some embodiments, the checkpoint modulator is an ADORA2A antagonist. ADORA2A-binding proteins (e.g., antibodies) are known in the art and are disclosed, e.g., in U.S. Patent Application Publication No. 2014/0322236, which is incorporated by reference herein.

B7-H3. B7-H3 (also known as CD276) belongs to the B7 superfamily, a group of molecules that costimulate or down-modulate T-cell responses. B7-H3 potently and consistently down-modulates human T-cell responses (see, e.g., Leitner et al. (2009) *Eur. J. Immunol.* 39(7): 1754-64). Multiple immune checkpoint modulators specific for B7-H3 have been developed and may be used as disclosed herein. In some embodiments, the immune checkpoint modulator is an agent that modulates the activity and/or expression of B7-H3. In some embodiments, the immune checkpoint modulator is an agent that binds to B7-H3 (e.g., an anti-B7-H3 antibody). In some embodiments, the checkpoint modulator is an B7-H3 agonist. In some embodiments, the checkpoint modulator is an B7-H3 antagonist. In some embodiments, the immune checkpoint modulator is an anti-B7-H3-binding protein selected from the group consisting of DS-5573 (Daiichi Sankyo, Inc.), enoblituzumab (MacroGenics, Inc.), and 8H9 (Sloan Kettering Institute for Cancer Research; see, e.g., Ahmed et al. (2015) J. Biol. Chem. 290(50): 30018-29). In some embodiments, the immune checkpoint modulator is a B7-H3-binding protein (e.g., an antibody). B7-H3-binding proteins (e.g., antibodies) are known in the art and are disclosed, e.g., in U.S. Pat. Nos. 9,371,395, 9,150,656, 9,062,110, 8,802,091, 8,501,471, 8,414,892; U.S. Patent Application Publication Nos. 2015/0352224, 2015/0297748, 2015/0259434, 2015/0274838, 2014/032875, 2014/0161814, 2013/0287798, 2013/0078234, 2013/0149236, 2012/02947960, 2010/0143245, 2002/0102264; PCT Publication Nos. WO 2016/106004, WO 2016/033225, WO 2015/181267, WO 2014/057687, WO 2012/147713, WO 2011/109400, WO 2008/116219, WO 2003/075846, WO 2002/032375; and Shi et al. (2016) *Mol. Med. Rep.* 14(1): 943-8, each of which is incorporated by reference herein.

B7-H4. B7-H4 (also known as 08E, OV064, and V-set domain-containing T-cell activation inhibitor (VTCN1)), belongs to the B7 superfamily. By arresting cell cycle, B7-H4 ligation of T cells has a profound inhibitory effect on the growth, cytokine secretion, and development of cytotoxicity. Administration of B7-H4Ig into mice impairs antigen-specific T cell responses, whereas blockade of endogenous B7-H4 by specific monoclonal antibody promotes T cell responses (see, e.g., Sica et al. (2003) Immunity 18(6): 849-61). Multiple immune checkpoint modulators specific for B7-H4 have been developed and may be used as disclosed herein. In some embodiments, the immune checkpoint modulator is an agent that modulates the activity and/or expression of B7-H4. In some embodiments, the immune checkpoint modulator is an agent that binds to B7-H4 (e.g., an anti-B7-H4 antibody). In some embodiments, the immune checkpoint modulator is a B7-H4-binding protein (e.g., an antibody). In some embodiments, the checkpoint modulator is an B7-H4 agonist. In some embodiments, the checkpoint modulator is an B7-H4 antagonist. B7-H4-binding proteins (e.g., antibodies) are known in the art and are disclosed, e.g., in U.S. Pat. Nos. 9,296,822, 8,609,816, 8,759,490, 8,323,645; U.S. Patent Application Publication Nos. 2016/0159910, 2016/0017040, 2016/0168249, 2015/0315275, 2014/0134180, 2014/0322129, 2014/0356364, 2014/0328751, 2014/0294861, 2014/0308259, 2013/0058864, 2011/0085970, 2009/0074660, 2009/0208489; and PCT Publication Nos. WO 2016/040724, WO 2016/070001, WO 2014/159835, WO 2014/100483, WO 2014/100439, WO 2013/067492, WO 2013/025779, WO 2009/073533, WO 2007/067991, and WO 2006/104677, each of which is incorporated by reference herein.

BTLA. B and T Lymphocyte Attenuator (BTLA), also known as CD272, has HVEM (Herpesvirus Entry Mediator) as its ligand. Surface expression of BTLA is gradually downregulated during differentiation of human $CD8^+$ T cells from the naïve to effector cell phenotype, however tumor-specific human $CD8^+$ T cells express high levels of BTLA (see, e.g., Derre et al. (2010) J. Clin. Invest. 120 (1):

157-67). Multiple immune checkpoint modulators specific for BTLA have been developed and may be used as disclosed herein. In some embodiments, the immune checkpoint modulator is an agent that modulates the activity and/or expression of BTLA. In some embodiments, the immune checkpoint modulator is an agent that binds to BTLA (e.g., an anti-BTLA antibody). In some embodiments, the immune checkpoint modulator is a BTLA-binding protein (e.g., an antibody). In some embodiments, the checkpoint modulator is an BTLA agonist. In some embodiments, the checkpoint modulator is an BTLA antagonist. BTLA-binding proteins (e.g., antibodies) are known in the art and are disclosed, e.g., in U.S. Pat. Nos. 9,346,882, 8,580,259, 8,563,694, 8,247,537; U.S. Patent Application Publication Nos. 2014/0017255, 2012/0288500, 2012/0183565, 2010/0172900; and PCT Publication Nos. WO 2011/014438, and WO 2008/076560, each of which is incorporated by reference herein.

CTLA-4. Cytotoxic T lymphocyte antigen-4 (CTLA-4) is a member of the immune regulatory CD28-B7 immunoglobulin superfamily and acts on naïve and resting T lymphocytes to promote immunosuppression through both B7-dependent and B7-independent pathways (see, e.g., Kim et al. (2016) J. Immunol. Res., Article ID 4683607, 14 pp.). CTLA-4 is also known as called CD152. CTLA-4 modulates the threshold for T cell activation. See, e.g., Gajewski et al. (2001) J. Immunol. 166(6): 3900-7. Multiple immune checkpoint modulators specific for CTLA-4 have been developed and may be used as disclosed herein. In some embodiments, the immune checkpoint modulator is an agent that modulates the activity and/or expression of CTLA-4. In some embodiments, the immune checkpoint modulator is an agent that binds to CTLA-4 (e.g., an anti-CTLA-4 antibody). In some embodiments, the checkpoint modulator is an CTLA-4 agonist. In some embodiments, the checkpoint modulator is an CTLA-4 antagonist. In some embodiments, the immune checkpoint modulator is a CTLA-4-binding protein (e.g., an antibody) selected from the group consisting of ipilimumab (Yervoy; Medarex/Bristol-Myers Squibb), tremelimumab (formerly ticilimumab; Pfizer/AstraZeneca), JMW-3B3 (University of Aberdeen), and AGEN1884 (Agenus). Additional CTLA-4 binding proteins (e.g., antibodies) are known in the art and are disclosed, e.g., in U.S. Pat. No. 8,697,845; U.S. Patent Application Publication Nos. 2014/0105914, 2013/0267688, 2012/0107320, 2009/0123477; and PCT Publication Nos. WO 2014/207064, WO 2012/120125, WO 2016/015675, WO 2010/097597, WO 2006/066568, and WO 2001/054732, each of which is incorporated by reference herein.

IDO. Indoleamine 2,3-dioxygenase (IDO) is a tryptophan catabolic enzyme with immune-inhibitory properties. Another important molecule is TDO, tryptophan 2,3-dioxygenase. IDO is known to suppress T and NK cells, generate and activate Tregs and myeloid-derived suppressor cells, and promote tumor angiogenesis. Prendergast et al., 2014, Cancer Immunol Immunother. 63 (7): 721-35, which is incorporated by reference herein.

Multiple immune checkpoint modulators specific for IDO have been developed and may be used as disclosed herein. In some embodiments, the immune checkpoint modulator is an agent that modulates the activity and/or expression of IDO. In some embodiments, the immune checkpoint modulator is an agent that binds to IDO (e.g., an IDO binding protein, such as an anti-IDO antibody). In some embodiments, the checkpoint modulator is an IDO agonist. In some embodiments, the checkpoint modulator is an IDO antagonist. In some embodiments, the immune checkpoint modulator is selected from the group consisting of Norharmane, Rosmarinic acid, COX-2 inhibitors, alpha-methyl-tryptophan, and Epacadostat. In one embodiment, the modulator is Epacadostat.

KIR. Killer immunoglobulin-like receptors (KIRs) comprise a diverse repertoire of MHICI binding molecules that negatively regulate natural killer (NK) cell function to protect cells from NK-mediated cell lysis. KIRs are generally expressed on NK cells but have also been detected on tumor specific CTLs. Multiple immune checkpoint modulators specific for KIR have been developed and may be used as disclosed herein. In some embodiments, the immune checkpoint modulator is an agent that modulates the activity and/or expression of KIR. In some embodiments, the immune checkpoint modulator is an agent that binds to KIR (e.g., an anti-KIR antibody). In some embodiments, the immune checkpoint modulator is a KIR-binding protein (e.g., an antibody). In some embodiments, the checkpoint modulator is an KIR agonist. In some embodiments, the checkpoint modulator is an KR antagonist. In some embodiments the immune checkpoint modulator is lirilumab (also known as BMS-986015; Bristol-Myers Squibb). Additional KTR binding proteins (e.g., antibodies) are known in the art and are disclosed, e.g., in U.S. Pat. Nos. 8,981,065, 9,018,366, 9,067,997, 8,709,411, 8,637,258, 8,614,307, 8,551,483, 8,388,970, 8,119,775; U.S. Patent Application Publication Nos. 2015/0344576, 2015/0376275, 2016/0046712, 2015/0191547, 2015/0290316, 2015/0283234, 2015/0197569, 2014/0193430, 2013/0143269, 2013/0287770, 2012/0208237, 2011/0293627, 2009/0081240, 2010/0189723; and PCT Publication Nos. WO 2016/069589, WO 2015/069785, WO 2014/066532, WO 2014/055648, WO 2012/160448, WO 2012/071411, WO 2010/065939, WO 2008/084106, WO 2006/072625, WO 2006/072626, and WO 2006/003179, each of which is incorporated by reference herein.

LAG-3, Lymphocyte-activation gene 3 (LAG-3, also known as CD223) is a CD4-related transmembrane protein that competitively binds MHC II and acts as a co-inhibitory checkpoint for T cell activation (see, e.g., Goldberg and Drake (2011) Curr. Top. Microbiol. Immunol. 344: 269-78). Multiple immune checkpoint modulators specific for LAG-3 have been developed and may be used as disclosed herein. In some embodiments, the immune checkpoint modulator is an agent that modulates the activity and/or expression of LAG-3. In some embodiments, the immune checkpoint modulator is an agent that binds to LAG-3 (e.g., an anti-PD-1 antibody). In some embodiments, the checkpoint modulator is an LAG-3 agonist. In some embodiments, the checkpoint modulator is an LAG-3 antagonist. In some embodiments, the immune checkpoint modulator is a LAG-3-binding protein (e.g., an antibody) selected from the group consisting of pembrolizumab (Keytruda; formerly lambrolizumab; Merck & Co., Inc.), nivolumab (Opdivo; Bristol-Myers Squibb), pidilizumab (CT-011, CureTech), SHR-1210 (Incyte/Jiangsu Hengrui Medicine Co., Ltd.), MEDIO680 (also known as AMP-514; Amplimmune Inc./Medimmune), PDR001 (Novartis), BGB-A317 (BeiGene Ltd.), TSR-042 (also known as ANBO11; AnaptysBio/Tesaro, Inc.), REGN2810 (Regeneron Pharmaceuticals, Inc./Sanofi-Aventis), and PF-06801591 (Pfizer). Additional PD-1-binding proteins (e.g., antibodies) are known in the art and are disclosed, e.g., in U.S. Pat. Nos. 9,181,342, 8,927,697, 7,488,802, 7,029,674; U.S. Patent Application Publication Nos. 2015/0152180, 2011/0171215, 2011/0171220; and PCT Publication Nos. WO 2004/056875, WO 2015/

036394, WO 2010/029435, WO 2010/029434, WO 2014/194302, each of which is incorporated by reference herein.

PD-1. Programmed cell death protein 1 (PD-1, also known as CD279 and PDCD1) is an inhibitory receptor that negatively regulates the immune system. In contrast to CTLA-4 which mainly affects naïve T cells, PD-1 is more broadly expressed on immune cells and regulates mature T cell activity in peripheral tissues and in the tumor microenvironment. PD-1 inhibits T cell responses by interfering with T cell receptor signaling. PD-1 has two ligands, PD-L1 and PD-L2. Multiple immune checkpoint modulators specific for PD-1 have been developed and may be used as disclosed herein. In some embodiments, the immune checkpoint modulator is an agent that modulates the activity and/or expression of PD-1. In some embodiments, the immune checkpoint modulator is an agent that binds to PD-1 (e.g., an anti-PD-1 antibody). In some embodiments, the checkpoint modulator is an PD-1 agonist. In some embodiments, the checkpoint modulator is an PD-1 antagonist. In some embodiments, the immune checkpoint modulator is a PD-1-binding protein (e.g., an antibody) selected from the group consisting of pembrolizumab (Keytruda; formerly lambrolizumab; Merck & Co., Inc.), nivolumab (Opdivo; Bristol-Myers Squibb), pidilizumab (CT-011, CureTech), SHR-1210 (Incyte/Jiangsu Hengrui Medicine Co., Ltd.), MEDIO680 (also known as AMP-514; Amplimmune Inc./Medimmune), PDR001 (Novartis), BGB-A317 (BeiGene Ltd.), TSR-042 (also known as ANBO11; AnaptysBio/Tesaro, Inc.), REGN2810 (Regeneron Pharmaceuticals, Inc./Sanofi-Aventis), and PF-06801591 (Pfizer). Additional PD-1-binding proteins (e.g., antibodies) are known in the art and are disclosed, e.g., in U.S. Pat. Nos. 9,181,342, 8,927,697, 7,488,802, 7,029,674; U.S. Patent Application Publication Nos. 2015/0152180, 2011/0171215, 2011/0171220; and PCT Publication Nos. WO 2004/056875, WO 2015/036394, WO 2010/029435, WO 2010/029434, WO 2014/194302, each of which is incorporated by reference herein.

PD-L1/PD-L2. PD ligand 1 (PD-L1, also knows as B7-H1) and PD ligand 2 (PD-L2, also known as PDCDILG2, CD273, and B7-DC) bind to the PD-1 receptor. Both ligands belong to the same B7 family as the B7-1 and B7-2 proteins that interact with CD28 and CTLA-4. PD-L1 can be expressed on many cell types including, for example, epithelial cells, endothelial cells, and immune cells. Ligation of PDL-1 decreases IFNγ, TNFα, and IL-2 production and stimulates production of IL10, an anti-inflammatory cytokine associated with decreased T cell reactivity and proliferation as well as antigen-specific T cell anergy. PDL-2 is predominantly expressed on antigen presenting cells (APCs). PDL2 ligation also results in T cell suppression, but where PDL-1-PD-1 interactions inhibits proliferation via cell cycle arrest in the G1/G2 phase, PDL2-PD-1 engagement has been shown to inhibit TCR-mediated signaling by blocking B7:CD28 signals at low antigen concentrations and reducing cytokine production at high antigen concentrations. Multiple immune checkpoint modulators specific for PD-L1 and PD-L2 have been developed and may be used as disclosed herein.

In some embodiments, the immune checkpoint modulator is an agent that modulates the activity and/or expression of PD-L1. In some embodiments, the immune checkpoint modulator is an agent that binds to PD-L1 (e.g., an anti-PD-L1 antibody). In some embodiments, the checkpoint modulator is an PD-L1 agonist. In some embodiments, the checkpoint modulator is an PD-L1 antagonist. In some embodiments, the immune checkpoint modulator is a PD-L1-binding protein (e.g., an antibody or a Fc-fusion protein) selected from the group consisting of durvalumab (also known as MEDI-4736; AstraZeneca/Celgene Corp./Medimmune), atezolizumab (Tecentriq; also known as MPDL3280A and RG7446; Genetech Inc.), avelumab (also known as MSB0010718C; Merck Serono/AstraZeneca); MDX-1105 (Medarex/Bristol-Meyers Squibb), AMP-224 (Amplimmune, GlaxoSmithKline), LY3300054 (Eli Lilly and Co.). Additional PD-L1-binding proteins are known in the art and are disclosed, e.g., in U.S. Patent Application Publication Nos. 2016/0084839, 2015/0355184, 2016/0175397, and PCT Publication Nos. WO 2014/100079, WO 2016/030350, WO2013181634, each of which is incorporated by reference herein.

In some embodiments, the immune checkpoint modulator is an agent that modulates the activity and/or expression of PD-L2. In some embodiments, the immune checkpoint modulator is an agent that binds to PD-L2 (e.g., an anti-PD-L2 antibody). In some embodiments, the checkpoint modulator is an PD-L2 agonist. In some embodiments, the checkpoint modulator is an PD-L2 antagonist. PD-L2-binding proteins (e.g., antibodies) are known in the art and are disclosed, e.g., in U.S. Pat. Nos. 9,255,147, 8,188,238; U.S. Patent Application Publication Nos. 2016/0122431, 2013/0243752, 2010/0278816, 2016/0137731, 2015/0197571, 2013/0291136, 2011/0271358; and PCT Publication Nos. WO 2014/022758, and WO 2010/036959, each of which is incorporated by reference herein.

TIM-3. T cell immunoglobulin mucin 3 (TIM-3, also known as Hepatitis A virus cellular receptor (HAVCR2)) is a A type I glycoprotein receptor that binds to S-type lectin galectin-9 (Gal-9). TIM-3, is a widely expressed ligand on lymphocytes, liver, small intestine, thymus, kidney, spleen, lung, muscle, reticulocytes, and brain tissue. Tim-3 was originally identified as being selectively expressed on IFN-γ-secreting Th1 and Tc1 cells (Monney et al. (2002) Nature 415: 536-41). Binding of Gal-9 by the TIM-3 receptor triggers downstream signaling to negatively regulate T cell survival and function. Multiple immune checkpoint modulators specific for TIM-3 have been developed and may be used as disclosed herein. In some embodiments, the immune checkpoint modulator is an agent that modulates the activity and/or expression of TIM-3. In some embodiments, the immune checkpoint modulator is an agent that binds to TIM-3 (e.g., an anti-TIM-3 antibody). In some embodiments, the checkpoint modulator is an TIM-3 agonist. In some embodiments, the checkpoint modulator is an TIM-3 antagonist. In some embodiments, the immune checkpoint modulator is an anti-TIM-3 antibody selected from the group consisting of TSR-022 (AnaptysBio/Tesaro, Inc.) and MGB453 (Novartis). Additional TIM-3 binding proteins (e.g., antibodies) are known in the art and are disclosed, e.g., in U.S. Pat. Nos. 9,103,832, 8,552,156, 8,647,623, 8,841,418; U.S. Patent Application Publication Nos. 2016/0200815, 2015/0284468, 2014/0134639, 2014/0044728, 2012/0189617, 2015/0086574, 2013/0022623; and PCT Publication Nos. WO 2016/068802, WO 2016/068803, WO 2016/071448, WO 2011/155607, and WO 2013/006490, each of which is incorporated by reference herein.

VISTA. V-domain Ig suppressor of T cell activation (VISTA, also known as Platelet receptor Gi24) is an Ig super-family ligand that negatively regulates T cell responses. See, e.g., Wang et al., 2011, J. Exp. Med. 208: 577-92. VISTA expressed on APCs directly suppresses $CD4^+$ and $CD8^+$ T cell proliferation and cytokine production (Wang et al. (2010) J Exp Med. 208(3): 577-92). Multiple immune checkpoint modulators specific for VISTA have been developed and may be used as disclosed herein. In some embodiments, the immune checkpoint modulator is an agent that modulates the activity and/or expression of VISTA. In some embodiments, the immune checkpoint modulator is an agent that binds to VISTA (e.g., an anti-VISTA antibody). In some embodiments, the checkpoint modulator is an VISTA agonist. In some embodiments, the checkpoint modulator is an VISTA antagonist. In some embodiments, the immune checkpoint modulator is a VISTA-binding protein (e.g., an antibody) selected from the group consisting of TSR-022 (AnaptysBio/Tesaro, Inc.) and MGB453 (Novartis). VISTA-binding proteins (e.g., antibodies) are known in the art and are disclosed, e.g., in U.S. Patent Application Publication Nos. 2016/0096891, 2016/0096891; and PCT Publication Nos. WO 2014/190356, WO 2014/197849, WO 2014/190356 and WO 2016/094837, each of which is incorporated by reference herein.

Methods are provided for the treatment of oncological disorders by administering a composition comprising one or more postcellular signaling factors produced by cells exposed to a stress condition, in combination with at least one immune checkpoint modulator to a subject. In certain embodiments, the immune checkpoint modulator stimulates the immune response of the subject. For example, in some embodiments, the immune checkpoint modulator stimulates or increases the expression or activity of a stimulatory immune checkpoint (e.g. CD27, CD28, CD40, CD122, OX40, GITR, ICOS, or 4-1BB). In some embodiments, the immune checkpoint modulator inhibits or decreases the expression or activity of an inhibitory immune checkpoint (e.g. A2A4, B7-H3, B7-H4, BTLA, CTLA-4, IDO, KIR, LAG3, PD-1, PD-L1, PD-L2, TIM-3 or VISTA).

In certain embodiments the immune checkpoint modulator targets an immune checkpoint molecule selected from the group consisting of CD27, CD28, CD40, CD122, OX40, GITR, ICOS, 4-1BB, A2A4, B7-H3, B7-H4, BTLA, CTLA-4, IDO, KIR, LAG3, PD-1, PD-L1, PD-L2, TIM-3 and VISTA. In certain embodiments the immune checkpoint modulator targets an immune checkpoint molecule selected from the group consisting of CD27, CD28, CD40, CD122, OX40, GITR, ICOS, 4-1BB, A2A4, B7-H3, B7-H4, BTLA, IDO, KIR, LAG3, PD-1, PD-L1, PD-L2, TIM-3 and VISTA. In a particular embodiment, the immune checkpoint modulator targets an immune checkpoint molecule selected from the group consisting of CTLA-4, PD-L1 and PD-1. In a further particular embodiment the immune checkpoint modulator targets an immune checkpoint molecule selected from PD-L1 and PD-1.

In some embodiments, more than one (e.g. 2, 3, 4, 5 or more) immune checkpoint modulator is administered to the subject. Where more than one immune checkpoint modulator is administered, the modulators may each target a stimulatory immune checkpoint molecule, or each target an inhibitory immune checkpoint molecule. In other embodiments, the immune checkpoint modulators include at least one modulator targeting a stimulatory immune checkpoint and at least one immune checkpoint modulator targeting an inhibitory immune checkpoint molecule. In certain embodiments, the immune checkpoint modulator is a binding protein, for example, an antibody. The term "binding protein", as used herein, refers to a protein or polypeptide that can specifically bind to a target molecule, e.g. an immune checkpoint molecule. In some embodiments the binding protein is an antibody or antigen binding portion thereof, and the target molecule is an immune checkpoint molecule. In some embodiments the binding protein is a protein or polypeptide that specifically binds to a target molecule (e.g., an immune checkpoint molecule). In some embodiments the binding protein is a ligand. In some embodiments, the binding protein is a fusion protein. In some embodiments, the binding protein is a receptor. Examples of binding proteins that may be used in the methods of the invention include, but are not limited to, a humanized antibody, an antibody Fab fragment, a divalent antibody, an antibody drug conjugate, a scFv, a fusion protein, a bivalent antibody, and a tetravalent antibody.

The term "antibody", as used herein, refers to any immunoglobulin (Ig) molecule comprised of four polypeptide chains, two heavy (H) chains and two light (L) chains, or any functional fragment, mutant, variant, or derivation thereof. Such mutant, variant, or derivative antibody formats are known in the art. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass. In some embodiments, the antibody is a fill-length antibody. In some embodiments, the antibody is a murine antibody. In some embodiments, the antibody is a human antibody. In some embodiments, the antibody is a humanized antibody. In other embodiments, the antibody is a chimeric antibody. Chimeric and humanized antibodies may be prepared by methods well known to those of skill in the art including CDR grafting approaches (see, e.g., U.S. Pat. Nos. 5,843,708; 6,180,370; 5,693,762; 5,585,089; and 5,530,101), chain shuffling strategies (see, e.g., U.S. Pat. No. 5,565,332; Rader et al. (1998) PROC. NAT'L. ACAD. SCI. USA 95: 8910-8915), molecular modeling strategies (U.S. Pat. No. 5,639,641), and the like.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) NATURE 341: 544-546; and WO 90/05144 A1, the contents of which are herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) SCIENCE 242:423-426; and Huston et al. (1988) PROC. NAT'L. ACAD. SCI. USA 85:5879-5883). Such single chain antibodies are also intended to be encompassed within the term "antigen-binding portion" of an antibody. Other forms of single chain antibodies, such as diabodies are also encompassed. Antigen binding portions can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers found that certain sub-portions within Kabat CDRs adopt nearly identical peptide backbone conformations, despite having great diversity at the level of amino acid sequence (Chothia et al. (1987) J. MOL. BIOL. 196: 901-917, and Chothia et al. (1989) NATURE 342: 877-883). These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan et al. (1995) FASEB J. 9: 133-139, and MacCallum et al. (1996) J. MOL. BIOL. 262(5): 732-45. Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

The term "humanized antibody", as used herein refers to non-human (e.g., murine) antibodies that are chimeric immunoglobulins, immunoglobulin chains, or fragments thereof (such as Fv, Fab, Fab', F(ab')2 or other antigen-binding subsequences of antibodies) which contain minimal sequence derived from a non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al. (1986) NATURE 321: 522-525; Reichmann et al. (1988) NATURE 332: 323-329; and Presta (1992) CURR. OP. STRUCT. BIOL. 2: 593-596, each of which is incorporated by reference herein in its entirety.

The term "immunoconjugate" or "antibody drug conjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the immunoconjugate. Additionally, the immunoconjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

A "bivalent antibody" refers to an antibody or antigen-binding fragment thereof that comprises two antigen-binding sites. The two antigen binding sites may bind to the same antigen, or they may each bind to a different antigen, in which case the antibody or antigen-binding fragment is characterized as "bispecific." A "tetravalent antibody" refers to an antibody or antigen-binding fragment thereof that comprises four antigen-binding sites. In certain embodiments, the tetravalent antibody is bispecific. In certain embodiments, the tetravalent antibody is multispecific, i.e. binding to more than two different antigens.

Fab (fragment antigen binding) antibody fragments are immunoreactive polypeptides comprising monovalent antigen-binding domains of an antibody composed of a polypeptide consisting of a heavy chain variable region ($V_H$) and heavy chain constant region 1 ($C_{H1}$) portion and a poly peptide consisting of a light chain variable (VL) and light chain constant ($C_L$) portion, in which the $C_L$ and $C_{H1}$ portions are bound together, preferably by a disulfide bond between Cys residues.

Immune checkpoint modulator antibodies include, but are not limited to, at least 4 major categories: i) antibodies that block an inhibitory pathway directly on T cells or natural killer (NK) cells (e.g., PD-1 targeting antibodies such as nivolumab and pembrolizumab, antibodies targeting TIM-3, and antibodies targeting LAG-3, 2B4, CD160, A2aR, BTLA, CGEN-15049, and KIR), ii) antibodies that activate stimulatory pathways directly on T cells or NK cells (e.g., antibodies targeting OX40, GITR, and 4-1BB), iii) antibodies that block a suppressive pathway on immune cells or relies on antibody-dependent cellular cytotoxicity to deplete suppressive populations of immune cells (e.g., CTLA-4 targeting antibodies such as ipilimumab, antibodies targeting VISTA, and antibodies targeting PD-L2, Gr1, and Ly6G), and iv) antibodies that block a suppressive pathway directly on cancer cells or that rely on antibody-dependent cellular cytotoxicity to enhance cytotoxicity to cancer cells (e.g., rituximab, antibodies targeting PD-L1, and antibodies targeting B7-H3, B7-H4, Gal-9, and MUC1). Examples of checkpoint inhibitors include, e.g., an inhibitor of CTLA-4, such as ipilimumab or tremelimumab; an inhibitor of the PD-1 pathway such as an anti-PD-1, anti-PD-L1 or anti-PD-L2 antibody. Exemplary anti-PD-1 antibodies are described in WO 2006/121168, WO 2008/156712, WO 2012/145493, WO 2009/014708 and WO 2009/114335. Exemplary anti-PD-L1 antibodies are described in WO 2007/005874, WO 2010/077634 and WO 2011/066389, and exemplary anti-PD-L2 antibodies are described in WO 2004/007679.

In a particular embodiment, the immune checkpoint modulator is a fusion protein, for example, a fusion protein that modulates the activity of an immune checkpoint modulator.

In one embodiment, the immune checkpoint modulator is a therapeutic nucleic acid molecule, for example a nucleic acid that modulates the expression of an immune checkpoint protein or mRNA. Nucleic acid therapeutics are well known in the art. Nucleic acid therapeutics include both single stranded and double stranded (i.e., nucleic acid therapeutics having a complementary region of at least 15 nucleotides in length) nucleic acids that are complementary to a target sequence in a cell. In certain embodiments, the nucleic acid therapeutic is targeted against a nucleic acid sequence encoding an immune checkpoint protein.

Antisense nucleic acid therapeutic agents are single stranded nucleic acid therapeutics, typically about 16 to 30 nucleotides in length, and are complementary to a target nucleic acid sequence in the target cell, either in culture or in an organism.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) Mol Cancer Ther 1:347-355. The antisense RNA molecule may have about 15-30 nucleotides that are complementary to the target mRNA. Patents directed to antisense nucleic acids, chemical modifications, and therapeutic uses include, for example: U.S. Pat. No. 5,898,031 related to chemically modified RNA-containing therapeutic compounds; U.S. Pat. No. 6,107,094 related methods of using these compounds as therapeutic agents; U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality of RNA nucleosides and at least one chemical modification. The entire contents of each of the patents listed in this paragraph are incorporated herein by reference.

Nucleic acid therapeutic agents for use in the methods of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims. The RNAi agents that are used in the methods of the invention include agents with chemical modifications as disclosed, for example, in WO/2012/037254, and WO 2009/073809, the entire contents of each of which are incorporated herein by reference.

Immune checkpoint modulators may be administered at appropriate dosages to treat the oncological disorder, for example, by using standard dosages. One skilled in the art would be able, by routine experimentation, to determine what an effective, non-toxic amount of an immune checkpoint modulator would be for the purpose of treating oncological disorders. Standard dosages of immune checkpoint modulators are known to a person skilled in the art and may be obtained, for example, from the product insert provided by the manufacturer of the immune checkpoint modulator. Examples of standard dosages of immune checkpoint modulators are provided in Table 1 below. In other embodiments, the immune checkpoint modulator is administered at a dosage that is different (e.g. lower) than the standard dosages of the immune checkpoint modulator used to treat the oncological disorder under the standard of care for treatment for a particular oncological disorder.

TABLE 1

Exemplary Standard Dosages of Immune Checkpoint Modulators

| Immune Checkpoint Modulator | Immune Checkpoint Molecule Targeted | Exemplary Standard Dosage |
| --- | --- | --- |
| Ipilimumab (Yervoy ™) | CTLA-4 | 3 mg/kg administered intravenously over 90 minutes every 3 weeks for a total of 4 doses |
| Pembrolizumab (Keytruda ™) | PD-1 | 2 mg/kg administered as an intravenous infusion over 30 minutes every 3 weeks until disease progression or unacceptable toxicity |
| Atezolizumab (Tecentriq ™) | PD-L1 | 1200 mg administered as an intravenous infusion over 60 minutes every 3 weeks |

In certain embodiments, the administered dosage of the immune checkpoint modulator is 5%, 10%, 20%, 30%, 40%, 50%, 60%, 70%, 80%, or 90% lower than the standard dosage of the immune checkpoint modulator for a particular oncological disorder. In certain embodiments, the dosage administered of the immune checkpoint modulator is 95%, 90%, 85%, 80%, 75%, 70%, 65%, 60%, 55%, 50%, 45%, 40%, 35%, 30%, 25%, 20%, 15%, 10% or 5% of the standard dosage of the immune checkpoint modulator for a particular oncological disorder. In one embodiment, where a combination of immune checkpoint modulators are administered, at least one of the immune checkpoint modulators is administered at a dose that is lower than the standard dosage of the immune checkpoint modulator for a particular oncological disorder. In one embodiment, where a combination of immune checkpoint modulators are administered, at least two of the immune checkpoint modulators are administered at a dose that is lower than the standard dosage of the immune checkpoint modulators for a particular oncological disorder. In one embodiment, where a combination of immune checkpoint modulators are administered, at least three of the immune checkpoint modulators are administered at a dose that is lower than the standard dosage of the immune checkpoint modulators for a particular oncological disorder. In one embodiment, where a combination of immune checkpoint modulators are administered, all of the immune checkpoint modulators are administered at a dose that is lower than the standard dosage of the immune checkpoint modulators for a particular oncological disorder.

In some embodiments, additional immunotherapeutics that may be administered in combination with the composition comprising one or more postcellular signaling factors include, but are not limited to, Toll-like receptor (TLR) agonists, cell-based therapies, cytokines and cancer vaccines.

In some embodiments, additional immunotherapeutics that may be administered in combination with the STING agonist and the purinergic receptor agonist include, but are not limited to, Toll-like receptor (TLR) agonists, cell-based therapies, cytokines and cancer vaccines.

2. TLR Agonists

TLRs are single membrane-spanning non-catalytic receptors that recognize structurally conserved molecules derived from microbes. TLRs together with the Interleukin-1 receptor form a receptor superfamily, known as the "Interleukin-1 Receptor/Toll-Like Receptor Superfamily." Members of this family are characterized structurally by an extracellular leucine-rich repeat (LRR) domain, a conserved pattern of juxtamembrane cysteine residues, and an intracytoplasmic signaling domain that forms a platform for downstream signaling by recruiting TIR domain-containing adapters including MyD88, TIR domain-containing adaptor (TRAP), and TIR domain-containing adaptor inducing IFNβ (TRIF) (O'Neill et al., 2007, Nat Rev Immunol 7, 353).

The TLRs include TLR1, TLR2, TLR3, TLR4, TLR5, TLR6, TLR7, TLR8, TLR9, and TLR10. TLR2 mediates cellular responses to a large number of microbial products including peptidoglycan, bacterial lipopeptides, lipoteichoic acid, mycobacterial lipoarabinomannan and yeast cell wall components. TLR4 is a transmembrane protein which belongs to the pattern recognition receptor (PRR) family. Its activation leads to an intracellular signaling pathway NF-κB and inflammatory cytokine production which is responsible for activating the innate immune system. TLR5 is known to recognize bacterial flagellin from invading mobile bacteria, and has been shown to be involved in the onset of many diseases, including inflammatory bowel disease.

TLR agonists are known in the art and are described, for example, in US2014/0030294, which is incorporated by reference herein in its entirety. Exemplary TLR2 agonists include mycobacterial cell wall glycolipids, lipoarabinomannan (LAM) and mannosylated phosphatidylinositol (PIIM), MALP-2 and Pam3Cys and synthetic variants thereof. Exemplary TLR4 agonists include lipopolysaccharide or synthetic variants thereof (e.g., MPL and RC529) and lipid A or synthetic variants thereof (e.g., aminoalkyl glucosaminide 4-phosphates). See, e.g., Cluff et al., 2005, Infection and Immunity, p. 3044-3052:73; Lembo et al., 2008, The *Journal of* Immunology 180, 7574-7581; and Evans et al., 2003, Expert Rev Vaccines 2:219-29. Exemplary TLR5 agonists include flagellin or synthetic variants thereof (e.g., A pharmacologically optimized TLR5 agonist with reduced immunogenicity (such as CBLB502) made by deleting portions of flagellin that are non-essential for TLR5 activation).

Additional TLR agonists include Coley's toxin and Bacille Calmette-Guérin (BCG). Coley's toxin is a mixture consisting of killed bacteria of species *Streptococcus pyogenes* and *Serratia marcescens*. See Taniguchi et al., 2006, Anticancer Res. 26 (6A): 3997-4002. BCG is prepared from a strain of the attenuated live bovine tuberculosis *bacillus, Mycobacterium bovis*. See Venkataswamy et al., 2012, Vaccine. 30 (6): 1038-1049.

3. Cell Based Therapies

Cell-based therapies for the treatment of cancer include administration of immune cells (e.g. T cells, tumor-infiltrating lymphocytes (TILs), Natural Killer cells, and dendritic cells) to a subject. In autologous cell-based therapy, the immune cells are derived from the same subject to which they are administered. In allogeneic cell-based therapy, the immune cells are derived from one subject and administered to a different subject. The immune cells may be activated, for example, by treatment with a cytokine, before administration to the subject. In some embodiments, the immune cells are genetically modified before administration to the subject, for example, as in chimeric antigen receptor (CAR) T cell immunotherapy.

In some embodiments, the cell-based therapy include an adoptive cell transfer (ACT). ACT typically consists of three parts: lympho-depletion, cell administration, and therapy with high doses of IL-2. Types of cells that may be administered in ACT include tumor infiltrating lymphocytes (TILs), T cell receptor (TCR)-transduced T cells, and chimeric antigen receptor (CAR) T cells.

Tumor-infiltrating lymphocytes are immune cells that have been observed in many solid tumors, including breast cancer. They are a population of cells comprising a mixture of cytotoxic T cells and helper T cells, as well as B cells, macrophages, natural killer cells, and dendritic cells. The general procedure for autologous TIL therapy is as follows: (1) a resected tumor is digested into fragments; (2) each fragment is grown in IL-2 and the lymphocytes proliferate destroying the tumor; (3) after a pure population of lymphocytes exists, these lymphocytes are expanded; and (4) after expansion up to $10^{11}$ cells, lymphocytes are infused into the patient. See Rosenberg et al., 2015, Science 348 (6230):62-68, which is incorporated by reference herein in its entirety.

TCR-transduced T cells are generated via genetic induction of tumor-specific TCRs. This is often done by cloning the particular antigen-specific TCR into a retroviral backbone. Blood is drawn from patients and peripheral blood mononuclear cells (PBMCs) are extracted. PBMCs are stimulated with CD3 in the presence of IL-2 and then transduced with the retrovirus encoding the antigen-specific TCR. These transduced PBMCs are expanded further in vitro and infused back into patients. See Robbins et al., 2015, Clinical Cancer Research 21(5):1019-1027, which is incorporated by reference herein in its entirety.

Chimeric antigen receptors (CARs) are recombinant receptors containing an extracellular antigen recognition domain, a transmembrane domain, and a cytoplasmic signaling domain (such as CD3ξ, CD28, and 4-1BB). CARs possess both antigen-binding and T-cell-activating functions. Therefore, T cells expressing CARs can recognize a wide range of cell surface antigens, including glycolipids, carbohydrates, and proteins, and can attack malignant cells expressing these antigens through the activation of cytoplasmic costimulation. See Pang et al., 2018, Mol Cancer 17: 91, which is incorporated by reference herein in its entirety.

In some embodiments, the cell-based therapy is a Natural Killer (NK) cell-based therapy. NK cells are large, granular lymphocytes that have the ability to kill tumor cells without any prior sensitization or restriction of major histocompatibility complex (MHC) molecule expression. See Uppendahl et al., 2017, Frontiers in Immunology 8: 1825. Adoptive transfer of autologous lymphokine-activated killer (LAK) cells with high-dose IL-2 therapy have been evaluated in human clinical trials. Similar to LAK immunotherapy, cytokine-induced killer (CIK) cells arise from peripheral blood mononuclear cell cultures with stimulation of anti-CD3 mAb, IFN-γ, and IL-2. CIK cells are characterized by a mixed T-NK phenotype (CD3+CD56+) and demonstrate enhanced cytotoxic activity compared to LAK cells against ovarian and cervical cancer. Human clinical trials investigating adoptive transfer of autologous CIK cells following primary debulking surgery and adjuvant carboplatin/paclitaxel chemotherapy have also been conducted. See Liu et al., 2014, J Immunother 37(2): 116-122.

In some embodiments, the cell-based therapy is a dendritic cell-based immunotherapy. Vaccination with dendritic cells (DC)s treated with tumor lysates has been shown to increase therapeutic antitumor immune responses both in vitro and in vivo. See Jung et al., 2018, Translational Oncology 11(3): 686-690. DCs capture and process antigens, migrate into lymphoid organs, express lymphocyte costimulatory molecules, and secrete cytokines that initiate immune responses. They also stimulate immunological effector cells (T cells) that express receptors specific for tumor-associated antigens and reduce the number of immune repressors such as CD4+CD25+Foxp3+ regulatory T (Treg) cells. For example, a DC vaccination strategy for renal cell carcinoma (RCC), which is based on a tumor cell lysate-DC hybrid, showed therapeutic potential in preclinical and clinical trials. See Lim et al., 2007, Cancer Immunol Immunother 56: 1817-1829.

4. Cytokines

Several cytokines including IL-2, IL-12, IL-15, IL-18, and IL-21 have been used in the treatment of cancer for activation of immune cells such as NK cells and T cells. IL-2 was one of the first cytokines used clinically, with hopes of inducing antitumor immunity. As a single agent at high dose IL-2 induces remissions in some patients with renal cell carcinoma (RCC) and metastatic melanoma. Low dose IL-2 has also been investigated and aimed at selectively ligating the IL-2 αβγ receptor (IL-2Rαβγ) in an effort to reduce toxicity while maintaining biological activity. See Romee et al., 2014, Scientifica, Volume 2014, Article ID 205796, 18 pages, which is incorporated by reference herein in its entirety.

Interleukin-15 (IL-15) is a cytokine with structural similarity to Interleukin-2 (IL-2). Like IL-2, IL-15 binds to and signals through a complex composed of IL-2/IL-15 receptor beta chain (CD122) and the common gamma chain (gamma-C, CD132). Recombinant IL-15 has been evaluated for treatment of solid tumors (e.g. melanoma, renal cell carcinoma) and to support NK cells after adoptive transfer in cancer patients. See Romee et al., cited above.

IL-12 is a heterodimeric cytokine composed of p35 and p40 subunits (IL-12a and R chains), originally identified as "NK cell stimulatory factor (NKSF)" based on its ability to enhance NK cell cytotoxicity. Upon encounter with pathogens, IL-12 is released by activated dendritic cells and macrophages and binds to its cognate receptor, which is primarily expressed on activated T and NK cells. Numerous preclinical studies have suggested that IL-12 has antitumor potential. See Romee et al., cited above.

IL-18 is a member of the proinflammatory IL-1 family and, like IL-12, is secreted by activated phagocytes. IL-18 has demonstrated significant antitumor activity in preclinical animal models, and has been evaluated in human clinical trials. See Robertson et al., 2006, Clinical Cancer Research 12: 4265-4273.

IL-21 has been used for antitumor immunotherapy due to its ability to stimulate NK cells and CD8+ T cells. For ex vivo NK cell expansion, membrane bound IL-21 has been expressed in K562 stimulator cells, with effective results. See Denman et al., 2012, PLoS One 7(1)e30264. Recombinant human IL-21 was also shown to increase soluble CD25 and induce expression of perforin and granzyme B on CD8+ cells. IL-21 has been evaluated in several clinical trials for treatment of solid tumors. See Romee et al., cited above.

5. Cancer Vaccines

Therapeutic cancer vaccines eliminate cancer cells by strengthening a patients' own immune responses to the cancer, particularly CD8+ T cell mediated responses, with the assistance of suitable adjuvants. The therapeutic efficacy of cancer vaccines is dependent on the differential expression of tumor associated antigens (TAAs) by tumor cells relative to normal cells. TAAs derive from cellular proteins and should be mainly or selectively expressed on cancer cells to avoid either immune tolerance or autoimmunity effects. See Circelli et al., 2015, Vaccines 3(3): 544-555. Cancer vaccines include, for example, dendritic cell (DC) based vaccines, peptide/protein vaccines, genetic vaccines, and tumor cell vaccines. See Ye et al., 2018, J Cancer 9(2): 263-268.

The combination therapies of the present invention may be utilized for the treatment of oncological disorders.

In some embodiments, the combination therapy of the one or more posteellular signaling factors and the additional therapeutic agent inhibits tumor cell growth. Accordingly, the invention further provides methods of inhibiting tumor cell growth in a subject, comprising administering a composition comprising one or more postcellular signaling factors and at least one additional therapeutic agent to the subject, such that tumor cell growth is inhibited. In certain embodiments, treating cancer comprises extending survival or extending time to tumor progression as compared to a control. In some embodiments, the control is a subject that is treated with the additional therapeutic agent, but is not treated with the composition comprising one or more postcellular signaling factors. In some embodiments, the control is a subject that is treated with the composition comprising one or more postcellular signaling factors, but is not treated with the additional therapeutic agent. In some embodiments, the control is a subject that is not treated with the additional therapeutic agent or the composition comprising one or more postcellular signaling factors. In certain embodiments, the subject is a human subject. In some embodiments, the subject is identified as having a tumor prior to administration of the first dose of the composition comprising one or more postcellular signaling factors or the first dose of the additional therapeutic agent. In certain embodiments, the subject has a tumor at the time of the first administration of the composition comprising one or more postcellular signaling factors or at the time of first administration of the additional therapeutic agent.

In certain embodiments, at least 1, 2, 3, 4, or 5 cycles of the combination therapy are administered to the subject. The subject is assessed for response criteria at the end of each cycle. The subject is also monitored throughout each cycle for adverse events (e.g., clotting, anemia, liver and kidney function, etc.) to ensure that the treatment regimen is being sufficiently tolerated.

It should be noted that more than one additional therapeutic agent, e.g., 2, 3, 4, 5, or more additional therapeutic agents, may be administered in combination with the composition comprising one or more postcellular signaling factors.

In one embodiment, administration of the composition comprising one or more postcellular signaling factors and the additional therapeutic agent as described herein results in one or more of reducing tumor size, weight or volume, increasing time to progression, inhibiting tumor growth and/or prolonging the survival time of a subject having an oncological disorder. In certain embodiments, administration of the composition comprising one or more postcellular signaling factors and the additional therapeutic agent reduces tumor size, weight or volume, increases time to progression, inhibits tumor growth and/or prolongs the survival time of the subject by at least 1%, 2%, 3%, 4%, 5%, 10%, 20%, 30%, 40%, 50%, 60%, 70%, 80%, 90%, 100%, 200%, 300%, 400% or 500% relative to a corresponding control subject that is administered the composition comprising one or more posteellular signaling factors alone or the additional therapeutic agent alone. In certain embodiments, administration of the composition comprising one or more postcellular signaling factors and the additional therapeutic agent reduces tumor size, weight or volume, increases time to progression, inhibits tumor growth and/or prolongs the survival time of a population of subjects afflicted with an oncological disorder by at least 1%, 2%, 3%, 4%, 5%, 10%, 20%, 30%, 40%, 50%, 60%, 70%, 80%, 90%, 100%, 200%, 300%, 400% or 500% relative to a corresponding population of control subjects afflicted with the oncological disorder that is administered the composition comprising one or more postcellular signaling factors alone or the additional therapeutic agent alone. In other embodiments, administration of the composition comprising one or more postcellular signaling factors and the additional therapeutic agent stabilizes the oncological disorder in a subject with a progressive oncological disorder prior to treatment.

In certain embodiments, treatment with the composition comprising one or more postcellular signaling factors and the additional therapeutic agent (e.g. an immunotherapeutic) is combined with a further anti-neoplastic agent such as the standard of care for treatment of the particular cancer to be treated, for example by administering a standard dosage of one or more antineoplastic (e.g. chemotherapeutic) agents. The standard of care for a particular cancer type can be determined by one of skill in the art based on, for example, the type and severity of the cancer, the age, weight, gender, and/or medical history of the subject, and the success or failure of prior treatments. In certain embodiments of the invention, the standard of care includes any one of or a combination of surgery, radiation, hormone therapy, antibody therapy, therapy with growth factors, cytokines, and chemotherapy. In one embodiment, the additional antineoplastic agent is not an agent that induces iron-dependent cellular disassembly and/or an immune checkpoint modulator.

In some embodiments, the combination therapy of the STING agonist and purinergic receptor agonist and the additional therapeutic agent inhibits tumor cell growth. Accordingly, the invention further provides methods of inhibiting tumor cell growth in a subject, comprising administering a STING agonist, a purinergic receptor agonist, and at least one additional therapeutic agent to the subject, such that tumor cell growth is inhibited. In certain embodiments, treating cancer comprises extending survival or extending time to tumor progression as compared to a control. In some embodiments, the control is a subject that is treated with the additional therapeutic agent, but is not treated with the STING agonist and/or purinergic receptor agonist. In some embodiments, the control is a subject that is treated with the STING agonist and purinergic receptor agonist, but is not treated with the additional therapeutic agent. In some embodiments, the control is a subject that is not treated with the additional therapeutic agent, the STING agonist, or the purinergic receptor agonist. In certain embodiments, the subject is a human subject. In some embodiments, the subject is identified as having a tumor prior to administration of the first dose of the STING agonist and/or purinergic receptor agonist or the first dose of the additional therapeutic agent. In certain embodiments, the subject has a tumor at the time of the first administration of the STING agonist and/or purinergic receptor agonist, or at the time of first administration of the additional therapeutic agent.

In certain embodiments, at least 1, 2, 3, 4, or 5 cycles of the combination therapy comprising the STING agonist, purinergic receptor agonist and one or more additional therapeutic agents are administered to the subject. The subject is assessed for response criteria at the end of each cycle. The subject is also monitored throughout each cycle for adverse events (e.g., clotting anemia, liver and kidney function, etc.) to ensure that the treatment regimen is being sufficiently tolerated.

It should be noted that more than one additional therapeutic agent, e.g., 2, 3, 4, 5, or more additional therapeutic agents, may be administered in combination with the STING agonist and purinergic receptor agonist.

In one embodiment, administration of the STING agonist, the purinergic receptor agonist and the additional therapeutic agent as described herein results in one or more of, reducing tumor size, weight or volume, increasing time to progression, inhibiting tumor growth and/or prolonging the survival time of a subject having an oncological disorder. In certain embodiments, administration of the STING agonist, the purinergic receptor agonist and the additional therapeutic agent reduces tumor size, weight or volume, increases time to progression, inhibits tumor growth and/or prolongs the survival time of the subject by at least 1%, 2%, 3%, 4%, 5%, 10%, 20%, 30%, 40%, 50%, 60%, 70%, 80%, 90%, 100%, 200%, 300%, 400% or 500% relative to a corresponding control subject that is administered the STING agonist and the purinergic receptor agonist, but is not administered the additional therapeutic agent. In certain embodiments, administration of the STING agonist, the purinergic receptor agonist and the additional therapeutic agent reduces tumor size, weight or volume, increases time to progression, inhibits tumor growth and/or prolongs the survival time of a population of subjects afflicted with an oncological disorder by at least 1%, 2%, 3%, 4%, 5%, 10%, 20%, 30%, 40%, 50%, 60%, 70%, 80%, 90%, 100%, 200%, 300%, 400% or 500% relative to a corresponding population of control subjects afflicted with the oncological disorder that is administered the STING agonist and purinergic receptor agonist, but is not administered the additional therapeutic agent. In other embodiments, administration of the STING agonist, the purinergic receptor agonist and the additional therapeutic agent stabilizes the oncological disorder in a subject with a progressive oncological disorder prior to treatment.

In certain embodiments, treatment with the STING agonist, the purinergic receptor agonist and the additional therapeutic agent (e.g. an immunotherapeutic) is combined with a further anti-neoplastic agent such as the standard of care for treatment of the particular cancer to be treated, for example by administering a standard dosage of one or more antineoplastic (e.g. chemotherapeutic) agents. The standard of care for a particular cancer type can be determined by one of skill in the art based on, for example, the type and severity of the cancer, the age, weight, gender, and/or medical history of the subject, and the success or failure of prior treatments. In certain embodiments of the invention, the standard of care includes any one of or a combination of surgery, radiation, hormone therapy, antibody therapy, therapy with growth factors, cytokines, and chemotherapy. In one embodiment, the additional anti-neoplastic agent is not an agent that induces iron-dependent cellular disassembly and/or an immune checkpoint modulator.

Additional anti-neoplastic agents suitable for use in the methods disclosed herein include, but are not limited to, chemotherapeutic agents (e.g., alkylating agents, such as Altretamine, Busulfan, Carboplatin, Carmustine, Chlorambucil, Cisplatin, Cyclophosphamide, Dacarbazine, Lomustine, Melphalan, Oxaliplatin, Temozolomide, Thiotepa; antimetabolites, such as 5-fluorouracil (5-FU), 6-mercaptopurine (6-MP); Capecitabine (Xeloda®), Cytarabine (Ara-C®), Floxuridine, Fludarabine, Gemcitabine (Gemzar®), Hydroxyurea, Methotrexate, Pemetrexed (Alimta®); anti-tumor antibiotics such as anthracyclines (e.g., Daunorubicin, Doxorubicin (Adriamycin®), Epirubicin, Idarubicin), Actinomycin-D, Bleomycin, Mitomycin-C, Mitoxantrone (also acts as a topoisomerase II inhibitor); topoisomerase inhibitors, such as Topotecan, Irinotecan (CPT-11), Etoposide (VP-16), Teniposide, Mitoxantrone (also acts as an anti-tumor antibiotic); mitotic inhibitors such as Docetaxel, Estramustine, Ixabepilone, Paclitaxel, Vinblastine, Vincristine, Vinorelbine; corticosteroids such as Prednisone, Methylprednisolone (Solumedrol®), Dexamethasone (Decadron®); enzymes such as L-asparaginase, and bortezomib (Velcade®)). Anti-neoplastic agents also include biologic anti-cancer agents, e.g., anti-TNF antibodies, e.g., adalimumab or infliximab; anti-CD20 antibodies, such as rituximab, anti-VEGF antibodies, such as bevacizumab; anti-HIER2 antibodies, such as trastuzumab; anti-RSV, such as palivizumab.

VII. Methods for Identification of Agents that Induce Cellular Disassembly and Production of Immunostimulatory Postcellular Signaling Factors In addition to the agents that induce cellular disassembly and production of immunostimulatory postcellular signaling factors known in the art and described herein, the disclosure further relates to methods for identifying other compounds that induce cellular disassembly and production of immunostimulatory postcellular signaling factors.

For example, in certain aspects, the disclosure relates to a method of screening for an agent that induces production of immunostimulatory postcellular signaling factors in a cell, the method comprising: (a) providing a plurality of test agents (e.g., a library of test agents); and (b) evaluating each of the plurality of test agents for the ability to induce production of immunostimulatory postcellular signaling factors in a cell.

In some embodiments, evaluating the test agents for the ability to induce production of immunostimulatory postcellular signaling factors comprises contacting cells or tissue with each of the plurality of test agents.

Any of the methods described herein for evaluating immune response may be used for evaluating the test agents for the ability to induce production of immunostimulatory postcellular signaling factors.

In one embodiment, evaluating each of the plurality of test agents for the ability to induce production of immunostimulatory postcellular signaling factors in a cell comprises culturing an immune cell together with cells contacted with each of the plurality of test agents or exposing an immune cell to postcellular signaling factors produced by cells contacted with each of the plurality of test agents and measuring the level or activity of NFκB, IRF or STING in the immune cell.

In one embodiment, the immune cell is a THP-1 cell. For example, NFκB and IRF activity may be measured in commercially available TH1-Dual cells (InvivoGen, San Diego, Calif.). TH1-Dual cells are human monocyte cells that induce reporter proteins upon activation of either NFKB or IRF pathways. The THP-1 cells may be cultured with cells contacted with the test agents or exposed to postcellular signaling factors produced by cells contacted with the test agents and then mixed with either 200 µl QuantiBlue (InvivoGen, San Diego, Calif.) or 50 µl QuantiLuc for detection of NFKB and IRF activity. NFKB and IRF activity may be quantified by measuring absorbance or luminescence on a Molecular Devices plate reader.

In one embodiment, evaluating each of the plurality of test agents comprises culturing T cells together with cells contacted with the test agents or exposing T cells to postcellular signaling factors produced by cells contacted with the test agents and measuring the activation and proliferation of the T cells.

In one embodiment, the immune cell is a macrophage. For example, NFκB and IRF activity may be measured in commercially available Raw-Dual™ and J774-Dual™ macrophage cells (InvivoGen, San Diego, Calif.). Raw-Dual™ and J774-Dual™ cells are mouse macrophage cell lines that induce reporter proteins upon activation of either NFKB or IRF pathways. The macrophage cells may be cultured with cells contacted with the selected candidate immunostimulatory agent or exposed to postcellular signaling factors produced by cells contacted with the selected candidate immunostimulatory agent and then mixed with either 200 µl QuantiBlue (InvivoGen, San Diego, Calif.) or 50 µl QuantiLuc for detection of NFKB and IRF activity. NFKB and IRF activity may be quantified by measuring absorbance or luminescence on a Molecular Devices plate reader.

In one embodiment, the immune cell is a dendritic cell. For example, co-stimulatory markers (e.g. CD80, CD86) or markers of enhanced antigen presentation (e.g. MHCII) can be measured in dendritic cells by flow cytometry. The dendritic cells may be cultured with cells contacted with the selected candidate immunostimulatory agent or exposed to compounds produced by cells contacted with the selected candidate immunostimulatory agent and then stained with antibodies specific to cell surface markers indicative of activation status. Subsequently, the expression level of these markers is determined by flow cytometry.

The ability of the test agents to induce production of immunostimulatory postcellular signaling factors may also be evaluated by measuring pro-immune cytokine levels in macrophages and/or dendritic cells. For example, in some embodiments, evaluating the test agents comprises culturing macrophage cells and/or dendritic cells with cells contacted with the test agents or contacting macrophage cells and/or dendritic cells with postcellular signaling factors produced by cells contacted with the test agents and measuring levels of pro-immune cytokines (e.g. IFN-α, IL-1, IL-12, IL-18, IL-2, IL-15, IL-4, IL-6, TNF-α, IL-17 and GMCSF). Pro-immune cytokine levels may be determined by methods known in the art, such as ELISA.

VIII. Methods for Identification of Immunostimulatory Postcellular Signaling Factors Produced by Cells Exposed to a Stress Condition Applicants have shown that treatment of cells with particular stress conditions (e.g. nutrient deprivation) results in the production and release of postcellular signaling factors that increase immune activity. These immunostimulatory postcellular signaling factors may be used in the treatment of disorders that may benefit from increased immune activity, such as cancer and infections.

For example, in certain aspects, the disclosure relates to a method of identifying an immunostimulatory postcellular signaling factor, the method comprising: (a) exposing a cell to a stress condition; (b) isolating one or more postcellular signaling factors produced by the cell after exposure to the stress condition; and (c) assaying the one or more postcellular signaling factors for the ability to stimulate immune response.

The one or more postcellular signaling factors produced by the cell may be isolated, for example, by separating the cell from the medium in which it is grown (e.g. by centrifugation) and subjecting this conditioned medium to further analysis. For example, in some embodiments, the conditioned medium is extracted with organic solvent followed by HPLC fractionation. In other embodiments, the conditioned medium is subjected to size exclusion chromatography and different fractions are collected. For example, conditioned medium may be applied to a size exclusion column and fractionated on FPLC.

The ability of the postcellular signaling factors to modulate immune response may be assayed by contacting the postcellular signaling factors with an immune cell and evaluating immune activity. Any of the methods described herein for measuring immune response such as measuring the level or activity of NFkB, IRF and/or STING, the level or activity of macrophages, the level or activity of monocytes, the level or activity of dendritic cells, the level or activity of CD4+, CD8+ or CD3+ cells, the level or activity of T cells, and the level or activity of a pro-immune cytokine may be used to measure the ability of the postcellular signaling factors to modulate immune response. For example, in some embodiments, collected fractions containing the postcellular signaling factors are applied to THP-1 Dual cells and NFKB and/or IRF1 reporter activity is assessed. Positive hit fractions are confirmed by their ability to induce NFKB or IRF activity in THP1 Dual cells. Positive hit fractions may be further characterized by mass spectrometry (large molecules) or NMR (small molecules) to identify particular compounds with immune activity. The immune activity of the individual compounds or species may be tested by the addition of synthetic or recombinant forms of such compounds or species to THP1 Dual Cells followed by measurement of NFKB or IRF activity, as described above.

The immune activity of the posteellular signaling factors may be determined by applying the postcellular signaling factors to macrophages, monocytes, dendritic cells, CD4+, CD8+ or CD3+ cells, and/or T cells and measuring the level or activity of the cells. For example, in one embodiment, the assaying comprises treating an immune cell with the one or more postcellular signaling factors and measuring the level or activity of NFκB activity in the immune cell. In one embodiment, the assaying comprises treating T cells with the one or more postcellular signaling factors and measuring the activation or proliferation of the T cells. In one embodiment, the assaying comprises contacting an immune cell with the one or more postcellular signaling factors and measuring the level or activity of NFκB, IRF or STING in the immune cell. In one embodiment, the immune cell is a THP-1 cell.

The immunostimulatory activity of the postcellular signaling factors may also be evaluated in animal models, e.g. an animal cancer model. For example, in some embodiments, a postcellular signaling factor is administered to an animal and an immune response is measured in the animal, for example, by measuring changes in the level or activity of NFκB, IRF and/or STING, the level or activity of macrophages, the level or activity of monocytes, the level or activity of dendritic cells, the level or activity of CD4+, CD8+ or CD3+ cells, the level or activity of T cells, and the level or activity of a pro-immune cytokine after administration of the postcellular signaling factor.

In one embodiment, the method further comprises selecting a postcellular signaling factor that stimulates immune response.

Postcellular signaling factors that are produced at higher levels in cells exposed to a stress condition relative to cells that are not exposed to a stress condition may be identified by comparing levels of postcellular signaling factors in treated and untreated cells. For example, in one embodiment, the method further comprises: i) measuring the level of the one or more postcellular signaling factors produced by the cell after exposure to the stress condition; ii) comparing the level of the one or more postcellular signaling factors produced by the cell after exposure to the stress condition to the level of the one or more test agents in a control cell that is not exposed to the stress condition; and iii) selecting postcellular signaling factors that exhibit increased levels in the cell exposed to the stress condition relative to the control cell to generate the one or more postcellular signaling factors for assaying in step (c).

In certain aspects, the disclosure provides methods of decreasing immune response by administering to a cell, tissue or subject a purinergic receptor antagonist alone or in combination with a Stimulator of Interferon Genes (STING) antagonist. The decrease in immune response may be used, for example, for treatment of a disorder such as an autoimmune disorder, allergy, or an inflammatory disorder.

IX. Purinergic Receptor Antagonists

Purinergic receptors, also known as purinoceptors, are a family of plasma membrane molecules that are found in almost all mammalian tissues. Within the field of purinergic signalling, these receptors have been implicated in learning and memory, locomotor and feeding behavior, and sleep. More specifically, they are involved in several cellular functions, including proliferation and migration of neural stem cells, vascular reactivity, apoptosis and cytokine secretion. These functions have not been well characterized and the effect of the extracellular microenvironment on their function is also poorly understood.

There are five known distinct classes of purinergic receptors, known as P1, P2X, P2Y, P2Z, P2U and P2T receptors, and they are so classified based on their respective activation molecules. For instance, P1 receptors such as $A_1$, $A_{2A}$, $A_{2B}$ and $A_3$ receptors, are G protein-coupled receptors activated by adenosine. P2Y receptors, such as P2Y2, P2Y4 P2Y6, P2Y11, P2Y12, P2Y13 and P2Y14, are also G protein-coupled receptors but are activated by nucleotides such as ATP, ADP, UTP, UDP and UDP-glucose. P2X receptors are ligand-gated ion channels activated by ATP.

The term "purinergic receptor antagonist" as used herein refers to any chemical entity, including but not limited to a small molecule, a nucleoside, a nucleotide, a nucleobase, a sugar, a nucleic acid, an amino acid, a polysaccharide, a peptide, a polypeptide, a protein, an antibody, an aptamer (e.g., DNA/RNA/XNA/peptide aptamers) or a complex comprising any combination of the aforementioned chemical entities, that inhibits a purinergic receptor.

In one embodiment, the purinergic receptor antagonist used in a method of the invention is a P2 receptor antagonist. In one embodiment, the purinergic receptor antagonist is a P2Y receptor antagonist (e.g., P2Y1, P2Y2, P2Y4, P2Y6, P2Y11 or P2Y12 receptor antagonist). In one embodiment, the purinergic receptor antagonist is a P2Y2, P2Y4 or P2Y6 receptor antagonist. In one embodiment, the purinergic receptor antagonist is a P2Y1 receptor antagonist. In one embodiment, the purinergic receptor antagonist is a P2Y2 receptor antagonist. In one embodiment, the purinergic receptor antagonist is a P2Y4 receptor antagonist. In another embodiment, the purinergic receptor antagonist is a P2Y6 receptor antagonist. In one embodiment, the purinergic receptor antagonist is a P2Y11 receptor antagonist. In one embodiment, the purinergic receptor antagonist is a P2Y12 receptor antagonist.

A "P2Y receptor antagonist" as used herein refers to any chemical entity, including but not limited to a small molecule, a nucleoside, a nucleotide, a nucleobase, a sugar, a nucleotide-sugar, an N-acetylated nucleotide-sugar, a nucleic acid, an amino acid, a polysaccharide, a peptide, a polypeptide, a protein, an antibody, an aptamer (e.g., DNA/RNA/XNA/peptide aptamers) or a complex comprising any combination of the aforementioned chemical entities, that inhibits a P2Y receptor (e.g., P2Y1, P2Y2, P2Y4, P2Y6, P2Y11 or P2Y12 receptor agonist).

P2Y receptors initiate an intracellular cascade of events that lead to an increase in the cytosolic concentration of calcium ions. Accordingly, a P2Y receptor antagonist may be identified by treating a cell with a chemical entity and a known P2Y receptor agonist (e.g. UTP) and measuring intracellular calcium ion concentrations. For example, commercially available fluorescent dyes such as fluo-4 and fura-2 (Thermo Fisher Scientific, Waltham, Mass.) that fluoresce at greater intensity when bound to $Ca^{2+}$ may be used to measure intracellular $Ca^{2+}$ concentrations. Cells such as 1321N1 astrocytoma cells may be stably transfected with a P2Y receptor for use in the assay. Fluorescence may be measured, for example, by using a TriStar LB 942 plate reader (Berthold Technologies GmbH & Co. KG, Bad Wildbad, Germany). A decrease in intracellular $Ca^{2+}$ concentrations in response to treatment with the chemical entity and the P2Y receptor agonist relative to treatment with the P2Y receptor agonist alone would indicate that the chemical entity is a P2Y receptor antagonist.

In some embodiments, the P2Y receptor antagonist inhibits activation of Phospholipase-C (PLC) and/or Protein Kinase-C (PKC). Accordingly, in some embodiments, a P2Y receptor antagonist may be identified by treating a cell with a chemical entity and a known P2Y receptor agonist and assaying for PLC and/or PKC activity using utilizing assays commonly known in the art, for example as described in (Durban et al., 2007, European *Journal of* Lipid Science and Technology 109(5): 469-473; and Glickman et al., 2004, Assay Guidance Manual, Editors Sittampalam et al., Eli Lilly & Company and the National Center for Advancing Translational Sciences, Bethesda (Md.); the entire content of each of which is incorporated by reference herein in its entirety. A decrease in PLC and/or PKC activation in response to treatment with the combination of the chemical entity and the P2Y receptor agonist relative to the P2Y receptor agonist alone would indicate that the chemical entity is a P2Y receptor antagonist.

In some embodiments, the P2Y2 receptor antagonist regulates chemotaxis of macrophages and immune cells. In some embodiments, the P2Y2 receptor antagonist regulates neutrophil degranulation. In some embodiments, the P2Y2 receptor antagonist regulates proliferation and migration of smooth muscle cells. In some embodiments, the P2Y2 receptor antagonist regulates secretion of chloridion in epithelial cells. In some embodiments, the P2Y2 receptor antagonist regulates secretion of water and mucin from epithelial cells. Accordingly, in some embodiments, a P2Y2 receptor antagonist may be identified by assaying for any one or more of chemotaxis of macrophages and immune cells, neutrophil degranulation, proliferation and migration of smooth muscle cells, secretion of chloridion in epithelial cells, and/or secretion of water and mucin from epithelial cells using assays commonly known in the art, for example as described in Xu et al., 2018, Bioorganic and Medicinal Chemistry 26: 366-374; and Linden et al., 2019, Annual Review of Immunology 37:325-47, Liu et al., 2012, Med Chem 20: 1155; Muller et al., 2017, Oncotarget 8: 35962-72; the contents of each of which are incorporated by reference herein in their entirety. A modulation of chemotaxis of macrophages and immune cells, neutrophil degranulation, proliferation and migration of smooth muscle cells, secretion of chloridion in epithelial cells, and/or secretion of water and mucin from epithelial cells in response to treatment with the chemical entity and a known P2Y receptor agonist relative to the P2Y receptor agonist alone would indicate that the chemical entity is a P2Y (e.g., P2Y2) receptor antagonist.

In one embodiment, the purinergic receptor antagonist (e.g., P2Y receptor antagonist, such as a P2Y2, P2Y4 or P2Y6 receptor antagonist) is a small molecule compound or a nucleotide as defined herein. Non-limiting examples of small molecule and nucleotide-based purinergic receptor antagonists (e.g., P2Y2, P2Y4 or P2Y6 receptor antagonist) are described in International Patent Application Nos. WO 2004/047749, WO 2011/054947, WO 2012/114268, WO 2014/097140, WO 2014/115072, WO 2014/057078, WO 2014/057080, WO 2015/118019, WO 2012/036193, U.S. Pat. Nos. 8,106,073, 7,964,616, 7,709,469, 7,723,367, 7,741,493, 7,923,448, 8,580,812, US Patent Application Publication Nos. 2012/0264708, 2014/0037576, 2012/0034165, 2011/0267708, 2015/0004179, 2010/0105068, 2010/0286390, 2010/0184802, 2012/0172366, 2012/0190680, 2014/0163035, 2014/0275096, 2014/0275120, 2014/0275015, 2014/0275056, 2011/0092481, 2012/0157494, 2012/0149718, 2011/0071143, 2011/0028502, 2012/0157436, 2010/0311749, 2011/0046137, 2010/0075968, EP Patent Application Publication Nos. 1448535 and 2604265, and Park et al. (*Expert Opinion on Therapeutic Patents*, 2017, 27(3): 257-267.

In one embodiment, the purinergic receptor antagonist (e.g., P2Y receptor antagonist, such as a P2Y2, P2Y4 or P2Y6 receptor antagonist) is a compound selected from the following:

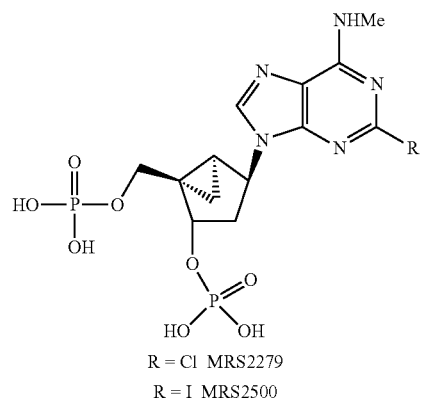
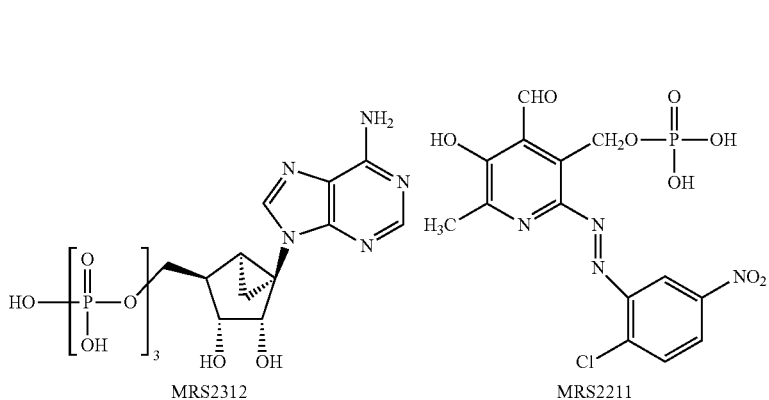
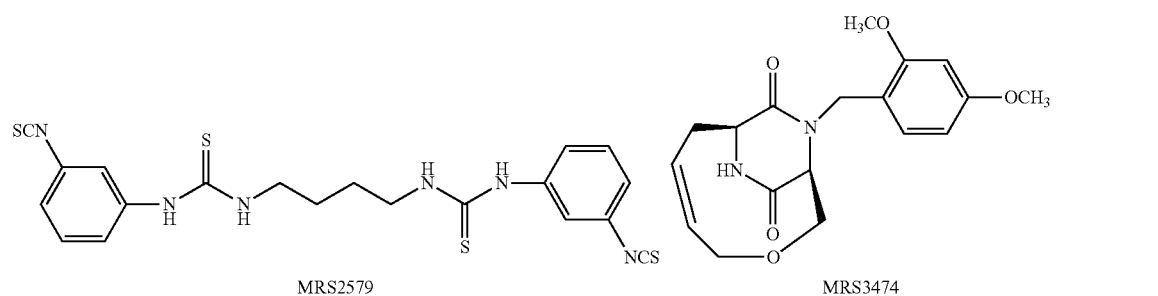
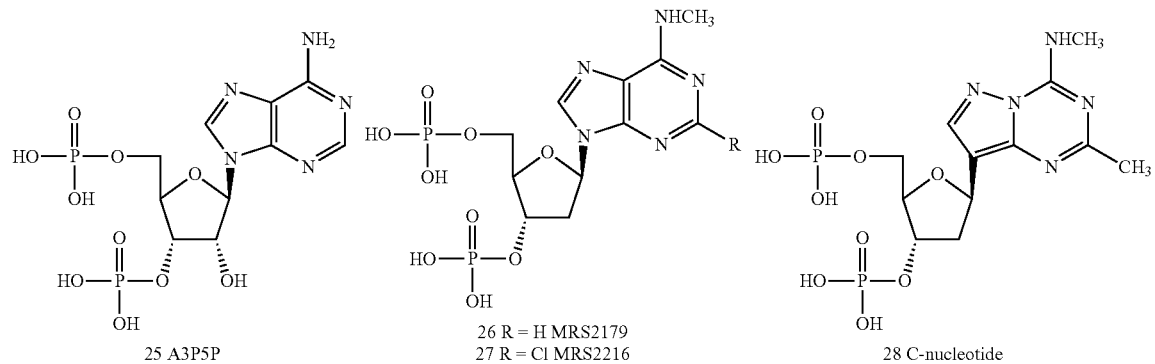
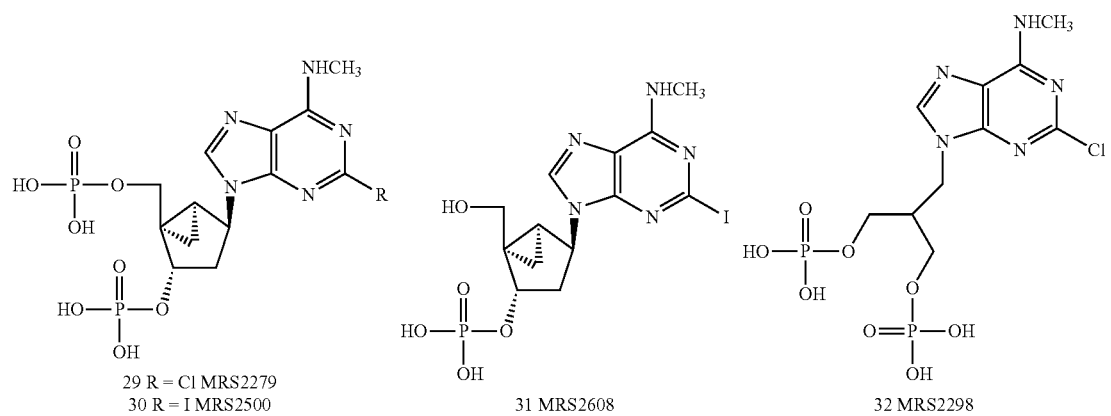

145 146
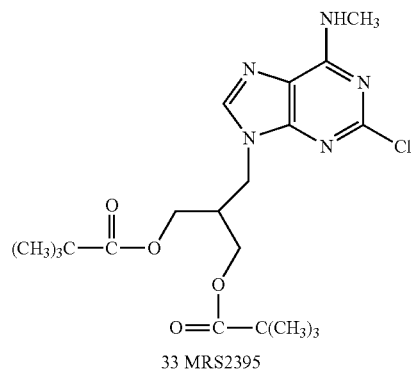
33 MRS2395
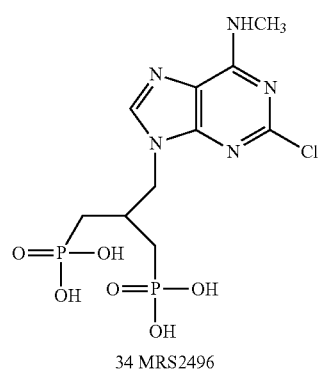
34 MRS2496
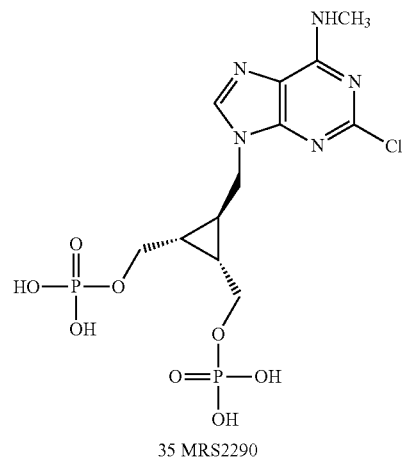
35 MRS2290
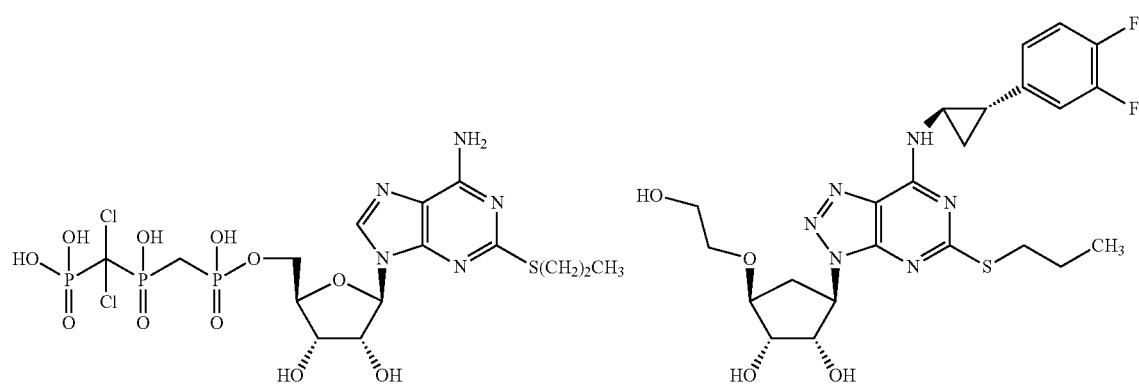
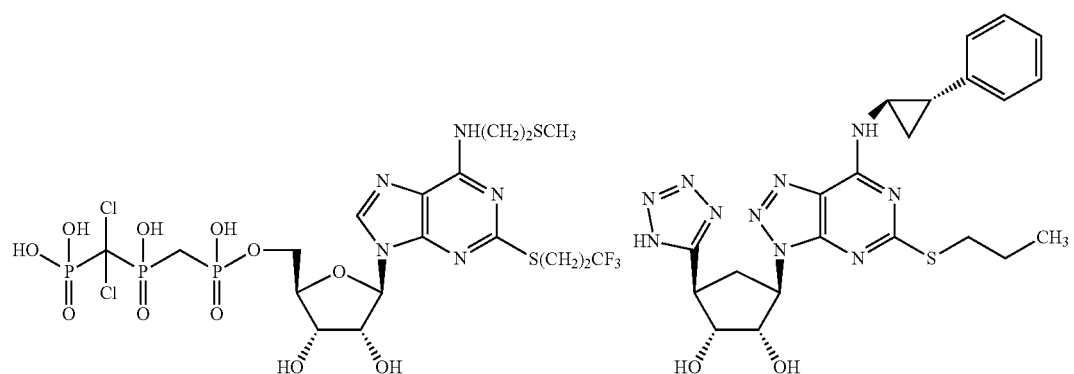

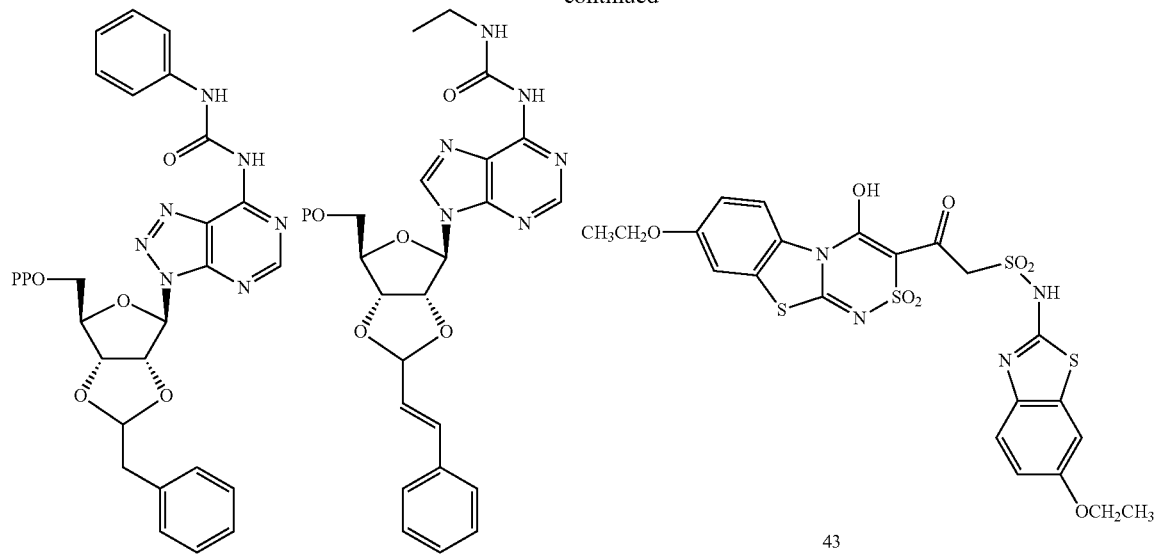
43
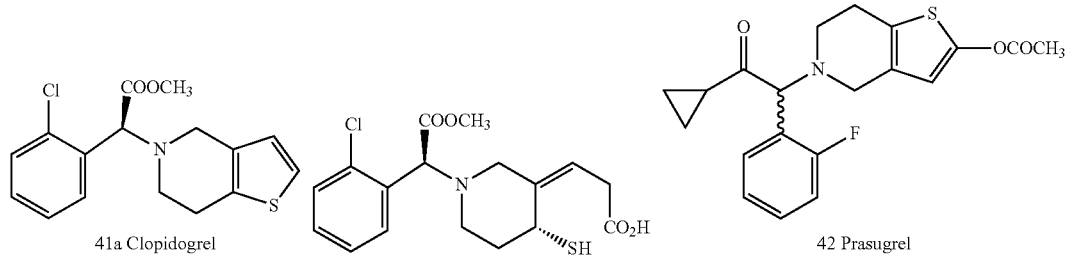
41a Clopidogrel
42 Prasugrel
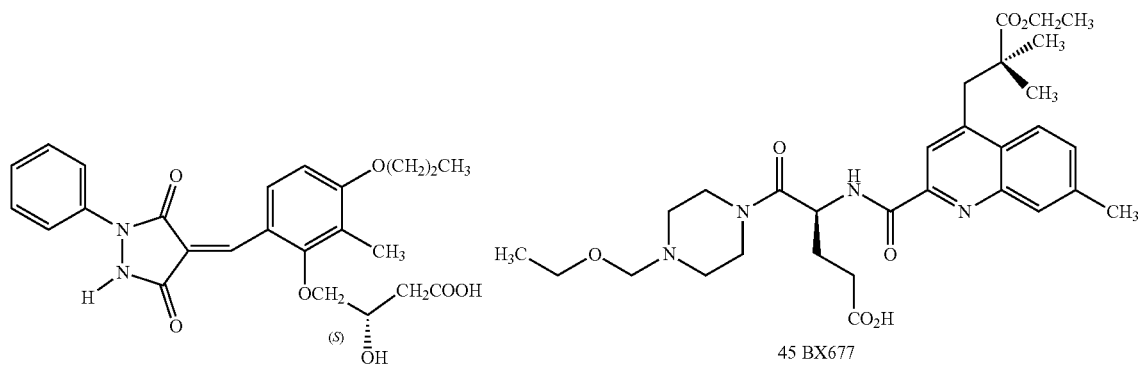
45 BX677
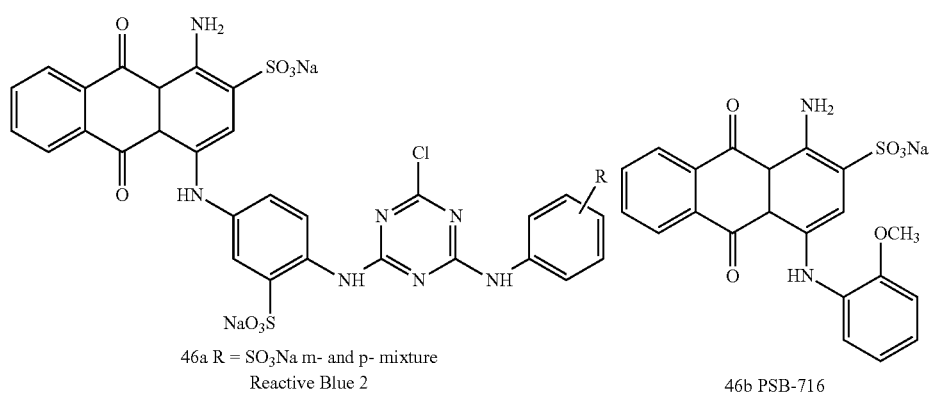
46a R = SO3Na m- and p- mixture
Reactive Blue 2
46b PSB-716

-continued
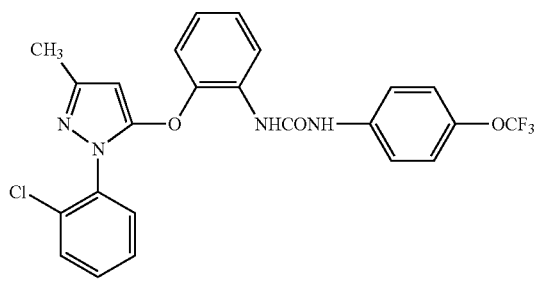
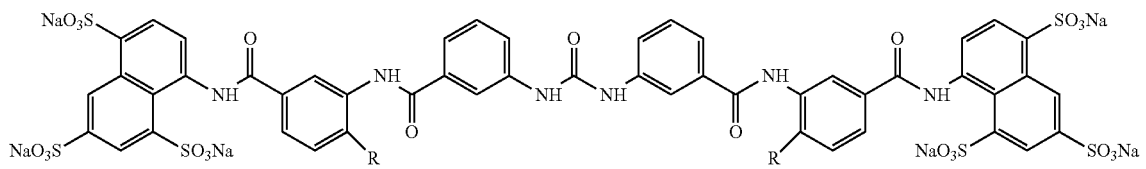
48a R = CH₃ Suramin
48b R = F NF157
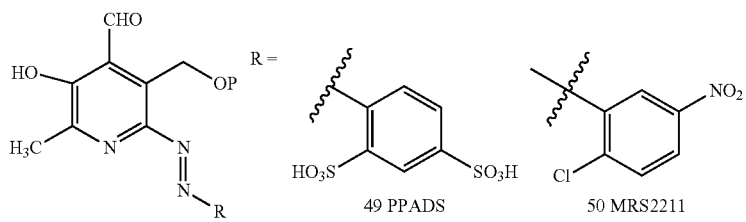
49 PPADS
50 MRS2211
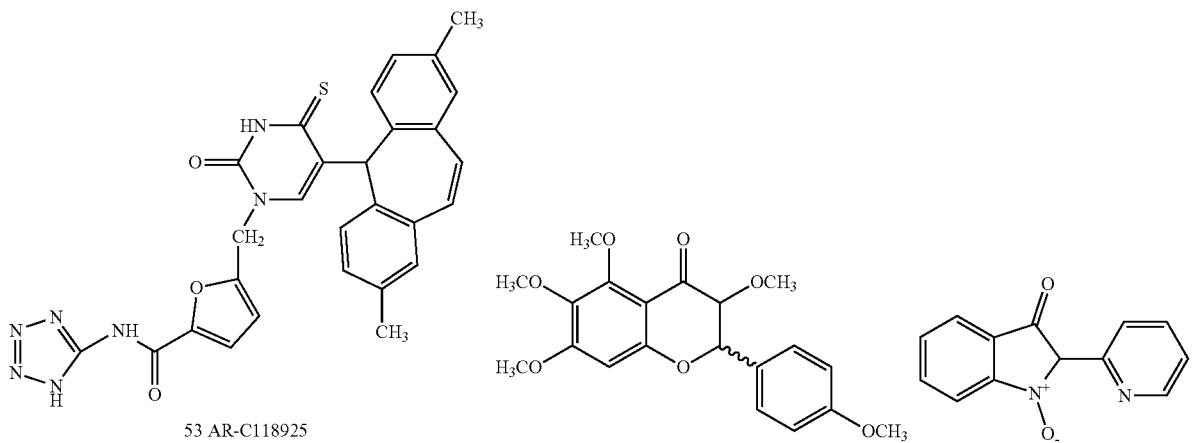
53 AR-C118925
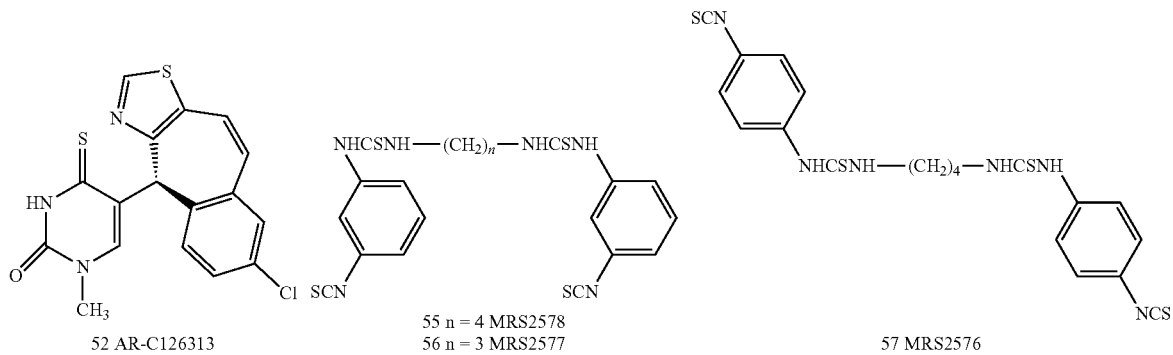
52 AR-C126313
55 n = 4 MRS2578
56 n = 3 MRS2577
57 MRS2576

-continued
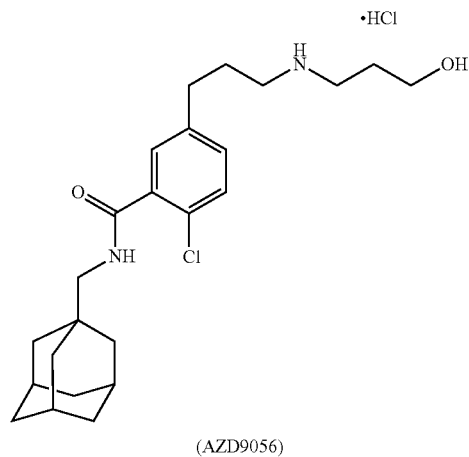
(AZD9056)
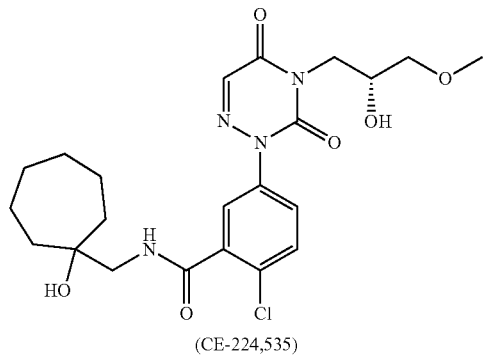
(CE-224,535)
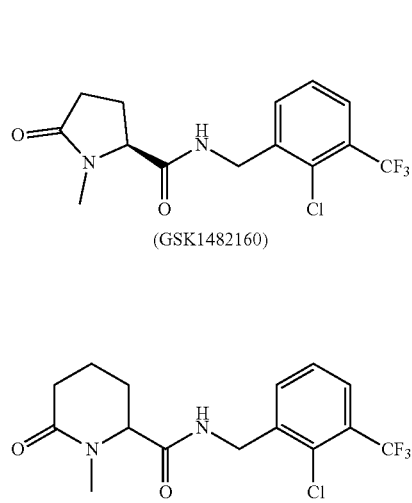
(GSK1482160)
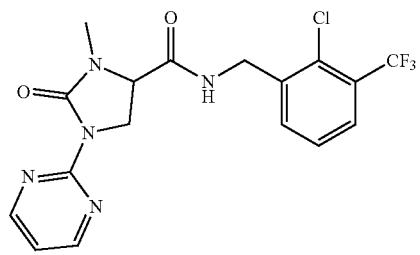
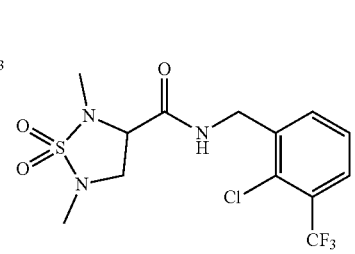
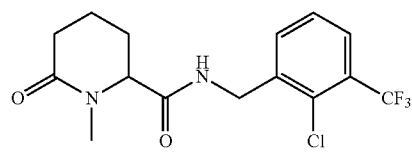
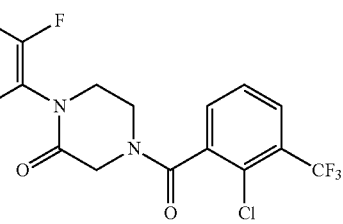
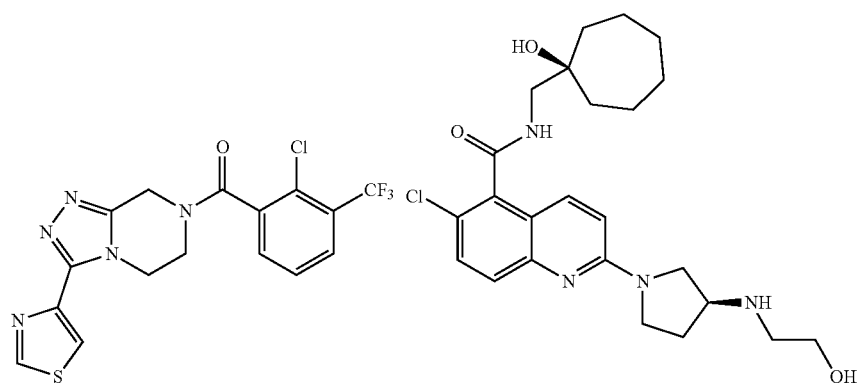
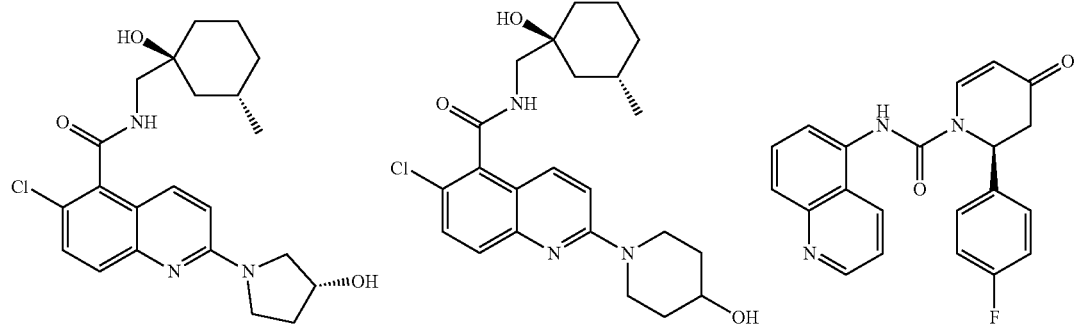

-continued
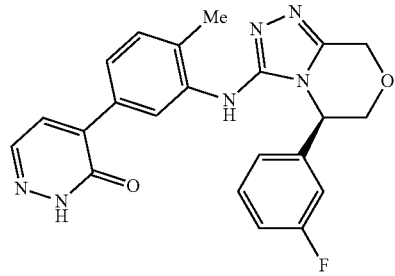
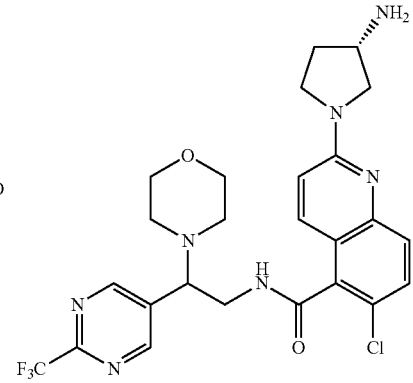
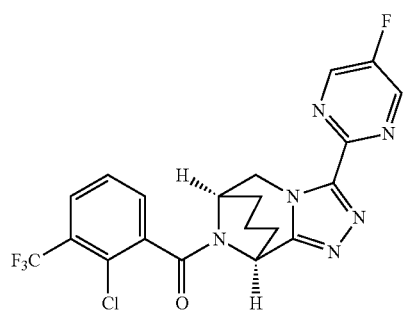
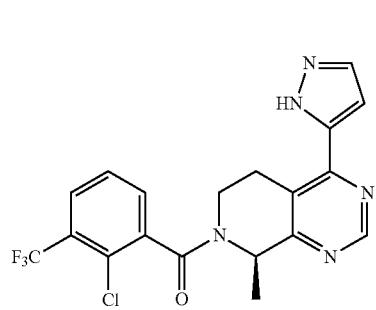
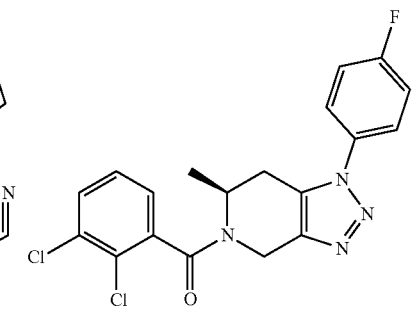
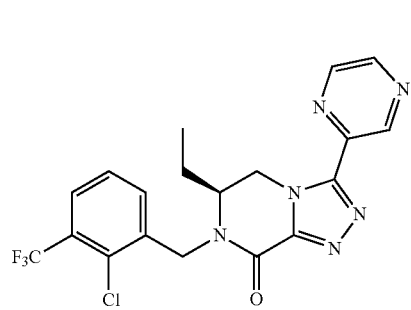
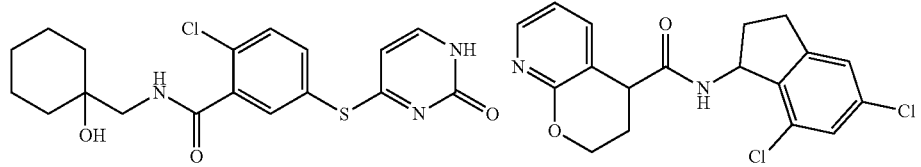
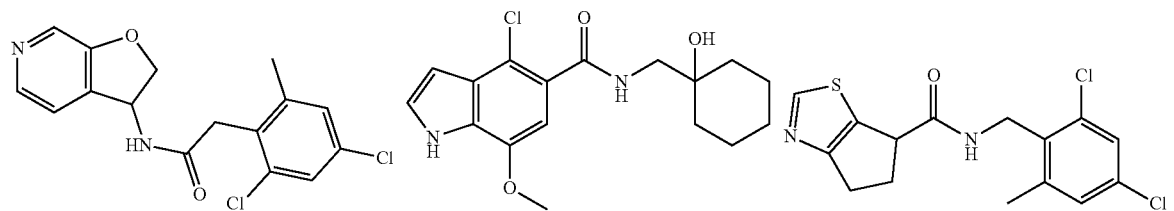
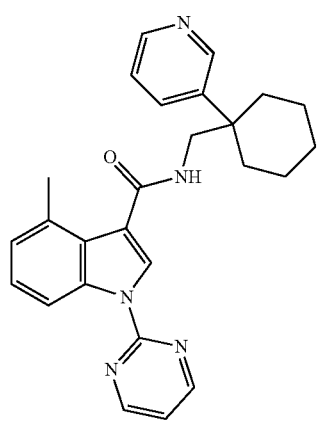
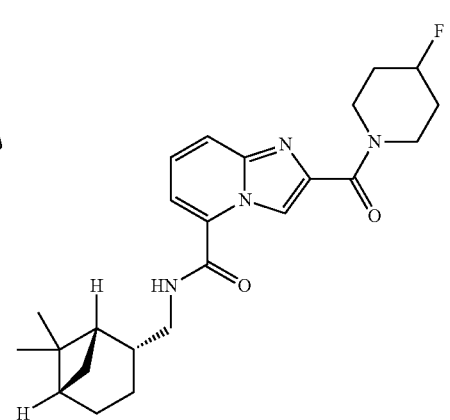

-continued
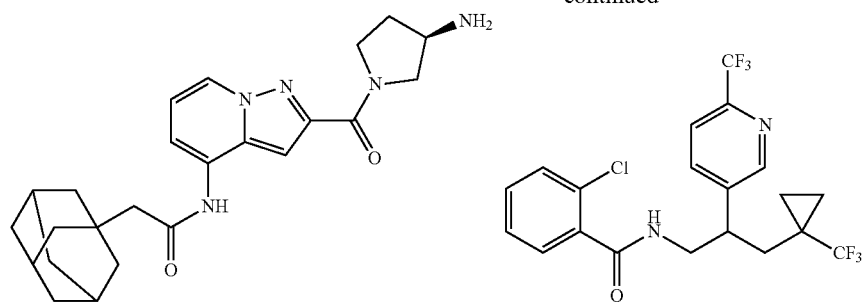
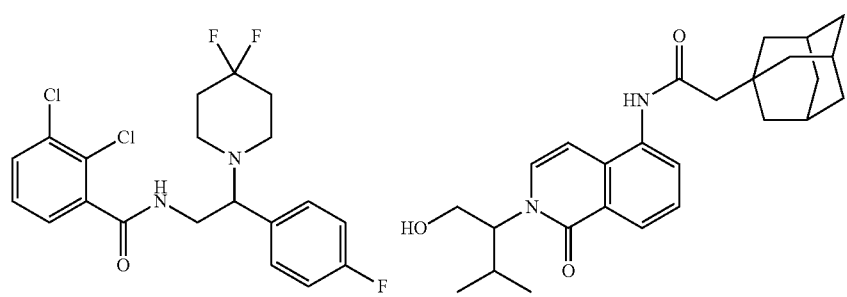
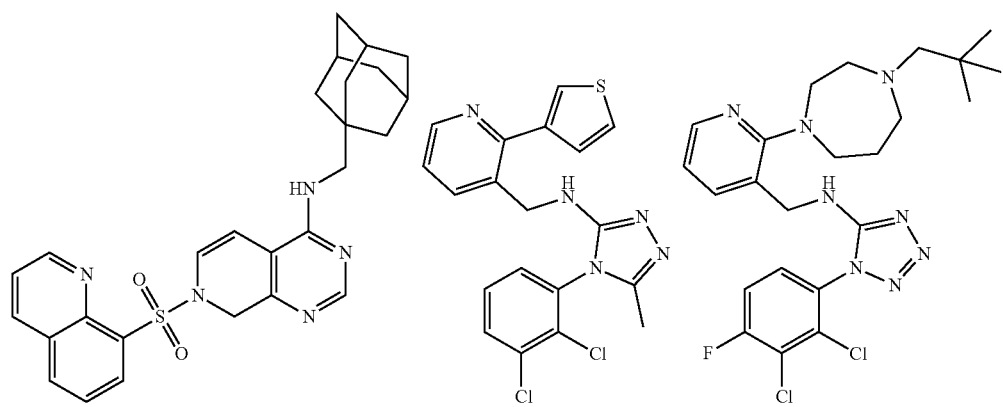
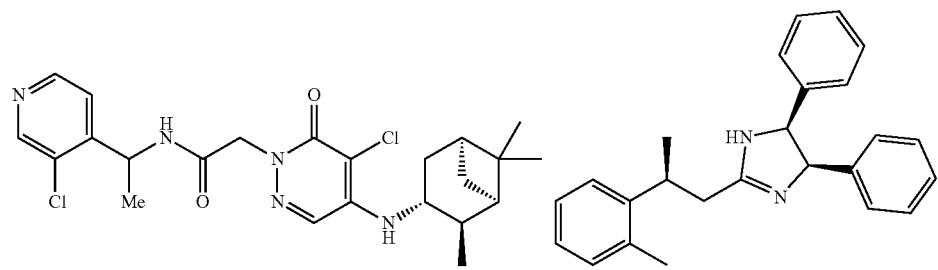
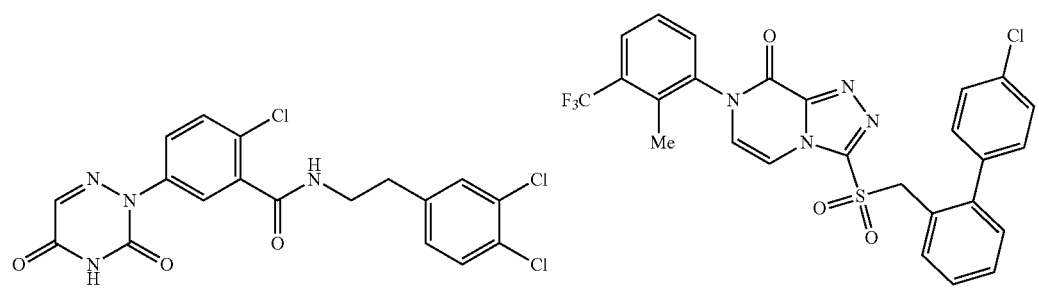

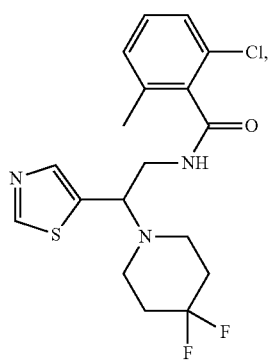

EVT 401, and AFC-5128, or a pharmaceutically acceptable salt, free acid, an analogue, a regioisomer, a stereoisomer or a tautomer thereof.

In one particular embodiment, the purinergic receptor antagonist is a P2Y2, P2Y4 or P2Y6 antagonist, and is a compound selected from the following:

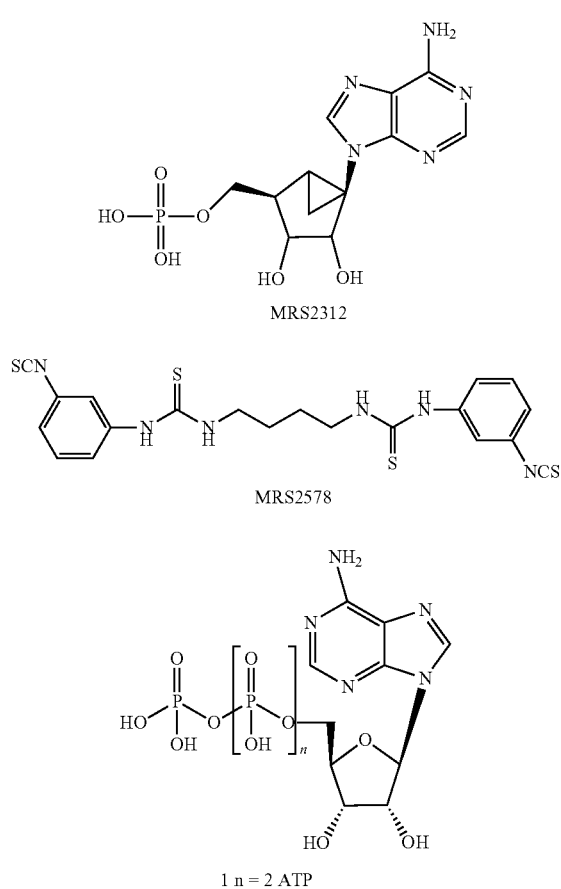

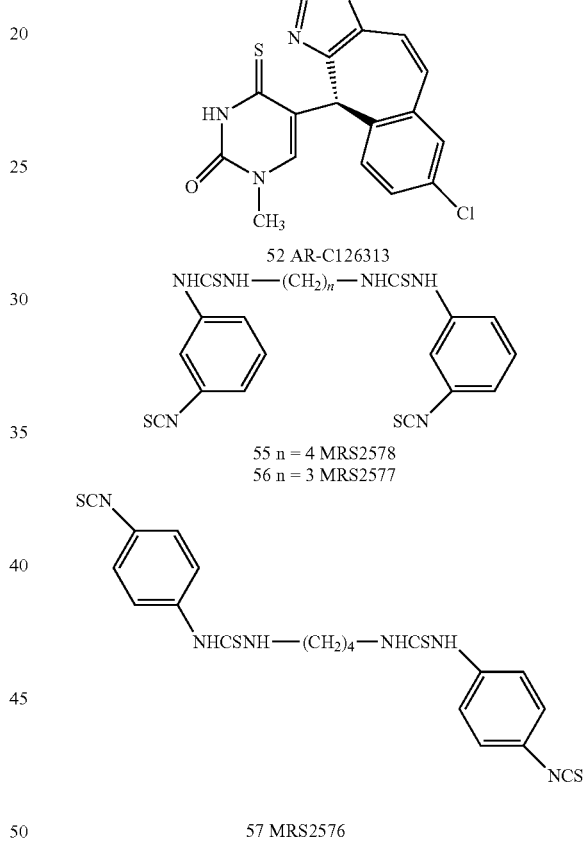

or a pharmaceutically acceptable salt, free acid, an analogue, a regioisomer, a stereoisomer or a tautomer thereof.

X. STING Antagonists

In some embodiments, the purinergic receptor antagonist is administered in combination with a Stimulator of Interferon Genes (STING) antagonist. STING is an adaptor protein anchored in the endoplasmic reticulum (ER). In its basal state, STING exists as a dimer, with its C-terminal domain residing in the cytosol; however, in the presence of cytosolic DNA (typically due to viral, bacterial, or parasitic infections) STING undergoes conformational changes and transits from the ER through the Golgi to perinuclear endosomes. Consequently, STING recruits TANK-binding kinase 1 (TBK1), which phosphorylates STING, rendering it more accessible for the binding of the transcription factor IFN-regulatory factor 3 (IRF3). TBK1 then phosphorylates IRF3, which translocates to the nucleus to drive transcription of interferon-β (IFN-0) and other innate immune genes. Bacterial cyclic-dinucleotides (CDNs) are natural ligands of STING and link the presence of cytosolic DNA to the activation of STING. For example, bacteria and mammalian cells generate CDNs via the DNA sensor cyclic GMP-AMP synthase (cGAS/MB21D1), which catalyzes the synthesis of cyclic GMP-AMP (cGAMP) from GTP and ATP upon DNA binding. Cells from cGAS-deficient mice were unable to produce type I IFNs in response to cytosolic DNA. Upon DNA exposure within the cytosol, cGAS is the major receptor that directly binds DNA, leading to cGAMP production, which in turn engages STING to trigger the remaining signaling events that drive IFN-β expression. STING pathway activation within antigen presenting cells (APCs) in the tumor microenvironment leads to production of IFN-β and the spontaneous generation of antitumor CD8+ T cell responses, allowing for control of the growth of several transplantable tumor cell models. See Corrales et al., 2016, J Clin. Invest. 126(7): 2404-2411.

The term "STING antagonist" as used herein refers to any chemical entity, including but not limited to a small molecule, an oncogene, a nucleoside, a nucleotide, a nucleobase, a sugar, a nucleic acid, an amino acid, a polysaccharide, a peptide, a polypeptide, a protein, an antibody, an aptamer (e.g., DNA/RNA/XNA/peptide aptamers) or a complex comprising any combination of the aforementioned chemical entities, that inhibits the STING pathway. In some embodiments, the STING antagonist interacts directly with the STING protein. In some embodiments, the STING antagonist interacts with a downstream component of the STING pathway, for example, cyclic GMP-AMP synthase (cGAS), TBK1, IRF3 or IFN-β. In some embodiments, the STING antagonist reduces the level or activity of one or more components of the STING pathway, e.g. STING, cyclic GMP-AMP synthase (cGAS), TBK1, IRF3 and/or IFN-β.

A chemical entity may be identified as a STING antagonist, for example, by treating a cell with the chemical entity in combination with a known STING agonist (e.g. cGMP) and measuring IRF3 activity. For example, an IRF reporter cell such as THP1-Dual™ cells (InvivoGen) may used to identify STING antagonists. THP1-Dual™ cells are human THP1 monocytes that have been engineered to contain an inducible IRF reporter construct. IRF activity is measured in these cells by assessing the activity of a secreted luciferase. A decrease in IRF activity in cells treated with the chemical entity and the STING agonist relative to cells treated with the STING agonist alone would indicate that the chemical entity is a STING antagonist.

A chemical entity may also or alternatively be identified as a STING antagonist by treating a cell with the chemical entity in combination with a known STING agonist (e.g. cGMP) and measuring IFN-β expression and/or activity. For example, antigen presenting cells (APCs), PBMCs, dendritic cells or the THP1-Dual™ cells described above may be treated with the chemical entity and the STING agonist and then IFN-β expression measured by methods known in the art, such as ELISA. An IFN-β reporter cell line such as B16-Blue IFN reporter cells (InvivoGen) may also be used to measure IFN-β expression in response to treatment with the chemical entity and the STING agonist. For the reporter cell line, IFN-β expression may be measured by adding the substrate QUANTI-Blue (InvivoGen) and measuring color intensity using a spectrophotometer at 620-655 nm. See Woo et al., 2014, Immunity 41(5): 830-842, which is incorporated by reference herein in its entirety. A decrease in IFN-β expression and/or activity in the cells treated with the chemical entity and the STING agonist relative to cells treated with the STING agonist alone would indicate that the compound is a STING antagonist.

Another method that may alternatively or additionally be used for identifying a chemical entity as a STING antagonist is through a HepAD38-derived reporter cell line that expresses firefly luciferase in response to the activation of the cyclic GMP-AMP synthase (cGAS)-STING pathway. The reporter cells are treated with the chemical entity and the STING agonist and the luciferase signal produced by the cells is measured several hours after treatment. See Liu et al., 2017, Antiviral Research 147: 37-46, which is incorporated by reference herein in its entirety. A decrease in luciferase activity in the reporter cells treated with the chemical entity and the STING agonist relative to cells treated with the STING agonist alone would indicate that the compound is a STING antagonist.

In one embodiment, the STING antagonist administered in combination with a purinergic receptor antagonist (e.g., a P2Y receptor antagonist, such as a P2Y2, P2Y4 or P2Y6 antagonist) is a small molecule compound as defined herein. Non-limiting examples of small molecule STING antagonists are described in WO 2019/069269, WO 2019/055750, WO 2018/234808, WO 2018/234805, WO 2017/123657, Haag et al. (*Nature*, 2018, 559:269-273), and Koch et al. (*ACS Chem Biol.*, 2018, 13(4):1066-1081), each incorporated herein by reference in its entirety.

In one embodiment, the STING antagonist is a kinase inhibitor, such as a TBK1 kinase inhibitor (e.g., staurosporine, BX765 and MRT67307). In some embodiments, the STING antagonist is an inhibitor of the ATP6V1A gene. The ATP6V1A gene encodes a component of vacuolar ATPase, a multisubunit enzyme that mediates acidification of eukaryotic intracellular organelles.

In one embodiment, the STING antagonist is a cyclic dinucleotide (CDN) compound. Although most CDNs have been characterized as STING agonists, some CDNs have been shown to function as STING antagonists instead. Accordingly, in one embodiment, the STING antagonist is a CDN compound represented by the following structural formula:

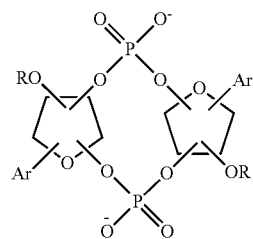

or a pharmaceutically acceptable salt, a free acid, a regioisomer, a stereoisomer or a tautomer thereof wherein Ar, for each instance, is independently optionally substituted monocyclic or bicyclic heteroaryl having at least one nitrogen atom (e.g., 1, 2, 3 or 4) and optionally one or more heteroatoms selected from O and S; wherein R, for each instance, is independently hydrogen or an optionally substituted $C_1$-$C_4$ alkyl; wherein each oxygen atom in the two phosphate groups and the OR groups is optionally and independently substituted with S; wherein each OR group and each O⁻ is optionally substituted with a halogen (e.g., F, Cl). In one embodiment, each Ar is independently selected from the group consisting of
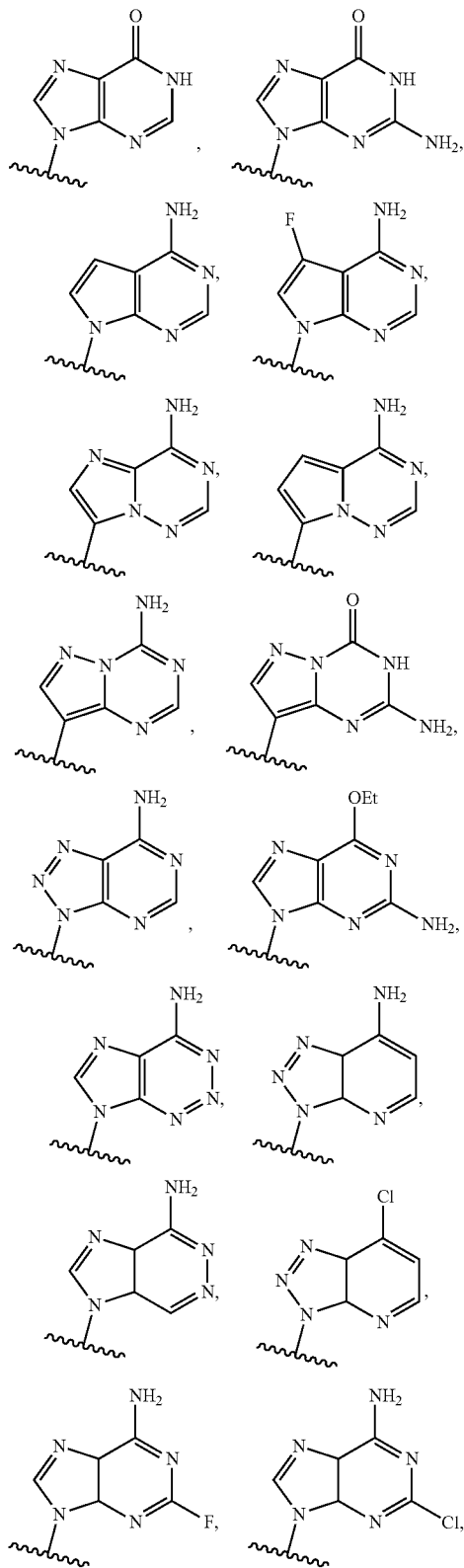
-continued
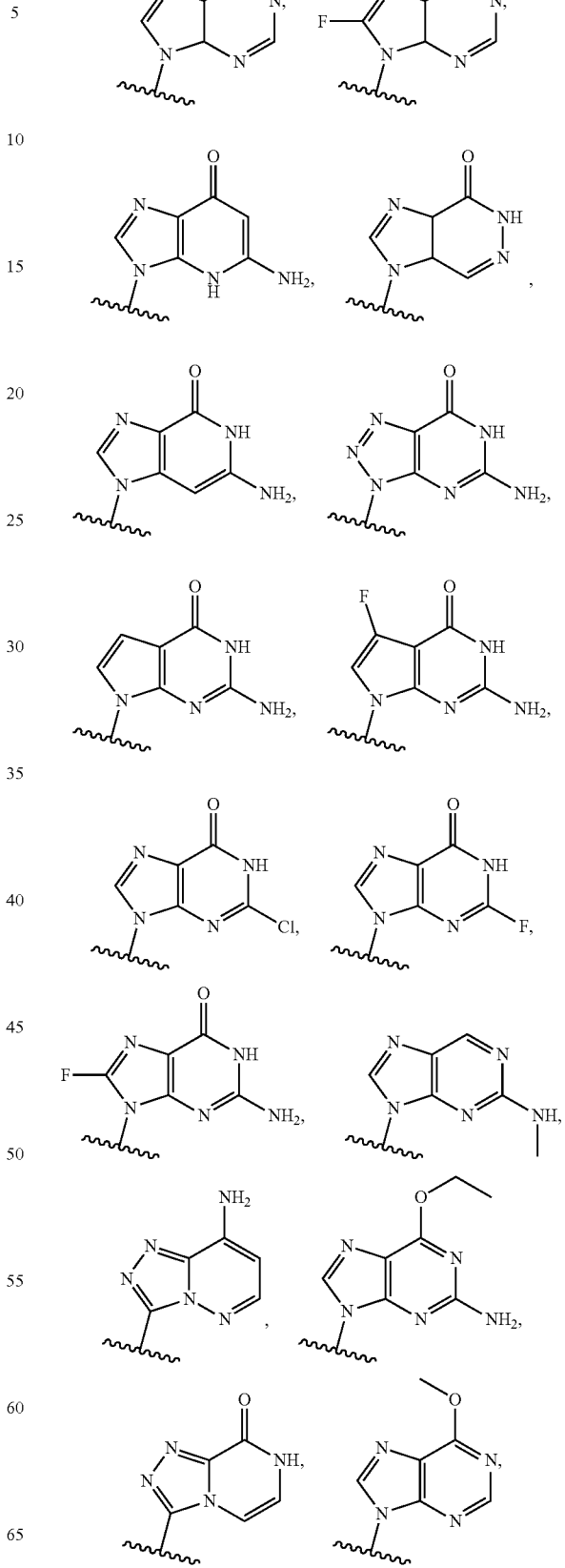

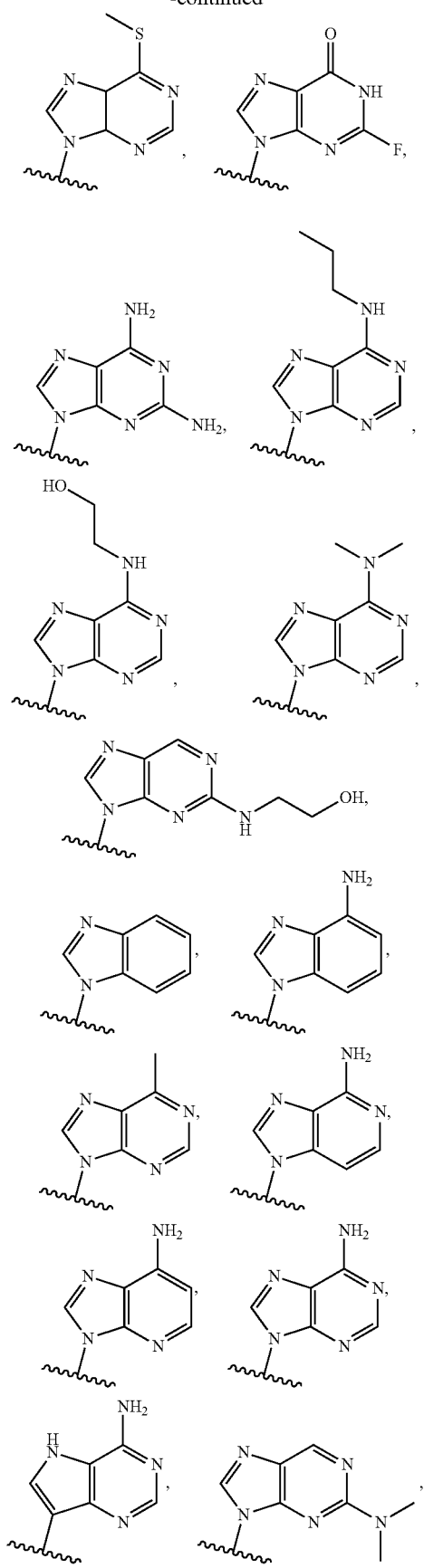

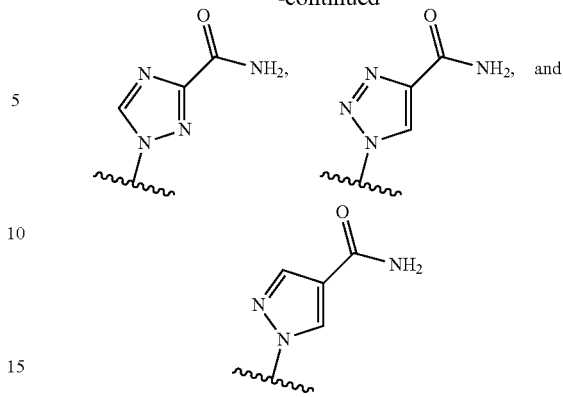

In one embodiment, the STING antagonist is an imidazole derivative, including dimeric forms of imidazole-based compounds. Although some amidobenzimidazole and dimeric amidobenzimidazole compounds have been characterized as STING agonists, certain imidazole derivatives have been shown to function instead as STING antagonists. Accordingly, in one embodiment, the STING antagonist is a dimeric compound represented by the following structural formula:

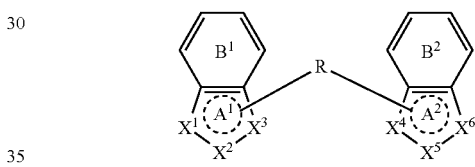

or a pharmaceutically acceptable salt, a free acid, a regioisomer, a stereoisomer or a tautomer thereof wherein one or two of $X^1$, $X^2$ and $X^3$ is/are nitrogen while the other(s) is/are carbon; wherein one or two of $X^4$, $X^5$ and $X^6$ is/are nitrogen while the other(s) is/are carbon; wherein R is an optionally substituted $C_1$-$C_6$ alkyl, $C_2$-$C_6$ alkenyl or $C_2$-$C_6$ alkynyl covalently linked to ring $A^1$ and ring $A^2$; each of rings $A^1$, $A^2$, $B^1$ and $B^2$ is optionally substituted.

In one embodiment, the STING antagonist is an amido-substituted bi-heterocyclic compound represented by the following formula:

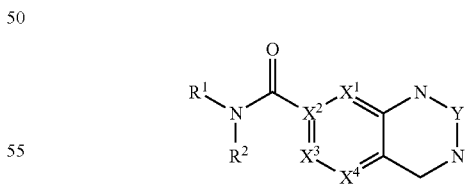

or a pharmaceutically acceptable salt, a free acid, a regioisomer, a stereoisomer or a tautomer thereof the bi-heterocyclic ring is optionally further substituted; wherein Y is C, O, or S; $X^1$, $X^2$, $X^3$ and $X^4$ are each independent C or N; and R1 and R2 are each independently an optionally substituted alkyl, an optionally substituted alkenyl, an optionally substituted alkynyl, an optionally substituted cycloalkyl, an optionally substituted aryl, an optionally substituted heteroaryl, or an optionally substituted heterocyclyl.

In one embodiment, the STING antagonist is a compound selected from the following:

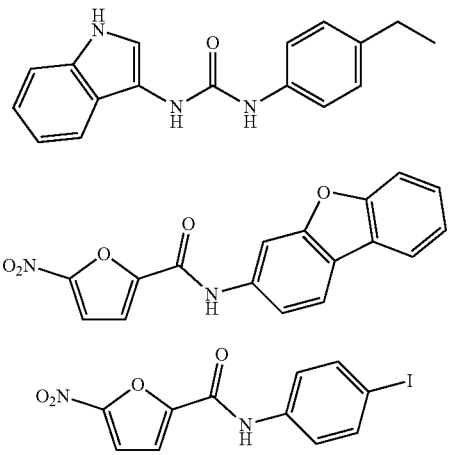

or a pharmaceutically acceptable salt, a free acid, a regioisomer, a stereoisomer or a tautomer thereof.

In one embodiment, the STING antagonist is an oncogene, an oncoprotein, or a nucleic acid. Non-limiting examples of oncogene, oncoprotein and nucleic acid STING antagonists are described in Lau et al. (Science, 2015, 350(6260):568-571), Corrales et al. (*Journal of Immunology*, 2016, 196(7): 3191-3198), Maringer et al. (*Cytokine & Growth Factor Reviews*, 2014, 25(6):669-679), Shaikh et al. (*Microbial Pathogenesis*, 2019, 132:162-162), and Wang et al. (*Nucleic Acids Research*, 2018, 46(8): 4054-4071), each of which is incorporated by reference herein in its entirety. In some embodiments, the STING antagonist is a viral oncogene or oncoprotein, or a fragment thereof. In some embodiments the viral oncogene or oncoprotein is selected from the group consisting of E6 (e.g. HPV18 E6), E7 (e.g. HPV18 E7), E1A (e.g. hAd5 E1A) and SV40 Large T antigen.

XI. Methods of Decreasing Immune Activity

The purinergic receptor antagonists (e.g., P2Y receptor antagonist, such as a P2Y2, P2Y4 or P2Y6 receptor antagonists) described herein may be used to decrease immune activity in a cell, tissue or in a subject, for example, a subject who would benefit from decreased immune activity. For example, in some aspects, the disclosure relates to a method of decreasing immune activity in a cell, tissue or subject, the method comprising administering to the cell, tissue or subject a purinergic receptor antagonist in an amount sufficient to decrease the immune activity relative to a cell, tissue or subject that is not treated with the purinergic receptor antagonist. In some embodiments, the purinergic receptor antagonist is administered in combination with a STING antagonist in an amount sufficient to decrease the immune activity relative to a cell, tissue or subject that is not treated with the purinergic receptor antagonist and/or the STING antagonist.

In some aspects, the disclosure relates to a method of decreasing immune activity in a cell, the method comprising administering to the cell a purinergic receptor antagonist (e.g., a P2Y receptor antagonist, such as a P2Y2, P2Y4 or P2Y6 antagonist) wherein the purinergic receptor antagonist are administered in an amount sufficient to decrease the immune activity relative to a cell that is not treated with the the purinergic receptor antagonist. In some embodiments, the purinergic receptor antagonist is administered in combination with a STING antagonist in an amount sufficient to decrease the immune activity relative to a cell that is not treated with the purinergic receptor antagonist and/or the STING antagonist.

In some aspects, the disclosure relates to a method of decreasing immune activity in a target tissue, the method comprising administering to the target tissue a purinergic receptor antagonist (e.g., a P2Y receptor antagonist, such as a P2Y2, P2Y4 or P2Y6 antagonist), wherein the purinergic receptor antagonist is administered in an amount sufficient to decrease the immune activity relative to a tissue that is not treated with the purinergic receptor antagonist. In some embodiments, the purinergic receptor antagonist is administered in combination with a STING antagonist in an amount sufficient to decrease the immune activity relative to a tissue that is not treated with the purinergic receptor antagonist and/or the STING antagonist.

In some aspects, the disclosure relates to a method of decreasing immune activity in a subject, the method comprising administering to the subject a purinergic receptor antagonist, wherein the purinergic receptor antagonist (e.g., a P2Y receptor antagonist, such as a P2Y2, P2Y4 or P2Y6 antagonist) is administered in an amount sufficient to decrease the immune activity relative to a subject that is not treated with the purinergic receptor antagonist. In one embodiment, the subject is in need of a decreased immune activity. In some embodiments, the purinergic receptor antagonist is administered in combination with a STING antagonist in an amount sufficient to decrease the immune activity relative to a tissue that is not treated with the purinergic receptor antagonist and/or the STING antagonist.

According to some methods of the disclosure, immune activity may be regulated by interaction of the purinergic receptor antagonist (optionally in combination with the STING antagonist) with a broad range of immune cells, including, for example, any one or more of mast cells, Natural Killer (NK) cells, basophils, neutrophils, monocytes, macrophages, dendritic cells, eosinophils, lymphocytes (e.g. B-lymphocytes (B-cells)), and T-lymphocytes (T-cells)).

Decreasing Immune Activity

The purinergic receptor antagonists (e.g., a P2Y receptor antagonist, such as a P2Y2, P2Y4 or P2Y6 antagonist) and STING antagonists described herein may decrease immune activity in a tissue or subject by decreasing the level or activity of any one or more of the immune cells described herein, for example, macrophages, monocytes, dendritic cells, and CD4+, CD8+ or CD3+ cells (e.g. CD4+, CD8+ or CD3+ T cells) in the tissue or subject. For example, in one embodiment, the purinergic receptor antagonist is administered in an amount sufficient to decrease in the tissue or subject one or more of the level or activity of macrophages, the level or activity of monocytes, the level or activity of dendritic cells, the level or activity of T cells, and the level or activity of CD4+, CD8+ or CD3+ cells (e.g. CD4+, CD8+ or CD3+ T cells). In one embodiment, the purinergic receptor antagonist and the STING antagonist are administered in an amount sufficient to decrease in the tissue or subject one or more of the level or activity of macrophages, the level or activity of monocytes, the level or activity of dendritic cells, the level or activity of T cells, and the level or activity of CD4+, CD8+ or CD3+ cells (e.g. CD4+, CD8+ or CD3+ T cells).

The purinergic receptor antagonist and the STING antagonist may also decrease immune activity in a cell, tissue or subject by decreasing the level or activity of a pro-immune cytokine. For example, in some embodiments, the purinergic receptor antagonist is administered in an amount sufficient to decrease in a cell, tissue or subject the level or activity of a pro-immune cytokine. In some embodiments, the STING antagonist and the purinergic receptor antagonist are administered in an amount sufficient to decrease in a cell, tissue or subject the level or activity of a pro-immune cytokine. In one embodiment, the pro-immune cytokine is selected from IFN-α, IL-1, IL-12, IL-18, IL-2, IL-15, IL-4, IL-6, TNF-α, IL-17 and GMCSF.

The the purinergic receptor antagonist and the STING antagonist may also decrease immune activity in a cell, tissue or subject by decreasing the level or activity of positive regulators of the immune response such as nuclear factor kappa-light-chain-enhancer of activated B cells (NFkB), interferon regulatory factor (IRF), and stimulator of interferon genes (STING). For example, in some embodiments, the purinergic receptor antagonist is administered in an amount sufficient to decrease in a cell, tissue or subject the level or activity of NFkB, IRF and/or STING. In some embodiments, the STING antagonist and the purinergic receptor antagonist are administered in an amount sufficient to decrease in a cell, tissue or subject the level or activity of NFkB, IRF and/or STING.

In some aspects, the disclosure relates to a method of decreasing the level or activity of NFkB in a cell, tissue or subject, comprising administering to the cell, tissue or subject a purinergic receptor antagonist (e.g., a P2Y receptor antagonist, such as a P2Y2, P2Y4 or P2Y6 antagonist) in an amount sufficient to decrease the level or activity of NFkB relative to a cell, tissue or subject that is not treated with the purinergic receptor antagonist.

In some aspects, the disclosure relates to a method of decreasing the level or activity of NFkB in a cell, tissue or subject, comprising administering to the cell, tissue or subject, in combination, a STING antagonist and a purinergic receptor antagonist (e.g., a P2Y receptor antagonist, such as a P2Y2, P2Y4 or P2Y6 antagonist) in an amount sufficient to decrease the level or activity of NFkB relative to a cell, tissue or subject that is not treated with the STING antagonist and/or the purinergic receptor antagonist.

In one embodiment, the subject is in need of a decreased level or activity of NFkB.

In one embodiment, the level or activity of NFkB is decreased by at least 10%, 20%, 30%, 40%, 50%, 60%, 70%, 80%, 90% or 99% relative to a cell, tissue or subject that is not treated with the agent that inhibits iron-dependent cellular disassembly.

In some aspects, the disclosure relates to a method of decreasing the level or activity of IRF or STING in a cell, tissue or subject, comprising administering to the cell, tissue or subject, a purinergic receptor antagonist (e.g., a P2Y receptor antagonist, such as a P2Y2, P2Y4 or P2Y6 antagonist) in an amount sufficient to decrease the level or activity of IRF or STING relative to a cell, tissue or subject that is not treated with the purinergic receptor antagonist.

In some aspects, the disclosure relates to a method of decreasing the level or activity of IRF or STING in a cell, tissue or subject, comprising administering to the cell, tissue or subject, in combination, a STING antagonist and a purinergic receptor antagonist (e.g., a P2Y receptor antagonist, such as a P2Y2, P2Y4 or P2Y6 antagonist) in an amount sufficient to decrease the level or activity of IRF or STING relative to a cell, tissue or subject that is not treated with the STING antagonist and/or the purinergic receptor antagonist.

In one embodiment, the subject is in need of a decreased level or activity of IRF or STING.

In one embodiment, the level or activity of IRF or STING is decreased by at least 10%, 20%, 30%, 40%, 50%, 60%, 70%, 80%, 90% or 99% relative to a cell, tissue or subject that is not treated with the STING antagonist and/or the purinergic receptor antagonist.

In some aspects, the disclosure relates to a method of decreasing the level or activity of macrophages, monocytes, dendritic cells or T cells in a tissue or subject, comprising administering to the tissue or subject a purinergic receptor antagonist (e.g., a P2Y receptor antagonist, such as a P2Y2, P2Y4 or P2Y6 antagonist) in an amount sufficient to decrease the level or activity of macrophages, monocytes, dendritic cells or T cells relative to a tissue or subject that is not treated with the purinergic receptor antagonist.

In some aspects, the disclosure relates to a method of decreasing the level or activity of macrophages, monocytes, dendritic cells or T cells in a tissue or subject, comprising administering to the tissue or subject, in combination, a STING antagonist and a purinergic receptor antagonist (e.g., a P2Y receptor antagonist, such as a P2Y2, P2Y4 or P2Y6 antagonist) in an amount sufficient to decrease the level or activity of macrophages, monocytes, dendritic cells or T cells relative to a tissue or subject that is not treated with the STING antagonist and/or the purinergic receptor antagonist.

In one embodiment, the subject is in need of a decreased level or activity of macrophages, monocytes, dendritic cells or T cells.

In one embodiment, the level or activity of macrophages, monocytes, dendritic cells, or T cells is decreased by at least 10%, 20%, 30%, 40%, 50%, 60%, 70%, 80%, 90% or 99% relative to a tissue or subject that is not treated with the agent that inhibits iron-dependent cellular disassembly.

In some aspects, the disclosure relates to a method of decreasing the level or activity of CD4+, CD8+, or CD3+ cells in a tissue or subject, comprising administering to the subject a purinergic receptor antagonist (e.g., a P2Y receptor antagonist, such as a P2Y2, P2Y4 or P2Y6 antagonist) in an amount sufficient to decrease the level or activity of CD4+, CD8+, or CD3+ cells relative to a tissue or subject that is not treated with the purinergic receptor antagonist.

In some aspects, the disclosure relates to a method of decreasing the level or activity of CD4+, CD8+, or CD3+ cells in a tissue or subject, comprising administering to the subject, in combination, a STING antagonist and a purinergic receptor antagonist (e.g., a P2Y receptor antagonist, such as a P2Y2, P2Y4 or P2Y6 antagonist) in an amount sufficient to decrease the level or activity of CD4+, CD8+, or CD3+ cells relative to a tissue or subject that is not treated with the STING antagonist and/or the purinergic receptor antagonist.

In one embodiment, the subject is in need of a decreased level or activity of CD4+, CD8+, or CD3+ cells.

In one embodiment, the level or activity of CD4+, CD8+, or CD3+ cells is decreased by at least 10%, 20%, 30%, 40%, 50%, 60%, 70%, 80%, 90% or 99% relative to a tissue or subject that is not treated with the STING antagonist and/or the purinergic receptor antagonist.

In some aspects, the disclosure relates to a method of decreasing the level or activity of a pro-immune cytokine in a cell, tissue or subject, comprising administering to the cell, tissue or subject a purinergic receptor antagonist (e.g., a P2Y receptor antagonist, such as a P2Y2, P2Y4 or P2Y6 antagonist) in an amount sufficient to decrease the level or activity of the pro-immune cytokine relative to a cell, tissue or subject that is not treated with the the purinergic receptor antagonist.

In some aspects, the disclosure relates to a method of decreasing the level or activity of a pro-immune cytokine in a cell, tissue or subject, comprising administering to the cell, tissue or subject, in combination, a STING antagonist and a purinergic receptor antagonist (e.g., a P2Y receptor antagonist, such as a P2Y2, P2Y4 or P2Y6 antagonist) in an amount sufficient to decrease the level or activity of the pro-immune cytokine relative to a cell, tissue or subject that is not treated with the STING antagonist and/or the purinergic receptor antagonist.

In one embodiment, the subject is in need of a decreased level or activity of a pro-immune cytokine.

In one embodiment, the level or activity of the pro-immune cytokine is decreased by at least 10%, 20%, 30%, 40%, 50%, 60%, 70%, 80%, 90% or 99% relative to a cell, tissue or subject that is not treated with the STING antagonist and/or the purinergic receptor antagonist.

In one embodiment, the pro-immune cytokine is selected from IFN-α, IL-1, IL-12, IL-18, IL-2, IL-15, IL-4, IL-6, TNF-α, IL-17 and GMCSF.

In one embodiment, the method further includes, before the administration, evaluating the cell, tissue or subject for one or more of the level or activity of NFkB; the level or activity of macrophages; the level or activity of monocytes; the level or activity of dendritic cells; the level or activity of CD4+ cells, CD8+ cells, or CD3+ cells; the level or activity of T cells; and the level or activity of a pro-immune cytokine.

In one embodiment, the method further includes, after the administration, evaluating the cell, tissue or subject for one or more of the level or activity of NFkB; the level or activity of macrophages; the level or activity of monocytes; the level or activity of dendritic cells; the level or activity of CD4+ cells, CD8+ cells or CD3+ cells; the level or activity of T cells; and the level or activity of a pro-immune cytokine.

Regulatory T cells (Tregs) are a class of CD4+CD25+ T cells that suppress the activity of other immune cells. Tregs are central to immune system homeostasis, and play a major role in maintaining tolerance to self-antigens and in modulating the immune response to foreign antigens. Multiple autoimmune and inflammatory diseases, including Type 1 Diabetes (T1D), Systemic Lupus Erythematosus (SLE), and Graft-versus-Host Disease (GVHD) have been shown to have a deficiency of Treg cell numbers or Treg function. One assay to determine Treg activity measures the phosphorylation of the signal transduction protein STAT5, measured by flow cytometry with an antibody specific for the phosphorylated protein (pSTAT5). STAT5 is essential for Treg development, and a constitutively activated form of STAT5 expressed in CD4+CD25+ cells is sufficient for the production of Treg cells in the absence of IL-2 (Mahmud, S. A., et al., 2013, JAKSTAT 2:e23154). Therefore, measurement of phosphorylated STAT5 (pSTAT5) in Treg cells provides a method for determining activation of these cells. Another assay for functional activation measures proliferation of Treg cells. Treg proliferation can be measured by tritiated thymidine incorporation into purified Treg cells, by an increase in Treg cell numbers in a mixed population of cells measured by flow cytometry and the frequencies of CD4+CD25+FOXP3+ or the CD4+CD25+CD127− marker phenotypes, by increased expression in Treg cells of proliferation-associated cell cycle proteins, such as Ki-67, or by measurement of the cell division-associated dilution of a vital fluorescent dye such as carboxyfluorescein succinimidyl ester (CFSE) by flow cytometry in Treg cells. Another assay for functional activation of Tregs is the increased stability of Tregs. pTreg cells are thought by some to be unstable, and have the potential to differentiate into Th1 and Th17 effector T cells. Activation of Tregs can stabilize Tregs and prevent this differentiation (Chen, Q., et al., 2011, J Immunol. 186:6329-37). Another outcome of stimulation of Tregs is the stimulation of the level of Treg functional effector molecules, such as CTLA4, GITR, LAG3, TIGIT, IL-10, CD39, and CD73, which contribute to the immunosuppressive activity of Tregs. Production of these effector molecules by Tregs may be determined by methods known in the art, such as ELISA.

XII. Methods of Treating Disorders That Would Benefit from Decreased Immune Activity Applicants have shown that combinations of a STING agonist and a purinergic receptor agonist (e.g., a P2Y receptor antagonist, such as a P2Y2, P2Y4 or P2Y6 antagonist) increase immune response as evidenced by increases in IRF activity in immune cells. These results suggest that a purinergic receptor antagonist, optionally in combination with a STING antagonist, would decrease immune response by preventing the induction of immunostimulatory activity. Accordingly, administration of a purinergic receptor antagonist (e.g., a P2Y receptor antagonist, such as a P2Y2, P2Y4 or P2Y6 antagonist) optionally in combination with a STING antagonist may be used to treat disorders that would benefit from decreased immune activity, such as inflammatory diseases or conditions including inflammation, acute organ injury, tissue damage, sepsis, ischemia, atherosclerosis, neurodegenerative disorders, and immune-related diseases or conditions.

Inflammatory Diseases or Conditions

In some aspects, the present disclosure relates to a method of treating an inflammatory disease or condition comprising administering to the subject a purinergic receptor antagonist (e.g., a P2Y receptor antagonist, such as a P2Y2, P2Y4 or P2Y6 antagonist) in an amount sufficient to treat the inflammatory disease or condition in the subject.

In some aspects, the present disclosure relates to a method of treating an inflammatory disease or condition comprising administering to the subject, in combination, a STING antagonist and a purinergic receptor antagonist (e.g., a P2Y receptor antagonist, such as a P2Y2, P2Y4 or P2Y6 antagonist) in an amount sufficient to treat the inflammatory disease or condition in the subject.

In some embodiments, the inflammatory disease or condition is an inflammatory disease or condition in which iron-dependent cellular disassembly (e.g. ferroptosis) is detrimental.

In some embodiments, the inflammatory disease or condition is selected from the group consisting of inflammation (e.g. sterile inflammation), acute organ injury, tissue damage, sepsis, ischemia, and atherosclerosis.

In some embodiments, the inflammatory disease is an autoimmune disease or immune-related disease or condition. Autoimmune diseases are diseases in which the immune system attacks its own proteins, cells, and tissues. Autoimmune diseases include diseases that affect organs such as the heart, kidney, liver, lung, reproductive organs, digestive system, or skin. Autoimmune diseases include diseases that affect glands, including the endocrine, adrenal, thyroid, salivary and exocrine glands, and the pancreas. Autoimmune diseases can also be multi-glandular. Autoimmune diseases can target one or more tissues, for example connective tissue, muscle, or blood. Autoimmune diseases can target the nervous system or eyes, ears or vascular system. Autoimmune diseases can also be systemic, affecting multiple organs, tissues and/or systems. In some embodiments, an autoimmune disease or condition is an inflammatory disease or condition.

Non-limiting examples of autoimmune or immune-related diseases or conditions include systemic lupus erythematosus, rheumatoid arthritis, Type I diabetes, Type II diabetes, multiple sclerosis (MS), allergies, asthma, psoriasis, amyotrophic lateral sclerosis (ALS), organ transplant/graft-vs-host disease (GVHD), and ulcerative colitis.

In some embodiments, the immune-related condition is an allergy or allergic condition, for example, an allergy or allergic condition in which iron-dependent cellular disassembly (e.g. ferroptosis) is detrimental. An allergy or allergic condition is a hypersensitive reaction to allergens (e.g. lipids or proteins) in the environment. Allergens are antigens to which atopic patients respond with IgE antibody responses subsequently leading to allergic reactions. Allergens include environmental allergens (e.g. house dust mite, birch pollen, grass pollen, cat antigens, cockroach antigens), or food allergens (e.g. cow milk, peanut, shrimp, soybean), or a combination thereof. IgE molecules are important in allergic responses because of their role in effector cell (mast cell, basophiles and eosinophiles) activation. Allergies and allergic conditions include but are not limited to asthma, chronic obstructive pulmonary disease, hay fever (seasonal rhinitis), hives, and eczema.

In some embodiments, the immune-related condition is an autoinflammatory condition. Autoinflammatory conditions result from a dysfunction in the innate immune system, and constitute a broad range of genetically mediated conditions characterized by recurrent attacks of systemic inflammation with primary physical manifestations of fever, rash, serositis, lymphadenopathy, and musculoskeletal symptoms. Genetic mutations that usually cause some dysregulation of the innate immune system underlie the etiology of autoinflammatory conditions.

In some embodiments, the disorder is neuroinflammation. Neuroinflammation is a chronic inflammation of the nervous system and is often associated with brain injury and neurodegenerative disorders. Neurodegenerative disorders involve the progressive loss of structure or function of neurons, and may involve death of neurons. In some embodiments, the disorder is a neurodegenerative disorder, e.g. Parkinson's disease, Huntington's disease, or Alzheimer's disease. See Chen et al., 2015, J. Biol. Chem. 290: 28097-28106, which is incorporated by reference herein in its entirety. In some embodiments, the condition is traumatic or hemorrhagic brain injury. See Stockwell et al., 2017, Cell 171: 273-285, which is incorporated by reference herein in its entirety.

XIII. Pharmaceutical Compositions and Modes of Administration

The pharmaceutical compositions described herein may be administered to a subject in any suitable formulation. These include, for example, liquid, semi-solid, and solid dosage forms, The preferred form depends on the intended mode of administration and therapeutic application.

In certain embodiments the composition is suitable for oral administration. In certain embodiments, the formulation is suitable for parenteral administration, including topical administration and intravenous, intraperitoneal, intramuscular, and subcutaneous, injections. In a particular embodiment, the composition is suitable for intravenous administration.

Pharmaceutical compositions for parenteral administration include aqueous solutions of the active compounds in water-soluble form. For intravenous administration, the formulation may be an aqueous solution. The aqueous solution may include Hank's solution, Ringer's solution, phosphate buffered saline (PBS), physiological saline buffer or other suitable salts or combinations to achieve the appropriate pH and osmolarity for parenterally delivered formulations. Aqueous solutions can be used to dilute the formulations for administration to the desired concentration. The aqueous solution may contain substances which increase the viscosity of the solution, such as sodium carboxymethyl cellulose, sorbitol, or dextran. In some embodiments, the formulation includes a phosphate buffer saline solution which contains sodium phosphate dibasic, potassium phosphate monobasic, potassium chloride, sodium chloride and water for injection.

Formulations suitable for topical administration include liquid or semi-liquid preparations suitable for penetration through the skin, such as liniments, lotions, creams, ointments or pastes, and drops suitable for administration to the eye, ear, or nose. Formulations suitable for oral administration include preparations containing an inert diluent or an assimilable edible carrier. The formulation for oral administration may be enclosed in hard or soft shell gelatin capsule, or it may be compressed into tablets, or it may be incorporated directly with the food of the diet. When the dosage unit form is a capsule, it may contain, in addition to materials of the above type, a liquid carrier. Various other materials may be present as coatings or to otherwise modify the physical form of the dosage unit. Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically.

As will be readily apparent to one skilled in the art, the useful in vivo dosage to be administered and the particular mode of administration will vary depending upon the age, body weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, animal models, and in vitro studies.

In certain embodiments, the composition is delivered orally. In certain embodiments, the composition is administered parenterally. In certain embodiments, the compositions is delivered by injection or infusion. In certain embodiments, the composition is delivered topically including transmucosally. In certain embodiments, the composition is delivered by inhalation. In one embodiment, the compositions provided herein may be administered by injecting directly to a tumor. In some embodiments, the compositions may be administered by intravenous injection or intravenous infusion. In certain embodiments, administration is systemic. In certain embodiments, administration is local.

In certain aspects, the present disclosure relates to a pharmaceutical composition comprising a STING agonist and/or a purinergic receptor agonist. In some embodiments, the STING agonist and the purinergic receptor agonist are administered in separate pharmaceutical compositions. In some embodiments, the STING agonist and the purinergic receptor agonist are administered in the same pharmaceutical composition.

In certain aspects, the present disclosure relates to a pharmaceutical composition comprising a STING antagonist and/or a purinergic receptor antagonist. In some embodiments, the STING antagonist and the purinergic receptor antagonist are administered in separate pharmaceutical compositions. In some embodiments, the STING antagonist and the purinergic receptor antagonist are administered in the same pharmaceutical composition.

EXAMPLES

Example 1: IRF Signaling in Human THP1 Monocytes Treated with Nutrient-Deprived or UV-treated HeLa Cells Experimental Design HeLa cervical cancer cells were grown in DMEM containing 10% FBS (standard culture conditions), or in PBS (nutrient-deprivation) for 48 hours. Alternatively, HeLa cervical cancer cells were grown in either DMEM containing 10% FBS (standard culture conditions) and exposed to UV irradiation. Cell bodies were pelleted and resuspended in fresh tissue culture medium and co-cultured with THP1-Dual cells for an additional 24 hrs. THP1 supernatants were then assessed for NfkB or IRF reporter activity. The results of two experiments are shown (FIG. 1A).

Materials and Methods

HeLa cells were acquired from the ATCC (catalog no. CCL 2.2) and were cultured in DMEM containing 10% FBS. THP1-Dual cells, which are human monocytes that report on both the NfkB and IRF pathways, were purchased from Invivogen (cat no. thpd-nfis) and were cultured in RPMI containing 10% FBS and 100 µg/ml normocin.

Conclusion

HeLa cells cultured in PBS (nutrient-deprivation) elicited increased IRF transcriptional activity in co-cultured THP1 monocytes (FIGS. 1A and 1B).

Example 2: Conditioned Medium from Nutrient-Deprived HeLa Cells in Combination with the STING Agonist 2'3'-cGAMP Induces IRF and NfkB Activity in Human THP1 Monocytes Experimental Design HeLa cervical cancer cells were grown in either DMEM containing 10% FBS (standard culture conditions), or in PBS (nutrient-deprivation) for 48 hours. Conditioned media from each condition was then transferred to THP1-Dual cells in the presence of 300 ng/ml of 2'3'-cGAMP (purchased from Invivogen, cat no. tlrl-nacga23, and resuspended in water). THP1 cells treated with conditioned media were incubated for an additional 24 hours. THP1 supernatants were then assessed for NfkB or IRF reporter activity.

Materials and Methods

HeLa cells were acquired from the ATCC (catalog no. CCL 2.2) and were cultured in DMEM containing 10% FBS. THP1-Dual cells, which are human monocytes that report on both the NfkB and IRF pathways, were purchased from Invivogen (cat no. thpd-nfis) and were cultured in RPMI containing 10% FBS and 100 µg/ml normocin.

To generate conditioned media, 3 million HeLa cells were seeded in a 10 cm dish in DMEM containing 10% FBS. Cells were left overnight to adhere and then plates were washed 3× with PBS prior to replacing media with either fresh DMEM containing 10% FBS, or with PBS. Cells were incubated for 48 hours, and then the conditioned media was removed, spun down and sterile filtered.

To measure IRF or NfkB pathway activation, 35,000 THP1-Dual cells/well were seeded in a 96-well plate (100 µl/well). 100 µl of HeLa conditioned media was transferred to each well, plus or minus 2'3'-cGAMP (300 ng/ml final concentration). After a 24 hour incubation period, IRF and NfkB activity were measured. To measure IRF activity, 50 µl of THP1 supernatant was transferred to a 96-well plate, and 50 µl of QuantiLuc reagent was added to each well immediately prior to reading luminescence by a platereader. To measure NfkB activity, 50 µl of THP1 supernatant was transferred to a 96-well plate containing 200 µl of QuantiBlue reagent. The plate was then incubated at room temperature for 2-3 hours prior to reading the absorbance at 655 nm.

Conclusion

As shown in FIGS. 2A and 2B, treatment of THP1 monocytes with nutrient-starved HeLa cell conditioned media (grown in PBS) increased IRF and NFKB signaling when tested in combination with 2'3'-cGAMP. Conditioned media from HeLa cells grown under standard culture conditions (i.e. DMEM+10% FBS), on the other hand, only slightly induced IRF and NFKB signaling when tested in combination with 2'3'-cGAMP.

Example 3: Nutrient-Deprived HeLa Cells in Combination with the STING Agonist 2'3'-cGAMP Induces IFN-Beta Secretion from Human THP1 Monocytes or J774 Macrophages Experimental Design HeLa cervical cancer cells were grown in PBS (nutrient-deprivation) for 48 hours. THP1 cells were then treated with the HeLa-PBS (nutrient deprived) conditioned media in the presence and absence of 2'3'-cGAMP. THP1 supernatants were then assayed for the secretion of IFN-beta, a cytokine regulated by IRF. The same experiment was additionally performed using the mouse macrophage cell line J774 in place of the THP1 cells.

Materials and Methods

HeLa cells were cultured in DMEM containing 10% FBS. THP1-Dual cells were cultured in RPMI containing 10% FBS and 100 µg/ml normocin.

To generate conditioned media, 3 million HeLa cells were seeded in a 10 cm dish in DMEM containing 10% FBS. Cells were left overnight to adhere and then plates were washed 3× with PBS prior to replacing media with either fresh DMEM containing 10% FBS, or with PBS. Cells were incubated for 48 hours, and then the conditioned media was removed, spun down and sterile filtered.

500,000 THP1-Dual cells/well were seeded in a 24-well plate. 500 µl (1:1 dilution) of each condition was added to the well (PBS; PBS+300 ng/ml cGAMP; HeLa-PBS CM; HeLa-PBS CM+300 ng/ml cGAMP) and incubated for 24 hours. Cell supernatants were then spun down and sterile filtered prior to performing ELISA assay. ELISA assay was performed using the human IFN-beta DuoSet ELISA kit (DY814-05) and following the protocol provided by the manufacturer.

The same experiment was additionally performed using J774 cells (ATCC, TIB-67). In brief 500,000 cells/well were seeded in a 24-well plate. After cell adherence, media was refreshed, and HeLa conditioned media was added either in the presence or absence of 2'3'-cGAMP (as described above). After 24 hours J774 supernatant was removed an assayed for IFN-beta secretion as described above.
Conclusion
As shown in FIGS. 3A and 3B, for both THP1 monocytes, and J774 macrophages, IFN-beta secretion increased when cells were exposed to HeLa/PBS conditioned media in combination with 2'3'-cGAMP.

Example 4: Conditioned Medium from Nutrient-Deprived HeLa Cells in Combination with STING Agonist Cyclic Dinucleotides Induces IRF Activity in Human THP1 Monocytes Experimental Design
THP1 cells were treated with dose response curves of either a cyclic dinucleotide (CDN) alone or in combination with HeLa-PBS conditioned media. The CDNs used were all purchased from Invivogen: 2'3'-cGAMP (tlrl-nacga23), 3'3'-cGAMP (tlrl-nacga), 2'3'-cyclic-di-GMP (tlrl-nacdg23), 3'3'cGAMP-fluorinated (tlrl-nacgaf), c-di-GMP-fluorinated (tlrl-nacdgf), and 2'3'-cGAM(PS)2(Rp/Sp) (tlrl-nacga2srs).
Materials and Methods
THP1-Dual cells (acquired from Invivogen) were seeded at 35,000 cells/well in a 96-well plate (100 μl/well). In a separate treatment plate, a 3-fold dose-response curve of each CDN was prepared, starting at 40 μg/ml, in either plain PBS or in combination with HeLa-PBS conditioned media (conditioned media prepared as previously described). 100 μl of compound treatment was transferred to THP1 cells (1:1 dilution) and cells were incubated for 24 hours. THP1 supernatants were subsequently removed and assayed for IRF activity.
Conclusion
As shown in FIG. 4A-4F, each of the tested CDNs displayed IRF inducing activity on its own in THP1-Dual cells, and each of these CDNs also displayed synergistic activation of IRF when combined with HeLa-PBS conditioned media.

Example 5: Conditioned Medium from Multiple Types of Nutrient-Deprived Cells in Combination with the STING Agonist 2'3'-cGAMP Induces IRF Activity in Human THP1 Monocytes Experimental Design
THP1 cells were treated with the conditioned media of multiple cell types in either DMEM containing 10% FBS (standard culture conditions), or PBS (nutrient deprivation) in combination with 2'3'-cGAMP (acquired from Invivogen). THP1 cells were then assayed for induction of IRF activity.
Materials and Methods
The cell types tested were as follows: A549 (human lung epithelial adenocarcinoma cells), A427 (human lung epithelial carcinoma cells), J774 (mouse macrophage cells), AMJ2C11 (mouse macrophage cells), PANC1 (human pancreatic cancer cells), MLE12 (mouse lung epithelial cells), RAW264 (mouse leukemia cells), Calu-1 (human non-small-cell lung cancer cells), MCF7 (human breast cancer cells). All cells were acquired from ATCC.
For each cell type, 3 million cells were plated in DMEM with 10% FBS on a 10 cm dish. After adherence, cells were washed 3× with PBS and media was replaced with either fresh DMEM containing 10% FBS, or with PBS. Cells were incubated for 48 hours prior to removal, centrifugation and sterile filtration of the conditioned media.
THP1-Dual cells were plated at 35,000 cells/well in 96-well format. To each well, 100 μl of conditioned media was added (in triplicate) in the presence or absence of 2'3'-cGAMP (300 ng/ml). THP1-Dual cells were then incubated for 24 hours with conditioned media prior to assaying IRF induction.
Conclusion
As shown in FIG. 5A-5I, conditioned media from several different nutrient-deprived cells in combination with 2'3'-cGAMP induced IRF activation in human monocytes.

Example 6: Induction of IRF in Human THP1 Monocytes Mediated by Conditioned Medium from Nutrient-Deprived Cells and the STING Agonist cGAMP is Inhibited by Subtype Specific Purinergic Receptor Antagonists Experimental Design
THP1 cells were treated with cGAMP or cGAMP in combination with HeLa-PBS conditioned media, and then dosed with various purinergic receptors antagonists. Purinergic receptors, of which there are many subtypes, are GPCRs that are activated by nucleotides and nucleotide analogs. The purinergic receptor antagonist compounds tested were all ordered from Tocris: AR-C 118925 (P2RY2 antagonist), MRS 2179 (P2RY1 antagonist), AR-C 69931 (P2Y12 antagonist), A740003 (P2RX7 antagonist)
Materials and Methods
THP1-Dual cells (acquired from Invivogen) were seeded at 35,000 cells/well in a 96-well plate (100 μl/well). In a separate treatment plate, a 3-fold dose-response curve of each purinergic receptor antagonist was prepared, starting at 20 μM, in either 2'3'-cGAMP alone or 2'3'-cGAMP in combination with HeLa-PBS conditioned media (conditioned media prepared as described in examples above). 100 μl from the treatment plate was then transferred to THP1 cells (1:1 dilution), and the cells were incubated for 24 hours. THP1 supernatants were removed and tested for IRF activity.
Conclusion
As shown in FIGS. 6A-6D, the synergistic induction of IRF activity by cGAMP in combination with HeLa-PBS conditioned media was inhibited by AR-C 118925, which is a P2Y2 specific purinergic receptor antagonist.

Example 7: Combination of STING Agonist (cGAMP) and Purinergic Receptor P2Y2 Agonist (PSB1114) Induces IRF Activity in Human THP1 Monocytes Experimental Design
THP1 cells were co-treated with cGAMP and a dose-response curve of an agonist of the purinergic receptor P2Y2, PSB 1114 (acquired from Tocris). After 24 hours, the THP1 supernatant was assayed for IRF induction.
Materials and Methods
THP1 cells, acquired from Invivogen, were seeded at 35,000 cells/well in 96-well format, in 100 μl media. In a separate treatment plate, a dose curve of PSB 1114, starting at 20 μM, was prepared in either plain PBS, or in the presence of cGAMP. 100 μl from treatment plate was transferred to THP1 cells (1:1 dilution), and cells were incubated for 24 hours prior to IRF and NfkB read-out.

Conclusion

As shown in FIGS. 7A and 7B, the combination of PSB 1114 (a P2Y2 agonist) and 2'3'-cGAMP (a STING agonist) induced IRF signaling in human THP1 monocytes.

Example 8: Combination of STING Agonist (cGAMP) and Purinergic Receptor P2Y2 Agonist (Diquafosol) Induces IRF Activity in Human THP1 Monocytes Experimental Design THP1 cells were co-treated with cGAMP and a dose-response curve of the P2Y2 agonist Diquafosol. After 24 hours, THP1 supernatant was assayed for IRF and NfkB induction.

Materials and Methods

THP1 cells, acquired from Invivogen, were seeded at 35,000 cells/well in 96-well format, in 100 μl media. In a separate treatment plate, a dose curve of Diquafosol (acquired from MedChemExpress), starting at 100 μM, was prepared in either plain PBS, or in the presence of cGAMP. 100 μl from treatment plate was transferred to THP1 cells (1:1 dilution), and cells were incubated for 24 hours prior to IRF and NfkB read-outs.

Conclusion

As depicted in FIGS. 8A-8B, a combination of the P2Y2 agonist Diquafosol and the STING agonist cGAMP induced IRF signaling in human monocytes. In a related experiment, combinations of the STING agonist cGAMP with purinergic receptor agonist nucleotide triphosphates also induced IRF signaling in human monocytes (data not shown).

Example 9: Conditioned Medium from Nutrient Starved HeLa Cells in Combination with a STING Agonist (ADU-S100) Induces IRF Activity in Human THP1 Monocytes Experimental Design THP1 cells were co-treated with nutrient starved (PBS) HeLa conditioned media and a dose-response curve of the STING agonist ADU-S100 (acquired from Chemietek). After 24 hours, the THP1 supernatant was assayed for IRF induction.

Materials and Methods

THP1 cells, acquired from Invivogen, were seeded at 35,000 cells/well in 96-well format, in 100 μl media. In a separate treatment plate, a dose curve of ADU-S100, starting at 20 μM, was prepared in either PBS, or in the presence of nutrient-starved HeLa conditioned media. 100 μl from the treatment plate was transferred to the THP1 cells (1:1 dilution), and the cells were incubated for 24 hours prior to IRF reporter read-out.

Conclusion

As depicted in FIG. 9, treatment of THP1 monocytes with nutrient starved (PBS) HeLa conditioned media in combination with the STING agonist ADU-S100 strongly increased IRF signaling.

Example 10: Combination of STING Agonist (ADU-S100) and Purinergic Receptor P2Y2 Agonist (Diquafosol) Induces IRF Activity in Human THP1 Monocytes Experimental Design THP1 cells were co-treated with ADU-S100 and a dose-response curve of the P2Y2 agonist Diquafosol. After 24 hours, the THP1 supernatant was assayed for IRF induction.

Materials and Methods

THP1 cells, acquired from Invivogen, were seeded at 35,000 cells/well in 96-well format, in 100 μl media. In a separate treatment plate, a dose curve of Diquafosol (acquired from MedChemExpress), starting at 100 μM, was prepared in either plain PBS, or in the presence of ADU-S100 (2 μM). 100 μl from the treatment plate was transferred to THP1 cells (1:1 dilution), and the cells were incubated for 24 hours prior to IRF and NfkB read-outs.

Conclusion

As depicted in FIG. 10A-10B, the STING agonist ADU-S100 synergizes with the P2Y2 agonist Diquafosol to induce IRF signaling in human monocytes.

Example 11: Method for Screening Nucleotides in Combination with the STING Agonist cGAMP for Activation of Human THP1 Monocytes Experimental Design THP1 cells are co-treated with a dose-curve of various nucleotides in the presence or absence of cGAMP. After 24 hours the THP1 supernatants are assayed for IRF activity.

Materials and Methods

THP1 cells, acquired from Invivogen, are seeded at 35,000 cells/well in 96-well format, in 100 μl media. In a separate treatment plate, a dose curve of the indicated nucleotide is prepared in the presence of absence of cGAMP. 100 μl from the treatment plate is transferred to THP1 cells (1:1) dilution, and the cells are incubated for 24 hours prior to IRF read-out.

Example 12: Induction of an Anti-Tumor/Pro-Inflammatory Response In Vivo by Treatment of 4T1 Breast Tumor Xenografts with Conditioned Medium from Nutrient Starved 4T1 Breast Cancer Cells and the STING Agonist ADU-S100

BALB/C mice are subcutaneously injected with $1\times10^6$ 4T1 breast cancer cells. Mice are dosed intratumorally by injection with Vehicle, conditioned medium from nutrient starved 4T1 breast cancer cells alone, or a combination of the conditioned medium and ADU-S100 when tumors reach a median size of 150-200 mm$^3$. The conditioned medium is prepared by culturing the 4T1 breast cancer cells in PBS (nutrient-deprivation) for 48 hours.

Forty-eight hours after dosing, immunophenotyping is performed on tumor infiltrating cells, lymphocytes, and splenocytes to characterize the recruitment and activation status of myeloid and lymphoid cells. Immunophenotyping is performed either by immunohistochemistry/immunofluorescence staining of tumor sections, or by first dissociating the tumor into single cell suspensions and then subjecting the cells to flow cytometry (J Vis Exp., 2015, (98): 52657; J Natl Cancer Inst. 2015 Feb. 3; 107(3); Cancer Discov. 2012 July; 2(7):608-23.). Compared to vehicle, an induction of a pro-inflammatory response by conditioned medium from nutrient starved 4T1 breast cancer cells alone or in combination with ADU-S100 is assessed by an increased recruitment of monocytes, macrophages and T cells into the tumor microenvironment. Further, anti-tumor immune responses are assessed by determining increases in activation markers in macrophages, (MHCII and CD80) CD11+ CD103+ Dendritic cells (MHCII) and in both CD4 and CD8 T cells (Ki67 and CD69) without concomitant activation of CD4+FoxP3+ T-regulatory cells. In addition, the inhibition of tumor growth by conditioned medium from nutrient starved 4T1 breast cancer cells alone or in combination with ADU-S100 is assessed by measurements of tumor size over a three-week period or until tumors reach a maximum size of 2000 mm$^3$.

Example 13: Induction of a Systemic Anti-Tumor/Pro-Inflammatory Response In Vivo by Local Treatment of 4T1 Breast Tumor Xenografts with Conditioned Medium from Nutrient Starved 4T1 Breast Cancer Cells and the STING Agonist ADU-S100

BALB/C mice are subcutaneously injected with 1×10$^6$ 4T1 breast cancer cells at two different sites within the body. Mice are dosed intratumorally with Vehicle, conditioned medium from nutrient starved 4T1 breast cancer cells alone, or a combination of the conditioned medium and ADU-S100 at one tumor site when tumors reach a median size of 150-200 mm$^3$. The conditioned medium is prepared by culturing the 4T1 breast cancer cells in PBS (nutrient-deprivation) for 48 hours. The inhibition of tumor growth by conditioned medium from nutrient starved 4T1 breast cancer cells alone or in combination with ADU-S100 is assessed by measurements of tumor size of both the treated and non-treated (contralateral) tumor over a three-week period or until tumors reach a maximum size of 2000 mm$^3$. In addition, engagement of systemic adaptive immune responses is assessed by analyzing the tumor infiltrating lymphocytes (TILs) within the contralateral tumor site. Therapeutically relevant adaptive immune responses in the contralateral tumor are assessed by either quantitative increases in T effector cell number (FoxP3-CD4+ T cells, CD8+ T cells) or by increased activation status of T cells (CD69, ki67), macrophages (MHCII and CD80) or CD11+ CD103+ Dendritic cells (MHCII).

Example 14: Use of Conditioned Medium from Nutrient Starved Melanoma Cells and the STING Agonist ADU-S100 to Treat Melanoma in a Human Clinical Trial A randomized controlled trial (RCT) is conducted to evaluate the safety and efficacy of conditioned medium from nutrient starved melanoma cells alone or in combination with ADU-S100 following multiple infusions of conditioned medium from nutrient starved melanoma cells alone, in combination with ADU-S100 or in further combination with pembrolizumab, compared to multiple infusions of pembrolizumab, in the treatment of melanoma patients that have failed 1 or 2 cancer treatment regimens. The conditioned medium is prepared by culturing melanoma cells in PBS (nutrient-deprivation) for 48 hours.

One hundred patients with advanced RCC that failed cancer treatment regimens were randomized to receive conditioned medium from nutrient starved melanoma cells alone, a combination of the conditioned medium with ADU-S100, pembrolizumab alone, conditioned medium from nutrient starved renal carcinoma cells in combination with pembrolizumab, or a combination of the conditioned medium, ADU-S100 and pembrolizumab. Patients are required to have not received prior treatment with pembrolizumab and not have active autoimmune disease or medical conditions requiring systemic immunosuppression. Tumor assessments begin on week 8 following commencement of therapy and continue every 8 weeks thereafter for the first year and every 12 weeks until progression or treatment discontinuation. The efficacy of the conditioned medium from nutrient starved melanoma cells is assessed by assessment of overall survival rates.

Example 15: Induction of Anti-Tumor Immune Response In Vivo by Conditioned Medium from B16.BL6 Melanoma Cells, the STING Agonist ADU-S100 and Anti-CTLA4 Antibody (9D9) Treatment of B16.BL6 Melanoma Tumor Xenografts C57/BL6 mice are subcutaneously injected with 1×10$^5$ B16.BL6 melanoma cells. Mice are dosed intratumorally with Vehicle, conditioned medium from B16.BL6 melanoma cells, ADU-S100, a combination of the conditioned medium and ADU-S100, anti-CTLA4 antibody 9D9 (10 mg/kg, i.p.), a combination of conditioned medium from B16.BL6 melanoma cells and 9D9, or a combination of the conditioned medium, ADU-S100 and 9D9. The conditioned medium is prepared by culturing the B16.BL6 melanoma cells in PBS for 48 hours. Mice are dosed when tumors reach a median size of 150-200 mm$^3$. 48 hours later immunophenotyping is performed on tumor infiltrating cells, lymphocytes and splenocytes to characterize the recruitment and activation status of myeloid and lymphoid cells. Compared to vehicle, an induction of a maximal pro-inflammatory response by the combinations of conditioned medium from B16.BL6 melanoma cells, ADU-S100 and 9D9 treatment is assessed by an increased recruitment of CD3$^+$ T cells into the tumor microenvironment compared to each treatment alone. In addition, the maximal inhibition of tumor growth by the combination therapies compared to each treatment alone is assessed by measurements of tumor size over a three-week period or until tumors reach a maximum size of 2000 mm$^3$.

Example 16: Induction of an Anti-Tumor/Pro-Inflammatory Response In Vivo by Treatment of 4T1 Breast Tumor Xenografts with a Combination of a STING Agonist (ADU-S100) and a Purinergic Receptor P2Y2 Agonist (Diquafosol)

BALB/C mice are subcutaneously injected with 1×10$^6$ 4T1 breast cancer cells. Mice are dosed intratumorally by injection with Vehicle or a combination of ADU-S100 and Diquafosol when tumors reach a median size of 150-200 mm$^3$. 48 hours later immunophenotyping is performed on tumor infiltrating cells, lymphocytes, and splenocytes to characterize the recruitment and activation status of myeloid and lymphoid cells. Immunophenotyping is performed either by immunohistochemistry/immunofluorescence staining of tumor sections, or by first dissociating the tumor into single cell suspensions and then subjecting the cells to flow cytometry (J Vis Exp., 2015, (98): 52657; J Natl Cancer Inst. 2015 Feb. 3; 107(3); Cancer Discov. 2012 July; 2(7):608-23.). Compared to vehicle, an induction of a pro-inflammatory response by ADU-S100 and Diquafosol treatment is assessed by an increased recruitment of monocytes, macrophages and T cells into the tumor microenvironment. Further, anti-tumor immune responses are assessed by determining increases in activation markers in macrophages, (MHCII and CD80) CD11+CD103+ Dendritic cells (MHCII) and in both CD4 and CD8 T cells (Ki67 and CD69) without concomitant activation of CD4+ FoxP3+ T-regulatory cells. Further, enhanced IRF response is confirmed by increases in cytokine expression, particularly type I interferon (e.g. IFNβ). In addition, the inhibition of tumor growth by ADU-S100 and Diquafosol is assessed by measurements

Example 17: Induction of a Systemic Anti-Tumor/Pro-Inflammatory Response In Vivo by Local Treatment of 4T1 Breast Tumor Xenografts with a Combination of a STING Agonist (ADU-S100) and a Purinergic Receptor P2Y2 Agonist (Diquafosol)

BALB/C mice are subcutaneously injected with $1\times10^6$ 4T1 breast cancer cells at two different sites within the body. Mice are dosed intratumorally with Vehicle or ADU-5100 and Diquafosol at one tumor site when tumors reach a median size of 150-200 mm$^3$. The inhibition of tumor growth by ADU-5100 and Diquafosol is assessed by measurements of tumor size of both the treated and non-treated (contralateral) tumor over a three-week period or until tumors reach a maximum size of 2000 mm$^3$. In addition, engagement of systemic adaptive immune responses is assessed by analyzing the tumor infiltrating lymphocytes (TILs) within the contralateral tumor site. Therapeutically relevant adaptive immune responses in the contralateral tumor are assessed by either quantitative increases in T effector cell number (FoxP3-CD4+ T cells, CD8+ T cells) or by increased activation status of T cells (CD69, ki67), macrophages (MHCII and CD80) or CD11+CD103+ Dendritic cells (IICII).

Example 18: Use of a Combination of a STING Agonist (ADU-S100) and a Purinergic Receptor P2Y2 Agonist (Diquafosol) to Treat Melanoma in a Human Clinical Trial A randomized controlled trial (RCT) is conducted to evaluate the safety and efficacy of ADU-S100 and Diquafosol following multiple infusions of a combination of ADU-S100 and Diquafosol alone or in further combination with pembrolizumab, compared to multiple infusions of pembrolizumab, in the treatment of melanoma patients that have failed 1 or 2 cancer treatment regimens.

One hundred patients with advanced melanoma that failed cancer treatment regimens are randomized to receive either a combination of ADU-5100 and Diquafosol alone, pembrolizumab alone or ADU-S100 and Diquafosol in further combination with pembrolizumab. Patients are required to have not received prior treatment with pembrolizumab and not have active autoimmune disease or medical conditions requiring systemic immunosuppression. Tumor assessments begin on week 8 following commencement of therapy and continue every 8 weeks thereafter for the first year and every 12 weeks until progression or treatment discontinuation. The efficacy of the combination of ADU-S100 and Diquafosol is assessed by assessment of overall survival rates.

Example 19: Induction of Anti-Tumor Immune Response In Vivo by a Combination of a STING Agonist (ADU-S100), a Purinergic Receptor P2Y2 Agonist (Diquafosol), and Anti-CTLA4 Antibody (9D9) Treatment of B16.BL6 Melanoma Tumor Xenografts C57/BL6 mice are subcutaneously injected with $1\times10^5$ B16.BL6 melanoma cells. Mice are dosed intratumorally with Vehicle, a combination of ADU-S100 and Diquafosol, anti-CTLA4 antibody 9D9 (10 mg/kg, i.p.), or a combination of ADU-S100, Diquafosol and 9D9. Mice are dosed when tumors reach a median size of 150-200 mm$^3$. 48 hours later immunophenotyping is performed on tumor infiltrating cells, lymphocytes and splenocytes to characterize the recruitment and activation status of myeloid and lymphoid cells. Compared to vehicle, an induction of a maximal pro-inflammatory response by the combination of ADU-S100, Diquafosol and 9D9 treatment is assessed by an increased recruitment of CD3+ T cells into the tumor microenvironment compared to either treatment alone. In addition, the maximal inhibition of tumor growth by the combination therapy compared to either treatment alone is assessed by measurements of tumor size over a three-week period or until tumors reach a maximum size of 2000 mm$^3$.

Example 20: Testing the Inhibition of Pro-Inflammatory Signaling by a Purinergic Receptor P2Y2 Antagonist (AR-C 118925), Alone or in Combination with a STING Antagonist (H-151), in an In Vivo Model of Injury and Regeneration C57/BL6 mice are treated with either vehicle, a purinergic receptor P2Y2 antagonist (AR-C 118925), or a combination of a STING antagonist (H-151) and purinergic receptor P2Y2 antagonist (AR-C 118925) by intraperitoneal injection and subjected to a renal ischemia-reperfusion injury. Briefly, mice are exposed by flank incision and clamped for 60 minutes. After releasing the clamp, flank incisions are closed with sutures. Sham surgeries are performed in a similar manner but without clamping renal vessels. Inflammation of the outer medulla is assessed 2 days and 7 days post-surgery. The anti-inflammatory effect of the purinergic receptor P2Y2 antagonist (AR-C 118925) or the combination of the STING antagonist and the purinergic receptor antagonist is assessed by a decrease in macrophage and neutrophil recruitment as assessed by histology (F4/80 staining for macrophages and Napthol AS-D chloroacetate esterase staining) and/or flow-cytometry.

Example 21: Testing the Inhibition of Ulcerative Colitis in Mice by a Purinergic Receptor P2Y2 Antagonist (AR-C 118925), Alone or in Combination with a STING Antagonist (H-151)

C57/B6 mice are treated with vehicle, a purinergic receptor P2Y2 antagonist (AR-C 118925), or a combination of a STING antagonist (H-151) and purinergic receptor P2Y2 antagonist (AR-C 118925), by intraperitoneal injection before the induction of colitis by administration of 3-4% dextran sodium sulfate in the drinking water for 5 days. An anti-inflammatory effect of the purinergic receptor P2Y2 antagonist (AR-C 118925), and of the combination of the STING antagonist and the purinergic receptor antagonist, as compared to vehicle is assessed by decreased colon length, decreased diarrhea, and decreased weight loss. In addition, inhibition of neutrophil recruitment (innate immune response) by the purinergic receptor P2Y2 antagonist (AR-C 118925) or the combination of the STING antagonist and the purinergic receptor antagonist is assessed by decreased myeloperoxidase activity in the colon (compared to vehicle).

Example 22: Effects of a STING Agonist (ADU-S100), a Purinergic Receptor (P2Y2) Agonist (Diquafosol), and Combinations Thereof on Tumor Growth and Survival in a Mouse Model of Cancer Test BALB/c mice were injected subcutaneously in the right flank with $1\times10^6$ A20 B-cell lymphoma tumor cells (in a 0.1 mL cell suspension). Sixteen days after tumor cell implantation, on Day 1 of the study, animals were sorted into ten groups (n=10) with individual tumor volumes between 48 and 100 mm$^3$ and a group mean tumor volume of 81 mm$^3$. Five groups of mice were dosed according in the following treatment groups.

Group 1 received Vehicle (PBS) intratumorally once per day.

Group 2 received 1 µg/kg of the STING agonist (ADU-S100) intratumorally once per day.

Group 3 received 50 µg/kg of the STING agonist (ADU-S100) intratumorally once per day.

Group 4 received 10 mg/animal of the purinergic receptor agonist (diquafosol testrasodium) intratumorally once per day.

Group 5 received 1 µg/kg ADU-S100 intratumorally combined with 10 mg/animal of diquafosol testrasodium intratumorally once per day.

ADU-S100 and Diquafosol tetrasodum were dosed intratumorally (itu) in a total volume of 50 µL of therapeutic agents; combination therapies were administered as single injections containing 2×25 µL of 2× dosing solutions.

Tumors were measured using calipers twice per week.

Results

As shown in FIG. 12, the combination of the P2Y2 agonist and the lower dose of the STING agonist (Group 5) had a much greater effect on increasing survival relative to the P2Y2 agonist alone (10 mg/animal of diquafosol testrasodium, Group 4) or the lower dose of the STING agonist alone (1 µg/kg of ADU-S100, Group 2).

Conclusions

Combination of a STING agonist and a purinergic receptor (P2Y2) agonist had a greater effect on improving survival in a mouse model of cancer than either compound alone.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

Each reference, patent, and patent application referred to in the instant application is hereby incorporated by reference in its entirety as if each reference were noted to be incorporated individually.

The invention claimed is:

1. A method of treating a cancer in a subject, comprising administering to the subject, in combination (a) a Stimulator of Interferon Genes (STING) agonist, wherein the STING agonist is a cyclic dinucleotide, and (b) a P2Y2 receptor agonist compound selected from:

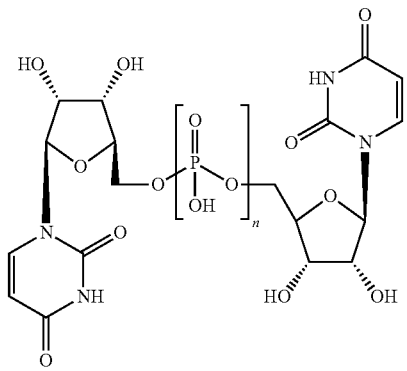

68a n = 2 Up$_2$U
68b n = 3 Up$_3$U
68c n = 4 Up$_4$U, Diquafosol
68d n = 6 Up$_6$U

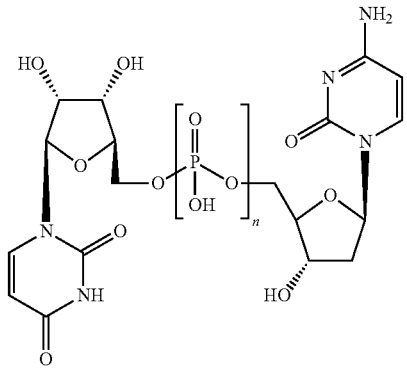

69 Up$_4$dC, INS37217, Denufosol

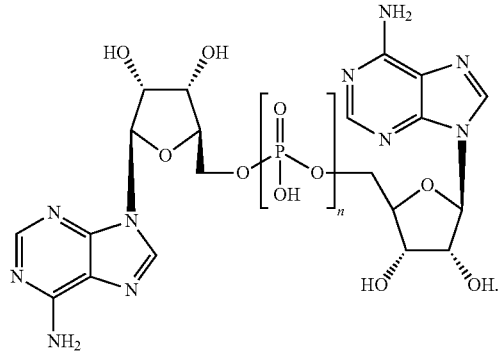

70a n = 3 Ap$_3$A
70b n = 4 Ap$_4$A
70c n = 5 Ap$_5$A or a pharmaceutically acceptable salt thereof, thereby treating the cancer in the subject.

2. The method of claim 1, wherein the method comprises administering the STING agonist and the P2Y2 receptor agonist in an amount sufficient to increase immune activity, increase the level or activity of IRF, and/or increase the level or activity of NF-κB in the subject relative to a subject that is treated with the STING agonist alone, wherein a response of the cancer to treatment is improved relative to a treatment with the STING agonist alone.

3. The method of claim 1, wherein the method further comprises administering an immunotherapeutic to the subject.

4. The method of claim 1, wherein the cancer is responsive to an immune checkpoint therapy.

5. The method of claim 4, wherein the cancer is selected from the group consisting of squamous cell head and neck cancer, melanoma, Merkel cell carcinoma, hepatocellular carcinoma, renal cell carcinoma, cervical cancer, small cell lung cancer, non-small cell lung cancer, triple negative breast cancer, esophageal cancer, stomach cancer, Hodgkin's lymphoma, B-cell lymphoma, and bladder cancer.

6. The method of claim 1, wherein the cancer is lymphoma.

7. The method of claim 1, wherein the cancer is colon cancer.

8. The method of claim 1, wherein the STING agonist is administered intratumorally or intravenously.

9. The method of claim 1, wherein the P2Y2 receptor agonist is administered intratumorally or intravenously.

10. The method of claim 1, wherein the subject is human.

11. The method of claim 1, wherein the cyclic dinucleotide is selected from the group consisting of cGAMP, 2'3'-cGAMP, 3'3'-cGAMP, 3'3'-cGAMP-F, c-di-GMP-F, Rp/Sp, MK-1454, ADU-S100, and Disodium dithio-(RP, RP)-[cyclic [A(2',5')pA(3',5')p]] [Rp,Rp]-Cyclic(adenosine-(2',5') monophosphorothioateadenosine-(3',5')-monophosphorothioate).

12. The method of claim 11, wherein the P2Y2 receptor agonist is diquafosol, denufosol, Ap4A, or a pharmaceutically acceptable salt thereof.

13. The method of claim 11, wherein the P2Y2 receptor agonist is $Up_2U$, $Up_3U$, diquafasol, $Up_6U$, or a pharmaceutically acceptable salt thereof.

14. The method of claim 11, wherein the P2Y2 receptor agonist is diquafosol or a pharmaceutically acceptable salt thereof.

15. The method of claim 11, wherein the P2Y2 receptor agonist is denufosol or a pharmaceutically acceptable salt thereof.

16. The method of claim 1, wherein the cyclic dinucleotide is ADU-S100 or MK-1454.

17. The method of claim 16, wherein the P2Y2 receptor agonist is diquafosol, denufosol, Ap4A, or a pharmaceutically acceptable salt thereof.

18. The method of claim 16, wherein the P2Y2 receptor agonist is $Up_2U$, $Up_3U$, diquafasol, $Up_6U$, or a pharmaceutically acceptable salt thereof.

19. The method of claim 16, wherein the P2Y2 receptor agonist is diquafosol or a pharmaceutically acceptable salt thereof.

20. The method of claim 16, wherein the P2Y2 receptor agonist is denufosol or a pharmaceutically acceptable salt thereof.

21. The method of claim 1, wherein the cyclic dinucleotide is a compound represented by the following structural formula:

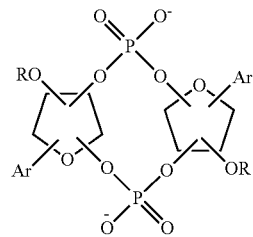

or a pharmaceutically acceptable salt thereof; wherein Ar, for each instance, is independently optionally substituted monocyclic or bicyclic heteroaryl having at least one nitrogen atom and optionally one or more heteroatoms selected from O and S; wherein R, for each instance, is independently hydrogen or an optionally substituted $C_1$-$C_4$ alkyl; wherein each oxygen atom in the two phosphate groups and the OR groups is optionally and independently substituted with S; wherein each OR group and each O⁻ is optionally substituted with a halogen.

22. The method of claim 1, wherein the cyclic dinucleotide is ADU-S100.

23. The method of claim 22, wherein the P2Y2 receptor agonist is diquafosol, denufosol, Ap4A, or a pharmaceutically acceptable salt thereof.

24. The method of claim 22, wherein the P2Y2 receptor agonist is diquafosol or a pharmaceutically acceptable salt thereof.

25. The method of claim 22, wherein the P2Y2 receptor agonist is denufosol or a pharmaceutically acceptable salt thereof.

26. The method of claim 1, wherein the P2Y2 receptor agonist is diquafosol, denufosol, $Ap_4A$, or a pharmaceutically acceptable salt thereof.

27. The method of claim 1, wherein the P2Y2 receptor agonist is $Up_2U$, $Up_3U$, diquafasol, $Up_6U$, or a pharmaceutically acceptable salt thereof.

28. The method of claim 1, wherein the P2Y2 receptor agonist is diquafosol or a pharmaceutically acceptable salt thereof.

29. The method of claim 1, wherein the P2Y2 receptor agonist is denufosol or a pharmaceutically acceptable salt thereof.

30. A method of treating a cancer in a subject, comprising administering to the subject, in combination (a) a Stimulator of Interferon Genes (STING) agonist, wherein the STING agonist is ADU-S100 or MK-1454, and (b) a P2Y2 receptor agonist, wherein the P2Y2 receptor agonist is diquafosol, denufosol, Ap4A, or a pharmaceutically acceptable salt thereof, wherein a response of the cancer to treatment is improved relative to a treatment with the STING agonist alone.

* * * * *